(12) United States Patent
Wollacott et al.

(10) Patent No.: US 10,513,553 B2
(45) Date of Patent: *Dec. 24, 2019

(54) COMPOSITIONS AND METHODS FOR TREATING AND PREVENTING INFLUENZA

(71) Applicant: VISTERRA, INC., Waltham, MA (US)

(72) Inventors: Andrew M. Wollacott, Milton, MA (US); Karthik Viswanathan, Acton, MA (US); Jose Miguel Trevejo, Lexington, MA (US); Susan Sloan, Newton, MA (US); Zachary Shriver, Winchester, MA (US); Maciej Boni, Providence, RI (US)

(73) Assignee: VISTERRA, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,235

(22) Filed: Nov. 11, 2016

(65) Prior Publication Data

US 2017/0137498 A1 May 18, 2017

Related U.S. Application Data

(60) Provisional application No. 62/315,977, filed on Mar. 31, 2016, provisional application No. 62/299,141, filed on Feb. 24, 2016, provisional application No. 62/255,262, filed on Nov. 13, 2015.

(51) Int. Cl.
C07K 16/10 (2006.01)
A61K 39/00 (2006.01)

(52) U.S. Cl.
CPC .... C07K 16/1018 (2013.01); *A61K 2039/505* (2013.01); *A61K 2039/54* (2013.01); *A61K 2039/545* (2013.01); *C07K 2317/34* (2013.01); *C07K 2317/565* (2013.01); *C07K 2317/76* (2013.01); *C07K 2317/92* (2013.01); *C07K 2317/94* (2013.01)

(58) Field of Classification Search
CPC ............ C07K 16/1018; C07K 2317/92; C07K 2317/34; C07K 2317/94; C07K 2317/565; C07K 2317/76; C07K 14/005; C07K 14/255; A61K 2039/54; A61K 2039/545; A61K 2039/505; A61K 38/162; A61K 39/3955; A61K 39/42; A61K 2300/00; A61K 39/00; A61K 39/12; A61K 2039/55516; A61K 38/164; A61K 2039/5258; A61K 2039/523; A61K 2039/55544; A61K 2039/55594; A61K 2039/6068; A61K 35/74; A61K 39/285; A61K 2039/70; A61K 39/02; A61K 39/04; A61K 35/76; A61K 39/275; C12Q 2600/118; C12N 7/00; C12N 2320/30; C12N 33/56983; C12N 15/86; C12N 2710/24034; C12N 2710/24134; G01N 33/6854
See application file for complete search history.

(56) References Cited

U.S. PATENT DOCUMENTS

| | | | |
|---|---|---|---|
| 4,474,757 A | 10/1984 | Arnon et al. |
| 4,625,015 A | 11/1986 | Green et al. |
| 5,589,174 A | 12/1996 | Okuno et al. |
| 5,631,350 A | 5/1997 | Okuno et al. |
| 5,684,146 A | 11/1997 | Okuno et al. |
| 6,337,070 B1 | 1/2002 | Okuno et al. |
| 6,720,409 B2 | 4/2004 | Okuno et al. |
| 7,255,859 B1 | 8/2007 | Emrich et al. |
| 7,527,800 B2 | 5/2009 | Yang et al. |
| 7,537,768 B2 | 5/2009 | Luke et al. |
| 7,566,454 B2 | 7/2009 | Lu et al. |
| 7,566,458 B2 | 7/2009 | Yang et al. |
| 7,572,620 B2 | 8/2009 | Olsen et al. |
| 7,879,326 B2 | 2/2011 | Foung et al. |
| 8,124,092 B2 | 2/2012 | Lanzavecchia |
| 8,192,927 B2 | 6/2012 | Van Den Brink et al. |
| 8,383,121 B2 | 2/2013 | Qian et al. |
| 8,444,986 B2 | 5/2013 | Qian et al. |
| 8,470,327 B2 | 6/2013 | Throsby et al. |
| 8,486,406 B2 | 7/2013 | Burioni et al. |
| 8,540,994 B2 | 9/2013 | Ho et al. |
| 8,540,995 B2 | 9/2013 | Mookkan et al. |
| 8,540,996 B2 | 9/2013 | Qian et al. |
| 8,574,581 B2 | 11/2013 | Qian et al. |
| 8,574,830 B2 | 11/2013 | Mookkan et al. |
| 8,603,467 B2 | 12/2013 | Chen et al. |
| 8,637,456 B2 | 1/2014 | Sasisekharan et al. |
| 8,637,644 B2 | 1/2014 | Ho et al. |
| 8,637,645 B2 | 1/2014 | Ho et al. |

(Continued)

FOREIGN PATENT DOCUMENTS

| CA | 2872308 A1 * | 11/2013 | ............ A61K 45/06 |
|---|---|---|---|
| CN | 104602709 A * | 5/2015 | ............ A61K 45/06 |

(Continued)

OTHER PUBLICATIONS

Plans-Rubió P. The vaccination coverage required to establish herd immunity against influenza viruses. Prev Med. Jul. 2012;55(1): 72-7. Epub Mar. 4, 2012.*

Van den Dool C, Bonten MJ, Hak E, Heijne JC, Wallinga J. The effects of influenza vaccination of health care workers in nursing homes: insights from a mathematical model. PLoS Med. Oct. 28, 2008;5(10):e200.*

Shriver Z, Trevejo JM, Sasisekharan R. Antibody-Based Strategies to Prevent and Treat Influenza. Front Immunol. Jul. 13, 2015;6: 315. eCollection 2015.*

Kalenik B, Sawicka R, Góra-Sochacka A, Sirko A. Influenza prevention and treatment by passive immunization. Acta Biochim Pol. 2014;61(3):573-87. Epub Sep. 12, 2014.*

(Continued)

*Primary Examiner* — Rachel B Gill
(74) *Attorney, Agent, or Firm* — Lando & Anastasi, LLP

(57) ABSTRACT

This disclosure relates to peptide agents, e.g., antibodies and antigen-binding fragments thereof, that bind hemagglutinin protein of influenza viruses, and methods of their use.

22 Claims, 22 Drawing Sheets
Specification includes a Sequence Listing.

(56) References Cited

U.S. PATENT DOCUMENTS

| | | | |
|---|---|---|---|
| 8,802,110 B2 | 8/2014 | Raman et al. | |
| 8,871,207 B2 | 10/2014 | Lanzavecchia | |
| 8,877,200 B2 * | 11/2014 | Shriver | A61K 45/06 |
| | | | 424/159.1 |
| 9,096,657 B2 * | 8/2015 | Shriver | A61K 45/06 |
| 9,278,998 B2 | 3/2016 | Jayaraman et al. | |
| 9,334,309 B2 | 5/2016 | Sasisekharan et al. | |
| 9,572,861 B2 | 2/2017 | Sasisekharan et al. | |
| 9,587,010 B2 | 3/2017 | Lanzavecchia | |
| 9,683,030 B2 | 6/2017 | Raguram et al. | |
| 9,709,567 B2 | 7/2017 | Jayaraman et al. | |
| 9,745,352 B2 | 8/2017 | Raman et al. | |
| 9,982,037 B2 | 5/2018 | Raguram et al. | |
| 2002/0054882 A1 | 5/2002 | Okuno et al. | |
| 2005/0042229 A1 | 2/2005 | Yang et al. | |
| 2005/0287172 A1 | 12/2005 | Yang et al. | |
| 2006/0153871 A1 | 7/2006 | Olsen et al. | |
| 2006/0217338 A1 | 9/2006 | Lu et al. | |
| 2007/0286869 A1 | 12/2007 | Luke et al. | |
| 2008/0014205 A1 | 1/2008 | Horowitz et al. | |
| 2009/0060949 A1 | 3/2009 | Ho et al. | |
| 2009/0092620 A1 | 4/2009 | Moste et al. | |
| 2009/0106864 A1 | 4/2009 | Henry et al. | |
| 2009/0136530 A1 | 5/2009 | Yang et al. | |
| 2009/0234096 A1 | 9/2009 | Garry et al. | |
| 2009/0264362 A1 | 10/2009 | Garry et al. | |
| 2009/0291472 A1 | 11/2009 | Lu et al. | |
| 2009/0311265 A1 | 12/2009 | Van Den Brink et al. | |
| 2010/0021489 A1 | 1/2010 | Arnon et al. | |
| 2010/0036096 A1 | 2/2010 | Roosild et al. | |
| 2010/0040635 A1 | 2/2010 | Horowitz et al. | |
| 2010/0041740 A1 | 2/2010 | Wong et al. | |
| 2010/0061995 A1 * | 3/2010 | Carragher | A61K 31/7088 |
| | | | 424/147.1 |
| 2010/0080813 A1 | 4/2010 | Lanzavecchia | |
| 2010/0086555 A1 | 4/2010 | Lanzavecchia | |
| 2010/0145031 A1 | 6/2010 | Lanzavecchia et al. | |
| 2010/0278834 A1 | 11/2010 | Lanzavecchia | |
| 2010/0316654 A1 | 12/2010 | Horowitz et al. | |
| 2011/0014187 A1 | 1/2011 | Burioni et al. | |
| 2011/0033490 A1 | 2/2011 | Jayaraman et al. | |
| 2011/0038935 A1 | 2/2011 | Marasco et al. | |
| 2011/0065095 A1 | 3/2011 | Kida et al. | |
| 2011/0201547 A1 | 8/2011 | Sasisekharan et al. | |
| 2011/0274702 A1 | 11/2011 | Lanzavecchia | |
| 2011/0319600 A1 | 12/2011 | Ikuta et al. | |
| 2012/0020971 A1 | 1/2012 | Kauvar et al. | |
| 2012/0039898 A1 | 2/2012 | Throsby et al. | |
| 2012/0039899 A1 | 2/2012 | Olsen et al. | |
| 2012/0058124 A1 | 3/2012 | Kurosawa et al. | |
| 2012/0093823 A1 | 4/2012 | Van Den Brink et al. | |
| 2012/0093834 A1 | 4/2012 | Horowitz et al. | |
| 2012/0100142 A1 | 4/2012 | Crowe, Jr. et al. | |
| 2012/0100150 A1 | 4/2012 | Jiang et al. | |
| 2012/0107326 A1 | 5/2012 | Horowitz et al. | |
| 2012/0114664 A1 | 5/2012 | Lanzavecchia | |
| 2012/0128671 A1 | 5/2012 | Horowitz et al. | |
| 2012/0128684 A1 | 5/2012 | Marasco et al. | |
| 2012/0213819 A1 | 8/2012 | Tharakaraman et al. | |
| 2012/0219585 A1 | 8/2012 | Raman et al. | |
| 2012/0276115 A1 | 11/2012 | Van Den Brink et al. | |
| 2012/0282273 A1 | 11/2012 | Wrammert et al. | |
| 2013/0004505 A1 | 1/2013 | Chang et al. | |
| 2013/0022608 A1 | 1/2013 | Burioni et al. | |
| 2013/0202608 A1 | 8/2013 | Mookkan et al. | |
| 2013/0243792 A1 | 9/2013 | Vogels et al. | |
| 2013/0280248 A1 | 10/2013 | Ueno et al. | |
| 2013/0289246 A1 | 10/2013 | Crowe et al. | |
| 2013/0302348 A1 | 11/2013 | Raguram et al. | |
| 2013/0302349 A1 * | 11/2013 | Shriver | A61K 45/06 |
| | | | 424/159.1 |
| 2013/0309248 A1 | 11/2013 | Throsby et al. | |
| 2014/0011982 A1 | 1/2014 | Marasco et al. | |
| 2014/0046039 A1 | 2/2014 | Ahmed et al. | |
| 2014/0148581 A1 * | 5/2014 | Shriver | A61K 45/06 |
| | | | 530/387.3 |
| 2014/0206603 A1 | 7/2014 | Sasisekharan et al. | |
| 2014/0271655 A1 | 9/2014 | Lanzavecchia | |
| 2014/0335504 A1 | 11/2014 | Sasisekharan et al. | |
| 2015/0037352 A1 * | 2/2015 | Shriver | A61K 45/06 |
| | | | 424/159.1 |
| 2015/0147329 A1 | 5/2015 | Raman et al. | |
| 2016/0257732 A1 | 9/2016 | Benjamin et al. | |
| 2016/0266117 A1 | 9/2016 | Jayaraman et al. | |
| 2016/0317612 A1 | 11/2016 | Sasisekharan et al. | |
| 2017/0240617 A1 * | 8/2017 | Sloan | A61K 9/0019 |
| 2017/0306003 A1 | 10/2017 | Raguram et al. | |
| 2018/0009850 A1 | 1/2018 | Raman et al. | |
| 2019/0002536 A1 | 1/2019 | Shriver et al. | |
| 2019/0062407 A1 | 2/2019 | Raguram et al. | |
| 2019/0142931 A1 | 5/2019 | Tharakaraman et al. | |

FOREIGN PATENT DOCUMENTS

| | | | |
|---|---|---|---|
| EP | 0044710 A1 | 1/1982 | |
| EP | 0417191 B1 | 3/1993 | |
| EP | 2363415 A2 | 9/2011 | |
| EP | 2846832 A1 * | 3/2015 | A61K 45/06 |
| JP | 62-051700 | 3/1987 | |
| JP | 2008104450 A | 5/2008 | |
| JP | 2011-160681 A | 8/2011 | |
| JP | 2011528901 A | 12/2011 | |
| WO | 1984/00687 A1 | 3/1984 | |
| WO | 2002/46235 A1 | 6/2002 | |
| WO | 2007/089753 A2 | 8/2007 | |
| WO | 2007/134327 A2 | 11/2007 | |
| WO | 2007/149715 A2 | 12/2007 | |
| WO | 2008/028946 A2 | 3/2008 | |
| WO | 2008/033105 A1 | 3/2008 | |
| WO | 2008/091657 A1 | 7/2008 | |
| WO | 2008/110937 A2 | 9/2008 | |
| WO | 2008/118970 A2 | 10/2008 | |
| WO | 2008/140415 A1 | 11/2008 | |
| WO | 2008/154813 A1 | 12/2008 | |
| WO | 2009/035412 A1 | 3/2009 | |
| WO | 2009/035420 A1 | 3/2009 | |
| WO | 2009/073163 A1 | 6/2009 | |
| WO | 2009/073330 A2 | 6/2009 | |
| WO | 2009/079259 A2 | 6/2009 | |
| WO | 2009/099394 A1 | 8/2009 | |
| WO | 2009/111865 A1 | 9/2009 | |
| WO | 2009/115972 A1 | 9/2009 | |
| WO | 2009/119722 A1 | 10/2009 | |
| WO | 2009/121004 A2 | 10/2009 | |
| WO | 2009/133249 A1 | 11/2009 | |
| WO | 2009/144667 A1 | 12/2009 | |
| WO | 2009/147248 A2 | 12/2009 | |
| WO | 2010/006144 A2 | 1/2010 | |
| WO | 2010/010466 A2 | 1/2010 | |
| WO | 2010/010467 A2 | 1/2010 | |
| WO | 2010/027818 A2 | 3/2010 | |
| WO | 2010/040281 A1 | 4/2010 | |
| WO | 2010/040572 A2 | 4/2010 | |
| WO | 2010/046775 A2 | 4/2010 | |
| WO | 2010/073647 A1 | 7/2010 | |
| WO | 2010/074656 A1 | 7/2010 | |
| WO | 2010/127252 A2 | 11/2010 | |
| WO | 2010/130636 A1 | 11/2010 | |
| WO | 2010/132604 A2 | 11/2010 | |
| WO | 2010/140114 A1 | 12/2010 | |
| WO | 2011003100 A2 | 1/2011 | |
| WO | 2011/041391 A1 | 4/2011 | |
| WO | 2011/044570 A2 | 4/2011 | |
| WO | 2011/068143 A1 | 6/2011 | |
| WO | 2011/087092 A1 | 7/2011 | |
| WO | 2011/093217 A1 | 8/2011 | |
| WO | 2011/096302 A1 | 8/2011 | |
| WO | 2011094445 A1 | 8/2011 | |
| WO | 2011/117848 A1 | 9/2011 | |
| WO | 2011/160083 A1 | 12/2011 | |
| WO | 2012/021786 A2 | 2/2012 | |
| WO | 2012/026878 A1 | 3/2012 | |
| WO | 2012/029997 A1 | 3/2012 | |

(56) References Cited

FOREIGN PATENT DOCUMENTS

| WO | 2012040406 | A2 | 3/2012 | | |
|---|---|---|---|---|---|
| WO | 2012/045001 | A2 | 4/2012 | | |
| WO | 2012/054745 | A1 | 4/2012 | | |
| WO | 2012047941 | A2 | 4/2012 | | |
| WO | 2012/072788 | A1 | 6/2012 | | |
| WO | 2012/096994 | A2 | 7/2012 | | |
| WO | 2013/007770 | A1 | 1/2013 | | |
| WO | 2013/011347 | A1 | 1/2013 | | |
| WO | 2013/020074 | A2 | 2/2013 | | |
| WO | 2013/030604 | A1 | 3/2013 | | |
| WO | 2013/044840 | A1 | 4/2013 | | |
| WO | 2013/048153 | A2 | 4/2013 | | |
| WO | 2013/059524 | A2 | 4/2013 | | |
| WO | 2013/081371 | A1 | 6/2013 | | |
| WO | 2013/081463 | A2 | 6/2013 | | |
| WO | 2013/086052 | A2 | 6/2013 | | |
| WO | 2013/089496 | A1 | 6/2013 | | |
| WO | 2013/114885 | A1 | 8/2013 | | |
| WO | 2013/132007 | A1 | 9/2013 | | |
| WO | 2013/169377 | A1 | 11/2013 | | |
| WO | WO-2013170139 | A1 | * | 11/2013 | ............. A61K 45/06 |
| WO | 2014124319 | A2 | 8/2014 | | |
| WO | 2015051010 | A1 | 4/2015 | | |
| WO | 2015112994 | A1 | 7/2015 | | |
| WO | 2017083627 | A1 | 5/2017 | | |
| WO | 2017147248 | A1 | 8/2017 | | |

OTHER PUBLICATIONS

Lambert LC, Fauci AS. Influenza vaccines for the future. N Engl J Med. Nov. 18, 2010;363(21):2036-44.*
He W, Mullarkey CE, Duty JA, Moran TM, Palese P, Miller MS. Broadly neutralizing anti-influenza virus antibodies: enhancement of neutralizing potency in polyclonal mixtures and IgA backbones. J Virol. Apr. 2015;89(7):3610-8. Epub Jan. 14, 2015.*
Soema PC, Kompier R, Amorij JP, Kersten GF. Current and next generation influenza vaccines: Formulation and production strategies. Eur J Pharm Biopharm. Aug. 2015;94:251-63. Epub Jun. 3, 2015.*
Wu JT, Lee CK, Cowling BJ, Yuen KY. Logistical feasibility and potential benefits of a population-wide passive immunotherapy program during an influenza pandemic. Influenza Other Respir Viruses. May 2011;5 Suppl 1:226-9.*
Gronvall GK, Rambhia KJ, Adalja A, Cicero A, Ingelsby T, Kadlec R. Next-Generation Monoclonal Antibodies: Challenges and Opportunities. Center for Biosecurity of UPMC. Final Report—Feb. 2013.*
Oh HL, Akerström S, Shen S, Bereczky S, Karlberg H, Klingström J, Lal SK, Mirazimi A, Tan YJ. An antibody against a novel and conserved epitope in the hemagglutinin 1 subunit neutralizes numerous H5N1 influenza viruses. J Virol. Aug. 2010;84(16):8275-86. Epub Jun. 2, 2010.*
Wu JT, Lee CK, Cowling BJ, Yuen KY. Logistical feasibility and potential benefits of a population-wide passive-immunotherapy program during an influenza pandemic. Proc Natl Acad Sci U S A. Feb. 16, 2010;107(7):3269-74. doi: 10.1073/pnas.0911596107. Epub Feb. 1, 2010.*
Song A, Myojo K, Laudenslager J, Harada D, Miura T, Suzuki K, Kuni-Kamochi R, Soloff R, Ohgami K, Kanda Y. Evaluation of a fully human monoclonal antibody against multiple influenza A viral strains in mice and a pandemic H1N1 strain in nonhuman primates. Antiviral Res. Nov. 2014;111:60-8. Epub Sep. 16, 2014.*
Ter Meulen J. Monoclonal antibodies for prophylaxis and therapy of infectious diseases. Expert Opin Emerg Drugs. Nov. 2007;12(4): 525-40.*
Baranovich et al. "The Hemagglutinin Stem-Binding Monoclonal Antibody VIS410 Controls Influenza Virus-Induced Acute Respiratory Distress Syndrome" Antimicrobial Agents and Chemotherapy (2016) vol. 60, No. 4, pp. 2118-2131.

Berry, C.M., et al., "Passive Broad-Spectrum Influenza Immunoprophylaxis", Influenza Research and Treatment, vol. 2014, Article ID 267594, pp. 1-9; Published Sep. 22, 2014.
Boni et al., "Virulence attenuation during an influenza A/H5N1 pandemic," Phil Trans R Soc B (2012) 368(1614), 12 pages.
Chen et al "Humanized antibodies with broad-spectrum neutralization to avian influenza virus H1N1", Antiviral Research, vol. 87, No. 1, Jul. 1, 2010 pp. 81-84.
Clementi et al. "Broad-range neutralizing anti-influenza A human monoclonal antibodies: new perspectives in therapy and prophylaxis" New Microbiologica (2012) vol. 35, pp. 399-406.
ClinicalTrials.gov Identifier: NCT02045472, "A Study of VIS410 to Assess Safety and Pharmacokinetics," ClinicalTrial.gov updated May 13, 2015, clinicaltrials.gov/ct2/show/record/NCT02045472.
ClinicalTrials.gov Identifier: NCT02468115, "Influenza Challenge Study of VIS410 in Healthy Volunteers," ClinicalTrial.gov updated Apr. 4, 2016, clinicaltrials.gov/ct2/show/record/NCT02468115.
Communication Made to Inventors Prior to Mar. 14, 2013.
Corti et al. "A Neutralizing Antibody Selected from Plasma Cells that Binds to Group 1 and Group 2 Influenza A Hemagglutinins", Science vol. 333, No. 6044, Aug. 2011, pp. 850-856.
Dreyfus et al. "Highly Conserved Protective Epitopes on Influenza B Viruses" Science (2012) vol. 337, pp. 1343-1348.
Ekiert et al, "A Highly Conserved Neutralizing Epitope on Group 2 Influenza A Viruses", Science, vol. 333, No. 6044, Aug. 2011 pp. 843-850.
Ekiert et al."Broadly neutralizing antibodies against influenza virus and prospects for universal therapeies", Current Opinion in Virology, vol. 2, No. 2, Apr. 2012, pp. 134-141.
Ekiert et al., "Antibody recognition of a highly conserved influenza virus epitope" Science 324(5924):246-251 (2009).
Falconer et al., "Stabilization of a monoclonal antibody during purification and formulation by addition of basic amino acid excipients," J Chem Tech and Biotechnol (2011) vol. 86, Issue 7, pp. 942-948.
Ferguson et al., "Strategiesfor containing an emerging influenza pandemic in Southeast Asia," Nature (2005) vol. 437(7056), pp. 209-214.
Gamblin and Skehel, "Influenza hemagglutinin and neuraminidase membrane glycoproteins." J Biol Chem (2010) vol. 285, No. 37, pp. 28403-28409.
Germann et al., "Mitigation strategies for pandemic influenza in the United States," PNAS (2006) vol. 103, No. 15, pp. 5935-5940.
Gershoni et al., "Epitope Mapping: The First Step in Developing Epitope-Based Vaccines," Biodrugs (2007) vol. 21, No. 3, pp. 145-156.
International Search Report and Written Opinion for International Application No. PCT/US2016/061501 dated Feb. 8, 2017.
International Search Report and Written Opinion for PCT/US2013/040534 dated Sep. 2, 2013.
International Search Report and Written Opinion issued in International Application No. PCT/US2017/019053, dated Jun. 13, 2017.
Jefferson et al., "Oseltamivir for influenza in adults and children: systematic review of clinical study reports and summary of regulatory comments," BMJ (2014) vol. 348, Article g2545, 18 pages.
Krause et al. "A Broadly Neutralizing Human Monoclonal Antibody That Recognizes a Conserved, Novel Epitope on the Globular Head of the Influenza H1N1 Virus Hemagglutinin", Journal of Virology, vol. 85, No. 20, Oct. 15, 2011, pp. 10905-10908.
Kubota-Koketsu et al "Broad neutralizing human monoclonal antibodies against influenza virus from vaccinated healthy donors", Biochemical and Biophysical Research Communications, vol. 387, No. 1, Sep. 11, 2009 pp. 180-185.
Lachmann, P.J., "The Use of Antibodies in the Prophylaxis and Treatment of Infections", Emerging Microbes and Infections, Published Aug. 8, 2012, 1, e11, pp. 1-5.
Laursen et al. "Broadly neutralizing antibodies against influenza viruses", Antiviral Research, vol. 98, No. 3, Jun. 2013, pp. 476-483.
Longini et al., "Containing Pandemic Influenza at the Source" Science (2005) vol. 39, pp. 1083-1087.
Okuno et al., "A common neutralizing epitope conserved between the hemagglutinins of influenza A virus H1 and H2 strains." J Virol. 67(5):2552-2558 (1993).

(56) References Cited

OTHER PUBLICATIONS

Opposition paper filed in Chilean Application 3051-2014 by AG Pharmaceutical Labs Industrial Association, dated Sep. 9, 2015.
Pedotti et al., "Computational Docking of Antibody-Antigen Complexes, Opportunities and Pitfalls Illustrated by Influenza Hemagglutinin," Int J Mol Sci (2011), vol. 12, pp. 226-251.
Rogers and Paulson "Receptor determinants of human and animal influenza virus isolates: differences in receptor specificity of the H3 hemagglutinin based on species of origin" Virology. 127(2):361-373 (1983).
Rogers et al. "Single amino acid substitutions in influenza haemagglutinin change receptor binding specificity" Nature. 304(5921):76-78 (1983).
Rudikoff et al., "Single Amino Acid Substitution Altering Antigen-Binding Specificity", Proc. Natl. Acad. Sci., vol. 79, pp. 1979-1983, Mar. 1982.
Saelens "One Against All: A Broadly Influenza Neutralizing Manmade Monoclonal Antibody Passes Phase I" EBioMedicine 5 (2016) pp. 16-17.
Sauter et al. "Binding of influenza virus hemagglutinin to analogs of its cell-surface receptor, sialic acid: analysis by proton nuclear magnetic resonance spectroscopy and X-ray crystallography" Biochemistry. 31(40):9609-9621 (1992).
Shaman et al., "Forecasting season outbreaks of influenza," PNAS (2012) vol. 109, No. 50, pp. 20425-20430.
Shaman et al., "Real-time influenza forecasts during the 2012-2013 season," Nature Communications (2013) vol. 4, Article 2837, 10 pages.
Shriver and Viswanathan, "Design of a Broadly Neutralizing Antibody Targeting Influenza A" Visterra Inc. (2012) Retrieved from the Internet Aug. 8, 2013; www.visterrainc.com/pdf/ICAAC-VIS410-Presentation-Final-10Sept2012.pdf.
Skehel and Wiley "Receptor binding and membrane fusion in virus entry: the influenza hemagglutinin" Annu Rev Biochem. 69:531-569 (2000).
Smith, G.P., "Filamentous Fusion Phage: Novel Expression Vectors That Display Cloned Antigens on the Virion Surface", Science, 14:228(4705), pp. 1315-1317, 1985.
Soundararajan et al. "Networks link antigenic and receptor-binding sites of influenza hemagglutinin: Mechanistic insight into fitter strain propagation", Scientific Reports, vol. 1, Dec. 2011, pp. 1-7.
Sui et al., "Structural and functional bases for broad-spectrum neutralization of avian and human influenza A viruses" Nature Structural & Molecular Biology (2009) vol. 16, No. 3, pp. 265-273.
Sui et al., "Wide prevalence of heterosubtypic broadly neutralizing human anti-influenza A antibodies" Clin Infect Dis. 52(8):1003-1009 (2011).
Tan et al., "A pan-H1 anti-hemagglutinin monoclonal antibody with potent broad-spectrum efficacy in vivo" J Virol. 86(11):6179-6188 (2012).
Tharakaraman et al. "A broadly neutralizing human monoclonal antibody is effective against H7N9" PNAS (2015) vol. 112, No. 35, pp. 10890-10895.
Wang et al., "Antibody Structure, Instability, and Formulation," Journal of Pharmaceutical Sciences (2007) vol. 96, No. 1, pp. 1-26.
Wang et al., "Broadly protective monoclonal antibodies against H3 influenza viruses following sequential immunization with different hemagglutinins" PLoS Pathog. 6(2):e1000796 (2010).
Warne et al., "Development of high concentration protein biopharmaceuticals: The use of platform approaches in formulation development," European Journal of Pharmaceutics and Biopharmaceutics (2011), vol. 78, No. 2, pp. 208-212.
Whittle et al. "Broadly neutralizing human antibody that recognizes the receptor-binding pocket of influenza virus hemagglutinin", National Academy of Sciences Proceedings, vol. 108, No. 34, Aug. 23, 2011, pp. 14216-14221.
Wollacott et al., "Safety and Upper Respiratory Pharmacokinetics of the Hemagglutinin Stalk-Binding Antibody VIS410 Support Treatment and Prophylaxis Based on Population Modeling of Seasonal Influenza A Outbreaks," EBioMedicine (2016) vol. 5, No. 1, pp. 147-155.
Wrammert et al., "Broadly cross-reactive antibodies dominate the human B cell response against 2009 pandemic H1N1 influenza virus infection" J Exp Med. 208(1):181-193 (2011).
Hershberger et al., "Safety and efficacy of monocolonal antibody VIS410 in adults with uncomplicated influenza A infection: Results from a randomized, double-blind, phase-2, placebo-controlled study," EBioMedicine (2019) vol. 40, pp. 574-582.
Vasquez et al., "Connecting the sequence dots: shedding light on the genesis of antibodies reported to be designed in silico," MABS (2019) vol. 11, No. 5, pp. 803-808.

\* cited by examiner

SEQUENCE LISTING

```
<160> NUMBER OF SEQ ID NOS: 188

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Ala or Gly

<400> SEQUENCE: 1

Xaa Tyr Xaa Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val or Leu
<220> FEATURE:
<221> NAME/KEY: MOD_RES
<222> LOCATION: (4)..(4)
<223> OTHER INFORMATION: Tyr or Phe
```

-continued

```
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (8)..(8)
<223> OTHER INFORMATION: Tyr or Asn
<220> FEATURE:
<221> NAME/KEY: MOD_RES
<222> LOCATION: (9)..(9)
<223> OTHER INFORMATION: Lys or Arg

<400> SEQUENCE: 2

Val Xaa Ser Xaa Asp Gly Xaa Xaa Xaa Tyr Tyr Ala Asp Ser Val Gln
1               5                   10                  15

Gly

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Arg, Lys or Gln
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (15)..(15)
<223> OTHER INFORMATION: Gln or Ser
<220> FEATURE:
<221> NAME/KEY: MOD_RES
<222> LOCATION: (17)..(17)
<223> OTHER INFORMATION: Tyr, Leu or Val
<220> FEATURE:
<221> NAME/KEY: MOD_RES
<222> LOCATION: (18)..(18)
<223> OTHER INFORMATION: Phe or Leu
<220> FEATURE:
<221> NAME/KEY: MOD_RES
<222> LOCATION: (19)..(19)
<223> OTHER INFORMATION: Asn or Asp
<220> FEATURE:
<221> NAME/KEY: MOD_RES
<222> LOCATION: (20)..(20)
<223> OTHER INFORMATION: Pro or Tyr

<400> SEQUENCE: 3

Asp Xaa Xaa Leu Arg Xaa Leu Leu Tyr Phe Glu Trp Leu Ser Xaa Gly
1               5                   10                  15

Xaa Xaa Xaa Xaa
            20

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser or Asp

<400> SEQUENCE: 4

Gln Xaa Xaa Xaa Xaa Xaa Tyr Lys Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Thr, Ala, Tyr, His, Lys or Asp
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (7)..(7)
<223> OTHER INFORMATION: Ser or Thr

<400> SEQUENCE: 5

Trp Xaa Ser Xaa Xaa Glu Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or His
<220> FEATURE:
<221> NAME/KEY: MOD_RES
<222> LOCATION: (9)..(9)
<223> OTHER INFORMATION: Thr or Ser

<400> SEQUENCE: 6

Gln Gln Xaa Tyr Arg Thr Pro Pro Xaa
1               5

<210> SEQ ID NO 7
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (30)..(30)
<223> OTHER INFORMATION: Ser or Thr

<400> SEQUENCE: 7

Xaa Val Gln Leu Leu Glu Xaa Gly Gly Gly Leu Val Lys Pro Gly Gln
1               5                   10                  15

Ser Leu Lys Leu Ser Cys Ala Ala Ser Gly Phe Thr Phe Xaa
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Arg Gln Pro Pro Gly Lys Gly Leu Glu Trp Val Ala
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Gln
<220> FEATURE:
<221> NAME/KEY: MOD_RES
<222> LOCATION: (5)..(5)
<223> OTHER INFORMATION: Thr or Ala
<220> FEATURE:
<221> NAME/KEY: MOD_RES
<222> LOCATION: (6)..(6)
<223> OTHER INFORMATION: Thr or Met
<220> FEATURE:
<221> NAME/KEY: MOD_RES
```

```
<222> LOCATION: (7)..(7)
<223> OTHER INFORMATION: Leu or Val

<400> SEQUENCE: 10

Trp Gly Xaa Gly Xaa Xaa Xaa Thr Val Ser Ser
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (3)..(3)
<223> OTHER INFORMATION: Val or Gln
<220> FEATURE:
<221> NAME/KEY: MOD_RES
<222> LOCATION: (9)..(9)
<223> OTHER INFORMATION: Asp or Ser
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (12)..(12)
<223> OTHER INFORMATION: Ala or Ser
<220> FEATURE:
<221> NAME/KEY: MOD_RES
<222> LOCATION: (13)..(13)
<223> OTHER INFORMATION: Val or Ala
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu, Val or Arg
<220> FEATURE:
<221> NAME/KEY: MOD_RES
<222> LOCATION: (17)..(17)
<223> OTHER INFORMATION: Glu or Asp
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Thr or Ser
<220> FEATURE:
<221> NAME/KEY: MOD_RES
<222> LOCATION: (22)..(22)
<223> OTHER INFORMATION: Asn, Thr, Gln, Asp or Arg
<220> FEATURE:
<221> NAME/KEY: MOD_RES
<222> LOCATION: (24)..(24)
<223> OTHER INFORMATION: Lys or Arg

<400> SEQUENCE: 11

Xaa Ile Xaa Met Thr Gln Ser Pro Xaa Xaa Xaa Xaa Xaa Xaa Xaa Gly
1               5                   10                  15

Xaa Arg Xaa Xaa Ile Xaa Cys Xaa Ser Ser
```

20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Gln or Lys
<220> FEATURE:
<221> NAME/KEY: MOD_RES
<222> LOCATION: (9)..(9)
<223> OTHER INFORMATION: Pro or Ala

<400> SEQUENCE: 12

Trp Tyr Gln Gln Lys Pro Gly Xaa Xaa Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp, Glu or Ser
<220> FEATURE:
<221> NAME/KEY: MOD_RES
<222> LOCATION: (24)..(24)
<223> OTHER INFORMATION: Ala or Pro
<220> FEATURE:
<221> NAME/KEY: MOD_RES
<222> LOCATION: (27)..(27)
<223> OTHER INFORMATION: Val, Phe, Lys or Asp
<220> FEATURE:
<221> NAME/KEY: MOD_RES
<222> LOCATION: (29)..(29)
<223> OTHER INFORMATION: Val or Thr

<400> SEQUENCE: 13

Gly Val Pro Xaa Arg Phe Ser Gly Ser Gly Ser Gly Thr Asp Phe Thr
1               5                   10                  15

Leu Thr Ile Ser Ser Leu Gln Xaa Glu Asp Xaa Ala Xaa Tyr Tyr Cys
                20                  25                  30

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Gln, Thr, Ser or Asn
<220> FEATURE:
<221> NAME/KEY: MOD_RES
<222> LOCATION: (7)..(7)
<223> OTHER INFORMATION: Leu or Val
<220> FEATURE:
<221> NAME/KEY: MOD_RES
<222> LOCATION: (8)..(8)
<223> OTHER INFORMATION: Asp or Glu

<400> SEQUENCE: 14

```
Phe Gly Xaa Gly Thr Lys Xaa Xaa Ile Lys
1               5                   10

<210> SEQ ID NO 15
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 16
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Thr Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser
```

```
<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17
```

| Glu | Val | Gln | Leu | Leu | Glu | Ser | Gly | Gly | Gly | Leu | Val | Lys | Pro | Gly | Gln |
|---|---|---|---|---|---|---|---|---|---|---|---|---|---|---|---|
| 1 | | | | 5 | | | | | 10 | | | | | 15 | |
| Ser | Leu | Lys | Leu | Ser | Cys | Ala | Ala | Ser | Gly | Phe | Thr | Phe | Thr | Ser | Tyr |
| | | | 20 | | | | | 25 | | | | | 30 | | |
| Gly | Met | His | Trp | Val | Arg | Gln | Pro | Pro | Gly | Lys | Gly | Leu | Glu | Trp | Val |
| | | 35 | | | | | 40 | | | | | 45 | | | |
| Ala | Val | Val | Ser | Tyr | Asp | Gly | Asn | Tyr | Lys | Tyr | Tyr | Ala | Asp | Ser | Val |
| 50 | | | | | 55 | | | | | 60 | | | | | |
| Gln | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Asp | Ser | Arg | Leu | Arg | Ser | Leu | Leu | Tyr | Phe | Glu | Trp | Leu | Ser |
| | | | 100 | | | | | 105 | | | | | 110 | | |
| Gln | Gly | Tyr | Phe | Asn | Pro | Trp | Gly | Ala | Gly | Thr | Thr | Leu | Thr | Val | Ser |
| | | | 115 | | | | | 120 | | | | | 125 | | |
| Ser | | | | | | | | | | | | | | | |

```
<210> SEQ ID NO 18
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

| Glu | Val | Gln | Leu | Leu | Glu | Ser | Gly | Gly | Gly | Leu | Val | Lys | Pro | Gly | Gln |
|---|---|---|---|---|---|---|---|---|---|---|---|---|---|---|---|
| 1 | | | | 5 | | | | | 10 | | | | | 15 | |
| Ser | Leu | Lys | Leu | Ser | Cys | Ala | Ala | Ser | Gly | Phe | Thr | Phe | Thr | Ser | Tyr |
| | | | 20 | | | | | 25 | | | | | 30 | | |
| Gly | Met | His | Trp | Val | Arg | Gln | Pro | Pro | Gly | Lys | Gly | Leu | Glu | Trp | Val |
| | | 35 | | | | | 40 | | | | | 45 | | | |
| Ala | Val | Leu | Ser | Tyr | Asp | Gly | Asn | Tyr | Lys | Tyr | Tyr | Ala | Asp | Ser | Val |
| 50 | | | | | 55 | | | | | 60 | | | | | |
| Gln | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Asp | Ser | Arg | Leu | Arg | Ser | Leu | Leu | Tyr | Phe | Glu | Trp | Leu | Ser |
| | | | 100 | | | | | 105 | | | | | 110 | | |
| Gln | Gly | Tyr | Phe | Asn | Pro | Trp | Gly | Ala | Gly | Thr | Thr | Leu | Thr | Val | Ser |
| | | | 115 | | | | | 120 | | | | | 125 | | |
| Ser | | | | | | | | | | | | | | | |

```
<210> SEQ ID NO 19
<211> LENGTH: 129
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 19

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Leu Ser Tyr Asp Gly Asn Tyr Lys Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Val Ser Phe Asp Gly Asn Asn Arg Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Ser Gly Val Leu Asp Tyr Trp Gly Gln Gly Ala Met Val Thr Val Ser
        115                 120                 125

Ser

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 22
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Gly Lys Gly Leu Glu Trp Val
            35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
            115                 120                 125

Ser

<210> SEQ ID NO 24
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Gly Lys Gly Leu Glu Trp Val
            35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
            115                 120                 125

Ser

<210> SEQ ID NO 25
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Gly Lys Gly Leu Glu Trp Val
            35                  40                  45

Ala Val Val Ser Tyr Asp Gly Asn Tyr Lys Tyr Tyr Ala Asp Ser Val

```
                    50                  55                  60
Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Gln Gly Thr Thr Leu Thr Val Ser
            115                 120                 125

Ser

<210> SEQ ID NO 26
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Lys Pro Gly Gln
  1               5                  10                  15

Ser Leu Lys Leu Ser Cys Ala Ala Ser Gly Phe Thr Phe Thr Ser Tyr
                 20                  25                  30

Ala Met His Trp Val Arg Gln Pro Pro Gly Lys Gly Leu Glu Trp Val
             35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Asp Ser Gln Leu Arg Thr Leu Leu Tyr Phe Glu Trp Leu Ser
                100                 105                 110

Gln Gly Tyr Phe Asn Pro Trp Gly Gln Gly Thr Thr Leu Thr Val Ser
            115                 120                 125

Ser

<210> SEQ ID NO 27
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Leu Glu Ser Gly Gly Gly Leu Val Lys Pro Gly Gln
  1               5                  10                  15

Ser Leu Lys Leu Ser Cys Ala Ala Ser Gly Phe Thr Phe Thr Ser Tyr
                 20                  25                  30

Ala Met His Trp Val Arg Gln Pro Pro Gly Lys Gly Leu Glu Trp Val
             35                  40                  45

Ala Val Val Ser Tyr Asp Gly Asn Tyr Lys Tyr Tyr Ala Asp Ser Val
         50                  55                  60

Gln Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Asp Ser Arg Leu Arg Thr Leu Leu Tyr Phe Glu Trp Leu Ser
            100                 105                 110

Gln Gly Tyr Phe Asp Pro Trp Gly Gln Gly Thr Thr Leu Thr Val Ser
        115                 120                 125

Ser
```

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110
```

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Ser
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110
```

<210> SEQ ID NO 30
<211> LENGTH: 111
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 30

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asp
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45
```

Lys Leu Leu Ile Tyr Trp Ala Ser Thr Arg Glu Ser Gly Val Pro Asp
            50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
                100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Phe Ala Ser Thr Arg Glu Ser Gly Val Pro Asp
    50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
                100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Phe Ala Ser Thr Arg Glu Ser Gly Val Pro Asp
    50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
                100                 105                 110

<210> SEQ ID NO 35

```
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Trp Ser
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Ser Gln Ser Pro Asp Thr Leu Ala Val Thr Leu Gly
1               5                   10                  15

Glu Arg Ala Ser Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Val Leu Ile Tyr Trp Ala Ser Ala Arg Glu Thr Gly Val Pro Glu
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Glu Ile Lys
            100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30
```

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Thr Gly Thr Lys Leu Asp Ile Lys
            100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
            100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Thr Gly Thr Lys Leu Asp Ile Lys
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn

```
                    20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
                100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
                100                 105                 110

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
```

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Gly Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Met Thr Gln Ser Pro Asp Thr Leu Ala Val Thr Leu Gly
1               5                   10                  15

Glu Arg Ala Thr Ile Gln Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Thr
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Asp Thr Val Ala Val Thr Val Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 49
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Val Met Thr Gln Ser Pro Asp Thr Val Ala Val Thr Leu Gly
1               5                   10                  15

Glu Arg Ala Thr Ile Asp Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Asp Thr Leu Ala Val Thr Val Gly
1               5                   10                  15

Glu Arg Ala Thr Ile Arg Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 51
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Asp Thr Leu Ala Val Ser Arg Gly
1               5                   10                  15

Glu Arg Ala Thr Ile Asp Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Glu Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
            85                  90                  95

Arg Thr Pro Pro Ser Phe Gly Gln Gly Thr Lys Val Glu Ile Lys
            100                 105                 110
```

<210> SEQ ID NO 53
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
            85                  90                  95

Arg Thr Pro Pro Ser Phe Gly Gln Gly Thr Lys Val Glu Ile Lys
            100                 105                 110
```

<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser His Leu Glu Ser Gly Val Pro Ser
    50                  55                  60

Arg Phe Ser Gly Ser Gly Ser Gly Thr Asp Phe Thr Leu Thr Ile Ser
65                  70                  75                  80
```

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Lys Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Lys Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 59
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser

```
                65                  70                  75                  80
Ser Leu Gln Pro Glu Asp Ala Thr Tyr Tyr Cys Gln Gln His Tyr
                    85                  90                  95

Arg Thr Pro Pro Ser Phe Gly Gln Gly Thr Lys Val Glu Ile Lys
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Tyr
                85                  90                  95

Arg Thr Pro Pro Ser Phe Gly Gln Gly Thr Lys Val Glu Ile Lys
            100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Arg Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 63
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggtacagc tcctcgaatc gggagggga ctggtcaaac cggtcaatc gctcaaactc        60 tcgtgtgcag cgtcaggttt tacgttcagc tcatatggga tgcactgggt ccgccagcct    120
ccgggaaagg gactggagtg gtggcagtc gtgtcgtatg acgggagcaa taagtactac     180
gccgattcag tgcaaggtcg gtttaccatt tcgagggata cagcaagaa cacgctctac     240 ttgcagatga actcacttag agcggaagat acggctgtgt actattgcgc aaagacaca    300 aagctgcgat ccctgttgta cttcgaatgg ttgtcctcgg gcttgcttga ctattggggg   360
cagggcgcca tggtcacagt atccagcgcg tcgactaagg ggccc                    405

<210> SEQ ID NO 64
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gagatcgtga tgacgcagag ccccgatagc ctcgctgtct cattgggga acgggccacg      60 attaactgca atcctcaca gtcggtgact ttcagctata gaattaccct ggcatggtat    120
cagcagaagc cgggtcaacc cccaaaactg ttgatctact gggcctccac acgcgagtcg   180
ggagtcccgg accgattttc gggttcaggg tccggcactg actttaccct cacaatttca   240
tcgcttcaag cggaggatgt agcagtgtac tattgtcagc agtattacag aacacctccc   300
accttcggag ggggaacgaa acttgacatc aagggatcc                          339

<210> SEQ ID NO 65
<211> LENGTH: 339
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 65

```
gagatcgtga tgacgcagag ccccgatagc ctcgctgtct cattggggga acgggccacg      60
attaactgca aatcctcaca gtcggtgact ttcgactata agaattacct ggcatggtat     120
cagcagaagc cgggtcaacc cccaaaactg ttgatctact gggcctccac acgcgagtcg     180
ggagtcccgg accgattttc gggttcaggg tccggcactg actttaccct cacaatttca     240
tcgcttcaag cggaggatgt agcagtgtac tattgtcagc agtattacag aacacctccc     300
accttcggag ggggaacgaa acttgacatc aagggatcc                            339
```

<210> SEQ ID NO 66
<211> LENGTH: 405
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66

```
gaagtgcaac tcctcgagtc aggaggaggt ttggtgaaac cgggtcagtc cttgaaactg      60
agctgtgcag caagcgggtt cacgtttacg tcgtacggca tgcactgggt acggcagcct    120
cccgggaagg gacttgaatg ggtcgccgtc atctcatacg acgggtcgta caatactat     180
gcggatagcg tgcaaggtcg cttcacaatt tcccgggaca attcgaagaa tacactgtat    240
cttcagatga actcgctcag ggctgaggac acggcggtct attactgcgc gaaggattcg    300
cgactcagat cccttttgta ctttgagtgg ctgtcgcagg ggtatttcaa cccatgggga    360
gccggaacca ctttgaccgt atcaagcgcg tcaacaaagg ggccc                    405
```

<210> SEQ ID NO 67
<211> LENGTH: 654
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67

```
gaaattgtaa tgacgcagag ccctgatagc cttgccgtgt ccctgggtga gagggcgaca      60
atcaattgta agtcatcaca gtcggtcacg tacaactaca agaactacct ggcgtggtat    120
caacagaaac ccgggcagcc gcccaaattg ctcatctatt gggcttcgac acgggagtcg    180
ggtgtgccag accgcttctc cgggtcagga tcgggaactg acttcacgtt gactatttcg    240
tccctccagg cagaagatgt agccgtctac tattgccaac agtattacag aacgccgcct    300
acatttggag gcgggaccaa acttgacatc aagggatccg tggccgcccc cagcgtcttc    360
atcttcccgc ccagcgacga gcagctgaag tcgggcacgg ccagcgtggt gtgcctcctg    420
aacaacttct accccgcga ggcgaaggtc cagtggaagg tggacaacgc cctgcagagc    480
gggaacagcc aggagagcgt gaccgagcag gactcgaagg acagcaccta cagcctcagc    540
agcaccctga cgctgagcaa ggccgactac gagaagcaca aggtctacgc ctgcgaggtg    600
acccaccagg ggctctcgag ccccgtgacc aagagcttca ccggggcga gtgc           654
```

<210> SEQ ID NO 68
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 68

Ser Tyr Ala Met His
1               5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Val Ser Tyr Asp Gly Asn Tyr Lys Tyr Tyr Ala Asp Ser Val Gln
1               5                   10                  15

Gly

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ser Arg Leu Arg Ser Leu Leu Tyr Phe Glu Trp Leu Ser Gln Gly
1               5                   10                  15

Tyr Phe Asn Pro
            20

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Ser Ile Thr Phe Asn Tyr Lys Asn Tyr Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Gly Ser Tyr Leu Glu Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 73

Gln Gln His Tyr Arg Thr Pro Pro Ser
1               5

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Val Arg Gln Pro Pro Gly Lys Gly Leu Glu Trp Val Ala
1               5                   10

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Gly Gln Gly Thr Thr Leu Thr Val Ser Ser
1               5                   10

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Asp Ile Gln Met Thr Gln Ser Pro Ser Ser Leu Ser Ala Ser Val Gly
1               5                   10                  15

Asp Arg Val Thr Ile Thr Cys Arg Ser Ser
            20                  25

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Tyr Gln Gln Lys Pro Gly Lys Ala Pro Lys Leu Leu Ile Tyr
1               5                   10                  15

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Gly Gln Gly Thr Lys Val Glu Ile Lys
1               5                   10

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

Lys Ser Ser Gln Ser Val Thr Tyr Asn Tyr Lys Asn Tyr Leu Ala
1               5                   10                  15

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Ala Ser Thr Arg Glu Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gln Tyr Tyr Arg Thr Pro Pro Thr
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Gly Met His
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ile Ser Tyr Asp Gly Ser Tyr Lys Tyr Tyr Ala Asp Ser Val Gln
1               5                   10                  15

Gly

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ser Glu Leu Arg Ser Leu Leu Tyr Phe Glu Trp Leu Ser Gln Gly
1               5                   10                  15

Tyr Phe Asn Pro
            20

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gly Ala Gly Thr Thr Leu Thr Val Ser Ser
1               5                   10

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Tyr Gln Gln Lys Pro Gly Gln Pro Pro Lys Leu Leu Ile Tyr
1               5                   10                  15

<210> SEQ ID NO 92
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Gly Gly Gly Thr Lys Leu Asp Ile Lys
1               5                   10

<210> SEQ ID NO 94
<211> LENGTH: 460
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 94

```
Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Pro Lys Ser Cys Asp Lys Thr His Thr Cys Pro
225                 230                 235                 240

Pro Cys Pro Gly Thr Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Glu Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380
```

```
Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
450                 455                 460

<210> SEQ ID NO 95
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
                100                 105                 110

Ser Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 96
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96
```

Ile Asp Glu Val Gln Leu Leu Glu Ser Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Ile Ser Tyr Asp Gly Ser Tyr Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 97
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Ser Asn Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Thr Lys Leu Arg Ser Leu Leu Tyr Phe Glu Trp
            100                 105                 110

Leu Ser Ser Gly Leu Leu Asp Tyr Trp Gly Gln Gly Ala Met Val Thr
            115                 120                 125

Val Ser Ser
    130

<210> SEQ ID NO 98
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
            35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 99
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
            35                  40                  45

Trp Val Ala Val Leu Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 100
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

```
Thr Tyr Ala Met His Trp Val Arg Gln Pro Pro Gly Lys Gly Leu Glu
            35                  40                  45

Trp Val Ala Val Leu Ser Tyr Asp Gly Asn Tyr Lys Tyr Tyr Ala Asp
 50                  55                  60

Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Ser Arg Leu Arg Ser Leu Leu Tyr Phe Glu Trp
                100                 105                 110

Leu Ser Gln Gly Tyr Phe Asn Pro Trp Gly Ala Gly Thr Thr Leu Thr
                115                 120                 125

Val Ser Ser
    130

<210> SEQ ID NO 101
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ile Asp Glu Val Gln Leu Leu Glu Ser Gly Gly Gly Leu Val Lys Pro
 1               5                  10                  15

Gly Gln Ser Leu Lys Leu Ser Cys Ala Ala Ser Gly Phe Thr Phe Ser
                20                  25                  30

Ser Tyr Gly Met His Trp Val Arg Gln Pro Pro Gly Lys Gly Leu Glu
            35                  40                  45

Trp Val Ala Val Ser Tyr Asp Gly Asn Asn Lys Tyr Tyr Ala Asp
 50                  55                  60

Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Ser Lys Leu Arg Ser Leu Leu Tyr Phe Glu Trp
                100                 105                 110

Leu Ser Ser Gly Leu Leu Asp Tyr Trp Gly Gln Gly Ala Met Val Thr
                115                 120                 125

Val Ser Ser
    130

<210> SEQ ID NO 102
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Asp Glu Val Gln Leu Leu Glu Ser Gly Gly Gly Leu Val Lys Pro
 1               5                  10                  15

Gly Gln Ser Leu Lys Leu Ser Cys Ala Ala Ser Gly Phe Thr Phe Thr
                20                  25                  30

Thr Tyr Ala Met His Trp Val Arg Gln Pro Pro Gly Lys Gly Leu Glu
            35                  40                  45
```

```
Trp Val Ala Val Val Ser Tyr Asp Gly Asn Asn Lys Tyr Tyr Ala Asp
 50                  55                  60

Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Lys Asp Ser Lys Leu Arg Ser Leu Leu Tyr Phe Glu Trp
                100                 105                 110

Leu Ser Ser Gly Leu Leu Asp Tyr Trp Gly Gln Gly Ala Met Val Thr
                115                 120                 125

Val Ser Ser
        130

<210> SEQ ID NO 103
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ile Asp Glu Val Gln Leu Leu Glu Ser Gly Gly Gly Leu Val Lys Pro
  1               5                  10                  15

Gly Gln Ser Leu Lys Leu Ser Cys Ala Ala Ser Gly Phe Thr Phe Thr
                 20                  25                  30

Thr Tyr Ala Met His Trp Val Arg Gln Pro Pro Gly Lys Gly Leu Glu
                 35                  40                  45

Trp Val Ala Val Val Ser Phe Asp Gly Asn Asn Arg Tyr Tyr Ala Asp
 50                  55                  60

Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Lys Asp Ser Gln Leu Arg Ser Leu Leu Tyr Phe Glu Trp
                100                 105                 110

Leu Ser Ser Gly Val Leu Asp Tyr Trp Gly Gln Gly Ala Met Val Thr
                115                 120                 125

Val Ser Ser
        130

<210> SEQ ID NO 104
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ile Asp Glu Val Gln Leu Leu Glu Ser Gly Gly Gly Leu Val Lys Pro
  1               5                  10                  15

Gly Gln Ser Leu Lys Leu Ser Cys Ala Ala Ser Gly Phe Thr Phe Thr
                 20                  25                  30

Ser Tyr Gly Met His Trp Val Arg Gln Pro Pro Gly Lys Gly Leu Glu
                 35                  40                  45

Trp Val Ala Val Val Ser Tyr Asp Gly Asn Tyr Lys Tyr Tyr Ala Asp
 50                  55                  60
```

```
Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Ser Lys Leu Arg Ser Leu Leu Tyr Phe Glu Trp
             100                 105                 110

Leu Ser Gln Gly Tyr Phe Asn Pro Trp Gly Ala Gly Thr Thr Leu Thr
         115                 120                 125

Val Ser Ser
    130

<210> SEQ ID NO 105
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ile Asp Glu Val Gln Leu Leu Glu Ser Gly Gly Gly Leu Val Lys Pro
 1               5                  10                  15

Gly Gln Ser Leu Lys Leu Ser Cys Ala Ala Ser Gly Phe Thr Phe Thr
             20                  25                  30

Ser Tyr Ala Met His Trp Val Arg Gln Pro Pro Gly Lys Gly Leu Glu
         35                  40                  45

Trp Val Ala Val Ser Tyr Asp Gly Asn Tyr Lys Tyr Tyr Ala Asp
     50                  55                  60

Ser Val Gln Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Asp Ser Arg Leu Arg Ser Leu Leu Tyr Phe Glu Trp
             100                 105                 110

Leu Ser Gln Gly Tyr Phe Asn Pro Trp Gly Gln Gly Thr Thr Leu Thr
         115                 120                 125

Val Ser Ser
    130

<210> SEQ ID NO 106
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ile Asp Gln Val Gln Leu Leu Glu Thr Gly Gly Gly Leu Val Lys Pro
 1               5                  10                  15

Gly Gln Ser Leu Lys Leu Ser Cys Ala Ala Ser Gly Phe Thr Phe Thr
             20                  25                  30

Ser Tyr Ala Met His Trp Val Arg Gln Pro Pro Gly Lys Gly Leu Glu
         35                  40                  45

Trp Val Ala Val Val Ser Tyr Asp Gly Asn Tyr Lys Tyr Tyr Ala Asp
     50                  55                  60

Ser Val Gln Gly Arg Phe Thr Ile Ser Arg Asp Asn Ser Lys Asn Thr
 65                  70                  75                  80
```

Leu Tyr Leu Gln Met Asn Ser Leu Arg Ala Glu Asp Thr Ala Val Tyr
            85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Gln Gly Thr Thr Leu Thr
        115                 120                 125

Val Ser Ser
    130

<210> SEQ ID NO 107
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Lys Asp Ser Gln Leu Arg Thr Leu Leu Tyr Phe Glu Trp
            100                 105                 110

Leu Ser Gln Gly Tyr Phe Asn Pro Trp Gly Gln Gly Thr Thr Leu Thr
        115                 120                 125

Val Ser Ser
    130

<210> SEQ ID NO 108
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Lys Asp Ser Arg Leu Arg Thr Leu Leu Tyr Phe Glu Trp
            100                 105                 110

Leu Ser Gln Gly Tyr Phe Asp Pro Trp Gly Gln Gly Thr Thr Leu Thr
        115                 120                 125

Val Ser Ser
    130

<210> SEQ ID NO 109
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Ser Tyr Asp Gly Ser Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
        115                 120                 125

Val Ser Ser
    130

<210> SEQ ID NO 110
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Tyr Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Phe Ser Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 112
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Phe Asp Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 113
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 113

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Thr
            20                  25                  30

Trp Ser Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Pro Thr Phe Gly Gly Gly Thr Lys Leu Asp Ile
            100                 105                 110

Lys

<210> SEQ ID NO 114
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 115
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45
```

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
            100                 105                 110

Lys

<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
            100                 105                 110

Lys

<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
            100                 105                 110
```

Lys

<210> SEQ ID NO 118
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ile Asp Glu Ile Val Met Ser Gln Ser Pro Asp Thr Leu Ala Val Thr
1               5                   10                  15

Leu Gly Glu Arg Ala Ser Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Val Leu Ile Tyr Trp Ala Ser Ala Arg Glu Thr Gly Val
    50                  55                  60

Pro Glu Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Glu Ile
            100                 105                 110

Lys

<210> SEQ ID NO 119
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 120
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Gly Trp Tyr Gln Gln Lys Pro Gly Lys
        35                  40                  45

Ala Pro Lys Leu Leu Ile Tyr Trp Gly Ser Tyr Leu Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 121
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Thr Gly Thr Lys Leu Asp Ile
            100                 105                 110

Lys

<210> SEQ ID NO 122
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

```
Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Ser Gly Thr Lys Leu Asp Ile
                100                 105                 110

Lys

<210> SEQ ID NO 123
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
                100                 105                 110

Lys

<210> SEQ ID NO 124
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
```

<210> SEQ ID NO 125
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Thr Gly Thr Lys Leu Asp Ile
            100                 105                 110

Lys

<210> SEQ ID NO 126
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Ser Gly Thr Lys Leu Asp Ile
            100                 105                 110

Lys

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 127

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 128
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
            100                 105                 110

Lys

<210> SEQ ID NO 129
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ile Asp Asp Ile Val Met Thr Gln Ser Pro Asp Thr Leu Ala Val Thr
1               5                   10                  15

Leu Gly Glu Arg Ala Thr Ile Gln Cys Lys Ser Ser Gln Thr Val Thr
            20                  25                  30

Phe Asn Tyr Lys Asn Tyr Leu Ala Trp Tyr Gln Gln Lys Pro Gly Gln

```
                35                  40                  45
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Thr Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
                100                 105                 110

Lys

<210> SEQ ID NO 130
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ile Asp Asp Ile Val Met Thr Gln Ser Pro Asp Thr Val Ala Val Thr
 1               5                   10                  15

Val Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
                100                 105                 110

Lys

<210> SEQ ID NO 131
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ile Asp Asp Ile Val Met Thr Gln Ser Pro Asp Thr Val Ala Val Thr
 1               5                   10                  15

Leu Gly Glu Arg Ala Thr Ile Asp Cys Lys Ser Ser Gln Thr Val Thr
                20                  25                  30

Phe Asn Tyr Lys Asn Tyr Leu Ala Trp Tyr Gln Gln Lys Pro Gly Gln
                35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95
```

His Tyr Arg Thr Pro Pro Ser Phe Gly Gln Gly Thr Lys Leu Asp Ile
            100                 105                 110

Lys

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ile Asp Asp Ile Val Met Thr Gln Ser Pro Asp Thr Leu Ala Val Thr
1               5                   10                  15

Val Gly Glu Arg Ala Thr Ile Arg Cys Lys Ser Ser Gln Thr Val Thr
            20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 133
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ile Asp Asp Ile Val Met Thr Gln Ser Pro Asp Thr Leu Ala Val Ser
1               5                   10                  15

Arg Gly Glu Arg Ala Thr Ile Asp Cys Lys Ser Ser Gln Thr Val Thr
            20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 134
<211> LENGTH: 113
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 134

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asp Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 135
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 135

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 136

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser His Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                 20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Lys Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys

<210> SEQ ID NO 138
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                 20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Asp Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys

<210> SEQ ID NO 139
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Lys Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 141
<211> LENGTH: 113
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 141

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Asp Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Arg Thr Pro Pro Ser Phe Gly Gln Gly Thr Lys Val Glu Ile
            100                 105                 110

Lys

<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30
```

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Ser Ile Thr Phe Asp Tyr Lys Asn Tyr Leu Ala
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Ser Ser Gln Ser Val Thr Phe Asn Tyr Lys Asn Tyr Leu Ala
1               5                   10                  15

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Trp Ala Ser Ala Arg Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Gln Gln His Tyr Arg Thr Pro Pro Thr
1               5

<210> SEQ ID NO 149
<211> LENGTH: 657
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149

```
gacattcaga tgactcagtc gccttcgtca ttgtccgcct ccgtgggtga tagggtcacg     60
atcacgtgcc ggagcagcca gtccatcacc ttcaattaca aaaactattt ggcatggtat    120
caacagaaac ccggaaaggc gccgaagctc ctgatctact ggggttcata tcttgagtcg    180
ggggtgccgt cgagattttc gggcagcgga tcagggacgg atttcacgct gaccatttcg    240
tcactccagc ccgaggactt tgcgacatat tactgtcaac agcactacag gacacccccca   300
tctttcggac aggggactaa agtagaaatc aagggatccg tggccgcccc cagcgtcttc    360
atcttcccgc ccagcgacga gcagctgaag tcgggcacgg ccagcgtggt gtgcctcctg    420
aacaacttct accccgcga ggcgaaggtc cagtggaagg tggacaacgc cctgcagagc    480
gggaacagcc aggagagcgt gaccgagcag gactcgaagg acagcaccta cagcctcagc    540
agcaccctga cgctgagcaa ggccgactac gagaagcaca aggtctacgc ctgcgaggtg    600
acccaccagg gctctcgag ccccgtgacc aagagcttca ccggggcga gtgctga        657
```

<210> SEQ ID NO 150
<211> LENGTH: 663
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150

```
gacattcaga tgactcagtc gccttcgtca ttgtccgcct ccgtgggtga tagggtcacg     60
atcacgtgcc ggagcagcca gtccatcacc ttcaattaca aaaactattt ggcatggtat    120
caacagaaac ccggaaaggc gccgaagctc ctgatctact ggggttcata tcttgagtcg    180
```

```
ggggtgccgt cgagattttc gggcagcgga tcagggacgg atttcacgct gaccatttcg    240
tcactccagc ccgaggactt tgcgacatat tactgtcaac agcactacag gacacccca     300 tctttcggac aggggactaa agtagaaatc aagggatccg tggccgcccc cagcgtcttc    360
atcttcccgc ccagcgacga gcagctgaag tcgggcacgg ccagcgtggt gtgcctcctg    420
aacaacttct accccgcga ggcgaaggtc cagtggaagg tggacaacgc cctgcagagc     480
gggaacagcc aggagagcgt gaccgagcag gactcgaagg acagcaccta cagcctcagc    540
agcaccctga cgctgagcaa ggccgactac gagaagcaca aggtctacgc ctgcgaggtg    600
acccaccagg ggctctcgag ccccgtgacc aagagcttca ccggggcga gtgctgagaa     660 ttc                                                                  663
```

```
<210> SEQ ID NO 151
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
caggtacaat tgcttgagac aggtggagga ctcgtgaagc caggtcagtc attgaaactg     60
agctgtgccg catccgggtt cacattcact tcctacgcga tgcactgggt ccgccagcct    120
cccggaaagg gacttgagtg ggtcgctgtg gtatcgtatg atgggaatta caaatactat    180
gcagactccg tgcaaggccg gtttacgatt agcagggaca actcgaagaa taccctttac    240
ctccaaatga actcgctccg agcggaggac acggcggtgt attactgcgc gaaggattca    300
cggttgagat cgctgctcta ttttgaatgg ttgtcacagg ggtacttcaa cccgtggggt    360
cagggaacaa cactgaccgt cagctcagcc tcgactaaag ggcccagcgt gttcccgctg    420 gccccagca gcaagagcac cagcggcggg accgccgccc tgggctgcct cgtcaaggac    480
tacttccccg agcccgtgac cgtgtcgtgg aacagcggcg cgctgacgag cggggtccac    540
accttcccgg ccgtgctgca gagcagcggc ctctactcgc tgagcagcgt ggtcaccgtg    600
cccagcagca gcctggggac ccagacgtac atctgcaacg tgaaccacaa gccctcgaac    660
accaaggtcg acaagaaggt ggagcccccg aagagctgcg acaaaactca cacatgccca    720
ccgtgcccag gtactgaact cctgggggga ccgtcagtct tcctcttccc cccaaaaccc    780
aaggacaccc tcatgatctc ccggaccct gaggtcacat gcgtggtggt ggacgtgagc    840
cacgaagacc ctgaggtcaa gttcaactgg tacgtggacg gcgtggaggt gcataatgcc    900
aagacaaagc cgcgggagga gcagtacaac agcacgtacc gtgtggtcag cgtcctcacc    960
gtcctgcacc aggactggct gaatggcaag gagtacaagt gcaaggtctc caacaaagcc   1020
ctcccagccc ccatcgagaa aaccatctcc aaagccaaag gtgagccccg agaaccacag   1080
gtgtacaccc tgcccccatc ccgggatgag ctgaccaaga accaggtcag cctgacctgc   1140
ctggtcaaag gcttctatcc cagcgacatc gccgtggagt gggagagcaa tgggcagccg   1200
gagaacaact acaagaccac gcctcccgtg ctggactccg acggctcctt cttcctctac   1260
agcaagctca ccgtggacaa gagcaggtgg cagcagggga acgtcttctc atgctccgtg   1320
atgcatgagg ctctgcacaa ccactacacg cagaagagcc tctccctgtc tccgggtaaa   1380
tga                                                                 1383
```

```
<210> SEQ ID NO 152
```

<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

```
gaagtacaat tgcttgagtc gggtggagga ctcgtgaagc caggtcagtc attgaaactg    60
agctgtgccg catccgggtt cacattcact tcctacgcga tgcactgggt ccgccagcct   120
cccggaaagg gacttgagtg ggtcgctgtg gtatcgtatg atgggaatta caaatactat   180
gcagactccg tgcaaggccg gtttacgatt agcagggaca actcgaagaa tacccttac    240
ctccaaatga actcgctccg agcggaggac acggcggtgt attactgcgc gaaggattca   300
cggttgagat cgctgctcta ttttgaatgg ttgtcacagg ggtacttcaa cccgtggggt   360
cagggaacaa cactgaccgt cagctcagcc tcgactaaag ggcccagcgt gttcccgctg   420
gcccccagca gcaagagcac cagcggcggg accgccgccc tgggctgcct cgtcaaggac   480
tacttccccg agcccgtgac cgtgtcgtgg aacagcggcg cgctgacgag cggggtccac   540
accttcccgg ccgtgctgca gagcagcggc ctctactcgc tgagcagcgt ggtcaccgtg   600
cccagcagca gcctggggac ccagacgtac atctgcaacg tgaaccacaa gccctcgaac   660
accaaggtcg acaagaaggt ggagcccccg aagagctgcg acggtaccca cacatgccca   720
ccgtgcccag gtactgaact cctgggggga ccgtcagtct tcctcttccc cccaaaaccc   780
aaggacaccc tcatgatctc ccggacccct gaggtcacat gcgtggtggt ggacgtgagc   840
cacgaagacc ctgaggtcaa gttcaactgg tacgtggacg gcgtggaggt gcataatgcc   900
aagacaaagc cgcgggagga gcagtacaac agcacgtacc gtgtggtcag cgtcctcacc   960
gtcctgcacc aggactggct gaatggcaag gagtacaagt gcaaggtctc caacaaagcc  1020
ctcccagccc ccatcgagaa aaccatctcc aaagccaaag gtgagccccg agaaccacag  1080
gtgtacaccc tgcccccatc ccgggatgag ctgaccaaga accaggtcag cctgacctgc  1140
ctggtcaaag gcttctatcc cagcgacatc gccgtggagt gggagagcaa tgggcagccg  1200
gagaacaact acaagaccac gcctcccgtg ctggactccg acggctcctt cttcctctac  1260
agcaagctca ccgtggacaa gagcaggtgg cagcaggga acgtcttctc atgctccgtg  1320
atgcatgagg ctctgcacaa ccactacacg cagaagagcc tctccctgtc tccgggtaaa  1380
tga                                                                1383
```

<210> SEQ ID NO 153
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Gln
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60
```

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
                100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Arg
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
                100                 105                 110

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Glu
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
                100                 105                 110

<210> SEQ ID NO 156
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Thr Arg Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 157
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Gln Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Arg Tyr Lys Asn Tyr Leu Ala Trp Tyr Gln Gln Lys Pro Gly Lys
```

```
            35                  40                  45
Ala Pro Lys Leu Leu Ile Tyr Trp Gly Ser Tyr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
                100                 105                 110

Lys

<210> SEQ ID NO 159
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ile Asp Asp Ile Gln Met Thr Gln Ser Pro Ser Ser Leu Ser Ala Ser
 1                5                  10                  15

Val Gly Asp Arg Val Thr Ile Thr Cys Arg Ser Ser Gln Ser Ile Thr
                 20                  25                  30

Phe Glu Tyr Lys Asn Tyr Leu Ala Trp Tyr Gln Gln Lys Pro Gly Lys
             35                  40                  45

Ala Pro Lys Leu Leu Ile Tyr Trp Gly Ser Tyr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
                100                 105                 110

Lys

<210> SEQ ID NO 160
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ile Asp Asp Ile Gln Met Thr Gln Ser Pro Ser Ser Leu Ser Ala Ser
 1                5                  10                  15

Val Gly Asp Arg Val Thr Ile Thr Cys Arg Ser Ser Gln Ser Ile Thr
                 20                  25                  30

Phe Asp Tyr Lys Asn Tyr Leu Ala Trp Tyr Gln Gln Lys Pro Gly Lys
             35                  40                  45

Ala Pro Lys Leu Leu Ile Tyr Trp Gly Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95
```

His Tyr Arg Thr Pro Pro Ser Phe Gly Gln Gly Thr Lys Val Glu Ile
                100                 105                 110
Lys

<210> SEQ ID NO 161
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 162
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Ser Phe Ser Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Thr Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 163
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

Glu Val Gln Leu Leu Glu Ser Gly Gly Gly Leu Arg Lys Pro Gly Gln
1               5                   10                  15

Ser Leu Lys Leu Ser Cys Ala Ala Ser Gly Phe Ser Phe Ser Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 164
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Val Thr Val Ser
        115                 120                 125

Ser

<210> SEQ ID NO 165
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Gln
            20                  25                  30

Tyr Lys Asn Tyr Leu Ala Trp Tyr Gln Gln Lys Pro Gly Lys Ala Pro
        35                  40                  45
```

```
Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Ser Ile Thr Trp Arg
                 20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Ser Ile Thr Trp Glu
                 20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 170
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser, Asp, Gln, Arg or Glu

<400> SEQUENCE: 170

Gln Xaa Xaa Xaa Xaa Xaa Tyr Lys Asn Tyr Leu Ala
1               5                   10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Trp Gly Gln Gly Thr Thr Val Thr Val Ser Ser
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ser Ile Thr Phe Glu Tyr Lys Asn Tyr Leu Ala
1               5                   10

<210> SEQ ID NO 173
<211> LENGTH: 329
<212> TYPE: PRT
<213> ORGANISM: Influenza A virus

<400> SEQUENCE: 173

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60
```

```
Thr Leu Ile Asp Ala Leu Leu Gly Asp Pro His Cys Asp Val Phe Gln
 65                  70                  75                  80

Asn Glu Thr Trp Asp Leu Phe Val Glu Arg Ser Lys Ala Phe Ser Asn
             85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg
                325

<210> SEQ ID NO 174
<211> LENGTH: 175
<212> TYPE: PRT
<213> ORGANISM: Influenza A virus

<400> SEQUENCE: 174

Gly Leu Phe Gly Ala Ile Ala Gly Phe Ile Glu Asn Gly Trp Glu Gly
  1               5                  10                  15

Met Ile Asp Gly Trp Tyr Gly Phe Arg His Gln Asn Ser Glu Gly Thr
             20                  25                  30

Gly Gln Ala Ala Asp Leu Lys Ser Thr Gln Ala Ala Ile Asp Gln Ile
         35                  40                  45

Asn Gly Lys Leu Asn Arg Val Ile Glu Lys Thr Asn Glu Lys Phe His
     50                  55                  60

Gln Ile Glu Lys Glu Phe Ser Glu Val Glu Gly Arg Ile Gln Asp Leu
 65                  70                  75                  80

Glu Lys Tyr Val Glu Asp Thr Lys Ile Asp Leu Trp Ser Tyr Asn Ala
             85                  90                  95

Glu Leu Leu Val Ala Leu Glu Asn Gln His Thr Ile Asp Leu Thr Asp
            100                 105                 110
```

Ser Glu Met Asn Lys Leu Phe Glu Lys Thr Arg Arg Gln Leu Arg Glu
            115                 120                 125

Asn Ala Glu Glu Met Gly Asn Gly Cys Phe Lys Ile Tyr His Lys Cys
        130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly
                165                 170                 175

<210> SEQ ID NO 175
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Ser Ile Ser Arg Asp Asn Ser Asn Asn Thr Leu His
65                  70                  75                  80

Leu Glu Met Asn Thr Leu Arg Thr Glu Asp Thr Ala Leu Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Pro Trp Gly Gln Gly Thr Leu Val Thr Val Thr
        115                 120                 125

Ser

<210> SEQ ID NO 176
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Val Gln Ser Gly Gly Gly Val Val Pro Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Tyr Lys Tyr Tyr Ala Asp Ser Val
    50                  55                  60

Arg Gly Arg Phe Thr Ile Ser Arg Asp Asn Ser Lys Asn Thr Leu Asn
65                  70                  75                  80

Leu Asp Met Asn Ser Leu Arg Thr Glu Asp Thr Ala Leu Tyr Tyr Cys
                85                  90                  95

```
Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser
```

<210> SEQ ID NO 177
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp Tyr Trp Gly Gln Gly Thr Leu Val Thr Val Ser
        115                 120                 125

Ser
```

<210> SEQ ID NO 178
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125
```

Ser

<210> SEQ ID NO 179
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Thr Glu Asp Thr Ala Leu Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser

<210> SEQ ID NO 180
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asp Ile Gln Met Thr Ser Gln Pro Asp Ser Leu Ala Val Ser Leu Gly
1               5                   10                  15

Ala Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Val Leu Ile Tyr Trp Ala Ser Ala Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 181
<211> LENGTH: 329
<212> TYPE: PRT
<213> ORGANISM: Influenza A virus

<400> SEQUENCE: 181

Thr Asn Ala Asp Thr Ile Cys Ile Gly Tyr His Ala Asn Asn Ser Thr
1               5                   10                  15

Asp Thr Val Asp Thr Val Leu Glu Lys Asn Val Thr Val Thr His Ser
            20                  25                  30

Val Asn Leu Leu Glu Asp Ser His Asn Gly Lys Leu Cys Lys Leu Lys
            35                  40                  45

Gly Ile Ala Pro Leu Gln Leu Gly Lys Cys Asn Ile Ala Gly Trp Leu
50                  55                  60

Leu Gly Asn Pro Glu Cys Asp Leu Leu Leu Thr Ala Ser Ser Trp Ser
65                  70                  75                  80

Tyr Ile Val Glu Thr Ser Asn Ser Glu Asn Gly Thr Cys Tyr Pro Gly
                85                  90                  95

Asp Phe Ile Asp Tyr Glu Glu Leu Arg Glu Gln Leu Ser Ser Val Ser
            100                 105                 110

Ser Phe Glu Lys Phe Glu Ile Phe Pro Lys Thr Ser Ser Trp Pro Asn
            115                 120                 125

His Glu Thr Thr Lys Gly Val Thr Ala Ala Cys Ser Tyr Ala Gly Ala
            130                 135                 140

Ser Ser Phe Tyr Arg Asn Leu Leu Trp Leu Thr Lys Lys Gly Ser Ser
145                 150                 155                 160

Tyr Pro Lys Leu Ser Lys Ser Tyr Val Asn Asn Lys Gly Lys Glu Val
                165                 170                 175

Leu Val Leu Trp Gly Val His His Pro Pro Thr Gly Thr Asp Gln Gln
            180                 185                 190

Ser Leu Tyr Gln Asn Ala Asp Ala Tyr Val Ser Val Gly Ser Ser Lys
            195                 200                 205

Tyr Asn Arg Arg Phe Thr Pro Glu Ile Ala Ala Arg Pro Lys Val Arg
210                 215                 220

Asp Gln Ala Gly Arg Met Asn Tyr Tyr Trp Thr Leu Leu Glu Pro Gly
225                 230                 235                 240

Asp Thr Ile Thr Phe Glu Ala Thr Gly Asn Leu Ile Ala Pro Trp Tyr
                245                 250                 255

Ala Phe Ala Leu Asn Arg Gly Ser Gly Ser Gly Ile Ile Thr Ser Asp
            260                 265                 270

Ala Pro Val His Asp Cys Asn Thr Lys Cys Gln Thr Pro His Gly Ala
            275                 280                 285

Ile Asn Ser Ser Leu Pro Phe Gln Asn Ile His Pro Val Thr Ile Gly
290                 295                 300

Glu Cys Pro Lys Tyr Val Arg Ser Thr Lys Leu Arg Met Ala Thr Gly
305                 310                 315                 320

Leu Arg Asn Ile Pro Ser Ile Gln Ser
                325

<210> SEQ ID NO 182
<211> LENGTH: 222
<212> TYPE: PRT
<213> ORGANISM: Influenza A virus

<400> SEQUENCE: 182

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asp Gly Ile

```
                35                  40                  45
Thr Asn Lys Val Asn Ser Val Ile Glu Lys Met Asn Thr Gln Phe Thr
 50                  55                  60

Ala Val Gly Lys Glu Phe Asn Asn Leu Glu Arg Arg Ile Glu Asn Leu
 65                  70                  75                  80

Asn Lys Lys Val Asp Asp Gly Phe Leu Asp Ile Trp Thr Tyr Asn Ala
                 85                  90                  95

Glu Leu Leu Val Leu Leu Glu Asn Glu Arg Thr Leu Asp Phe His Asp
                100                 105                 110

Ser Asn Val Arg Asn Leu Tyr Glu Lys Val Lys Ser Gln Leu Lys Asn
                115                 120                 125

Asn Ala Lys Glu Ile Gly Asn Gly Cys Phe Glu Phe Tyr His Lys Cys
130                 135                 140

Asp Asp Ala Cys Met Glu Ser Val Arg Asn Gly Thr Tyr Asp Tyr Pro
145                 150                 155                 160

Lys Tyr Ser Glu Glu Ser Lys Leu Asn Arg Glu Glu Ile Asp Gly Val
                165                 170                 175

Lys Leu Glu Ser Met Gly Val Tyr Gln Ile Leu Ala Ile Tyr Ser Thr
                180                 185                 190

Val Ala Ser Ser Leu Val Leu Leu Val Ser Leu Gly Ala Ile Ser Phe
                195                 200                 205

Trp Met Cys Ser Asn Gly Ser Leu Gln Cys Arg Ile Cys Ile
                210                 215                 220

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr
             20                  25                  30

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Ser or Thr
<220> FEATURE:
<221> NAME/KEY: MOD_RES
<222> LOCATION: (8)..(8)
<223> OTHER INFORMATION: Ala or Gly

<400> SEQUENCE: 184

Gly Phe Thr Phe Xaa Xaa Tyr Xaa Met His
 1               5                  10

<210> SEQ ID NO 185
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser or Asp

<400> SEQUENCE: 185

Xaa Ser Ser Gln Xaa Xaa Xaa Xaa Xaa Tyr Lys Asn Tyr Leu Ala
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser, Asp, Gln, Arg or Glu

<400> SEQUENCE: 186

Xaa Ser Ser Gln Xaa Xaa Xaa Xaa Xaa Tyr Lys Asn Tyr Leu Ala
1               5                   10                  15

<210> SEQ ID NO 187
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 187

```
gaaattgtaa tgacgcagag ccctgatagc cttgccgtgt ccctgggtga gagggcgaca    60
atcaattgta agtcatcaca gtcggtcacg tacaactaca agaactacct ggcgtggtat   120
caacagaaac ccgggcagcc gcccaaattg ctcatctatt gggcttcgac acgggagtcg   180
ggtgtgccag accgcttctc cgggtcagga tcgggaactg acttcacgtt gactatttcg   240
tccctccagg cagaagatgt agccgtctac tattgccaac agtattacag aacgccgcct   300
acatttggag gcgggaccaa acttgacatc aagggatccg tggccgcccc cagcgtcttc   360
atcttcccgc ccagcgacga gcagctgaag tcgggcacgg ccagcgtggt gtgcctcctg   420
aacaacttct accccgcga ggcgaaggtc cagtggaagg tggacaacgc cctgcagagc   480
gggaacagcc aggagagcgt gaccgagcag gactcgaagg acagcaccta cagcctcagc   540
agcaccctga cgctgagcaa ggccgactac gagaagcaca aggtctacgc ctgcgaggtg   600
acccaccagg ggctctcgag ccccgtgacc aagagcttca ccggggcga gtg           653
```

<210> SEQ ID NO 188
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 188

```
Glu Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Thr Tyr Asn
            20                  25                  30
Tyr Lys Asn Tyr Leu Ala Trp Tyr Gln Gln Lys Pro Gly Gln Pro Pro
        35                  40                  45
Lys Leu Leu Ile Tyr Trp Ala Ser Thr Arg Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Tyr Tyr
                85                  90                  95
Arg Thr Pro Pro Thr Phe Gly Gly Gly Thr Lys Leu Asp Ile Lys Gly
            100                 105                 110
Ser Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu
    210                 215
```

COMPOSITIONS AND METHODS FOR TREATING AND PREVENTING INFLUENZA

CROSS REFERENCE TO RELATED APPLICATIONS

This application claims the benefit of U.S. Provisional Application No. 62/255,262, filed Nov. 13, 2015, U.S. Provisional Application No. 62/299,141, filed Feb. 24, 2016, and U.S. Provisional Application No. 62/315,977, filed Mar. 31, 2016. The contents of the aforementioned applications are hereby incorporated by reference in their entirety.

SEQUENCE LISTING

The instant application contains a Sequence Listing which has been filed electronically in ASCII format and is hereby incorporated by reference in its entirety. Said ASCII copy, created on Nov. 2, 2016, is named P2029-700910_SL.txt and is 186,427 bytes in size.

BACKGROUND

Influenza is an infectious disease caused by RNA viruses of the family Orthomyxoviridae (the influenza viruses). Influenza viruses are classified based on core protein into three genera A, B and C that are further divided into subtypes determined by the viral envelope glycoproteins haemagglutinin (HA) and neuraminidase (NA). Influenza A viruses infect a range of mammalian and avian species, whereas type B and C infections are largely restricted to humans. Only types A and B cause human disease of any concern.

High mutation rates and frequent genetic reassortments of the influenza viruses contribute to great variability of the HA and NA antigens. Minor point mutations causing small changes ("antigenic drift") occur relatively often. Antigenic drift enables the virus to evade immune recognition, resulting in repeated influenza outbreaks during interpandemic years. Major changes in the HA antigen ("antigenic shift") are caused by reassortment of genetic material from different influenza A subtypes. Antigenic shifts resulting in new pandemic strains are rare events, occurring through reassortment between animal and human subtypes, for example in co-infected pigs.

Influenza A spreads around the world in seasonal epidemics, resulting in the deaths of between 250,000 and 500,000 people every year, and up to millions in some pandemic years. On average 41,400 people died each year in the United States between 1979 and 2001 from influenza.

SUMMARY

The disclosure is based, at least in part, on the discovery of human anti-HA antibodies comprising functional and structural properties disclosed herein, e.g., antibodies that bind a conserved region or epitope on influenza virus, and uses thereof.

Accordingly, the disclosure features binding agents, e.g., antibody molecules, or preparations, or isolated preparations thereof, that bind hemagglutinin (HA) from influenza viruses. In an embodiment, a binding agent, e.g., an antibody molecule, is broad spectrum, and binds more than one HA, e.g., an HA from one or both of Group 1 or Group 2 strains of influenza A viruses and/or one or more strains of influenza B viruses. Therefore, in some embodiments, a binding agent, e.g., an antibody molecule, featured in the disclosure can treat or prevent infection by a Group 1 influenza virus and a Group 2 influenza virus. In other embodiments, a binding agent, e.g., an antibody molecule, featured in the disclosure can treat or prevent infection by an influenza A virus and/or an influenza B virus. The binding agents, e.g., antibody molecules, share sufficient structural similarity with antibodies or variable regions disclosed herein such that they possess functional attributes of the antibodies disclosed herein. In some embodiments, the structural similarity can be in terms of three dimensional structure, or linear amino acid sequence, or both.

In an aspect, the disclosure features a method of treating a subject, e.g., a subject having influenza or at risk for influenza, the method comprising administering, or causing to be administered, to the subject an amount of an anti-HA antibody molecule described herein, e.g., Ab 044 (also known as VIS410 herein), of between 2 and 30 mg/kg, thereby treating the subject.

In an embodiment, the subject is treated for influenza, or a disorder associated with influenza. In an embodiment, the treatment comprises preventing the subject from influenza, or a disorder associated with influenza.

In an embodiment, the amount of the antibody molecule is between 5 and 25 mg/kg, between 10 and 20 mg/kg, between 12 and 18 mg/kg, between 14 and 16 mg/kg, between 13 and 18 mg/kg, between 8 and 16 mg/kg, between 13 and 16 mg/kg, between 11 and 16 mg/kg, between 10 and 15 mg/kg, between 11 and 15 mg/kg, between 8 and 12 mg/kg, or between 10 and 12 mg/kg.

In an embodiment, the amount of the antibody molecule is between 14.5 and 30 mg/kg, between 14.5 and 25 mg/kg, between 14.5 and 20 mg/kg, between 14.5 and 18 mg/kg, between 14.5 and 16 mg/kg; or between 14.5 and 15.5 mg/kg.

In an embodiment, the amount of the antibody molecule is between 15 and 30 mg/kg, between 15 and 25 mg/kg, between 15 and 20 mg/kg, between 15 and 18 mg/kg, between 15 and 16 mg/kg, or between 15 and 15.5 mg/kg.

In an embodiment, the amount of the antibody molecule is between 9 and 14 mg/kg, between 9 and 13 mg/kg, between 9 and 12 mg/kg, between 9 and 11 mg/kg, between 9 and 10 mg/kg, between 10 and 14 mg/kg, between 11 and 14 mg/kg, between 12 and 14 mg/kg, between 13 and 14 mg/kg, between 10 and 13 mg/kg, between 11 and 12 mg/kg, between 10 and 12 mg/kg, or between 10 and 11 mg/kg.

In an embodiment, the amount of the antibody molecule is 10 mg/kg, 11 mg/kg, 12 mg/kg, 13 mg/kg, 14 mg/kg, or 15 mg/kg. In an embodiment, the amount of the antibody molecule is 15 mg/kg. In an embodiment, the amount of the antibody is 10 mg/kg.

In an embodiment, the subject is administered a single dose of the antibody molecule. In an embodiment, the subject is administered a flat dose of the antibody molecule. In an embodiment, the amount of the antibody molecule administered is between 500 mg and 3000 mg, e.g., between 1000 mg and 3000 mg, between 1500 mg and 3000 mg, between 2000 mg and 3000 mg, between 1800 mg and 2500 mg, between 2500 mg and 3000 mg, between 500 mg and 2500 mg, between 500 mg and 2000 mg, between 500 mg and 1500 mg, between 500 mg and 1000 mg, between 1000 mg and 2500 mg, between 1500 mg and 2000 mg, or between 2000 mg and 2500 mg, e.g., 1500 mg, 1600 mg, 1700 mg, 1800 mg, 1900 mg, 2000 mg, 2100 mg, 2200 mg, 2300 mg, 2400 mg, or 2500 mg.

In an embodiment, the antibody molecule is administered intravenously. In an embodiment, the antibody molecule is administered intravenously over a period of 1-3 hours, e.g., 1-2 hours or 2-3 hours, e.g., 2 hours. In an embodiment, the subject is administered intravenously at a flat dose (e.g., a single flat dose) between 2000 mg and 2500 mg, e.g., between 2200 mg and 2400 mg, e.g., 2300 mg.

In an embodiment, the subject is infected, or is at risk of being infected, with an influenza virus chose from an H1N1 virus, an H3N2 virus, an H7N9 virus, or a combination thereof.

In an embodiment, the antibody molecule does not cause an antibody dependent enhancement (ADE) in the subject, e.g., as determined by a method described herein. In an embodiment, the antibody molecule is administered in an amount that does not cause an ADE in the subject, e.g., as determined by a method described herein.

In an embodiment, the antibody molecule does not cause viral resistance, e.g., as determined by a method described herein. In an embodiment, the antibody molecule is administered in an amount that does not cause viral resistance, e.g., as determined by a method described herein.

In an embodiment, the method further comprises detecting an anti-drug antibody (ADA) (e.g., an antibody that binds to or inhibits the anti-HA antibody molecule described herein) in a sample from the subject. In an embodiment, the antibody molecule is administered to a subject who has not developed, or has not been detected for having, an ADA to the antibody molecule.

In an embodiment, treating comprises preventing infection (e.g., influenza virus infection). In an embodiment, the influenza is a seasonal influenza.

In an embodiment, the method comprises administering the antibody molecule prior to the date, e.g., a day or range of days, of an epidemic peak of influenza or a disorder associated with influenza, e.g., wherein the date of the epidemic peak is an expected date for the epidemic peak determined prior to the occurrence of the epidemic peak.

In an embodiment, the epidemic peak is in a region that includes: the place (e.g., street address) where the subject lives; or the city, province or state, in which the subject lives.

In an embodiment, the antibody molecule is administered to a subject 1 to 15 weeks prior to the date of an epidemic peak; 2 to 10 weeks prior to the date of an epidemic peak; 3 to 8 weeks prior to the date of an epidemic peak; or 4 to 6 weeks prior to the date of an epidemic peak. In an embodiment, the antibody molecule is administered to a subject 4 to 8 weeks prior to the date of an epidemic peak.

In an embodiment, the subject is between 0 and 15 years of age; between 16 and 49 years of age; between 50 and 64 years of age; or 65 years of age or above. In another embodiment, the subject is at least 30, 40, 50, 60, or 65 years of age.

In an embodiment, the subject resides in a single family residence; a residence, e.g., single family residence, with at least 1 or 2 persons at least 65 years old; an institution, e.g., a retirement facility, assisted living facility, a hospital, nursing home; or an institution in which more than 2, 3, 5, 10, 20 or 30 unrelated people, e.g., people at least 65 years of age, reside.

In an embodiment, administering comprises an intravenous infusion. In an embodiment, administering includes a single intravenous infusion. In an embodiment, administering includes an intravenous infusion over at least 20, 30, 40, 50, 60, 90, or 120 minutes.

In an embodiment, the amount of the antibody molecule administered is between 10 and 15 mg/kg; the subject is over 65 years of age; and the antibody molecule is administered to the subject 1 to 15 weeks (e.g., 4 to 8 weeks) prior to the expected date of an epidemic peak in a region where the subject resides.

In an embodiment, the amount of the antibody molecule administered is between 14.5 and 15.5 mg/kg; the subject is over 65 years of age; and the antibody molecule is administered to the subject 1 to 15 weeks (e.g., 4 to 8 weeks) prior to the expected date of an epidemic peak in a region where the subject resides.

In an embodiment, the antibody molecule comprises:

(a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and (b) a light chain immunoglobulin variable region segment comprising: a CDR1 comprising the sequence Q-S-I-T-F-D-Y-K-N-Y-L-A (SEQ ID NO:145); a CDR2 comprising the sequence W-G-S-Y-L-E-S (SEQ ID NO:72); and a CDR3 comprising the sequence Q-Q-H-Y-R-T-P-P-S (SEQ ID NO:73).

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an embodiment, the method further comprises administering to the subject a second therapeutic agent, e.g., for influenza, or a disorder or symptom associated with influenza.

In an aspect, the disclosure features a method of protecting a population of subjects, e.g., from influenza or a disorder associated with influenza, comprising administering, and/or causing to be administered, an anti-HA antibody molecule described herein, e.g., Ab 044, to at least 2%, at least 4%, at least 6%, at least 8%, or at least 10% of the subjects in the population, thereby protecting the population.

In an embodiment, protection comprises, decreasing, in the population, one or more (e.g., two, three or all) of: the number of hospital admissions, e.g. of influenza infected individuals; the number incidents of influenza infection; the attack rate; or the number of deaths, e.g. of influenza infected individuals.

In an embodiment, the antibody molecule is administered to at least 2%, but not more than 5 or 10% of the subjects in the population. In another embodiment, the antibody molecule is administered to at least 4%, but nor more than 8 or 15% of the subjects of the population.

In an embodiment, the method decreases, in the population, one or more (e.g., two, three or all) of: the number of hospital admissions, e.g. of influenza infected individuals; the number incidents of influenza infection; the attack rate; or the number of deaths, e.g. of influenza infected individuals.

In an embodiment, (a) the percentage decrease in the number of hospital admissions, incidents of influenza infection, attack rate, or deaths, for the population, is greater than (b) the percentage of subjects in the population receiving the anti-HA antibody molecule. In an embodiment, (a) is at least 2, 3, 4, or 5 times greater than (b).

In an embodiment, the population is all the subjects present in a predefined area. In an embodiment, the population is all the subjects having a predefined characteristic, e.g., being at least 65 years of age, present in a predefined area. In an embodiment, the predefined area is or comprises a city, state, province or other political geographic area. In an embodiment, the predefined area is or comprises an area having a predefined number of subjects. In an embodiment, the predefined area is or comprises an area within a preselected distance of a preselected place or landmark.

In an embodiment, the method comprises administering, and/or causing to be administered, an amount of the antibody molecule of between 2 and 30 mg/kg, In an embodiment, the amount of the amount of the antibody molecule is between 5 and 25 mg/kg, between 10 and 20 mg/kg, between 12 and 18 mg/kg, between 14 and 16 mg/kg, between 13 and 18 mg/kg, between 8 and 16 mg/kg, between 11 and 16 mg/kg, between 13 and 16 mg/kg, between 10 and 15 mg/kg, between 11 and 15 mg/kg, between 8 and 12 mg/kg, or between 10 and 12 mg/kg.

In an embodiment, the amount of the antibody molecule is between 14.5 and 30 mg/kg, between 14.5 and 25 mg/kg, between 14.5 and 20 mg/kg, between 14.5 and 18 mg/kg, between 14.5 and 16 mg/kg; or between 14.5 and 15.5 mg/kg.

In an embodiment, the amount of the antibody molecule is between 15 and 30 mg/kg, between 15 and 25 mg/kg, between 15 and 20 mg/kg, between 15 and 18 mg/kg, between 15 and 16 mg/kg, or between 15 and 15.5 mg/kg.

In an embodiment, the amount of the antibody molecule is between 9 and 14 mg/kg, between 9 and 13 mg/kg, between 9 and 12 mg/kg, between 9 and 11 mg/kg, between 9 and 10 mg/kg, between 10 and 14 mg/kg, between 11 and 14 mg/kg, between 12 and 14 mg/kg, between 13 and 14 mg/kg, between 10 and 13 mg/kg, between 11 and 12 mg/kg, between 10 and 12 mg/kg, or between 10 and 11 mg/kg.

In an embodiment, the amount of the antibody molecule is 10 mg/kg, 11 mg/kg, 12 mg/kg, 13 mg/kg, 14 mg/kg, or 15 mg/kg. In an embodiment, the amount of the antibody molecule is 15 mg/kg. In an embodiment, the amount of the antibody is 10 mg/kg.

In an embodiment, the subject is at risk for influenza, e.g., seasonal influenza.

In an embodiment, the method comprises administering the antibody molecule prior to the date, e.g., a day or range of days, of an epidemic peak of influenza or a disorder associated with influenza, e.g., wherein the date of the epidemic peak is an expected date for the epidemic peak determined prior to the occurrence of the epidemic peak.

In an embodiment, the epidemic peak is in a region that includes: the place (e.g., street address) where the subject lives; or the city, province or state, in which the subject lives.

In an embodiment, the antibody molecule is administered, and/or causing to be administered, to a subject 1 to 15 weeks prior to the date of an epidemic peak; 2 to 10 weeks prior to the date of an epidemic peak; 3 to 8 weeks prior to the date of an epidemic peak; or 4 to 6 weeks prior to the date of an epidemic peak. In an embodiment, the antibody molecule is administered to a subject 4 to 8 weeks prior to the date of an epidemic peak.

In an embodiment, the subject is between 0 and 15 years of age; between 16 and 49 years of age; between 50 and 64 years of age; or 65 years of age or above. In another embodiment, the subject is at least 30, 40, 50, 55, 60, or 65 years of age. In an embodiment, the average age of the subjects in the population is at least 30, 40, 50, 55, 60, or 65.

In an embodiment, the subject resides in a single family residence; a residence, e.g., a single family residence, with at least 1 or 2 persons at least 65 years old; an institution, e.g., a retirement facility, assisted living facility, a hospital, nursing home; or an institution in which more than 2, 3, 5, 10, 20 or 30 unrelated people, e.g., people at least 65 years of age, reside.

In an embodiment, administering comprises an intravenous infusion. In an embodiment, administering includes a single intravenous infusion. In an embodiment, administering includes an intravenous infusion over at least 20, 30, 40, 50, 60, 90, or 120 minutes.

In an embodiment, the amount of the antibody molecule administered is between 10 and 15 mg/kg; the subject is over 65 years of age; and the antibody molecule is administered to the subject 1 to 15 weeks (e.g., 4 to 8 weeks) prior to the expected date of an epidemic peak in a region where the subject resides.

In an embodiment, the amount of the antibody molecule administered is between 14.5 and 15.5 mg/kg; the subject is over 65 years of age; and the antibody molecule is administered to the subject 1 to 15 weeks (e.g., 4 to 8 weeks) prior to the expected date of an epidemic peak in a region where the subject resides.

In an embodiment, the antibody molecule comprises:

(a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and (b) a light chain immunoglobulin variable region segment comprising: a CDR1 comprising the sequence Q-S-I-T-F-D-Y-K-N-Y-L-A (SEQ ID NO:145); a CDR2 comprising the sequence W-G-S-Y-L-E-S (SEQ ID NO:72); and a CDR3 comprising the sequence Q-Q-H-Y-R-T-P-P-S (SEQ ID NO:73).

In an embodiment, the antibody molecule comprises a heavy chain immunoglobulin variable region segment that comprises SEQ ID NO: 25. In an embodiment, the antibody molecule comprises a light chain immunoglobulin variable region segment that comprises SEQ ID NO: 52. In an embodiment, the antibody molecule comprises: a heavy chain immunoglobulin variable region segment that comprises SEQ ID NO: 25 and a light chain immunoglobulin variable region segment that comprises SEQ ID NO: 52. In an embodiment, the antibody molecule comprises a tetramer of: two heavy chain immunoglobulin variable region segments, each comprising SEQ ID NO: 25 and two light chain immunoglobulin variable region segments, each comprising SEQ ID NO: 52.

In an embodiment, the antibody molecule comprises a full length antibody. In an embodiment, the antibody molecule comprises a humanized antibody molecule. In an embodiment, the antibody molecule comprises two heavy claim variable regions and two light chain variable regions. In an embodiment, the antibody molecule is an IgG antibody. In an embodiment, the antibody molecule is a single chain antibody (scFv), a F(ab')$_2$ fragment, a Fab fragment, or an Fd fragment.

In an embodiment, the method further comprises administering to the subject a second therapeutic agent, e.g., for influenza, or a disorder or symptom associated with influenza.

In an aspect, the disclosure features an anti-HA antibody molecule described herein, e.g., Ab 044, of between 2 and 30 mg/kg, for use in a method of treating a subject, e.g., a subject having influenza or at risk for influenza. In an embodiment, the subject is treated for influenza or a disorder associated with influenza. In an embodiment, the treatment comprises preventing the subject from influenza or a disorder associated with influenza.

In an embodiment, the method comprises administering the anti-HA antibody to the subject in an amount between 10 and 15 mg/kg 1 to 15 weeks prior to the expected date of an epidemic peak of influenza (or a disorder associated with influenza) in a region where the subject resides. In another embodiment, the method comprises administering to the subject an anti-HA antibody molecule in an amount between 11 and 16 mg/kg.

In another aspect, the disclosure features an anti-HA antibody molecule described herein, e.g., Ab 044, for use in a method of protecting a population of subjects, e.g., from influenza or a disorder associated with influenza, wherein the anti-HA antibody molecule is used in at least 2%, at least 4%, at least 6%, at least 8%, or at least 10% of the subjects in the population.

In one aspect, the disclosure features an anti-hemagglutinin (anti-HA) binding agent, e.g., a specific binding agent, e.g., an antibody molecule, or preparation, or isolated preparation thereof, comprising one or more or all of the following properties:

(a) it fails to produce any escape mutants as determined by the failure of a viral titer to recover following at least 10, 9, 8, 7, 6, or 5 rounds of serial infections in cell culture with a mixture of the antibody molecule and an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004;

(b) it produces fewer escape mutants than does a reference anti-HA antibody molecule, e.g., Ab 67-11, FI6, FI28, C179, F10, CR9114, or CR6261, e.g., when tested by the method described in (a);

(c) it prevents infection by at least 1, 2, 3, 4 or 5 influenza subtypes of Group 1, and by at least 1, 2, 3, 4 or 5 influenza subtypes of Group 2;

(d) it inhibits fusogenic activity of the targeted HA;

(e) it treats or prevents infection by a Group 1 virus, such as where the virus is an H1, H5, or H9 virus; and it treats or prevents infection by a Group 2 virus, such as where the virus is an H3 or H7 virus;

(f) it treats or prevents infection by influenza A strains H1N1 and H3N2;

(g) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg;

(h) it treats or prevents infection by influenza A H5N1 strains;

(i) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg;

(j) the concentration of antibody molecule required for 50% neutralization of influenza A virus is less than 10 µg/mL;

(k) it treats or prevents infection by an influenza B virus, e.g., B/Wisconsin/1/2010;

(l) it is effective for prevention or treatment of infection, e.g., in humans or mice, with an influenza B virus, e.g., B/Wisconsin/1/2010, when administered at 10 mg/kg, 6 mg/kg, 4 mg/kg, 3 mg/kg, 2 mg/kg, or 1 mg/kg;

(m) the concentration of antibody molecule required for 50% neutralization of influenza B virus, e.g., B/Wisconsin/1/2010, virus is less than 10 µg/mL;

(n) it prevents or minimizes secondary infection (e.g., secondary bacterial infection) or effects thereof on a subject;

(o) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg;

(p) it binds an epitope which comprises or consists of the hemagglutinin trimer interface; and (q) it binds an epitope other than that bound by a reference anti-HA antibody molecule, e.g., Ab 67-11, FI6, FI28, C179, F10, CR9114, or CR6261, e.g., as determined by structural analysis, e.g., by X-ray crystallography or NMR spectroscopy; or (r) in an embodiment it binds to an epitope, e.g., it has an epitope that overlaps with or is the same as, of an antibody disclosed herein, e.g., as determined by mutational analysis or crystal structure analysis.

In one embodiment, the binding agent, e.g., an anti-HA antibody molecule, has one or more of the following characteristics: the anti-HA antibody molecule prevents infection by at least 1, 2, 3, 4 or 5 influenza subtypes of Group 1, and by at least 1, 2, 3, 4 or 5 influenza subtypes of Group 2; the concentration of the anti-HA antibody molecule required for 50% neutralization of influenza A virus is less than 10 µg/mL; or the anti-HA antibody molecule binds an epitope that comprises or consists of the hemagglutinin trimer interface.

In one embodiment, the binding agent, e.g., an anti-HA antibody molecule, featured in the disclosure treats or prevents infection by a Group 1 virus, such as where the virus is an H1, H2, H5, H6, H8, H9, H12, H11, H13, H16, or H17 virus; and treats or prevents infection by a Group 2 virus, such as where the virus is an H3, H4, H7, H10 or H15 virus. In one embodiment, the binding agent, e.g., an anti-HA antibody molecule, featured in the disclosure prevents infection by at least 1, 2, 3, 4, 5, 6, 7, 8, 9, 10 or 11 influenza subtypes of Group 1, and by at least 1, 2, 3, 4, 5 or 6 influenza subtypes of Group 2. In one embodiment, the binding agent, e.g., an anti-HA antibody molecule, featured in the disclosure treats or prevents infection by one or more of H1N1, H2N2, H5N1, and H9N2, and also treats or prevents infection by one or more of H3N2 and H7N7. In an embodiment, a binding agent, e.g., antibody molecule, binds, and in some embodiments, neutralizes: at least one strain from the Group 1 H1, e.g., H1a or H1b, cluster and at least one strain from the Group 2 H3 or H7 cluster. In an embodiment, a binding agent, e.g., antibody molecule, binds, and in some embodiments, neutralizes: at least one strain from the Group 1 H1, e.g., H1a or H1b, cluster and at least one influenza B strain, e.g., B/Wisconsin/1/2010. In an embodiment, a binding agent, e.g., antibody molecule, binds, and in certain embodiments, neutralizes: at least one strain from the Group 2 H3 or H7 cluster and at least one influenza B strain, e.g., B/Wisconsin/1/2010. In an embodiment, a binding agent, e.g., antibody molecule, binds, and in certain embodiments, neutralizes: at least one strain from the Group 1 H1, e.g., H1a or H1b, cluster, at least one strain from the Group 2 H3 or H7 cluster, and at least one influenza B strain, e.g., B/Wisconsin/1/2010. In one embodiment, the binding agent, e.g., an anti-HA antibody molecule, featured in the disclosure treats or prevents infection by one or more of influenza B viruses, e.g., B/Wisconsin/1/2010.

In one embodiment, the anti-HA antibody molecule is not an anti-HA antibody molecule previously described in the art. For example, the anti-HA antibody molecule is other than one or more or all of Ab 67-11 (U.S. Provisional Application No. 61/645,453), FI6 (FI6, as used herein, refers to any specifically disclosed FI6 sequence in U.S. Application Publication No. 2010/0080813, U.S. Application Publication No. 2011/0274702, International Publication No. WO2013/011347, or Corti et al., *Science* 333:850-856, 2011, published online Jul. 28, 2011; FIGS. 12A to 12C of International Publication No. WO2013/170139 or U.S. Application Publication No. 2013/0302349), FI28 (U.S. Application Publication No. 2010/0080813), C179 (Okuno et al., *J. Virol.* 67:2552-1558, 1993), F10 (Sui et al., *Nat. Struct. Mol. Biol.* 16:265, 2009), CR9114 (Dreyfus et al., *Science.* 2012; 337(6100):1343-1348; published online Aug. 9, 2012), or CR6261 (Ekiert et al., *Science* 324:246-251, 2009; published online Feb. 26, 2009).

In one embodiment, the binding agent, e.g., an anti-HA antibody molecule, neutralizes infection with H1N1 and H3N2 in vitro. In another embodiment, binding agent, e.g., an anti-HA antibody molecule, neutralizes infection with H1N1 and H3N2 in vivo. In one embodiment, the binding agent, e.g., an anti-HA antibody molecule, neutralizes infection with H5N1 in vitro. In another embodiment, binding agent, e.g., an anti-HA antibody molecule, neutralizes infection with H5N1 in vivo. In one embodiment, the binding agent, e.g., an anti-HA antibody molecule, neutralizes infection with an influenza B virus, e.g., B/Wisconsin/1/2010, in vitro. In another embodiment, the binding agent, e.g., an anti-HA antibody molecule neutralizes infection with an influenza B virus, e.g., B/Wisconsin/1/2010, in vivo.

In another embodiment, the concentration of the binding agent, e.g., an anti-HA antibody molecule, required for 50% neutralization of influenza A virus is 10 µg/mL or less, such as 9 µg/mL or less, 8 µg/mL or less, 7 µg/mL or less, 6 µg/mL or less, or 5 µg/mL or less. In another embodiment, the concentration of the binding agent, e.g., an anti-HA antibody molecule, required for 60% neutralization of influenza A virus, 50% neutralization of influenza A virus, or 40% neutralization of influenza A virus is 10 µg/mL or less, such as 9 µg/mL or less, 8 µg/mL or less, 7 µg/mL or less, 6 µg/mL or less, or 5 µg/mL or less.

In yet another embodiment, the binding agent, e.g., an anti-HA antibody molecule, is effective for prevention or treatment of infection, e.g., in humans or mice, with H1N1 and H3N2, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less. In still another embodiment, the binding agent, e.g., the anti-HA antibody molecule, is effective for prevention or treatment of infection, e.g., in humans or mice, with H5N1, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less.

In another embodiment, a binding agent, e.g., an anti-HA antibody molecule, is effective for the treatment or prevention of a Group 1 virus, where the Group 1 virus is H1, H5, or H9, and in another embodiment, the binding agent, e.g., an anti-HA antibody molecule, is effective for the treatment or prevention of a Group 2 virus, where the Group 2 virus is H3 or H7. In another embodiment, the concentration of the binding agent, e.g., an anti-HA antibody molecule, required for 50% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less. In another embodiment, the concentration of the binding agent, e.g., an anti-HA antibody molecule, required for 60% neutralization of influenza B virus, e.g., B/Wisconsin/1/2010, 50% neutralization of influenza B virus, e.g., B/Wisconsin/1/2010, or 40% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less.

In another embodiment, the binding agent, e.g., an anti-HA antibody molecule, is a full length tetrameric antibody, a single chain antibody (scFv), a F(ab')$_2$ fragment, a Fab fragment, or an Fd fragment. In another embodiment, the heavy chain of the antibody molecule is a γ1 heavy chain, and in yet another embodiment, the light chain of the antibody molecule is a κ light chain or a λ light chain. In yet another embodiment, the anti-HA antibody molecule featured in the disclosure is an IgG1 antibody.

In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f).

In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46. In an embodiment, the antibody molecule has one, two, three or all of the following properties: a) and aa); b) and bb); c) and cc); or d) and dd). In an embodiment, the molecule has properties c), cc), d), and dd).

In an embodiment, the binding agent, e.g., a specific binding agent, e.g., an antibody molecule, comprises one or both of: a heavy chain variable region comprising at least, or more than, 60, 65, 70, 75, 80, 85, 87, 90, 95, 98 or 99 percent homology with a heavy chain variable region from Table 3, Table 4A, or Table 4B, or FIG. 2, FIG. 13 or FIG. 17 of International Publication No. WO2013/170139 or U.S. Application Publication No. 2013/0302349; and a light chain variable region comprising at least, or more than, 60, 65, 70, 75, 80, 85, 87, 90, 95, 98 or 99 percent homology with light chain variable region from Table 3, Table 4A, or Table 4B, or FIG. 3, FIG. 14 or FIG. 17 International Publication No. WO2013/170139 or U.S. Application Publication No. 2013/0302349.

In an embodiment, the antibody molecule comprises a heavy chain variable region 25 (SEQ ID NO: 25), or a structurally or functionally related variable heavy chain region as described herein. In an embodiment, the antibody molecule comprises a light chain variable region 52 (SEQ ID NO: 52), 155 (SEQ ID NO: 155), or 45 (SEQ ID NO: 45), or a structurally or functionally related variable light chain region as described herein. In an embodiment, the antibody molecule comprises: a heavy chain variable region 25 (SEQ ID NO: 25), or a structurally or functionally related variable heavy chain region as described herein; and a light chain variable region 52 (SEQ ID NO: 52), 155 (SEQ ID NO: 155), or 45 (SEQ ID NO: 45), or a structurally or functionally related variable light chain region as described herein.

In an embodiment, the antibody molecule comprises a heavy chain variable region comprising one, two, or all of CDR1, CDR2, and CDR3, from heavy chain variable region 25 (SEQ ID NO: 25), or a structurally or functionally related variable heavy chain region as described herein. In an embodiment, the antibody molecule comprises a light chain variable region comprising one, two, or all of CDR1, CDR2, and CDR3, from light chain variable region 52 (SEQ ID NO: 52), 155 (SEQ ID NO: 155), or 45 (SEQ ID NO: 45), or a structurally or functionally related sequence as described herein. In an embodiment, the antibody molecule comprises: a heavy chain variable region comprising one, two, or all of CDR1, CDR2, and CDR3, from heavy chain variable region 25 (SEQ ID NO: 25), or a structurally or functionally related variable heavy chain region as described herein; and a light chain variable region comprising one, two, or all of CDR1, CDR2, and CDR3, from light chain variable region 52 (SEQ ID NO: 52), 155 (SEQ ID NO: 155), or 45 (SEQ ID NO: 45), or a structurally or functionally related variable light chain region as described herein.

In an embodiment, the antibody molecule comprises a heavy chain variable region from FIG. 2 or FIG. 13 of International Publication No. WO2013/170139 or U.S. Application Publication No. 2013/0302349 or a structurally or functionally related variable heavy chain region as described herein. In an embodiment, the antibody molecule comprises a light chain variable region from FIG. 3 or FIG. 14 of International Publication No. WO2013/170139 or U.S. Application Publication No. 2013/0302349, or a structurally or functionally related variable light chain region as described herein. In an embodiment, the antibody molecule comprises one, two, or all of, a CDR1, CDR2, and CDR3 from a heavy chain variable region from FIG. 2 or FIG. 13 International Publication No. WO2013/170139 or U.S. Application Publication No. 2013/0302349, or a structurally or functionally related sequence as described herein. In an embodiment, the antibody molecule comprises one, two, or all of, a CDR1, CDR2, and CDR3 from a light chain variable region from FIG. 3 or FIG. 14 International Publication No. WO2013/170139 or U.S. Application Publication No. 2013/0302349, or a structurally or functionally related sequence as described herein. In an embodiment, the antibody molecule comprises one, two or all of, HC CDR1, HC CDR2, and HC CDR3 and one, two or all of, LC CDR1, LC CDR2, and LC CDR3 from an antibody disclosed in Table 3, or a structurally or functionally related sequence as described herein.

In another embodiment, the antibody molecule comprises the light chain LC45 (SEQ ID NO: 45). In yet another embodiment, the antibody comprises the light chain LC45, and the heavy chain HC25 (SEQ ID NO: 25) or 24 (SEQ ID NO: 24). In one embodiment, the antibody molecule comprises the light chain Ab032 (SEQ ID NO: 45) and the heavy chain 25 (SEQ ID NO: 25). In yet another embodiment, the antibody molecule comprises light chain LC52 (SEQ ID NO: 52) and heavy chain HC25 (SEQ ID NO: 25).

In an embodiment, the antibody molecule comprises one or both of: a) one or more framework regions (FRs) from heavy chain disclosed herein. E.g., the antibody molecule comprises one or more or all of FR1, FR2, FR3, or FR4, or FR sequences that differ individually, or collectively, by no more than 1, 2, 3, 4, of 5 amino acid residues, e.g., conservative residues, from a heavy chain disclosed herein; and b) one or more framework regions (FRs) from light chain disclosed herein. E.g., the antibody molecule comprises one or more or all of FR1, FR2, FR3, or FR4, or FR sequences that differ individually, or collectively, by no more than 1, 2, 3, 4, of 5 amino acid residues, e.g., conservative residues, from light chain disclosed herein.

In one aspect, an anti-HA antibody molecule featured in the disclosure, or preparation, or isolated preparation thereof, comprises: (a) a heavy chain immunoglobulin variable domain comprising a sequence at least 60, 70, 80, 85, 87, 90, 95, 97, 98, or 99, e.g., 90%, homologous, to a heavy chain consensus sequence provided herein, e.g., the heavy chain consensus sequence provided in FIG. 2 or FIG. 13 of International Publication No. WO2013/170139 or U.S. Application Publication No. 2013/0302349, e.g., the heavy chain consensus sequence provided in FIG. 2 of International Publication No. WO2013/170139 or U.S. Application Publication No. 2013/0302349, SEQ ID NO: 161; and (b) a light chain immunoglobulin variable domain comprising a sequence at least 60, 70, 80, 85, 87, 90, 95, 97, 98, or 99, e.g., 95%, homologous, to a light chain consensus sequence provided herein, e.g., the light chain consensus sequence provided in FIG. 3 or FIG. 14 of International Publication No. WO2013/170139 or U.S. Application Publication No. 2013/0302349, e.g., the light chain consensus sequence provided in FIG. 3 of International Publication No. WO2013/170139 or U.S. Application Publication No. 2013/0302349, SEQ ID NO: 62.

For example, in one embodiment, the anti-HA antibody molecule featured in the disclosure comprises one or both of: (a) a heavy chain immunoglobulin variable domain comprising the sequence of SEQ ID NO: 161, or a sequence at least 87% identical to SEQ ID NO: 161; and (b) a light chain immunoglobulin variable domain comprising the sequence SEQ ID NO: 62, or a sequence at least 95% identical to SEQ ID NO: 62.

In another embodiment the antibody molecule comprises: (a) a heavy chain immunoglobulin variable domain comprising the sequence of SEQ ID NO: 161, or a sequence at least 87% identical to SEQ ID NO: 161; and (b) a light chain immunoglobulin variable domain comprising the sequence SEQ ID NO:62, or a sequence at least 95% identical to SEQ ID NO: 62, wherein said antibody molecule: (i) fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) produces fewer escape mutants than does a reference anti-HA antibody molecule, e.g., Ab 67-11, FI6, FI28, C179, F10, CR9114, or CR6261, such as when tested by the method described in (i).

In an embodiment, the disclosure features an antibody molecule comprising one or both of: (a) a heavy chain immunoglobulin variable region comprising the sequence of SEQ ID NO: 161, or a sequence that differs from SEQ ID NO:161 by not more than 1, 2, 3, 4, 5, 6, 8, 10, 11, 12, 13, 14, 15 or 16, e.g., by no more than 2, 3, 4, or 5 amino acids, e.g., conservative amino acids; and (b) a light chain immunoglobulin variable domain comprising the sequence SEQ ID NO:62, or a sequence that differs from SEQ ID NO:62 that differs by no more than 1, 2, 3, 4 or 5 amino acids, e.g., conservative amino acids.

In one embodiment, the 1, 2, 3, 4, 5, 6, 8, 10, 11, 12, 13, 14, 15 or 16 amino acid differences, e.g., conservative amino acid differences, in the heavy chain immunoglobulin variable region are in the FR regions of the heavy chain immunoglobulin variable domain. In another embodiment, the 1, 2, 3, 4 or 5 amino acid differences, e.g., conservative amino acid differences, in the light chain immunoglobulin variable domain are in the FR regions of the light chain immunoglobulin variable domain. In one embodiment, the amino acid differences in the heavy chain immunoglobulin variable region, or in the light chain immunoglobulin variable region, are conservative amino acid changes.

In an embodiment, the binding agent, e.g., an antibody molecule, binds to an epitope, e.g., it has an epitope that overlaps with or is the same as, of an antibody disclosed herein, e.g., as determined by mutational analysis or crystal structure analysis.

In an embodiment, the antibody molecule comprises one or both of: a) one or more framework regions (FRs) from heavy chain consensus sequence disclosed herein. e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain consensus sequence disclosed herein; and b) one or more framework regions (FRs) from light chain consensus sequence disclosed herein. e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain consensus disclosed herein. In an embodiment, the binding agent, e.g., an antibody molecule, specifically binds the HA antigen.

In another aspect, the disclosure features, a binding agent, e.g., an antibody molecule, or preparation, or isolated preparation thereof, comprising a structural or functional property of Ab 044.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-D-Y-K-N-Y-L-A (SEQ ID NO:145); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:52; or c) Ab 044.

The HA can be from a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecules or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry.

The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-D-Y-K-N-Y-L-A (SEQ ID NO:145); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:52; or c) Ab 044.

The HA can be HA1 or HA5, e.g., from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004 Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; or c) flow cytometry.

The antibody molecule can compete with the reference antibody such that binding of the reference antibody is decreased by 50% or more. In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52.

In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52, wherein, each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 52.

In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the $2^{nd}$ position; or N at the $7^{th}$ position and Q at the $16^{th}$ position in HC CDR2; (iii) a HC CDR3 comprising: R at the 3rd position (and optionally, L at the $3^{rd}$ position); (iv) a LC CDR1 comprising one or both of, e.g., one of: I at the 3rd position; or D at the 6th position in LC CDR1; (v) a LC CDR2 comprising one, two, or three of, e.g., one of: G at the $2^{nd}$ position; Y at the $4^{th}$ position; or L at the $5^{th}$ position in LC CDR2; (vi) a LC CDR3 comprising: S at the $9^{th}$ position in LC CDR3.

In an embodiment, the binding agent, e.g., an antibody molecule, comprises: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:52 (or a sequence that differs by no more than 1, 2, 3, 4 or 5 amino acids, e.g., conservative amino acids, therefrom).

In an embodiment, the binding agent, e.g., an antibody molecule, comprises one or both of: (a) a heavy chain immunoglobulin variable region segment comprising: a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising: a CDR1 comprising the sequence: Q-S-I-T-F-D-Y-K-N-Y-L-A (SEQ ID NO:145) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment, the binding agent, e.g., an antibody molecule, comprises one or both of: a) LC CDR1-3, that collectively, differ from the AB 044 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 044 HC CDR1-3 by no more than, 1, 2, 3, 4, 5, 6, 7, 8, 9, or 10, e.g., 1, 2, 3, or 4, amino acids, e.g., conservative amino acids.

In one embodiment, the antibody molecule comprises one or both of: (a) a heavy chain immunoglobulin variable region segment comprising SEQ ID NO: 25; and (b) a light chain variable region segment comprising SEQ ID NO: 52.

In an embodiment, the binding agent is an antibody molecule comprising one or both of: (a) a heavy chain immunoglobulin variable region segment comprising: a CDR1 comprising the sequence S-Y-A-M-H (SEQ ID NO:68) (or a sequence that differs by no more than, 1, 2, or 3, e.g., 1 or 2, amino acids, e.g., conservative amino acids, there from, optionally provided that at least 1 or 2 of the highlighted residue are not changed, e.g., both S and A are not changed); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V or both N and Q or all three of V, N, and Q are not changed); a CDR3 comprising the sequence D-S-R-L-R-S-L- L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising: a CDR1 comprising the sequence: Q-S-I-T-F-D-Y-K-N-Y-L-A (SEQ ID NO:145) (or a sequence that differs by no more than, 1, 2, 3, 4, or 5, e.g., 1 or 2, amino acids, e.g., conservative amino acids, therefrom, optionally provided that at least 1 or 2 of the highlighted residues are not changed, e.g., I or D is not changed); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2 or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2, amino acids, e.g., conservative amino acids, therefrom, optionally provided that at least 1 or both of the highlighted residues are not changed, e.g., S is not changed). In an embodiment a CDR of the light or heavy chain includes one of the highlighted residues, or one of the highlighted combinations of residues, for that CDR, (i.e., while other residues in that CDR might be changed, the highlighted residue or combination of residues, are not changed). E.g., in an embodiment, V or both N and Q, for heavy chain CDR2 are not changed.

In an embodiment, a CDR of the light and a CDR of the heavy chain each includes one of the highlighted residues, or one of the highlighted combinations of residues, for that CDR. In an embodiment each of two CDRs in the antibody molecule includes one of the highlighted residues, or one of the highlighted combinations of residues, for that CDR. In some embodiments, both are in the light chain. In some embodiments, both are in the heavy chain. In an embodiment each of the three CDRs in the heavy chain includes one of the highlighted residues, or one of the highlighted combinations of residues, for that CDR. In an embodiment each of the three CDRs in the light chain includes one of the highlighted residues, or one of the highlighted combinations of residues, for that CDR. In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged; (b) V or both N and Q or all three of V, N, and Q in HC CDR2 are unchanged; (c) R in HC CDR3 is unchanged; (d) One or both of I and D in LC CDR1 are unchanged. (e) 1, 2 or 3 of G, Y, and L in LC CDR2 are unchanged; or (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In one embodiment, the binding agent, e.g., an antibody molecule, comprises one or both of: (a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); a CDR3 comprising the sequence D-S-R-L-R-S-L-L-Y-F-E-W-L-S-Q-G-Y-F-N-P (SEQ ID NO:70); and (b) a light chain variable region segment comprising: a CDR1 comprising the sequence Q-S-I-T-F-D-Y-K-N-Y-L-A (SEQ ID NO:145); a CDR2 comprising the sequence W-G-S-Y-L-E-S (SEQ ID NO:72); and a CDR3 comprising the sequence Q-Q-H-Y-R-T-P-P-S (SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the antibody molecule comprises one or both of: a) one or more framework regions (FRs) from SEQ ID NO: 25 e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 52. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 52.

In one embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2, amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2, amino acids, e.g., conservative amino acids, therefrom); and (b) a light chain immunoglobulin variable region segment comprising one or more or all of: an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2, amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment, a FR of the light and a FR of the heavy chain each includes one of the highlighted residues, or one of the highlighted combinations of residues, for that FR. In an embodiment each of two FRs in the antibody molecule includes one of the highlighted residues, or one of the highlighted combinations of residues, for that FR. In some embodiments, both are in the light chain. In some embodiments, both are in the heavy chain. In an embodiment each of FR2 and FR3 in the heavy chain includes one of the highlighted residues, or one of the highlighted combinations of residues, for that FR. In an embodiment each of FR1 and FR2 in the heavy and light chain includes one of the highlighted residues for that FR. In an embodiment all of the highlighted residues in heavy chain FR1-4 are unchanged. In an embodiment all of the highlighted residues in light chain FR1-4 are unchanged. In an embodiment all of the highlighted residues in both heavy and light chain FR1-4 are unchanged. In an embodiment, sequence of FR1 of the heavy chain variable region segment is Q-V-Q-L-L-E-T-G-G-G-L-V-K-P-G-Q-S-L-K-L-S-C-A-A-S-G-F-T-F-T (SEQ ID NO: 74). In an embodiment, sequence of FR1 of the heavy chain variable region segment is E-V-Q-L-L-E-S-G-G-G-L-V-K-P-G-Q-S-L-K-L-S-C-A-A-S-G-F-T-F-T (SEQ ID NO: 173).

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f).

In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46.

In an embodiment, the antibody molecule has one, two, three or all of the following properties: a) and aa); b) and bb); c) and cc); d) and dd). In an embodiment, the molecule has properties c), cc), d), and dd).

In another aspect, the disclosure features, a binding agent, e.g., an antibody molecule, or preparation, or isolated preparation thereof, comprising a structural or functional property of Ab 069.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-E-Y-K-N-Y-L-A (SEQ ID NO:172); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:155; or c) Ab 069.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; c) flow cytometry.

The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds. In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-E-Y-K-N-Y-L-A (SEQ ID NO:172); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:155; or c) Ab 069.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding or lack thereof to mutant HA, e.g., if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; or d) (c) and one or both of (a) and (b);

Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; c) flow cytometry. The antibody molecule can compete with the reference antibody such that binding of the reference antibody is decreased by 50% or more.

In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155. In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155, wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 155. In an embodiment, the binding agent, e.g., an antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the 2nd position; or N at the 7$^{th}$ position and Q at the 16$^{th}$ position in HC CDR2; (iii) a HC CDR3 comprising: R at the 3rd position (and optionally, L at the 3$^{rd}$ position); (iv) a LC CDR1 comprising one or both of, e.g., one of: I at the 3rd position; or E at the 6th position in LC CDR1; (v) a LC CDR2 comprising one, two or three of, e.g., one of: G at the 2nd position; Y at the 4$^{th}$ position; or L at the 5$^{th}$ position in LC CDR2; (vi) a LC CDR3 comprising: S at the 9$^{th}$ position in LC CDR3. In an embodiment, the binding agent, e.g., an antibody molecule, comprises one or both of: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:155 (or a sequence that differs by no more than 1, 2, 3, 4 or 5 amino acids, e.g., conservative amino acids, therefrom). In one embodiment, the antibody molecule comprises one or both of: (a) a heavy chain immunoglobulin variable region segment comprising SEQ ID NO: 25; and (b) a light chain variable region segment comprising SEQ ID NO:155.

In an embodiment, the binding agent, e.g., an antibody molecule, comprises one or both of: (a) a heavy chain immunoglobulin variable region segment comprising: a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising: a CDR1 comprising the sequence: Q-S-I-T-F-E-Y-K-N-Y-L-A (SEQ ID NO: 172) or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment, the binding agent, e.g., an antibody molecule, comprises one or both of: a) LC CDR1-3, that collectively, differ from the AB 069 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 069 HC CDR1-3 by no more than, 1, 2, 3, 4, 5, 6, 7, 8, 9, or 10, e.g., 1, 2, 3, or 4, amino acids, e.g., conservative amino acids.

In an embodiment, the binding agent is an antibody molecule comprising one or both of: (a) a heavy chain immunoglobulin variable region segment comprising: a CDR1 comprising the sequence S-Y-A-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V or both N and Q or all three of V, N, and Q are not changed); a CDR3 comprising the sequence D-S-R-L-R-S-L-L-Y-F-E- W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom optionally provided that, R is not changed); and (b) a light chain variable region segment comprising: a CDR1 comprising the sequence: Q-S-I-T-F-E-Y-K-N-Y-L-A (SEQ ID NO: 172) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I or E is not changed); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that, at least one or both of the highlighted residues are not changed, e.g., S is not changed).

In an embodiment, a CDR of the light or heavy chain includes one of the highlighted residues, or one of the highlighted combinations of residues, for that CDR, (i.e., while other residues in that CDR might be changed, the highlighted residue or combination of residues, are not changed). In an embodiment a CDR of the light and a CDR of the heavy chain each includes one of the highlighted residues, or one of the highlighted combinations of residues, for that CDR. In an embodiment, each of two CDRs in the antibody molecule includes one of the highlighted residues, or one of the highlighted combinations of residues, for that CDR. In some embodiments, both are in the light chain. In some embodiments, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment, each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged; (b) V or both N and Q or all three of V, N, and Q in HC CDR2 are unchanged; (c) R in HC CDR3 is unchanged; (d) one or both of I and E in LC CDR1 are unchanged; (e) 1, 2 or 3 of G, Y, and L in LC CDR2 are unchanged; (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f). In one embodiment, the antibody molecule comprises one or both of: (a) a heavy chain immunoglobulin variable region segment comprising: a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); a CDR3 comprising the sequence D-S-R-L-R-S-L-L-Y-F-E-W-L-S-Q-G-Y-F-N-P (SEQ ID NO:70); and (b) a light chain variable region segment comprising: a CDR1 comprising the sequence Q-S-I-T-F-E-Y-K-N-Y-L-A (SEQ ID NO: 172); a CDR2 comprising the sequence W-G-S-Y-L-E-S (SEQ ID NO: 72); and a CDR3 comprising the sequence Q-Q-H-Y-R-T-P-P-S (SEQ ID NO: 73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the antibody molecule comprises one or both of: a) one or more framework regions (FRs) from SEQ ID NO: 25, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 155, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 155.

In one embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and (b) the light chain immunoglobulin variable region segment comprises one or more or all of: an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment, a FR of the light and a FR of the heavy chain each includes one of the highlighted residues, or one of the highlighted combinations of residues, for that FR. In an embodiment each of two FRs in the antibody molecule includes one of the highlighted residues, or one of the highlighted combinations of residues, for that FR. In some embodiments, both are in the light chain. In some embodiments, both are in the heavy chain. In an embodiment each of FR2 and FR3 in the heavy chain includes one of the highlighted residues, or one of the highlighted combinations of residues, for that FR. In an embodiment each of FR1 and FR2 in the heavy and light chain includes one of the highlighted residues for that FR. In an embodiment all of the highlighted residues in heavy chain FR1-4 are unchanged. In an embodiment all of the highlighted residues in light chain FR1-4 are unchanged. In an embodiment all of the highlighted residues in both heavy and light chain FR1-4 are unchanged.

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f).

In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46;

In an embodiment, the antibody molecule has one, two, three or all of the following properties: a) and aa); b) and bb); c) and cc); d) and dd). In an embodiment, the molecule has properties c), cc), d), and dd). In an embodiment, the molecule has properties c), cc), d), and dd).

In another aspect, the disclosure features, a binding agent, e.g., an antibody molecule, or preparation, or isolated preparation thereof, comprising a structural or functional property of Ab 032.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S (SEQ ID NO: 72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO: 45; or c) Ab 032.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry.

The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds. In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO:45; or c) Ab 32.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more.

In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45. In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 45.

In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the $2^{nd}$ position; or N at the $7^{th}$ position and Q at the $16^{th}$ position in HC CDR2; (iii) a HC CDR3 comprising: R at the 3rd position (and optionally, L at the $3^{rd}$ position); (iv) a LC CDR1 comprising: I at the 3rd position; (v) a LC CDR2 comprising one, two, or three of, e.g., one of: G at the 2${}^{nd}$ position; Y at the 4${}^{th}$ position; or L at the 5${}^{th}$ position in LC CDR2; (vi) a LC CDR3 comprising: S at the 9${}^{th}$ position in LC CDR3; In an embodiment, the binding agent, e.g., an antibody molecule, comprises one or both of: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:155 (or a sequence that differs by no more than 1, 2, 3, 4 or 5 amino acids, e.g., conservative amino acids, therefrom).

In one embodiment, the antibody molecule comprises one or both of: (a) a heavy chain immunoglobulin variable region segment comprising SEQ ID NO: 25; and (b) a light chain variable region segment comprising SEQ ID NO:155. In an embodiment, the binding agent, e.g., an antibody molecule, comprises one or both of: (a) a heavy chain immunoglobulin variable region segment comprising a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence: Q-S-I-T-F N-Y-K-N-Y-L-A (SEQ ID NO:71) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom). In an embodiment, the binding agent, e.g., an antibody molecule, comprises one or both of: a) LC CDR1-3, that collectively, differ from the AB 032 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 032 HC CDR1-3 by no more than, 1, 2, 3, 4, 5, 6, 7, 8, 9, or 10, e.g., 1, 2, 3, or 4, amino acids, e.g., conservative amino acids. In an embodiment, the binding agent is an antibody molecule comprising one or both of: (a) a heavy chain immunoglobulin variable region segment comprising a CDR1 comprising the sequence S-Y-A-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising a CDR1 comprising the sequence: Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S is not changed). In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment, a CDR of the light and a CDR of the heavy chain each includes one of the highlighted residues, or one of the highlighted combinations of residues, for that CDR. In an embodiment each of two CDRs in the antibody molecule includes one of the highlighted residues, or one of the highlighted combinations of residues, for that CDR. In some embodiments, both are in the light chain. In some embodiments, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged. (b) V or both N and Q or all three of V, N, and Q in HC CDR2 are unchanged. (c) R in HC CDR3 is unchanged. (d) I in LC CDR1 is unchanged. (e) 1, 2 or 3 of G, Y, and L in LC CDR2 are unchanged; (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In one embodiment, the antibody molecule comprises one or both of: (a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); a CDR3 comprising the sequence D-S-R-L-R-S-L-L-Y-F-E-W-L-S-Q-G-Y-F-N-P (SEQ ID NO:70); and (b) a light chain variable region segment comprising a CDR1 comprising the sequence Q-S-I-T-F-N-Y-K-N-Y-L-A (SEQ ID NO: 71); a CDR2 comprising the sequence W-G-S-Y-L-E-S (SEQ ID NO:72); and a CDR3 comprising the sequence Q-Q-H-Y-R-T-P-P-S (SEQ ID NO:73).

In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the antibody molecule comprises one or both of: a) one or more framework regions (FRs) from SEQ ID NO: 25, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 45, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In one embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-G-Q-S-L-K-L-S-C-A-A-S-G-F-T-F-T (SEQ ID NO:74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2 amino acids, e.g., conservative amino acids, therefrom); and (b) the light chain immunoglobulin variable region segment comprises one or more or all of: an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed.

In an embodiment, a FR of the light and a FR of the heavy chain each includes one of the highlighted residues, or one of the highlighted combinations of residues, for that FR. In an embodiment, each of two FRs in the antibody molecule includes one of the highlighted residues, or one of the highlighted combinations of residues, for that FR. In some embodiments, both are in the light chain. In some embodiments, both are in the heavy chain. In an embodiment each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment all of the highlighted residues in both heavy and light chain FR1-4 are unchanged.

In another embodiment, the binding agent, e.g., an antibody molecule, comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57. In an embodiment, the antibody molecule has properties: a) and b). In an embodiment, the antibody molecule has properties: c) and d). In an embodiment, the antibody molecule has properties: a; and c or d. In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f). In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57.

In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and c) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46; In an embodiment, the antibody molecule has one, two, three or all of the following properties: a) and aa); b) and bb); c) and cc); d) and dd). In an embodiment, the molecule has properties c), cc), d), and dd).

In another aspect, the disclosure features, a binding agent, e.g., an antibody molecule, or preparation, or isolated preparation thereof, comprising a structural or functional property of Ab 031. In an embodiment, the antibody molecule competes with a reference antibody molecule, e.g., an antibody molecule described herein, for binding to a substrate, e.g., an HA. The reference antibody molecule can be:

a) an antibody molecule comprising: i) a heavy chain immunoglobulin variable region segment comprising a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO:71); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 24; and (ii) a light chain variable region segment comprising SEQ ID NO:45; or c) Ab 031. The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c)

flow cytometry. The antibody molecule can compete with the reference antibody such that binding of the reference antibody is decreased by 50% or more.

In an embodiment, the antibody molecule binds to the same epitope, or a portion thereof, which the reference antibody molecule binds. In an embodiment, the antibody molecule does not bind to the same epitope, or a portion thereof, which the reference antibody molecule binds. In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-N-Y-K-N-Y-L-A (SEQ ID NO:71); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 24; and (ii) a light chain variable region segment comprising SEQ ID NO:45; or c) Ab 031. The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more. In an embodiment, the binding agent, e.g., an antibody molecule, comprises one or both of: a heavy chain variable region comprising least 60, 70, 80, 85, 90, 95, 98 or 99 percent homology with SEQ ID NO: 24; and a light chain variable region comprising least 60, 70, 80, 85, 90, 95, 98 or 99 percent homology with SEQ ID NO: 45. In an embodiment, the binding agent, e.g., an antibody molecule, comprises one or both of: a heavy chain variable region comprising least 60, 70, 80, 85, 90, 95, 98 or 99 percent homology with SEQ ID NO: 24; and a light chain variable region comprising least 60, 70, 80, 85, 90, 95, 98 or 99 percent homology with SEQ ID NO: 45, wherein, optionally, each HC CDR differs by no more than 1, 2, 3, 4 or 5 amino acids, e.g., 1 or 2, e.g., conservative amino acids, from the corresponding CDR of SEQ ID NO: 24 and each LC CDR differs by no more than 1, 2, 3, 4 or 5 amino acids, e.g., 1 or 2, e.g., conservative amino acids, from the corresponding CDR of SEQ ID NO: 45.

In an embodiment, the binding agent, e.g., an antibody molecule, comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein the antibody molecule comprises 1, 2, 3, 4, 5, or all of: (i) a HC CDR1 comprising: S at the 1st position and A at the 3rd position in HC CDR1; (ii) a HC CDR2 comprising one or both, e.g., one of: V at the 2nd position; or N at the $7^{th}$ position and Q at the $16^{th}$ position in HC CDR2; (iii) a HC CDR3 comprising: R at the 3rd position (and optionally, L at the $3^{rd}$ position); (iv) a LC CDR1 comprising: I at the 3rd position; (v) a LC CDR2 comprising one, two, or three of, e.g., one of: G at the 2nd position; Y at the $4^{th}$ position; or L at the $5^{th}$ position in LC CDR2; (vi) a LC CDR3 comprising: S at the $9^{th}$ position in LC CDR3.

In an embodiment, the binding agent comprises an antibody molecule comprising: (a) a heavy chain immunoglobulin variable region segment comprising SEQ ID NO:24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom). In one embodiment, the antibody molecule comprises one or both of: (a) a heavy chain immunoglobulin variable region segment comprising SEQ ID NO: 24; and (b) a light chain variable region segment comprising SEQ ID NO:45. In an embodiment, the binding agent, e.g., an antibody molecule, comprises one or both of: (a) a heavy chain immunoglobulin variable region segment comprising a CDR1 comprising the sequence S-Y-A-M-H (SEQ ID NO:68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO:69) (or a sequence that differs by no more than, 1, 2, 3, 4, or 5, e.g., 1 or 2 amino acids, e.g., conservative amino acids, therefrom); and a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence Q-S-I-T-F-N-Y-K-N-Y-L-A (SEQ ID NO:71) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO: 72) (or a sequence that differs by no more than, 1, 2, 3, 4, or 5, e.g., 1 or 2 amino acids, e.g., conservative amino acids, therefrom); and a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom).

In an embodiment, the binding agent, e.g., an antibody molecule, comprises one or both of: a) LC CDR1-3, that collectively, differ from the AB 031 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the AB 031 HC CDR1-3 by no more than, 1, 2, 3, 4, 5, 6, 7, 8, 9, or 10, e.g., 1, 2, 3, or 4, amino acids, e.g., conservative amino acids. In an embodiment, the binding agent, e.g., an antibody molecule, comprises one or both of: (a) a heavy chain immunoglobulin variable region segment comprising a CDR1 comprising the sequence S-Y-A-M-H (SEQ ID NO:68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y- A-D-S-V-Q-G (SEQ ID NO:69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO:70) (or a sequence that differs by no more than, 1, 2, 3, 4, or 5, e.g., 1 or 2 amino acids, e.g., conservative amino acids, therefrom optionally provided that, e.g., R is not changed); and (b) a light chain variable region segment comprising a CDR1 comprising the sequence Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S is not changed). In an embodiment a CDR of the light or heavy chain includes one of the highlighted residues, or one of the highlighted combinations of residues, for that CDR, (i.e., while other residues in that CDR might be changed, the highlighted residue or combination of residues, are not changed).

In an embodiment a CDR of the light and a CDR of the heavy chain each includes one of the highlighted residues, or one of the highlighted combinations of residues, for that CDR. In an embodiment each of two CDRs in the antibody molecule includes one of the highlighted residues, or one of the highlighted combinations of residues, for that CDR. In some embodiments, both are in the light chain. In some embodiments, both are in the heavy chain. In an embodiment each of the three CDRs in the heavy chain includes one of the highlighted residues, or one of the highlighted combinations of residues, for that CDR. In an embodiment each of the three CDRs in the light chain includes one of the highlighted residues, or one of the highlighted combinations of residues, for that CDR. In an embodiment each of the six CDRs in the heavy and light chain includes one of the highlighted residues, or one of the highlighted combinations of residues, for that CDR.

In one embodiment, the binding agent is an antibody molecule that comprises one or more or all of the following properties: (a) both S and A in HC CDR1 are unchanged; (b) V or both N and Q or all three of V, N, and Q in HC CDR2 are unchanged; (c) R in HC CDR3 is unchanged; (d) I in LC CDR1 is unchanged; (e) 1, 2 or 3 of G, Y, and L in LC CDR2 are unchanged; (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In the embodiment, the antibody molecule comprises one or both of: (a) a heavy chain immunoglobulin variable region segment comprising: a CDR1 comprising the sequence S-Y-A-M-H (SEQ ID NO:68); a CDR2 comprising the sequence V-V-S-Y-D-G-N-Y-K-Y-Y-A-D-S-V-Q-G (SEQ ID NO:69); and a CDR3 comprising the sequence D-S-R-L-R-S-L-L-Y-F-E-W-L-S-Q-G-Y-F-N-P (SEQ ID NO:70); and (b) a light chain variable region segment comprising a CDR1 comprising the sequence Q-S-I-T-F-N-Y-K-N-Y-L-A (SEQ ID NO:71); a CDR2 comprising the sequence W-G-S-Y-L-E-S (SEQ ID NO:72); and a CDR3 comprising the sequence Q-Q-H-Y-R-T-P-P-S (SEQ ID NO:73). In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/ 08/1934, or A/California/04/2009, or an H5N1 strain, e.g., A/Indonesia/5/2005 or A/Vietnam/1203/2004, or an influenza B virus, e.g., B/Wisconsin/1/2010); and (ii) it produces fewer escape mutants than does a reference anti-HA antibody molecule, e.g., Ab 67-11, FI6, FI28, C179, F10, CR9114, or CR6261, e.g., when tested by the method described in (i).

In an embodiment, the antibody molecule comprises one or both of: a) one or more framework regions (FRs) from SEQ ID NO: 24, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 24; and b) one or more framework regions (FRs) from SEQ ID NO: 45, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In one embodiment, the antibody molecule comprises: (a) a heavy chain immunoglobulin variable region segment that further comprises one or more or all of: an FR1 comprising the sequence E-V-Q-L-L-E-S-G-G-G-L-V-K-P-G-Q-S-L-K-L-S-C-A-A-S-G-F-T-F-T (SEQ ID NO:82) (or a sequence that differs by no more than, 1, 2, 3, 4, or 5, e.g., 1 or 2 amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2 amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N- S-L-R-A-E-D-T-A-V-Y-Y-C-A-K (SEQ ID NO:76) (or a sequence that differs by no more than, 1, 2, 3, 4, or 5, e.g., 1 or 2 amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2 amino acids, e.g., conservative amino acids, therefrom); and (a) a light chain immunoglobulin variable region segment further comprises one or more or all of: an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom). In an embodiment a FR of the light or heavy chain includes one of the highlighted residues, or one of the highlighted combinations of residues, for that FR, (i.e., while other residues in that FR might be changed, the highlighted residue or combination of residues, are not changed). E.g., in an embodiment, one, two or three of I, R, or L for heavy chain FR3 is not changed. In an embodiment a FR of the light and a FR of the heavy chain each includes one of the highlighted residues, or one of the highlighted combinations of residues, for that FR.

In an embodiment each of two FRs in the antibody molecule includes one of the highlighted residues, or one of the highlighted combinations of residues, for that FR. In some embodiments, both are in the light chain. In some embodiments, both are in the heavy chain. In an embodiment, each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment, all of the highlighted residues in both heavy and light chain FR1-4 are unchanged.

In one embodiment, the antibody molecule comprises: (a) the heavy chain immunoglobulin variable region segment comprises one or more or all of an FR1 comprising the sequence E-V-Q-L-L-E-S-G-G-G-L-V-K-P-G-Q-S-L-K-L-S-C-A-A-S-G-F-T-F-T (SEQ ID NO:82); an FR2 comprising the sequence W-V-R-Q-P-P-G-K-G-L-E-W-V-A (SEQ ID NO:75); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76); and an FR4 comprising the sequence W-G-Q-G-T-T-L-T-V-S-S (SEQ ID NO:77) or W-G-Q-G-T-T-V-T-V-S-S (SEQ ID NO:171); and (b) the light chain immunoglobulin variable region segment comprising one or more or all of an FR1 comprising the sequence D-I-Q-M-T-Q-S-P-S-S-L-S-A-S-V-G-D-R-V-T-I-T-C-R-S-S (SEQ ID NO:78); an FR2 comprising the sequence W-Y-Q-Q-K-P-G-K-A-P-K-L-L-I-Y (SEQ ID NO:79); an FR3 comprising the sequence G-V-P-S-R-F-S-G-S-G-S-G-T-D-F-T-L-T-I-S-S-L-Q-P-E-D-F-A-T-Y-Y-C(SEQ ID NO:80); and an FR4 comprising the sequence F-G-Q-G-T-K-V-E-I-K (SEQ ID NO:81).

In another embodiment, the antibody molecule comprises one or more or all of the following properties: (a) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (b) it produces fewer escape mutants than does a reference anti-HA antibody molecule, e.g., Ab 67-11, FI6, FI28, C179, F10, CR9114, or CR6261, e.g., when tested by the method described in (a); (c) it binds with high affinity to a hemagglutinin (HA) of at least 1, 2, 3, 4 or 5 influenza subtypes of Group 1 and at least 1, 2, 3, 4 or 5 influenza subtypes of Group 2; (d) it treats or prevents infection by at least 1, 2, 3, 4 or 5 influenza subtypes of Group 1, and by at least 1, 2, 3, 4 or 5 influenza subtypes of Group 2; (e) it inhibits fusogenic activity of the targeted HA; (f) it treats or prevents infection by a Group 1 virus, wherein the virus is an H1, H5, or H9 virus; and treats or prevents infection by a Group 2 virus, wherein the virus is an H3 or H7 virus; (g) it treats or prevents infection by influenza A strains H1N1 and H3N2; (h) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg; (i) it treats or prevents infection by influenza A strains H5N1; (j) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg; (k) it binds with high affinity to a hemagglutinin (HA) of an influenza B virus, e.g., B/Wisconsin/1/2010; (l) it treats or prevents infection by an influenza B virus, e.g., B/Wisconsin/1/2010; (m) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg, or 1 mg/kg; (n) the concentration of antibody molecule required for 50% neutralization of influenza A virus is less than 10 µg/mL; (o) the concentration of antibody molecule required for 50% neutralization of influenza B virus, e.g., B/Wisconsin/1/2010, is less than 10 µg/mL; (p) it prevents or minimizes secondary infection (e.g., secondary bacterial infection) or effects thereof on a subject; (q) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg; (r) it binds an epitope which comprises or consists of the hemagglutinin trimer interface; and (s) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In another aspect, the disclosure features an antibody molecule comprising: (a) a heavy chain immunoglobulin variable region segment comprising SEQ ID NO:24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom). In some embodiments, the antibody molecule comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza a virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and (ii) it produces fewer escape mutants than does a reference anti-HA antibody molecule, such as Ab 67-11, FI6, FI28, C179, F10, CR9114, or CR6261, such as when tested by the method described in (i).

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57. In an embodiment, the antibody molecule has properties: a) and b). antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f). In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc; and dd. In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff). In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46; In an embodiment, the antibody molecule has one, two, three or all of the following properties: a) and aa); b) and bb); c) and cc); d) and dd). In an embodiment, the molecule has properties c), cc), d), and dd).

In another aspect, the disclosure features, a binding agent, e.g., an antibody molecule, or preparation, or isolated preparation thereof, comprising a structural or functional property of one or both a heavy chain variable region and a light chain variable region disclosed herein.

In an embodiment, the antibody molecule competes with a reference antibody molecule, e.g., an antibody molecule described herein, for binding to a substrate, e.g., an HA. The reference antibody molecule can be: a) an antibody molecule comprising the heavy and light CDRs from: a heavy chain variable region from Table 3, Table 4A, or Table 4B, or FIG. 2, FIG. 13, or FIG. 17, of International Publication No. WO2013/170139 or U.S. Application Publication No. 2013/0302349; and a light chain variable region from Table 3, Table 4A, or Table 4B, or FIG. 3, FIG. 14, or FIG. 17, of International Publication No. WO2013/170139 or U.S. Application Publication No. 2013/0302349; b) an antibody molecule that comprises: (i) a heavy chain immunoglobulin variable region segment from Table 3, Table 4A, or Table 4B, or FIG. 2, FIG. 13, or FIG. 17, of International Publication No. WO2013/170139 or U.S. Application Publication No. 2013/0302349; and (ii) a light chain variable region segment from Table 3, Table 4A, or Table 4B, or FIG. 3, FIG. 14, or FIG. 17, of International Publication No. WO2013/170139 or U.S. Application Publication No. 2013/0302349; or c) an antibody disclosed herein.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Competition between the antibody molecule and a reference antibody molecule can be determined by evaluating the ability of one of the antibody molecule or the reference antibody molecule to decrease binding of the other to a substrate, e.g., HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more. In an embodiment, the antibody molecule binds to the same epitope, or a portion thereof, which the reference antibody molecule binds. In an embodiment, the antibody molecule does not bind to the same epitope, or a portion thereof, which the reference antibody molecule binds.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising the heavy and light CDRs from: a heavy chain variable region from Table 3, Table 4A, or Table 4B, or FIG. 2, FIG. 13, or FIG. 17, of International Publication No. WO2013/170139 or U.S. Application Publication No. 2013/0302349; and a light chain variable region from Table 3, Table 4A, or Table 4B, or FIG. 3, FIG. 14, or FIG. 17, of International Publication No. WO2013/170139 or U.S. Application Publication No. 2013/0302349; b) an antibody molecule that comprises: (i) a heavy chain immunoglobulin variable region segment from Table 3, Table 4A, or Table 4B, FIG. 2, FIG. 13, or FIG. 17, of International Publication No. WO2013/170139 or U.S. Application Publication No. 2013/0302349; and (ii) a light chain variable region segment from Table 3, Table 4A, or Table 4B, FIG. 3, FIG. 14, or FIG. 17, of International Publication No. WO2013/170139 or U.S. Application Publication No. 2013/0302349; or c) an antibody disclosed herein.

The HA can be HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, e.g. from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and d) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) Biacore analysis; b) ELISA assay; and c) flow cytometry. The antibody molecule can compete with the reference antibody such that binding of the reference antibody is decreased by 50% or more; d) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004; and e) (c) and one or both of (a) and (b).

Competition between the antibody molecule and a reference antibody molecule can be determined by evaluating the ability of one of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art.

In an embodiment, the binding agent, e.g., an antibody molecule, comprises one or both of: a heavy chain variable region comprising least 60, 70, 80, 85, 90, 95, 98 or 99 percent homology with a reference heavy chain from Table 3, Table 4A, or Table 4B, or FIG. 2, FIG. 13 or FIG. 17, of International Publication No. WO2013/170139 or U.S. Application Publication No. 2013/0302349; and a light chain variable region comprising least 60, 70, 80, 85, 90, 95, 98 or 99 percent homology with reference light chain from Table 3, Table 4A, or Table 4B, or FIG. 3, FIG. 14 or FIG. 17, of International Publication No. WO2013/170139 or U.S. Application Publication No. 2013/0302349, wherein, optionally, each HC CDR differs by no more than 1, 2, 3, 4 or 5 amino acids, e.g., 1 or 2, e.g., conservative amino acids, from the corresponding HC CDR from its reference heavy chain and each LC CDR differs by no more than 1, 2, 3, 4 or 5 amino acids, e.g., 1 or 2, e.g., conservative amino acids, from the corresponding CDR in its reference light chain. In an embodiment, the binding agent, e.g., an antibody molecule, comprises: a heavy chain variable region comprising least 60, 70, 80, 85, 90, 95, 98 or 99 percent homology with a heavy chain from Table 3 and a light chain variable region comprising least 60, 70, 80, 85, 90, 95, 98 or 99 percent homology with the corresponding light chain from Table 3. In an embodiment, the binding agent, e.g., an antibody molecule, comprises: a heavy chain variable region comprising least 60, 70, 80, 85, 90, 95, 98 or 99 percent homology with a heavy chain from Table 4A and a light chain variable region comprising least 60, 70, 80, 85, 90, 95, 98 or 99 percent homology with the corresponding light chain from Table 4A. In an embodiment, the binding agent, e.g., an antibody molecule, comprises: a heavy chain variable region comprising least 60, 70, 80, 85, 90, 95, 98 or 99 percent homology with a heavy chain from Table 4B and a light chain variable region comprising least 60, 70, 80, 85, 90, 95, 98 or 99 percent homology with the corresponding light chain from Table 4B.

In an embodiment, the binding agent, e.g., an antibody molecule, comprises one or both of: a heavy chain variable region from Table 3, Table 4A, or Table 4B, or FIG. 2, FIG. 13, or FIG. 17, of International Publication No. WO2013/170139 or U.S. Application Publication No. 2013/0302349; and a light chain variable region from Table 3, Table 4A, or Table 4B, or FIG. 3, FIG. 14, or FIG. 17, of International Publication No. WO2013/170139 or U.S. Application Publication No. 2013/0302349. In an embodiment, the binding agent, e.g., an antibody molecule, comprises: a heavy chain variable region from Table 3 and the corresponding light chain from Table 3; a heavy chain from Table 4A and the corresponding light chain from Table 4A; or a heavy chain from Table 4B and the corresponding light chain from Table 4B.

In an embodiment, the binding agent, e.g., an antibody molecule, comprises one or both of: (a) a heavy chain immunoglobulin variable region segment comprising a CDR1, a CDR2 and a CDR3 from a heavy chain sequence of Table 3, Table 4A, or Table 4B, or FIG. 2, FIG. 13, or FIG. 17, of International Publication No. WO2013/170139 or U.S. Application Publication No. 2013/0302349 (or CDRs that, individually or collectively, differ therefrom by no more than, 1, 2, 3, 4, or 5, e.g., 1 or 2 amino acids, e.g., conservative amino acids)); and (b) a light chain immunoglobulin variable region segment comprising a CDR1, a CDR2 and a CDR3 from a light chain sequence of Table 3, Table 4A, or Table 4B, or FIG. 3, FIG. 14, or FIG. 17, of International Publication No. WO2013/170139 or U.S. Application Publication No. 2013/0302349 (or CDRs that, individually or collectively, differ therefrom by no more than, 1, 2, 3, 4, or 5, e.g., 1 or 2 amino acids, e.g., conservative amino acids). In an embodiment, the binding agent, e.g., an antibody molecule, comprises one or both of: CDRs from a heavy chain of Table 3 and the light chain CDRs from the corresponding light chain from Table 3. In an embodiment, the binding agent, e.g., an antibody molecule, comprises one or both of: CDRs from a heavy chain of Table 4A and the light chain CDRs from the corresponding light chain from Table 4A. In an embodiment, the binding agent, e.g., an antibody molecule, comprises one or both of: CDRs from a heavy chain of Table 4B and the light chain CDRs from the corresponding light chain from Table 4B.

In some embodiments, the binding agent, e.g., an antibody molecule, comprises one or more or all of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); (ii) it produces fewer escape mutants than does a reference anti-HA antibody molecule, e.g., Ab 67-11, FI6, FI28, C179, F10, CR9114, or CR6261, e.g., when tested by the method described in (i); and (iii) it is other than Ab 67-11 and FI6.

In one embodiment, the antibody molecule comprises one or both of: (a) a heavy chain immunoglobulin variable region segment comprising a CDR1, a CDR2; and a CDR3 from a heavy chain sequence of FIG. 2, FIG. 13, or FIG. 17, of International Publication No. WO2013/170139 or U.S. Application Publication No. 2013/0302349; and (b) a light chain immunoglobulin variable region segment comprising a CDR1, a CDR2 and a CDR3 from a light chain sequence of FIG. 3, FIG. 14, or FIG. 17, of International Publication No. WO2013/170139 or U.S. Application Publication No. 2013/0302349. In one embodiment, the antibody molecule comprises: (a) a heavy chain immunoglobulin variable region segment from FIG. 2 or FIG. 17; and (b) a light chain immunoglobulin variable region segment from FIG. 3 or FIG. 17.

In one embodiment, the heavy chain immunoglobulin variable region further comprises an Isoleucine-Aspartate (Ile-Asp) dipeptide at the N-terminus. In another embodiment, the light chain immunoglobulin variable region further comprises an Ile-Asp dipeptide at the N-terminus. In yet another embodiment, both the heavy chain immunoglobulin variable region and the light chain immunoglobulin variable region or an antibody featured in the disclosure further comprises an Ile-Asp dipeptide at the N-terminus. In other embodiment the Ile-Asp dipeptide is absent from one or both the heavy and light chain.

In one embodiment, the binding agent, e.g., an antibody molecule, further comprises one or more or all of the following: (a) it treats or prevents infection by at least 1, 2, 3, 4 or 5 influenza subtypes of Group 1, and by at least 1, 2, 3, 4 or 5 influenza subtypes of Group 2; (b) it inhibits fusogenic activity of the targeted HA; (c) it treats or prevents infection by a Group 1 virus, wherein the virus is an H1, H5, or H9 virus; and treats or prevents infection by a Group 2 virus, wherein the virus is an H3 or H7 virus; (d) it treats or prevents infection by influenza A strains H1N1 and H3N2; (e) it is effective for prevention or treatment of infection, e.g., in humans or mice, with H1N1 and H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg; (f) it treats or prevents infection by influenza A strains H5N1; (g) it is effective for prevention or treatment of infection, e.g., in humans or mice, with H5N1 when administered at 50 mg/kg, 25 mg/kg, 10 mg/kg, 6 mg/kg, 5 mg/kg, 4 mg/kg, 3 mg/kg, 2 mg/kg, or 1 mg/kg; (h) it binds with high affinity to a hemagglutinin (HA) of an influenza B virus, e.g., B/Wisconsin/1/2010; (i) it treats or prevents infection by an influenza B virus, e.g., B/Wisconsin/1/2010; (j) it is effective for prevention or treatment of infection, e.g., in humans or mice, with an influenza B virus, e.g., B/Wisconsin/1/2010 when administered at 50 mg/kg, 25 mg/kg, 10 mg/kg, 6 mg/kg, 5 mg/kg, 4 mg/kg, 3 mg/kg, 2 mg/kg, or 1 mg/kg; (k) the concentration of antibody molecule required for 50% neutralization of influenza A virus is less than 10 μg/mL; (l) the concentration of antibody molecule required for 50% neutralization of influenza B virus, e.g., B/Wisconsin/1/2010, is less than 10 μg/mL; (m) it prevents or minimizes secondary infection (e.g., secondary bacterial infection) or effects thereof on a subject; (n) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg; (o) it binds an epitope which comprises or consists of the hemagglutinin trimer interface; and (p) it binds an epitope other than that bound by a reference anti-HA antibody molecule, e.g., Ab 67-11, FI6, FI28, C179, F10, CR9114, or CR6261, e.g., when tested by a method disclosed herein, e.g., by competition in an ELISA assay.

In an embodiment, the antibody molecule comprises one or both of: a) one or more framework regions (FRs) from heavy chain disclosed herein, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain disclosed herein; and b) one or more framework regions (FRs) from light chain disclosed herein, e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain disclosed herein.

In an embodiment, the binding agent, e.g., an antibody molecule, specifically binds the HA antigen. In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57. In an embodiment, the antibody molecule has properties: a) and b). In an embodiment, the antibody molecule has properties: c) and d). In an embodiment, the antibody molecule has properties: a); and c) or d). In an embodiment, the antibody molecule has properties: b); and c) or d). In an embodiment, the antibody molecule has properties: c); and a) or b). In an embodiment, the antibody molecule has properties: d); and a) or b). In an embodiment, the antibody molecule has properties: a), b), c) and d). In an embodiment, the antibody molecule has properties: a), b), c), d), e), and f). In an embodiment, the antibody molecule has a $K_D$ for H3 of equal to or less than $10^{-6}$, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$, wherein said $K_D$ is increased by no more than 2, or 5 fold, by a mutation or mutations in any of: c) H3 HA1 residues Q327, T328, or R329; or d) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and I324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff). In an embodiment, the antibody molecule has a $K_D$ for H1 of equal to or less than $10^{-6}$, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and I324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$, wherein said $K_D$ is increased by no more than 2, or 5 fold, by a mutation or mutations in any of: cc) H1 HA1 residues Q328 and S329; or dd) H1 HA2 residues G1, L2, F3, G4, and D46; In an embodiment, the antibody molecule has one, two, three or all of the following properties: a) and aa); b) and bb); c) and cc); d) and dd). In an embodiment, the molecule has properties c), cc), d), and dd).

In one aspect, the disclosure features an anti-hemagglutinin (anti-HA) binding agent, e.g., antibody molecule, or preparation, or isolated preparation thereof, comprising: (a) a heavy chain immunoglobulin variable region segment comprising one or more or all of a CDR1 comprising the sequence G-F-T-F-[S/T]-[S/T]-Y-[A/G]-M-H (SEQ ID NO:1), or a sequence that differs from SEQ ID NO:1 by no more than 1 or 2 residues; a CDR2 comprising the sequence V-[I/V/L]-S-[Y/F]-D-G-[S/N]-[Y/N]-[K/R]-Y-Y-A-D-S-V-Q-G (SEQ ID NO:2) or a sequence that differs from SEQ ID NO:2 by no more than 1 or 2 residues; and a CDR3 comprising the sequence D-[S/T]-[R/K/Q]-L-R-[S/T]-L-L-Y-F-E-W-L-S-[Q/S]-G-[Y/L/V]-[F/L]-[N/D]-[P/Y] (SEQ ID NO:3), or a sequence that differs from SEQ ID NO:3 by no more than 1 or 2 residues; and (b) a light chain variable region segment comprising one or more or all of a CDR1 comprising the sequence [K/R]-S-S-Q-[S/T]-[V/L/I]-[T/S]-[Y/F/W]-[N/S/D]-Y-K-N-Y-L-A (SEQ ID NO:4) or a sequence that differs from SEQ ID NO:4 by no more than 1 or 2 residues, or comprising the sequence [K/R]-S-S-Q-[S/T]-[V/L/I]-[T/S]-[Y/F/W]-[N/S/D/Q/R/E]-Y-K-N-Y-L-A (SEQ ID NO:170) or a sequence that differs from SEQ ID NO:170 by no more than 1 or 2 residues or [K/R]-S-S-Q-[S/T]-[V/L/I]-[T/S]-[Y/F/W]-[N/S/D/E]-Y-K-N-Y-L-A (SEQ ID NO:4) or a sequence that differs from SEQ ID NO:170 by no more than 1 or 2 residues; a CDR2 comprising the sequence W-[A/G]-S-[T/A/Y/H/K/D]-[R/L]-E-[S/T] (SEQ ID NO:5) or a sequence that differs from SEQ ID NO:5 by no more than 1 or 2 residues; a CDR3 comprising the sequence Q-Q-[Y/H]-Y-R-T-P-P-[T/S] (SEQ ID NO:6) or a sequence that differs from SEQ ID NO:6 by no more than 1 or 2 residues;

optionally, provided that, if the light chain variable region segment comprises: a CDR 1 comprising the sequence K-S-S-Q-S-V-T-Y-N-Y-K-N-Y-L-A (SEQ ID NO:83); a CDR2 comprising the sequence W-A-S-T-R-E-S (SEQ ID NO:84); and a CDR3 comprising the sequence Q-Q-Y-Y-R-T-P-P-T (SEQ ID NO:85); then the heavy chain variable region segment comprises one or more of the following: (a) CDRs other than the following: a CDR1 comprising the sequence S-Y-G-M-H (SEQ ID NO:86); a CDR2 comprising the sequence V-I-S-Y-D-G-S-Y-K-Y-Y-A-D-S-V-Q-G (SEQ ID NO:87); or a CDR3 comprising the sequence D-S-E-L-R-S-L-L-Y-F-E-W-L-S-Q-G-Y-F-N-P (SEQ ID NO:88); or (b) FRs other than the following: an FR1 other than E-V-Q-L-L-E-S-G-G-G-L-V-K-P-G-Q-S-L-K-L-S-C-A-A-S-G-F-T-F-T (SEQ ID NO:82); an FR2 other than W-V-R-Q-P-P-G-K-G-L-E-W-V-A (SEQ ID NO:75); an FR3 other than R-F-T-I-S-R-D-N-S-K-N-T-L-Y-L-Q-M-N-S-L-R-A-E-D-T-A-V-Y-Y-C-A-K (SEQ ID NO:76); or an FR4 other than W-G-A-G-T-T-L-T-V-S-S (SEQ ID NO:89); (c) a CDR1 where the amino residue at position 5 of SEQ ID NO:1 is an S, the amino acid residue at position 6 of SEQ ID NO:1 is a T, or the amino acid residue at position 8 of SEQ ID NO:1 is an A; (d) a CDR2 wherein the amino residue at position 2 of SEQ ID NO:2 is a V or an L, the amino acid at position 4 is an F, the amino acid at position 7 is an N, the amino acid at position 8 is a Y, or the amino acid at position 9 is a R; (e) a CDR3 wherein the amino residue at position 2 of SEQ ID NO:3 is a T, the amino acid residue at position 3 of SEQ ID NO:3 is an R, a K, or a Q, the amino acid residue at position 6 of SEQ ID NO:3 is a T, the amino acid residue at position 15 of SEQ ID NO:3 is an S, the amino acid residue at position 17 of SEQ ID NO:3 is an L, or a V, the amino acid residue at position 18 of SEQ ID NO:3 is an L, the amino acid residue at position 19 of SEQ ID NO:3 is a D, or the amino acid residue at position 20 of SEQ ID NO:3 is a Y; (f) an FR1 wherein the amino residue at position 11 of SEQ ID NO:7 is a Q, or the amino acid residue at position 7 of SEQ ID NO:7 is a T; (g) an FR4 wherein the amino residue at position 3 of SEQ ID NO:10 is a Q, the amino acid residue at position 5 of SEQ ID NO:10 is an A; the amino acid residue at position 6 of SEQ ID NO:10 is an M, or the amino acid residue at position 7 of SEQ ID NO:10 is a V; or (h) it produces fewer escape mutants than does a reference anti-HA antibody molecule, e.g., Ab 67-11, FI6, FI28, C179, F10, CR9114, or CR6261, e.g., when tested by a method disclosed herein, and also provided that, if the heavy chain immunoglobulin variable region segment comprises: a CDR1 comprising the sequence S-Y-G-M-H (SEQ ID NO:86); a CDR2 comprising the sequence V-I-S-Y-D-G-

S—Y-K-Y-Y-A-D-S-V-Q-G (SEQ ID NO:87); and a CDR3 comprising the sequence D-S-E-L-R-S-L-L-Y-F-E-W-L-S-Q-G-Y-F-N-P (SEQ ID NO:88), then the light chain variable region segment comprises one of more of the following: (a) CDRs other than the following: CDR1 KSSQSVTYNYK-NYLA (SEQ ID NO:83); CDR2 WASTRES (SEQ ID NO:84); or CDR3 QQYYRTPPT (SEQ ID NO:85); (b) FRs other than the following: FR1 comprising the sequence EIVMTQSPDSLAVSLGERATINC (SEQ ID NO:90); FR2 comprising the sequence WYQQKPGQPPKLLIY (SEQ ID NO:91); FR3 comprising the sequence GVPDRFSGSGS-GTDFTLTISSLQAEDVAVYYC (SEQ ID NO:92); or FR4 comprising the sequence FGGGTKLDIK (SEQ ID NO:93); (c) a CDR1 wherein the amino residue at position 1 of SEQ ID NO:4 is an R, the amino residue at position 5 of SEQ ID NO:4 is a T, the amino residue at position 6 of SEQ ID NO:4 is an L or an I, the amino residue at position 7 of SEQ ID NO:4 is an S, the amino residue at position 8 of SEQ ID NO:4 is an F or a W, or the amino residue at position 9 of SEQ ID NO:4 is an S or a D; (d) a CDR2 wherein the amino residue at position 2 of SEQ ID NO:5 is a G, the amino residue at position 4 of SEQ ID NO:5 is an A, a Y, an H, a K, or a D, the amino residue at position 5 of SEQ ID NO:5 is an L, the amino residue at position 7 of SEQ ID NO:5 is a T; (e) a CDR3 wherein the amino residue at position 3 of SEQ ID NO:6 is an H; the amino acid residue at position 9 of SEQ ID NO:6 is an S; (f) an FR1 wherein the amino residue at position 1 of SEQ ID NO:11 is a D; the amino residue at position 3 of SEQ ID NO:11 is a Q, the amino residue at position 9 of SEQ ID NO:11 is an S, the amino residue at position 10 of SEQ ID NO:11 is a T, the amino residue at position 11 of SEQ ID NO:11 is a V, the amino residue at position 12 of SEQ ID NO:11 is an S, the amino residue at position 13 of SEQ ID NO:11 is an A, the amino residue at position 14 of SEQ ID NO:11 is a T, the amino residue at position 15 of SEQ ID NO:11 is a V or an R, the amino residue at position 17 of SEQ ID NO:11 is a D, the amino residue at position 20 of SEQ ID NO:11 is an S, the amino residue at position 22 of SEQ ID NO:11 is a T, a Q, a D, or an R; (g) an FR2 wherein the amino residue at position 8 of SEQ ID NO:12 is a K; or the amino residue at position 9 of SEQ ID NO: 12 is an A; (h) an FR3 wherein the amino residue at position 4 of SEQ ID NO: 13 is an E or an S; the amino residue at position 24 of SEQ ID NO: 13 is a P, the amino residue at position 27 of SEQ ID NO: 13 is an F, a K, or a D, the amino residue at position 29 of SEQ ID NO: 13 is a T; (i) an FR4 wherein the amino residue at position 3 of SEQ ID NO:14 is a Q, a T, an S, or an N, the amino residue at position 7 of SEQ ID NO:14 is a V, or the amino residue at position 8 of SEQ ID NO:14 is an E; or (j) it produces fewer escape mutants than does a reference anti-HA antibody molecule, e.g., Ab 67-11, FI6, FI28, C179, F10, CR9114, or CR6261, e.g., when tested by a method disclosed herein; and further provided that if the light chain variable region segment comprises: a CDR 1 comprising the sequence K-S-S-Q-S-V-T-F-N-Y-K-N-Y-L-A (SEQ ID NO:146); a CDR2 comprising the sequence W-A-S-A-R-E-S (SEQ ID NO:147); and a CDR3 comprising the sequence Q-Q-H-Y-R-T-P-P-T (SEQ ID NO:148); then the heavy chain variable region segment comprises one or more of the following: CDRs other than the CDR's described at FIG. 12 of International Publication No. WO2013/170139 or U.S. Application Publication No. 2013/0302349; or FRs other than the FRs described at FIG. 12 of International Publication No. WO2013/170139 or U.S. Application Publication No. 2013/0302349.

In one embodiment, the heavy chain CDR sequences, collectively, differ from the recited sequences by no more than 5, 4, 3, 2 or 1 amino acid residues; and the light chain CDR sequences, collectively, differ from the recited sequences by no more than 5, 4, 3, 2 or 1 amino acid residues.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments featured in the disclosure are set forth in the accompanying drawings and the description below. Other features, objects, and advantages featured in the disclosure will be apparent from the description and drawings, and from the claims.

BRIEF DESCRIPTION OF THE DRAWINGS

FIG. 18 depicts the tolerance of VIS410 to existing sequence variation in its epitope.

FIG. 19 depicts the evolutionary trajectory of VIS410 epitope.

Figure 1A:
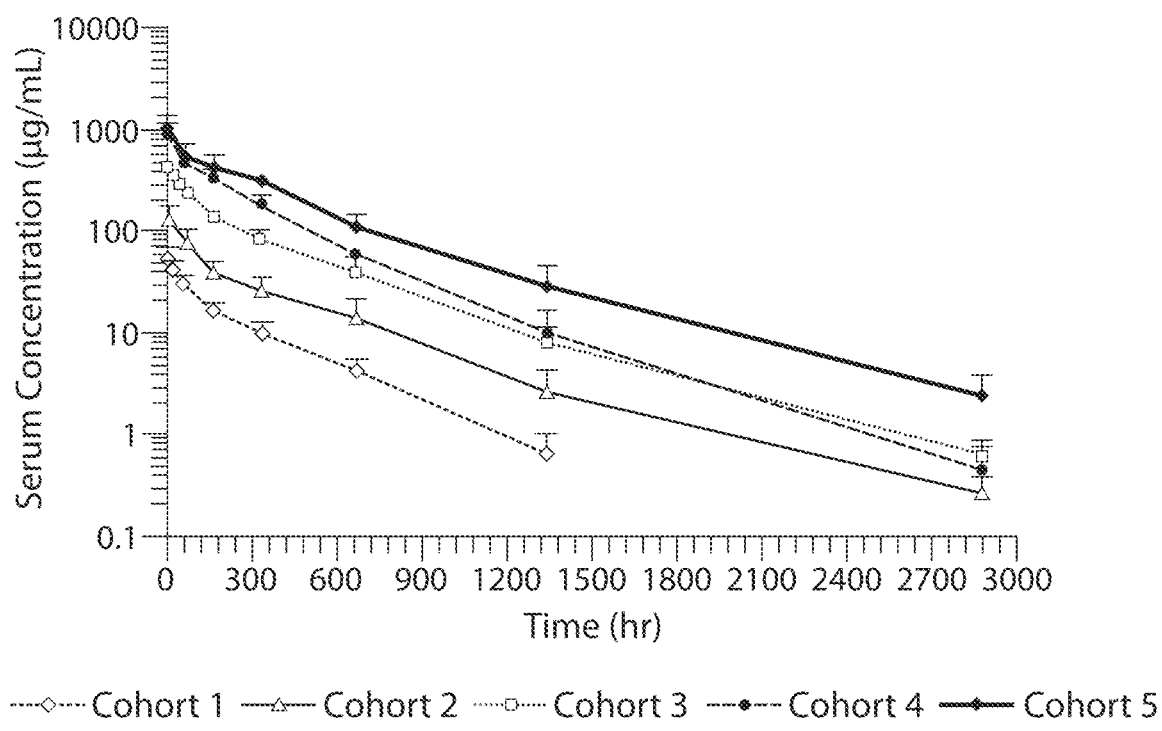
FIGS. 1A-1B depict the pharmacokinetic profiles of VIS410 in serum (FIG. 1A) and nasopharyngeal (FIG. 1B) samples. Mean concentrations along with the corresponding standard deviation at each time point were plotted on a logarithmic scale for each dose level. Cohort dose levels are as follows Cohort 1: 2 mg/kg; Cohort 2: 5 mg/kg; Cohort 3: 15 mg/kg; Cohort 4: 30 mg/kg; Cohort 5: 50 mg/kg.

Additional figures include FIGS. 1-27 of International Publication No. WO2013/170139 and U.S. Application Publication No. 2013/0302349, the contents of which are incorporated by reference in their entirety.

DETAILED DESCRIPTION

The disclosure is based, at least in part, on the design and synthesis of antibody molecules that can bind an epitope that is conserved across multiple hemagglutinin subtypes of influenza viruses (e.g., influenza A and influenza B viruses). For example, the antibody molecules described herein are useful as broad spectrum therapy against disease caused by at least one influenza A strain belonging to Group 1 and one influenza A strain belonging to Group 2 to neutralize infectivity of viruses belonging to both Group 1 and Group 2 (at least one subtype of each).

The antibody molecules were designed by a rational structure-based approach to target a region on the virus that is not fully accessible to the human immune system and, therefore, not amenable to antibody selection through more classical screening approaches. This rational-based approach to the design and development of broad-spectrum antibody molecules allows for the development of more efficacious vaccines for pandemic and seasonal influenza. This approach also allows for the advance preparation of pandemic vaccines so that they are ready to be employed against specific virus subtypes (e.g., avian virus subtypes) that may mutate to become human-adapted and highly transmissible. Vaccines (e.g., seasonal vaccines) that utilize the antibody molecules described herein can generate a more potent immune response without the use of adjuvants and provide broad protection against viral strain variation.

The antibody molecules described herein can be used, e.g., in methods of protecting a population of subjects from influenza. For example, the protection can include decreasing, in the population, the number of hospital admissions, e.g. of influenza infected individuals; the number incidents of influenza infection; the attack rate; or the number of deaths, e.g. of influenza infected individuals. In certain embodiments, the antibody molecules described herein can be used effectively and safely as either a single-dose therapeutic or prophylactic for influenza. Without wishing to be bound by theory, it is believed that in an embodiment, including the antibody molecules described herein in prophylaxis among the public health interventions for influenza (e.g., seasonal influenza) can result in beneficial effects, for example, lowering attack rates and reducing hospitalizations in high risk individuals.

Definitions

As used herein, the term "antibody molecule" refers to a polypeptide that comprises sufficient sequence from an immunoglobulin heavy chain variable region and/or sufficient sequence from an immunoglobulin light chain variable region, to provide antigen specific binding. It comprises full length antibodies as well as fragments thereof, e.g., Fab fragments, that support antigen binding. Typically an antibody molecule will comprise heavy chain CDR1, CDR2, and CDR3 and light chain CDR1, CDR2, and CDR3 sequence. Antibody molecules include human, humanized, CDR-grafted antibodies and antigen binding fragments thereof. In some embodiments, an antibody molecule comprises a protein that comprises at least one immunoglobulin variable region segment, e.g., an amino acid sequence that provides an immunoglobulin variable domain or immunoglobulin variable domain sequence.

The VH or VL chain of the antibody molecule can further include all or part of a heavy or light chain constant region, to thereby form a heavy or light immunoglobulin chain, respectively. In one embodiment, the antibody molecule is a tetramer of two heavy immunoglobulin chains and two light immunoglobulin chains.

An antibody molecule can comprise one or both of a heavy (or light) chain immunoglobulin variable region segment. As used herein, the term "heavy (or light) chain immunoglobulin variable region segment," refers to an entire heavy (or light) chain immunoglobulin variable region, or a fragment thereof, that is capable of binding antigen. The ability of a heavy or light chain segment to bind antigen is measured with the segment paired with a light or heavy chain, respectively. In some embodiment, a heavy or light chain segment that is less than a full length variable region will, when paired with the appropriate chain, bind with an affinity that is at least 20, 30, 40, 50, 60, 70, 80, 90, or 95% of what is seen when the full length chain is paired with a light chain or heavy chain, respectively.

An immunoglobulin variable region segment may differ from a reference or consensus sequence. As used herein, to "differ," means that a residue in the reference sequence or consensus sequence is replaced with either a different residue or an absent or inserted residue.

An antibody molecule can comprise a heavy (H) chain variable region (abbreviated herein as VH), and a light (L) chain variable region (abbreviated herein as VL). In another example, an antibody comprises two heavy (H) chain variable regions and two light (L) chain variable regions or antibody binding fragments thereof. The light chains of the immunoglobulin may be of type kappa or lambda. In one embodiment, the antibody molecule is glycosylated. An antibody molecule can be functional for antibody dependent cytotoxicity and/or complement-mediated cytotoxicity, or may be non-functional for one or both of these activities. An antibody molecule can be an intact antibody or an antigen-binding fragment thereof.

Antibody molecules include "antigen-binding fragments" of a full length antibody, e.g., one or more fragments of a full-length antibody that retain the ability to specifically bind to an HA target of interest. Examples of binding fragments encompassed within the term "antigen-binding fragment" of a full length antibody include (i) a Fab fragment, a monovalent fragment consisting of the VL, VH, CL and CH1 domains; (ii) a F(ab') or F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883. Antibody molecules include diabodies.

As used herein, an antibody refers to a polypeptide, e.g., a tetrameric or single chain polypeptide, comprising the structural and functional characteristics, particularly the antigen binding characteristics, of an immunoglobulin. Typically, a human antibody comprises two identical light chains and two identical heavy chains. Each chain comprises a variable region.

The variable heavy (VH) and variable light (VL) regions can be further subdivided into regions of hypervariability, termed "complementarity determining regions" ("CDR"), interspersed with regions that are more conserved, termed "framework regions" (FR). Human antibodies have three VH CDRs and three VL CDRs, separated by framework regions FR1-FR4. The extent of the FRs and CDRs has been precisely defined (see, Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

The heavy and light immunoglobulin chains can be connected by disulfide bonds. The heavy chain constant region typically comprises three constant domains, CH1, CH2 and CH3. The light chain constant region typically comprises a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "immunoglobulin" comprises various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\varepsilon$) with some subclasses among them (e.g., $\gamma 1$-$\gamma 4$). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure. Light chains are classified as either kappa or lambda ($\kappa$, $\lambda$). Each heavy chain class may be bound with either a kappa or lambda light chain.

Suitable antibodies include, but are not limited to, monoclonal, monospecific, polyclonal, polyspecific, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments.

In some embodiments, an antibody is a humanized antibody. A humanized antibody refers to an immunoglobulin comprising a human framework region and one or more CDR's from a non-human, e.g., mouse or rat, immunoglobulin. The immunoglobulin providing the CDR's is often referred to as the "donor" and the human immunoglobulin providing the framework often called the "acceptor," though in some embodiments, no source or no process limitation is implied. Typically a humanized antibody comprises a humanized light chain and a humanized heavy chain immunoglobulin.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay (1988) *Ann. Rev. Immunol.* 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that comprises an immunoglobulin variable domain sequence can associate with another immunoglobulin variable domain sequence to form a target binding structure (or "antigen binding site"), e.g., a structure that interacts with the target antigen.

As used herein, the term antibodies comprises intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibodies for use herein may be of any type (e.g., IgA, IgD, IgE, IgG, or IgM).

The antibody or antibody molecule can be derived from a mammal, e.g., a rodent, e.g., a mouse or rat, horse, pig, or goat. In embodiments, an antibody or antibody molecule is produced using a recombinant cell. In some embodiments an antibody or antibody molecule is a chimeric antibody, for example, from mouse, rat, horse, pig, or other species, bearing human constant and/or variable regions domains.

A binding agent, as used herein, is an agent that bind, e.g., specifically binds, a target antigen, e.g., HA. Binding agents of the invention share sufficient structural relationship with anti-HA antibody molecules disclosed herein to support specific binding to HA, and in some embodiments, other functional properties of an anti-HA antibody molecule disclosed herein. In some embodiments, a binding agent will exhibit a binding affinity of at least 10, 20, 30, 40, 50, 60, 70, 80, or 90% of an antibody molecule disclosed herein, e.g., an antibody molecule with which it shares, significant structural homology, e.g., CDR sequences. Binding agents can be naturally occurring, e.g., as are some antibodies, or synthetic. In an embodiment a binding agents is a polypeptide, e.g., an antibody molecule, e.g., an antibody. While some binding agents are antibody molecules, other molecules, e.g., other polypeptides, can also function as binding agents. Polypeptide binding agents can be monomeric or multimeric, e.g., dimeric, trimeric, or tetrameric and can be stabilized by intra- or interchain bonds, e.g., disulfide bonds. They can contain natural or non-naturally occurring amino acid residues. In some embodiments, binding agents are antibody molecules, or other polypeptides, that present one or more CDRs of antibody molecules disclosed herein or that otherwise mimic the structure of an antibody molecule disclosed herein. Binding agents can also comprise aptamers, nucleic acids or other molecular entities. A binding agent can be developed in a variety of ways, e.g., by immunization, by rational design, screening of random structures, or a combination of those or other approaches. Typically a binding agent will act by making contact with substantially the same epitope as an antibody molecule disclosed herein, e.g., an antibody molecule with which it shares, significant structural homology, e.g., CDR sequences. A binding agent can interact with amino acids, saccharides, or combinations thereof. Polypeptides other than antibodies can be used as a scaffold to present sequence, e.g., one or more, or a complete set of heavy chain and/or light chain CDRs, disclosed herein. Exemplary scaffolds include adnectin, zinc finger DNA-binding proteins. protein A, lipoclins, ankryin consensus repeat domain, thioredoxin, anticalins, centyrin, avimer domains, ubiquitin, peptidomimetics, stapled peptides, cystine-knot miniproteins, and IgNARs. In some embodiments, a binding agent is or comprises a nucleic acid, e.g., DNA, RNA or mixtures thereof. In some embodiments, a binding agent, e.g., a nucleic acid, shows secondary, tertiary, or quaternary structure. In some embodiments a binding agent, e.g., a nucleic acid, forms a structure that mimics the structure of an antibody molecule disclosed herein.

A broad spectrum binding agent, e.g., antibody molecule, as used herein, binds, a plurality of different HA molecules, and optionally neutralizes viruses comprising the different HA molecules. In an embodiment, it binds a first HA and binds a second HA from influenza A Group 1, and optionally neutralizes viruses comprising the first or second HA molecules. In an embodiment, it binds a first HA from an influenza A Group 1 virus, and binds a second HA from an influenza A Group 2 virus, and optionally neutralizes viruses comprising the different HA molecules. In an embodiment, it binds a first HA from an influenza A Group 1 or 2 virus and binds a HA from an influenza B virus, and optionally neutralizes viruses comprising the different HA molecules. In an embodiment, it binds, and in embodiments neutralizes, at least two different clades or clusters of virus, e.g., from different Groups. In some embodiments, it binds, and in some embodiments neutralizes, all or substantially all strains of Group 1 an/or Group 2 disclosed herein. In an embodiment, a binding agent, e.g., antibody molecule, binds, and in some embodiments, neutralizes: at least one strain from the Group 1 H1, e.g., H1a or H1b, cluster and at least one strain from the Group 2 H3 or H7 cluster. In an embodiment, a binding agent, e.g., antibody molecule, binds, and in some embodiments, neutralizes: at least one strain from the Group 1 H1, e.g., H1a or H1b, cluster and at least one influenza B strain. In an embodiment, a binding agent, e.g., antibody molecule, binds, and in some embodiments, neutralizes: at least one strain from the Group 2 H3 or H7 cluster and at least one influenza B strain. In an embodiment, a binding agent, e.g., antibody molecule, binds, and in some embodiments, neutralizes: at least one strain from the Group 1 H1, e.g., H1a or H1b, cluster, at least one strain from the Group 2 H3 or H7 cluster, and at least one influenza B strain. In some embodiments, binding agent, e.g., antibody molecule, binds, and optionally neutralizes or mediate infection of particular hosts, e.g., avian, camel, canine, cat, civet, equine, human, mouse, swine, tiger, or other mammal or bird.

The term "combination therapy", as used herein, refers to administration of a plurality of agents, e.g., wherein at least one binding agent, e.g., antibody molecule, disclosed herein is administered to a subject, e.g., a human subject. The introduction of the agents into the subject can be at different times. In some embodiments, the agents are administered in overlapping regimens, or such that the subject is simultaneously exposed to both agents, or such that the response of the subject is better than would be seen with either agent administered alone.

As used herein, an "escape mutant" is a mutated influenza strain that is resistant to neutralization by an anti-HA antibody molecule described herein. In some embodiments, an escape mutant is resistant to neutralization with a binding agent, e.g., antibody molecule, but its parent strain is neutralized by the binding agent, e.g., antibody molecule. Resistance can be tested by various methods, including, but not limited to, genotypic testing (e.g., Sanger sequencing/nested PCR-baseline and last qPCR sample (Ct<32)), and phenotypic testing (e.g., plaque reduction on primary sample, e.g., ViroSpot™ assay (e.g., virus titration–last post-baseline≥2 $Log_{10}$ $TCID_{50}$/mL) or IC50 single passage sample (e.g., antibody titration–last post-baseline≥1 $Log_{10}$ $TCID_{50}$/mL).

As used herein, "pandemic influenza" refers to a new viral strain that arises due to human adaptation of an influenza strain by mutation or by emergence of a strain by reassortment of different strains of influenza A. The resulting pandemic strain is significantly different from previous strains and most people will have little or no pre-existing immunity Symptoms and complications may be more severe and more frequent than those typical of seasonal influenza. Examples of past pandemic flu viruses include, e.g., the 2009 H1N1 'swine flu,' the 1957-58 H2N2 'Asian flu' and the 1968 H3N2 influenza strains.

The terms "purified" and "isolated" as used herein in the context of an antibody molecule, e.g., an antibody, or generally a polypeptide, obtained from a natural source, refers to a molecule which is substantially free of contaminating materials from the natural source, e.g., cellular materials from the natural source, e.g., cell debris, membranes, organelles, the bulk of the nucleic acids, or proteins, present in cells. Thus, a polypeptide, e.g., an antibody molecule, that is isolated includes preparations of a polypeptide having less than about 30%, 20%, 10%, 5%, 2%, or 1% (by dry weight) of cellular materials and/or contaminating materials. The terms "purified" and "isolated" when used in the context of a chemically synthesized species, e.g., an antibody molecule, refers to the species which is substantially free of chemical precursors or other chemicals which are involved in the syntheses of the molecule.

A preparation of binding agents, e.g., antibody molecules, as used herein, comprises a plurality of molecules of a binding agent, e.g., antibody molecule, described herein. In some embodiments, the binding agent, e.g., antibody molecule, makes up at least 60, 70, 80, 90, 95, 98, 99, 99.5 or 99.9%, of the preparation, or of the active ingredients of the preparation, by weight or number. In some embodiments, that binding agent is an antibody molecule which makes up at least 60, 70, 80, 90, 95, 98, 99, 99.5 or 99.9%, of the preparation, or of the active ingredients, or polypeptide ingredients, or antibody molecules, of the preparation, by weight or number. In some embodiments, the binding agent is an antibody molecule and the preparation contains no more than 30, 20, 10, 5, 2, 1, or 0.5%, by weight or number, of a contaminant, e.g., a reactant, solvent, precursor or other species, from the source, or used in the preparation, of the antibody molecule, e.g., a species from a cell, reaction mixture, or other system used to produce the antibody molecule.

As used herein, the term "prevent infection" means that a subject (e.g., a human) is less likely to be infected by influenza if the subject receives the antibody prior to (e.g., 1 day, 2 days, 1 week, 2 weeks, 3 weeks, or 1 month of more) before being exposed to influenza.

As used herein, "seasonal influenza" is a strain that is identical or closely related to strains that have been circulating in the human population in recent years and therefore most people are at least partially immune to it. Such a strain is not likely to cause severe disease. Symptoms can include fever, cough, runny nose, and muscle pain, and in rare cases, death can result from complications, such as pneumonia. Outbreaks follow predictable seasonal patterns, annually, and usually in fall and winter and in temperate climates. Infection due to seasonal influenza is commonly referred to as the flu.

As used herein, specific binding, means that a binding agent, e.g., an antibody molecule, binds its antigen with a $K_D$ of equal to or less than $10^{-5}$. In some embodiments, the antibody binds it's antigen with a $K_D$ of equal to or less than $10^{-6}$, $10^{-7}$, $10^{-8}$, $10^{-9}$, $10^{-10}$, $10^{-11}$, or $10^{-12}$.

As used herein, the term "therapeutically effective amount" refers to an amount of a therapeutic agent, e.g., a binding agent, e.g., an antibody molecule, which results in a positive outcome for the subject. In some embodiments, it can be statistically correlated with therapeutic effect or benefit, e.g., the lessening or prevention of a manifestation of an effect or a symptom, when administered to a population of subjects. In some embodiments, it is an amount that also provides a preselected, or reasonable, benefit/risk ratio. In some embodiments, it is an amount effective to reduce the incidence and/or severity of and/or to delay onset of one or more features, symptoms, or characteristics of a disease, disorder, or condition. A therapeutically effective amount is can be administered in a dosing regimen that may comprise one or multiple unit doses.

As used herein, the term "treat infection" means that a subject (e.g., a human) who has been infected with an influenza and experiences symptoms of the influenza (e.g., the flu), will in some embodiments, suffer less severe symptoms and/or will recover faster when the antibody molecule is administered than if the antibody is never administered. In some embodiments, when an infection is treated, an assay to detect virus in the subject will detect less virus after effective treatment for the infection. For example, a diagnostic assay using an antibody molecule, such as an antibody molecule described herein, will detect less or no virus in a biological sample of a patient after administration of an antibody molecule for the effective treatment of the viral infection. Other assays, such as PCR (e.g., qPCR) can also be used to monitor treatment in a patient, to detect the presence, e.g., decreased presence (or absence) after treatment of viral infection in the patient. Treatment can, e.g., partially or completely alleviate, ameliorate, relive, inhibit, reduce the severity of, and/or reduces incidence and optionally, delay onset of, one or more manifestations of the effects or symptoms, features, and/or causes of a particular disease, disorder, and/or condition (e.g., influenza). In some embodiments, treatment is of a subject who does not exhibit signs of the relevant disease, disorder and/or condition and/or of a subject who exhibits only early signs of the disease, disorder, and/or condition. In some embodiments, treatment is of a subject who exhibits one or more established signs of the relevant disease, disorder and/or condition. In some embodiments, treatment is of a subject diagnosed as suffering from influenza.

Calculations of "homology" or "sequence identity" or "identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Hemagglutinin (HA) Polypeptides and Influenza

Influenza viruses are negative sense, single-stranded, segmented RNA envelope viruses. Two glycoproteins, a hemagglutinin (HA) polypeptide and a neuraminidase (NA) polypeptide, are displayed on the outer surface of the viral envelope. There are several Influenza A subtypes, labeled according to an H number (for the type of hemagglutinin) and an N number (for the type of neuraminidase). There are 17 different H antigens (H1 to H17) and nine different N antigens (N1 to N9). Influenza strains are identified by a nomenclature based on the number of the strain's HA polypeptide and NA polypeptide subtypes, for example, H1N1, H1N2, H1N3, H1N4, H1N5, and the like.

HA is the major viral surface glycoprotein that mediates binding and entry of the virus into host cells and is a primary target of neutralizing antibody responses. HA is a trimer of three identical monomers. Each monomer is synthesized as a precursor, $HA_0$, that is proteolytically processed into two disulfide-bonded polypeptide chains, $HA_1$ and $HA_2$. The ectodomain of this protein has (i) a globular head domain possessing receptor binding activity and major antigenic determinants, (ii) a hinge region, and (iii) a stem region where a sequence critical for fusion, the fusion peptide, is located. The viral replication cycle is initiated when the virion attaches via its surface hemagglutinin proteins to sialylated glycan receptors on the host cell and enters the cell by endocytosis. The acidic environment in the endosome induces conformational changes in HA that expose the fusion peptide hidden within the stem region of the trimer. The exposed fusion peptide mediates the fusion of the viral and target cell membranes resulting in the release of the viral ribonucleoprotein into the cell cytoplasm.

Influenza A hemagglutinin subtypes have been divided into two main groups and four smaller clades, and these are further divided into clusters. Group 1 influenza A strains are divided into 3 clades: (i) H8, H9 and H12 ("the H9 cluster"); (ii) H1, H2, H5, H6 and H17 ("the H1a cluster"); and (iii) H11, H13 and H16 ("the H1b cluster"). Group 2 strains are divided into 2 clades: (i) H3, H4 and H14 ("the H3 cluster"); and (ii) H7, H10 and H15 ("the H7 cluster"). The H1b and the H1a clusters are classified together as the H1 cluster. The different HA subtypes do not necessarily share strong amino acid sequence identity, but their overall 3D structures are similar.

Of the 17 HA polypeptide subtypes, only 3 (H1, H2 and H3) have adapted for human infection. These subtypes have in common an ability to bind alpha 2,6 sialylated glycans. In contrast, their avian counterparts preferentially bind to alpha 2,3 sialylated glycans. HA polypeptides that have adapted to infect humans (e.g., of HA polypeptides from the pandemic H1N1 (1918) and H3N2 (1967-68) influenza subtypes) have been characterized by an ability to preferentially bind to α2,6 sialylated glycans in comparison with their avian progenitors that preferentially bind to α2,3 sialylated glycans (see, e.g., Skehel & Wiley, Annu Rev Biochem, 69:531, 2000; Rogers, & Paulson, Virology, 127:361, 1983; Rogers et al., Nature, 304:76, 1983; Sauter et al., Biochemistry, 31:9609, 1992

Further, HA polypeptides that mediate infection of humans preferentially bind to umbrella topology glycans over cone topology glycans (see, e.g., U.S. 2011/0201547). Without wishing to be bound by any particular theory, it has been proposed that the ability to infect human hosts correlates less with binding to glycans of a particular linkage, and more with binding to glycans of a particular topology, even though cone-topology glycans may be α2,6 sialylated glycans. In has been demonstrated that HA polypeptides that mediate infection of humans bind to umbrella topology glycans, often showing preference for umbrella topology glycans over cone topology glycans (See, for example, U.S. Application Publication Nos. 2009/0269342, 2010/0061990, 2009/0081193, and 2008/0241918, and International Publication No. WO2008/073161).

Mature HA polypeptides include three domains, (i) a globular domain (a.k.a., the head domain) consists mainly of the HA1 peptide and contains the receptor (sialylated glycoproteins)-binding region, (ii) a stalk domain (HA1 and HA2) where the membrane fusion peptide resides, and (iii) a transmembrane domain (HA2) that anchors hemagglutinin to the viral envelope. A set of amino acids in the interface of the HA1 and HA2 peptides is highly conserved across all influenza subtypes. The HA1/HA2 membrane proximal region (MPER), including a canonical alpha-helix, is also highly conserved across influenza subtypes.

HA polypeptides interact with the surface of cells by binding to a glycoprotein receptor, known as the HA receptor. Binding of an HA polypeptide to an HA receptor is predominantly mediated by N-linked glycans on the HA receptors. HA polypeptides on the surface of flu virus particles recognize sialylated glycans that are associated with HA receptors on the surface of the cellular host. Following replication of viral proteins and genome by the cellular machinery, new viral particles bud from the host to infect neighboring cells.

Currently, vaccines are administered to subjects, e.g., humans, to prevent the flu, e.g., to prevent infection or to minimize the effects of an infection with influenza virus. Traditional vaccines contain a cocktail of antigens from various strains of influenza and are administered to humans to prevent the human from getting infected with the virus. HA is the main target of influenza A-neutralizing antibodies, and HA undergoes continuous evolution driven by the selective pressure of the antibody response, which is primarily directed against the membrane-distal receptor-binding subdomain of the HA polypeptide. The subject, however, is protected only from strains that are identical to, or closely related to, the strains from which the antigens in the cocktail were derived. The human is still most vulnerable to infection by other strains of the flu that were not included in the cocktail. One of the advantages of the antibodies provided herein is their ability to bind an epitope of HA that is conserved across multiple strains of influenza A, and in some embodiments, influenza B. Thus, administration of an anti-HA antibody described herein will be more effective to protect an individual from infection from a broader spectrum of influenza (e.g., influenza A and, in some embodiments, influenza B) and conditions associate thereof (e.g., secondary infections, e.g., secondary bacterial infections). Further, the antibodies are effective in treating a subject after infection has occurred.

Anti-HA Antibody Molecules

Binding agents, and in particular, the antibody molecules described herein, can bind to influenza A viruses from both Group 1 and Group 2, and in some embodiments also bind influenza B viruses. For example, the antibody molecules described herein can bind to an HA polypeptide on at least 1, 2, 3, 4, 5, 6, 7, 8, 9, 10 or 11 strains from Group 1, and can also bind to an HA polypeptide on at least 1, 2, 3, 4, 5, or 6 strains from Group 2. In another example, the antibody molecules described herein can bind to an HA polypeptide on an influenza strain from at least 1, 2 or 3 clades from Group 1, and can also bind to an HA polypeptide on an influenza strain from one or both clades of Group 2. The antibody molecules described herein inhibit cell entry and thus targeting an early step in the infection process.

The binding agents, and in particular, the antibody molecules featured in the disclosure, can be effective to treat or prevent infection by seasonal or pandemic influenza strains. The binding agents, and in particular the antibody molecules described herein, can be characterized by their ability to prevent or treat a Group 1 or a Group 2 strain of influenza A viruses or, in some embodiments, a strain of influenza B viruses. The binding agents, and in particular the antibody molecules featured in the disclosure, are effective to prevent or treat infection by one or more strains of Group 1, one or more strains of Group 2, and also one or more strains of influenza B viruses. In an embodiment, the binding agent is used to treat or prevent an influenza virus infection caused by an influenza virus chose from an H1N1 virus, an H3N2 virus, an H7N9 virus, or a combination thereof.

The binding agents, and in particular the antibody molecules can be effective to treat the infection when administered the same day as the subject is exposed, or when administered, e.g., 1 day, 2 days, 3 days, 4 days or later after infection, or upon a first symptom experienced by the patient. In an embodiment, the antibody molecule does not cause an antibody dependent enhancement (ADE) in the subject, e.g., as determined by a method described herein. In an embodiment, the antibody molecule does not cause viral resistance, e.g., as determined by a method described herein.

Strains

The antibody molecules described herein are effective to treat one or more influenza strains of Group 1, one or more influenza strains of Group 2, and also one or more influenza B strains, and specific isolates within these strains. Certain antibody molecules may be more effective for treatment of certain isolates than other isolates. Exemplary influenza strains and isolates are described in the below Table 1. Affinity can also be in reference to a particular isolate of a given Group 1 or Group 2 strain for influenza A viruses or a strain for influenza B viruses. Exemplary isolates are as provided in the above Table 1. Other exemplary influenza virus strains and isolates are also described herein, e.g., in FIG. 18.

TABLE 1

Exemplary Influenza Strains and Isolates

| Type | Group | HA type | Isolate |
|---|---|---|---|
| A | 1 | H1N1 | A/PR/8/34 (aka PR-8) |
| | | | A/Solomon Islands/03/06 |
| | | | A/Solomon Islands/20/1999 |
| | | | A/California/07/2009 |
| | | | A/New Caledonia/20/99 |
| | | | A/Bangkok/10/83 |
| | | | A/Yamagata/120/86 |
| | | | A/Osaka/930/88 |
| | | | A/Suita/1/89 |
| | | | A/California/04/2009 |
| A | 1 | H2N2 | A/Okuda/57 |
| | | | A/Adachi/2/57 |
| | | | A/Kumamoto/1/65 |

TABLE 1-continued

Exemplary Influenza Strains and Isolates

| Type | Group | HA type | Isolate |
|---|---|---|---|
| | | | A/Kaizuka/2/65 |
| | | | A/Izumi/5/65 |
| | | | A/Chicken/PA/2004 |
| A | 1 | H5N1 | A/Vietnam/1203/04 |
| | | | A/Duck/Singapore/3/97 |
| | | | A/Duck/MN/1525/81 |
| A | 1 | H9N2 | A/Hong Kong/1073/2004 |
| | | | A/Swine/Hong Kong/9/98 |
| | | | A/Guinea fowl/HK/WF10/99 |
| A | 1 | H16N3 | A/black headed gull/Mongolia/1756/2006 |
| A | 2 | H3N2 | X-31 |
| | | | A/Victoria/3/75 |
| | | | A/Wyoming/03/2003 |
| | | | A/Wisconsin/67/2005 |
| | | | A/Brisbane/10/2007 |
| | | | A/California/7/2004 |
| | | | A/New York/55/2004 |
| | | | A/Moscow/10/1999 |
| | | | A/Aichi/2/68 |
| | | | A/Beijing/32/92/X-117 |
| | | | A/Fukuoka/C29/85 |
| | | | A/Sichuan/2/87 |
| | | | A/Ibaraki/1/90 |
| | | | A/Suita/1/90 |
| | | | A/Perth/16/2009 |
| | | | A/Uruguay/716/2007 |
| | | | A/Fujian/411/2003 |
| | | | A/Panama/2007/99 |
| | | | A/Shangdong/09/93 |
| A | 2 | H7N7 | A/Netherlands/219/2003 |
| B | | | B/Wisconsin/1/2010 |

Mechanisms of Inhibition

While not being limited by a specific mechanism, HA specific antibodies can inhibit infection by numerous methods, such as by blocking viral attachment to sialic acid residues on surface proteins on host cells, by interfering with the structural transition of HA that triggers fusion activity in the endosome, or by simultaneously inhibiting attachment and virus-cell fusion. In some embodiments, antibody molecules featured herein bind an epitope at the HA trimer interface. Structural changes at the trimer interface are important for fusion of the viral membrane and the endocytic membrane, and the antibody molecules described herein interfere with this critical step of infection. Assays to measure fusogenic activity of HA are known in the art. For example, one fusion assay measures syncytia formation, which occurs in cell-cell fusion events. Cells that express and display an influenza viral strain HA can be used in the assay. Membrane-anchored hemagglutinin in these cells is induced to convert to the fusion conformation by a brief (e.g., 3 minute) exposure to low pH (e.g., pH 5). A 2-3-hour incubation period follows to allow the cells to recover and fuse to form syncytia. A nuclear stain can be used to aid in the visualization of these fusion products, and their count is used as a gauge of fusion activity. A candidate anti-HA antibody can be added either before or after the low pH treatment to determine at which stage of the fusion process the antibody interferes.

Another type of fusion assay monitors content mixing. To measure content mixing, host cells (e.g., erythrocytes) are loaded with a dye (e.g., Lucifer yellow) to determine whether the contents of HA-bound host cells could be delivered to HA-expressing cells after exposure to fusion-inducing conditions (e.g., low pH, such as pH less than 6 or pH less than 5). If the dye fails to mix with the contents of the host cells, then the conclusion can be made that fusion is inhibited. See, e.g., Kemble et al., *J. Virol.* 66:4940-4950, 1992. In another example, a fusion assay is performed by monitoring lipid mixing. The lipid mixing assay can be performed by labeling host cells (e.g., erythrocytes) with a fluorescent dye (e.g., R18 (octadecylrhodamine)) or dye pairs (e.g., CPT-PC/DABS-PC) (for fluorescence resonance energy transfer), exposing the host cells and HA-expressing cells to fusion-inducing conditions, and assaying for fluorescence dequenching (FDQ). Lipid mixing leads to dilution of the label into the viral envelope and a consequent dequenching. A lag in dequenching or the absence of dequenching is indicative of membrane fusion inhibition. See, e.g., Kemble et al., *J. Virol.* 66:4940-4950, 1992; and Carr et al., *Proc. Natl. Acad. Sci.* 94:14306-14313, 1997.

Escape Mutants

In some embodiments, influenza strains will rarely if ever produce escape mutants when contacted with the featured antibody molecules. Escape mutants can be identified by methods known in the art. For example, an antibody featured in the disclosure will not produce an escape mutant when the cells are infected with the virus under prolonged or repeated exposure to anti-HA antibodies featured in the disclosure.

One exemplary method includes infection of cells (e.g. MDCK cells) with a fixed amount of influenza A viral particles in the presence of the antibody at a concentration known to attenuate infection rates by 50%. Viral progeny collected after each passaging is used to infect a fresh cell culture in the presence of the same or greater concentration of the antibody. After multiple cycles of infection, e.g., after 15 cycles, 12 cycles, 11 cycles, 10 cycles, 9 cycles, 8 cycles, 7 cycles, 6 cycles, or 5 cycles, of infection under these conditions, the HA nucleotide sequence extracted from 20 viral plaque picks is evaluated for enrichment for mutations that renders the viral isolate resistant to neutralization by the antibody (an escape mutant). If no mutants with reduced sensitivity to the antibody are detected after the multiple rounds of selection, e.g., after 11 rounds, 10 rounds, or 9 rounds of selection, the antibody is determined to be resistant to escape mutations (see, e.g., Throsby et al. (2008) PLoS One, volume 3, e3942).

In another example, an assay that measures minimum inhibitory concentration (MIC) of the neutralizing antibody can be used to identify escape mutants. The MIC of an antibody molecule is the lowest concentration of an antibody molecule that can be mixed with virus to prevent infection of cell culture with influenza. If escape mutants arise within a viral population, then the MIC of a particular antibody will be observed to increase with increased rounds of propagation under the antibody selective pressure, as the proportion of the viral particles that carry the resistance mutation within the population increased. Influenza escape mutants rarely if ever evolve in response to an anti-HA antibody molecule described herein, and therefore the MIC will stay the same over time.

Another assay suitable for monitoring for the development of escape mutants is a Cytopathic Effect (CPE) assay. A CPE assay monitors the ability of an antibody to neutralize (i.e., prevent infection by) an influenza strain. A CPE assay provides the minimal concentration of antibody required in cell culture to neutralize the virus. If escape mutants arise, than the CPE of a particular antibody will increase over time, as the antibody becomes less effective at neutralizing the virus. Viral strains rarely if ever produce escape mutants in response to an anti-HA antibody molecule described herein, and therefore the CPE will stay essentially the same over time.

Quantitative polymerase chain reaction (qPCR) can also be used to monitor for the development of escape mutants. qPCR is useful to monitor the ability of an antibody to neutralize (i.e., prevent infection by) an influenza strain. If an antibody effectively neutralizes a virus, then qPCR performed on cell culture samples will not detect presence of viral genomic nucleic acid. If escape mutants arise, than over time, qPCR will amplify more and more viral genomic nucleic acid. Escape mutants rarely if ever develop in response to an anti-HA antibody molecule described herein, and therefore qPCR will rarely if ever detect viral genomic nucleic acid, even after the passage of time.

Binding and Affinity

In some embodiments, the binding agents, particularly antibody molecules, featured herein bind to two or more of the following: at least one HA polypeptide from a Group 1 influenza strain (e.g., an H1, H2, H5, H6, H8, H9 H12, H11, H13, H16 or H17 polypeptide); at least one HA polypeptide from a Group 2 influenza strain (e.g., an H3, H4, H14, H7, H10, or H15 polypeptide); and at least one HA polypeptide from an influenza B strain. In an embodiment, a binding agent, e.g., an antibody molecule, has a $K_D$ for an HA from a Group 1 influenza strain (e.g., an H1, H2, H5, H6, H8, H9 H12, H11, H13, H16 or H17 polypeptide) of equal to or less than $10^{-6}$, $10^{-7}$, $10^{-8}$, $10^{-9}$, $10^{-10}$, $10^{-11}$, or $10^{-12}$. In an embodiment, a binding agent, e.g., an antibody molecule, has a $K_D$ for an HA from a Group 2 influenza strain (e.g., an H3, H4, H14, H7, H10, or H15 polypeptide) of equal to or less than $10^{-6}$, $10^{-7}$, $10^{-8}$, 10, $10^{-10}$, $10^{-11}$, or $10^{-12}$. In an embodiment, a binding agent, e.g., an antibody molecule, has a $K_D$ for an influenza B HA of equal to or less than $10^{-6}$, $10^{-7}$, $10^{-8}$, $10^{-9}$, $10^{-10}$, $10^{-11}$, or $10^{-12}$. In an embodiment, a binding agent, e.g., an antibody molecule, has: a) a first $K_D$ (representing an affinity for an HA from a Group 1 influenza strain, e.g., an H1, H2, H5, H6, H8, H9 H12, H11, H13, H16 or H17 polypeptide); and b) a second $K_D$ (representing an affinity for an HA from a Group 2 influenza strain, e.g., an H3, H4, H14, H7, H10, or H15 polypeptide), wherein the first and second $K_D$ are one or both of: both equal to or less than $10^{-8}$; and within 10 or 100 fold of each other;

In an embodiment, a binding agent, e.g., an antibody molecule, has a) a first $K_D$ (representing an affinity for an H1, e.g., the H1 from an H1N1 strain, e.g., A/South Carolina/1/1918, A/Puerto Rico/08/1934, or A/California/04/ 2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of: both equal to or less than $10^{-8}$; and within 10 or 100 fold of each other. In an embodiment, a binding agent, e.g., an antibody molecule, has: a) a first $K_D$ (representing an affinity for an H1, e.g., the H1 from an H1N1 strain, e.g., A/South Carolina/1/1918, A/Puerto Rico/ 08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of: both equal to or less than $10^{-8}$; and within 10 or 100 fold of each other.

In an embodiment, a binding agent, e.g., an antibody molecule, has: a) a first $K_D$ (representing an affinity for an HA from a Group 1 influenza strain, e.g., an H1, H2, H5, H6, H8, H9 H12, H11, H13, H16 or H17 polypeptide and/or an affinity for an HA from a Group 2 influenza strain, e.g., an H3, H4, H14, H7, H10, or H15 polypeptide); and b) a second $K_D$ (representing an affinity for an influenza B HA, e.g., from B/Wisconsin/1/2010); wherein the first and second $K_D$ are one or both of: both equal to or less than $10^{-8}$; and within 10 or 100 fold of each other. In an embodiment, a binding agent, e.g., an antibody molecule, has: a) a first $K_D$ (representing an affinity for an HA from a Group 1 influenza strain, e.g., an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, and/or an affinity for an HA from a Group 2 influenza strain, e.g., an H3 polypeptide, from an H3N2 strain, e.g., from A/Brisbane/59/2007); and b) a second $K_D$ (an affinity for an influenza B HA); wherein the first and second $K_D$ are: one or both of: both equal to or less than $10^{-8}$; and within 10 or 100 fold of each other.

(Sapidyne, Inc.). Relative binding affinity is expressed herein according to ELISA assay. As used herein, an anti-HA antibody that binds with "high affinity" to a Group 1 HA, to a Group 2 HA, and to an influenza B HA, can bind a Group 1 HA with a Kd less than or equal to 200 pM, e.g., less than or equal to 100 pM, as measured by ELISA, can bind a Group 2 HA with a Kd less than or equal to 200 pM, e.g., less than or equal to 100 pM, as measured by ELISA, and can bind an influenza B HA with a Kd less than or equal to 200 pM, e.g., less than or equal to 100 pM, as measured by ELISA.

Exemplary Anti-HA Antibody Molecules

Provided herein are antibodies that have one or more CDR sequences and one or more framework (FR) sequences as shown in Table 2.

TABLE 2

Heavy and Light Chain CDR and FR Sequences for Anti-HA Antibodies

| CDR/FR Region | Amino Acid Sequence | SEQ ID NO: |
|---|---|---|
| HC CDR1 | [S/T]Y[A/G]MH | 1 |
| HC CDR2 | V[I/V/L]S[Y/F]DG[S/N][Y/N][K/R]YYADSVQG | 2 |
| HC CDR3 | D[S/T][R/K/Q]LR[S/T]LLYFEWLS[Q/S]G[Y/L/V][F/L][N/D][P/Y] | 3 |
| LC CDR1 | Q[S/T][V/L/I][T/S][Y/F/W][N/S/D]YKNYLA | 4 |
| LC CDR1 | Q[S/T][V/L/I][T/S][Y/F/W][N/S/D/Q/R/E]YKNYLA | 170 |
| LC CDR2 | W[A/G]S[T/A/Y/H/K/D][R/L]E[S/T] | 5 |
| LC CDR3 | QQ[Y/H]YRTPP[T/S] | 6 |
| HC FR1 | [E/Q]VQLLE[S/T]GGGLVKPGQSLKLSCAASGFTF[S/T] | 7 |
| HC FR2 | WVRQPPGKGLEWVA | 8 |
| HC FR3 | RFTISRDNSKNTLYLQMNSLRAEDTAVYYCAK | 9 |
| HC FR4 | WG[A/Q]G[T/A][T/M][L/V]TVSS | 10 |
| LC FR1 | [E/D]I[V/Q]MTQSP[D/S][S/T][L/V][A/S][V/A][S/T][L/V/R]G[E/D]R[A/V][T/S]I[N/T/Q/D/R/A]C[K/R]SS | 11 |
| LC FR2 | WYQQKPG[Q/K][P/A]PKLLIY | 12 |
| LC FR3 | GVP[D/E/S]RFSGSGSGTDFTLTISSLQ[A/P]ED[V/F/K/D]A[V/T]YYC | 13 |
| LC FR4 | FG[G/Q/T/S/N]GTK[L/V][D/E]IK | 14 |

Figure 12A:
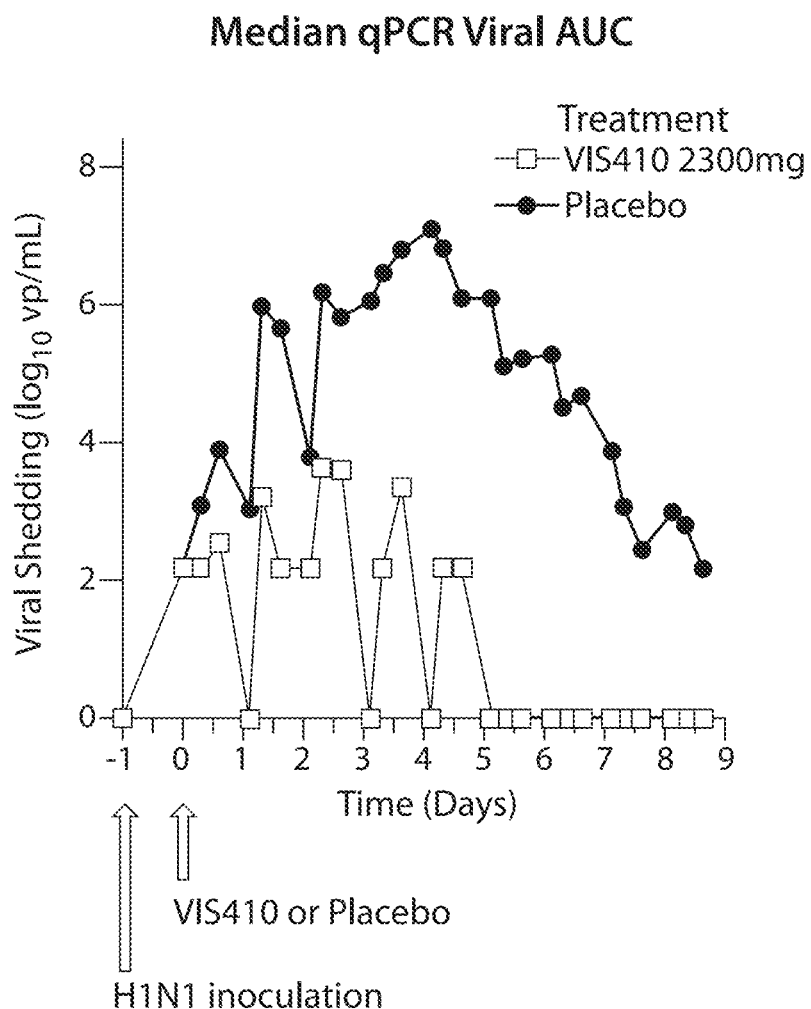
FIG. 12A depicts the median viral shedding versus time profiles of VIS410 compared to Placebo as measured by qRT-PCR in mITT population.
Figure 12B:
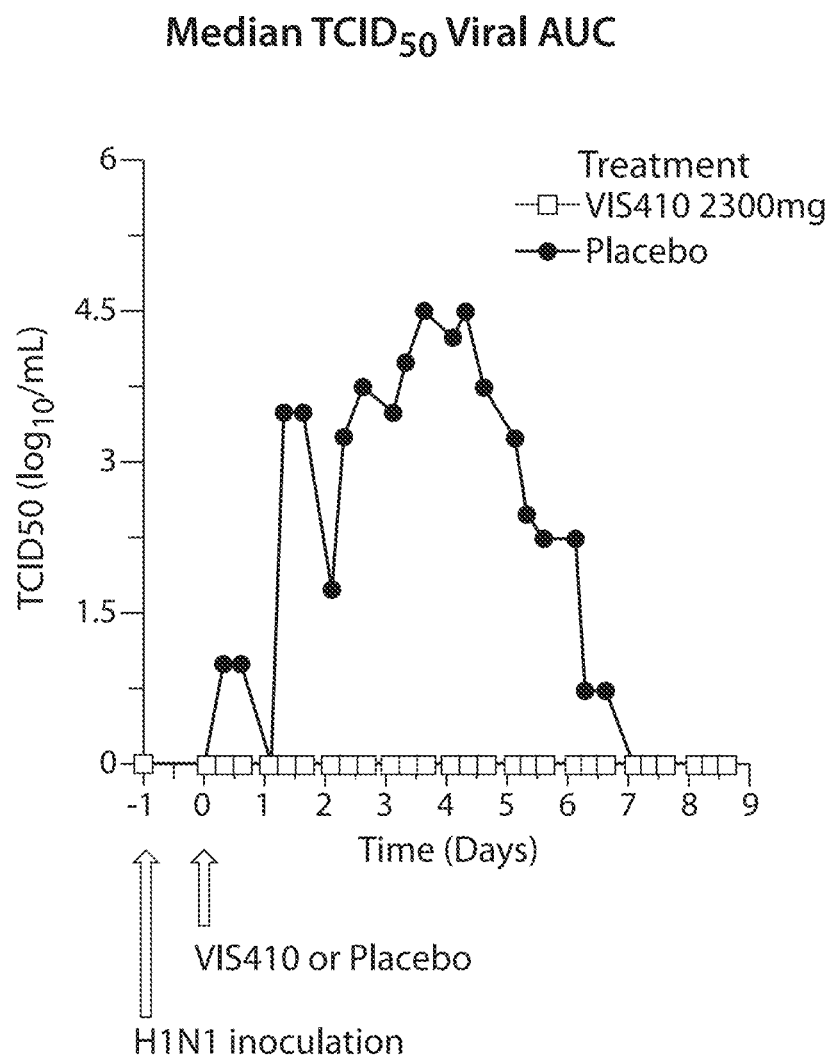
FIG. 12B depicts the median 50% tissue culture infective dose ($TCID_{50}$) time profiles of VIS410 compared to Placebo as measured by a cell based assay in mITT population.

In one embodiment, the antibody molecule binds to at least one HA polypeptide from a Group 1 influenza strain with a higher affinity than a reference anti-HA antibody, and to at least one HA polypeptide from a Group 2 influenza strain with a higher affinity than a reference anti-HA antibody. In another embodiment, the antibody molecule binds to at least one HA polypeptide from an influenza A strain with a higher affinity than a reference anti-HA antibody, and to at least one HA polypeptide from an influenza B strain with a higher affinity than a reference anti-HA antibody. Exemplary reference HA antibodies include Ab 67-11 (U.S. Provisional application No. 61/645,453, filed on the same date as the present application), FI6 (FI6, as used herein, refers to any specifically disclosed FI6 sequence in U.S. Application Publication No. 2010/0080813, US Application Publication No. 2011/0274702, International Publication No. WO2013/011347 or Corti et al., *Science* 333:850-856, 2011, published online Jul. 28, 2011; FIGS. 12A to 12C of International Publication No. WO2013/170139 or U.S. Application Publication No. 2013/0302349), FI28 (U.S. Application Publication No. 2010/0080813), and C179 (Okuno et al., *J. Virol.* 67:2552-1558, 1993), F10 (Sui et al., *Nat. Struct. Mol. Biol.* 16:265, 2009), CR9114 (Dreyfus et al., *Science.* 2012; 337(6100):1343-1348; published online Aug. 9, 2012), and CR6261 (Ekiert et al., *Science* 324:246-251, 2009; published online Feb. 26, 2009).

Affinity, or relative affinity or aviditiy, can be measured by methods known in the art, such as by ELISA assay (Enzyme Linked Immunosorbent Assay), Surface Plasmon Resonance (SPR, e.g., by a Biacore™ Assay), or KinExA® assay In one embodiment, the anti-HA antibody comprises a heavy chain and/or a light chain as defined in Table 3 below. The amino acid sequences of the variable heavy and light chains of Table 3 are provided in FIGS. 2 and 3, respectively, or in FIG. 17, of International Publication No. WO2013/170139 or U.S. Application Publication No. 2013/0302349.

TABLE 3

Heavy and Light Chain Amino Acid Sequence Designations for Anti-HA Antibodies

| | Antibody | HC | SEQ ID NO: | LC | SEQ ID NO: |
|---|---|---|---|---|---|
| 1. | Ab A18 | 15 | 15 | 28 | 28 |
| 2. | Ab 014 | 16 | 16 | 29 | 29 |
| 3. | Ab 028 | 16 | 16 | 30 | 30 |
| 4. | Ab 001 | 17 | 17 | 31 | 31 |
| 5. | Ab 002 | 18 | 18 | 31 | 31 |
| 6. | Ab 003 | 19 | 19 | 31 | 31 |
| 7. | Ab 009 | 17 | 17 | 32 | 32 |
| 8. | Ab 010 | 18 | 18 | 32 | 32 |
| 9. | Ab 011 | 19 | 19 | 32 | 32 |
| 10. | Ab 017 | 17 | 17 | 33 | 33 |
| 11. | Ab B18 | 18 | 18 | 33 | 33 |
| 12. | Ab 019 | 19 | 19 | 33 | 33 |
| 13. | Ab 025 | 17 | 17 | 34 | 34 |
| 14. | Ab 026 | 18 | 18 | 34 | 34 |
| 15. | Ab 027 | 19 | 19 | 34 | 34 |
| 16. | Ab 086 | 20 | 20 | 34 | 34 |
| 17. | Ab 154 | 21 | 21 | 29 | 29 |
| 18. | Ab 155 | 21 | 21 | 30 | 30 |
| 19. | Ab 157 | 22 | 22 | 29 | 29 |
| 20. | Ab 159 | 22 | 22 | 35 | 35 |
| 21. | Ab 160 | 17 | 17 | 36 | 36 |

TABLE 3-continued

Heavy and Light Chain Amino Acid Sequence Designations for Anti-HA Antibodies

| | Antibody | HC | SEQ ID NO: | LC | SEQ ID NO: |
|---|---|---|---|---|---|
| 22. | Ab 186 | 17 | 17 | 37 | 37 |
| 23. | Ab 187 | 17 | 17 | 38 | 38 |
| 24. | Ab 188 | 17 | 17 | 39 | 39 |
| 25. | Ab 189 | 17 | 17 | 40 | 40 |
| 26. | Ab 190 | 17 | 17 | 41 | 41 |
| 27. | Ab 191 | 17 | 17 | 42 | 42 |
| 28. | Ab 192 | 17 | 17 | 43 | 43 |
| 29. | Ab 193 | 17 | 17 | 44 | 44 |
| 30. | Ab 194 | 19 | 19 | 37 | 37 |
| 31. | Ab 195 | 19 | 19 | 38 | 38 |
| 32. | Ab 196 | 19 | 19 | 39 | 39 |
| 33. | Ab 197 | 19 | 19 | 40 | 40 |
| 34. | Ab 198 | 19 | 19 | 41 | 41 |
| 35. | Ab 199 | 19 | 19 | 42 | 42 |
| 36. | Ab 200 | 19 | 19 | 43 | 43 |
| 37. | Ab 202 | 17 | 17 | 45 | 45 |
| 38. | Ab 203 | 18 | 18 | 45 | 45 |
| 39. | Ab 204 | 19 | 19 | 45 | 45 |
| 40. | Ab 210 | 23 | 23 | 45 | 45 |
| 41. | Ab 211 | 17 | 17 | 46 | 46 |
| 42. | Ab 212 | 18 | 18 | 46 | 46 |
| 43. | Ab 213 | 19 | 19 | 46 | 46 |
| 44. | Ab 219 | 23 | 23 | 46 | 46 |
| 45. | Ab A001 | 24 | 24 | 47 | 47 |
| 46. | Ab A002 | 24 | 24 | 48 | 48 |
| 47. | Ab A003 | 24 | 24 | 49 | 49 |
| 48. | Ab 004 | 25 | 25 | 47 | 47 |
| 49. | Ab 005 | 25 | 25 | 48 | 48 |
| 50. | Ab 006 | 25 | 25 | 49 | 49 |
| 51. | Ab 007 | 26 | 26 | 47 | 47 |
| 52. | Ab 008 | 26 | 26 | 48 | 48 |
| 53. | Ab A009 | 26 | 26 | 49 | 49 |
| 54. | Ab A010 | 24 | 24 | 50 | 50 |
| 55. | Ab A011 | 24 | 24 | 51 | 51 |
| 56. | Ab 012 | 25 | 25 | 50 | 50 |
| 57. | Ab 013 | 25 | 25 | 51 | 51 |
| 58. | Ab A14 | 26 | 26 | 50 | 50 |
| 59. | Ab 015 | 26 | 26 | 51 | 51 |
| 60. | Ab 016 | 27 | 27 | 47 | 47 |
| 61. | Ab A017 | 27 | 27 | 48 | 48 |
| 62. | Ab C18 | 27 | 27 | 49 | 49 |
| 63. | Ab A019 | 27 | 27 | 50 | 50 |
| 64. | Ab 031 | 24 | 24 | 45 | 45 |
| 65. | Ab 032 | 25 | 25 | 45 | 45 |
| 66. | Ab 033 | 26 | 26 | 45 | 45 |
| 67. | Ab 034 | 27 | 27 | 45 | 45 |
| 68. | Ab 037 | 24 | 24 | 46 | 46 |
| 69. | Ab 038 | 25 | 25 | 46 | 46 |
| 70. | Ab 039 | 26 | 26 | 46 | 46 |
| 71. | Ab 040 | 27 | 27 | 46 | 46 |
| 72. | Ab 043 | 25 | 25 | 60 | 60 |
| 73. | Ab 044 | 25 | 25 | 52 | 52 |
| 74. | Ab 045 | 25 | 25 | 57 | 57 |
| 75. | Ab 046 | 25 | 25 | 59 | 59 |
| 76. | Ab 047 | 25 | 25 | 55 | 55 |
| 77. | Ab 048 | 25 | 25 | 58 | 58 |
| 78. | Ab 049 | 25 | 25 | 54 | 54 |
| 79. | Ab 050 | 25 | 25 | 56 | 56 |
| 80. | Ab 051 | 25 | 25 | 53 | 53 |
| 81. | Ab 052 | 25 | 25 | 61 | 61 |
| 82. | Ab 067 | 25 | 25 | 153 | 153 |
| 83. | Ab 068 | 25 | 25 | 154 | 154 |
| 84. | Ab 069 | 25 | 25 | 155 | 155 |
| 85. | Ab 070 | 25 | 25 | 156 | 156 |
| 86. | Ab 071 | 162 | 162 | 52 | 52 |
| 87. | Ab 072 | 163 | 163 | 52 | 52 |
| 88. | Ab 073 | 25 | 25 | 165 | 165 |
| 89. | Ab 074 | 25 | 25 | 166 | 166 |
| 90. | Ab 075 | 25 | 25 | 167 | 167 |
| 91. | Ab 076 | 25 | 25 | 168 | 168 |
| 92. | Ab 077 | 25 | 25 | 169 | 169 |
| 93. | Ab 078 | 164 | 164 | 52 | 52 |
| 94. | Ab 079 | 164 | 164 | 155 | 155 |
| 95. | Ab 080 | 164 | 164 | 166 | 166 |
| 96. | Ab 081 | 164 | 164 | 169 | 169 |

In one embodiment, the anti-HA antibody comprises a heavy chain as defined in Table 4A below, and/or a light chain as defined in Table 4A below.

TABLE 4A

Heavy and Light Chain Amino Acid Sequence Designations

| HC | SEQ ID NO: | LC | SEQ ID NO: |
|---|---|---|---|
| 15 | 15 | 28 | 28 |
| 16 | 16 | 29 | 29 |
| 17 | 17 | 30 | 30 |
| 18 | 18 | 35 | 35 |
| 19 | 19 | 31 | 31 |
| 21 | 21 | 32 | 32 |
| 22 | 22 | 33 | 33 |
| 20 | 20 | 34 | 34 |
| 23 | 23 | 36 | 36 |
| 24 | 24 | 45 | 45 |
| 25 | 25 | 46 | 46 |
| 26 | 26 | 37 | 37 |
| 27 | 27 | 38 | 38 |
| Hc consensus (HC161) | 161 | 39 | 39 |
| 162 | 162 | 40 | 40 |
| 163 | 163 | 41 | 41 |
| 164 | 164 | 42 | 42 |
| | | 43 | 43 |
| | | 44 | 44 |
| | | 47 | 47 |
| | | 48 | 48 |
| | | 49 | 49 |
| | | 50 | 50 |
| | | 51 | 51 |
| | | 52 | 52 |
| | | 53 | 53 |
| | | 54 | 54 |
| | | 55 | 55 |
| | | 56 | 56 |
| | | 57 | 57 |
| | | 58 | 58 |
| | | 59 | 59 |
| | | 60 | 60 |
| | | 61 | 61 |
| | | 153 | 153 |
| | | 154 | 154 |
| | | 155 | 155 |
| | | 156 | 156 |
| | | LC consensus (LC62) | 62 |
| | | 165 | 165 |
| | | 166 | 166 |
| | | 167 | 167 |
| | | 168 | 168 |
| | | 169 | 169 |

In one embodiment, an antibody featured in the disclosure comprises a heavy chain sequence as defined in Table 4A and a light chain sequence as defined in Table 4A.

In one embodiment, an antibody featured in the disclosure comprises a heavy chain sequence as defined herein, e.g., in Table 4A, where a dipeptide is fused to the N-terminus. Typically, the dipeptide is isoleucine-aspartic acid (Ile-Asp). In another embodiment, an antibody featured in the disclosure comprises a light chain sequence as defined herein, e.g., in Table 4A, where a dipeptide is fused to the N-terminus. Typically, the dipeptide is Ile-Asp. In yet another embodiment, an antibody featured in the disclosure comprises a heavy chain comprising an N-terminal Ile-Asp dipeptide and a light chain comprising an Ile-Asp dipeptide. In the propeptide sequence of the heavy chain or light chain polypeptide, the Ile-Asp dipeptide occurs between the signal sequence and FR1. Heavy chain and light chain variable sequences comprising an Ile-Asp dipeptide at the N-terminus are identified in Table 4B.

TABLE 4B

Heavy and Light Chain Amino Acid Sequence Designations, where the Sequence Includes an N-terminal Ile-Asp Dipeptide

| HC | SEQ ID NO: | LC | SEQ ID NO: |
|---|---|---|---|
| 15-ID | 96 | 28-ID | 110 |
| 16-ID | 97 | 29-ID | 111 |
| 17-ID | 98 | 30-ID | 112 |
| 18-ID | 99 | 35-ID | 113 |
| 19-ID | 100 | 31-ID | 114 |
| 21-ID | 101 | 32-ID | 115 |
| 22-ID | 102 | 33-ID | 116 |
| 20-ID | 103 | 34-ID | 117 |
| 23-ID | 104 | 36-ID | 118 |
| 24-ID | 105 | 45-ID | 119 |
| 25-ID | 106 | 46-ID | 120 |
| 26-ID | 107 | 37-ID | 121 |
| 27-ID | 108 | 38-ID | 122 |
| Hc consensus ID (161-ID) | 109 | 39-ID | 123 |
|  |  | 40-ID | 124 |
|  |  | 41-ID | 125 |
|  |  | 42-ID | 126 |
|  |  | 43-ID | 127 |
|  |  | 44-ID | 128 |
|  |  | 47-ID | 129 |
|  |  | 48-ID | 130 |
|  |  | 49-ID | 131 |
|  |  | 50-ID | 132 |
|  |  | 51-ID | 133 |
|  |  | 52-ID | 134 |
|  |  | 53-ID | 135 |
|  |  | 54-ID | 136 |
|  |  | 55-ID | 137 |
|  |  | 56-ID | 138 |
|  |  | 57-ID | 139 |
|  |  | 58-ID | 140 |
|  |  | 59-ID | 141 |
|  |  | 60-ID | 142 |
|  |  | 61ID | 143 |
|  |  | 153-ID | 157 |
|  |  | 154-ID | 158 |
|  |  | 155-ID | 159 |
|  |  | 156-ID | 160 |
|  |  | LC consensus ID (62-ID) | 144 |

In another embodiment, an antibody featured in the disclosure is other than an antibody known in the art. For example, the antibody is not Ab 67-11 (U.S. Provisional application No. 61/645,453) FI6 (FI6, as used herein, refers to any specifically disclosed FI6 sequence in U.S. Application Publication No. 2010/0080813, US Application Publication No. 2011/0274702, International Publication No. WO2013/011347 or Corti et al., *Science* 333:850-856, 2011, published online Jul. 28, 2011; FIGS. 12A to 12C of International Publication No. WO2013/170139 or U.S. Application Publication No. 2013/0302349), FI28 (U.S. Application Publication No. 2010/0080813), and C179 (Okuno et al., *J. Virol.* 67:2552-1558, 1993), F10 (Sui et al., *Nat. Struct. Mol. Biol.* 16:265, 2009), CR9114 (Dreyfus et al., *Science.* 2012; 337(6100):1343-1348; published online Aug. 9, 2012), and CR6261 (Ekiert et al., *Science* 324:246-251, 2009; published online Feb. 26, 2009). In one embodiment, an antibody featured in the disclosure is other than Ab 67-11 (U.S. Provisional application No. 61/645,453, filed on the same date as the present application).

Variants

Figure 2A:
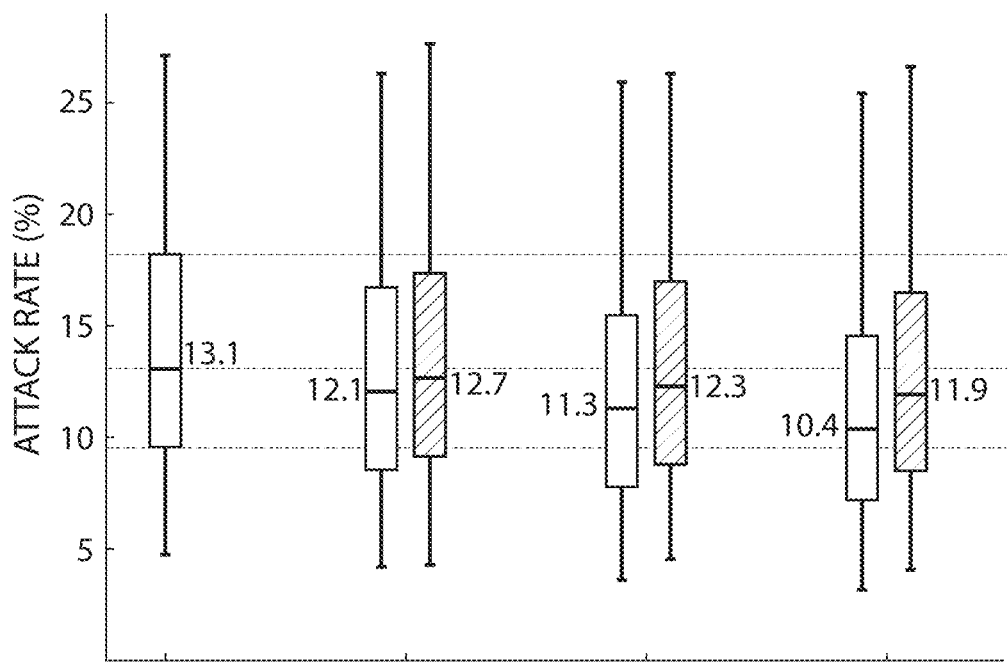
FIGS. 2A-2C depict the microsimulation results of VIS410 prophylactic use. Changes in attack rate (FIG. 2A), overall hospitalization rate (FIG. 2B), and hospitalization rate in individuals older than 65 years of age (FIG. 2C) as a function of the population-level prophylaxis coverage. The boxplots aggregate outcomes over time of administration and transmission setting, as these epidemiological variables might in some cases be difficult to predict. The boxplots for 0% coverage summarize 750 individual simulations, while the boxplots for 2% to 6% coverage summarize 3,750 simulations each. The yellow boxplots show results for VIS410 administration to the elderly only, while the white boxplots show general population VIS410 administration. The whiskers show the full range of outcomes, and the median value is shown next to the median line of each boxplot. With one exception, all pairwise comparisons between different coverage levels, when keeping the group administration method fixed ("all" or "elderly only"), show a statistically significant difference by the Mann-Whitney test (p=0.002); the one exception is in FIG. 2A when comparing no coverage to 2% coverage and distribution to the elderly only (significant at p=0.05). Note that in FIG. 2B when comparing elderly versus general population distribution, the Mann-Whitney p-values are p=0.21 (2% coverage), p=0.05 (4% coverage), and p=0.005 (6% coverage).
Figure 2B:
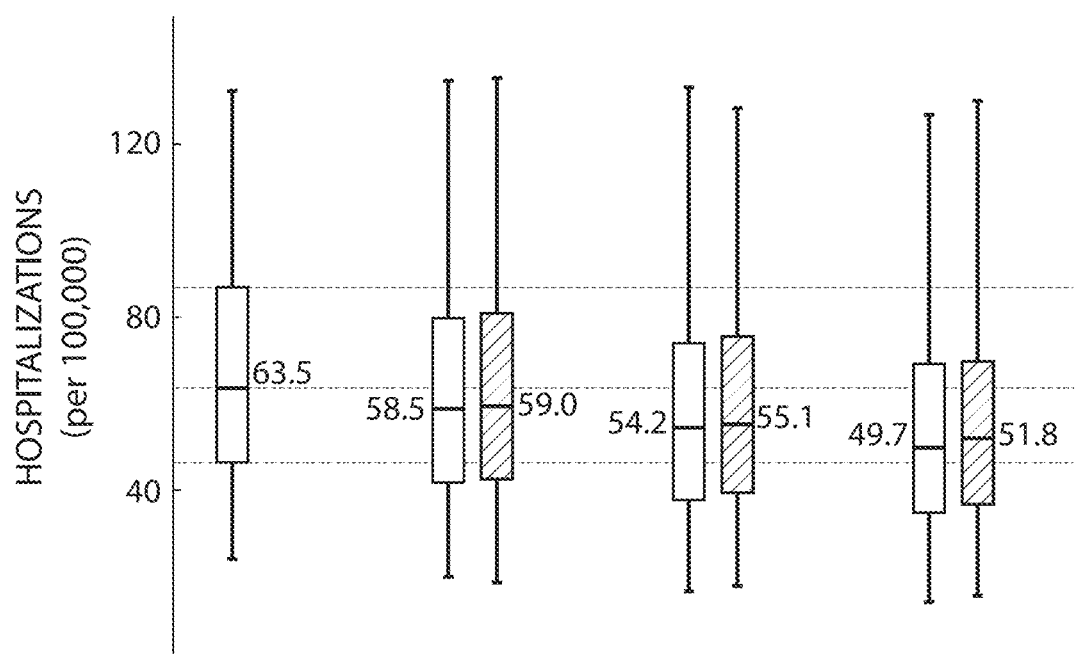
Figure 2C:
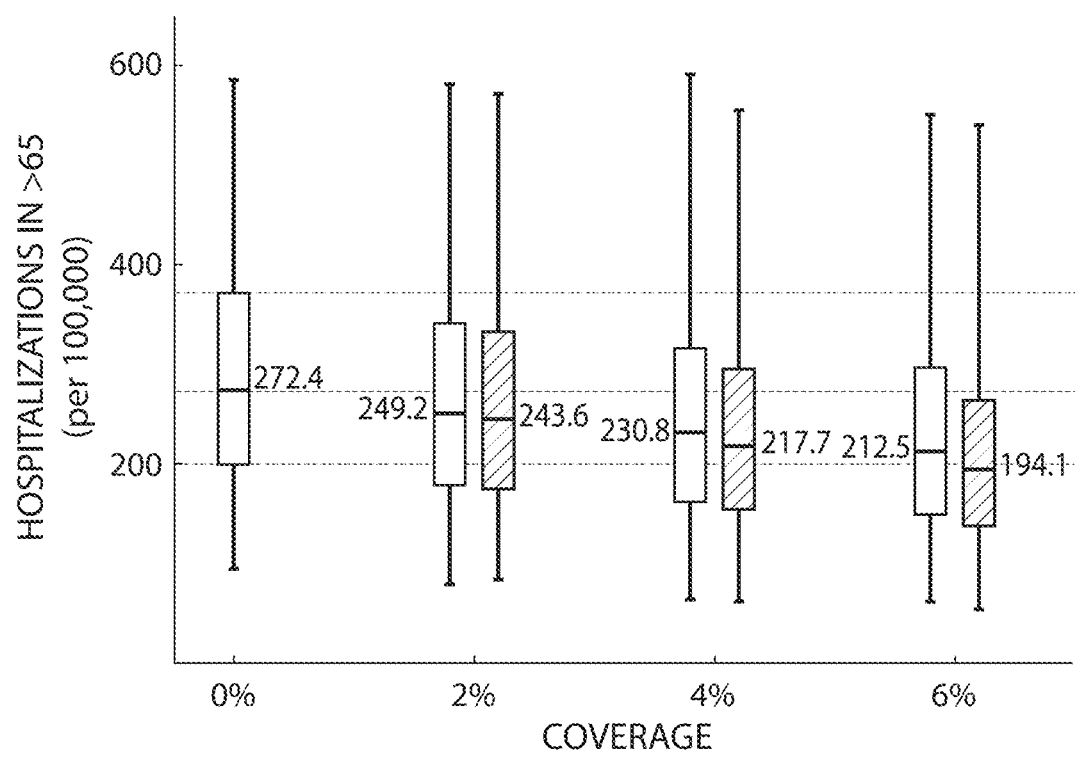
Figure 3:
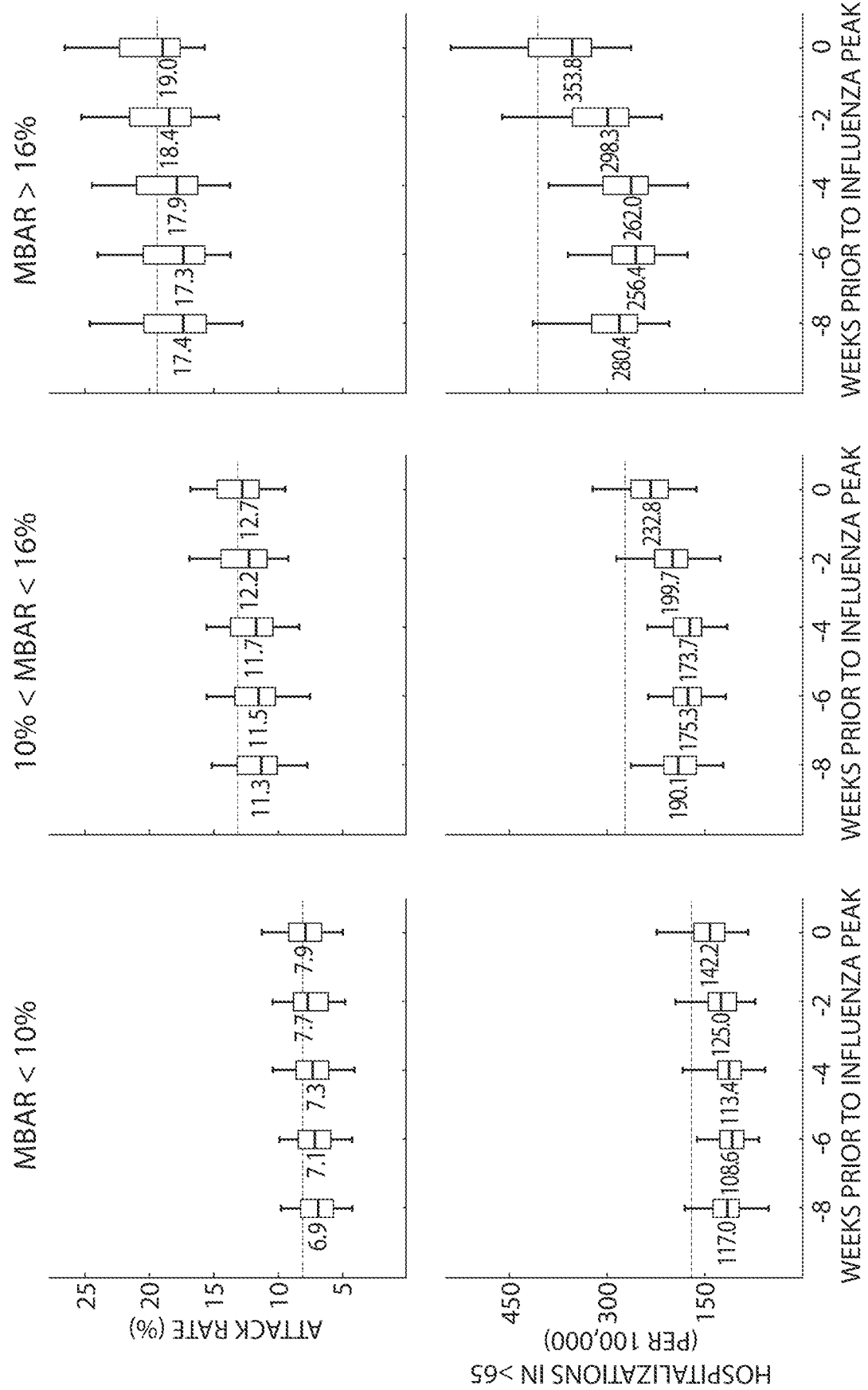
FIG. 3 depicts the results of VIS410 prophylactic use stratified by date of administration and transmission setting. Median baseline attack rate (MBAR) is used to separate the simulations into those that have low (<10%), medium (10%-16%), or high (>16%) median attack rates when coverage is zero. In these simulations, VIS410 was administered to the elderly only and coverage was set to 6%. Each boxplot corresponds to 250 simulations. The whiskers show the full range of outcomes, and the median value is shown next to the median line of each boxplot. The gray line denotes the baseline median for each scenario when coverage is zero.
Figure 13:
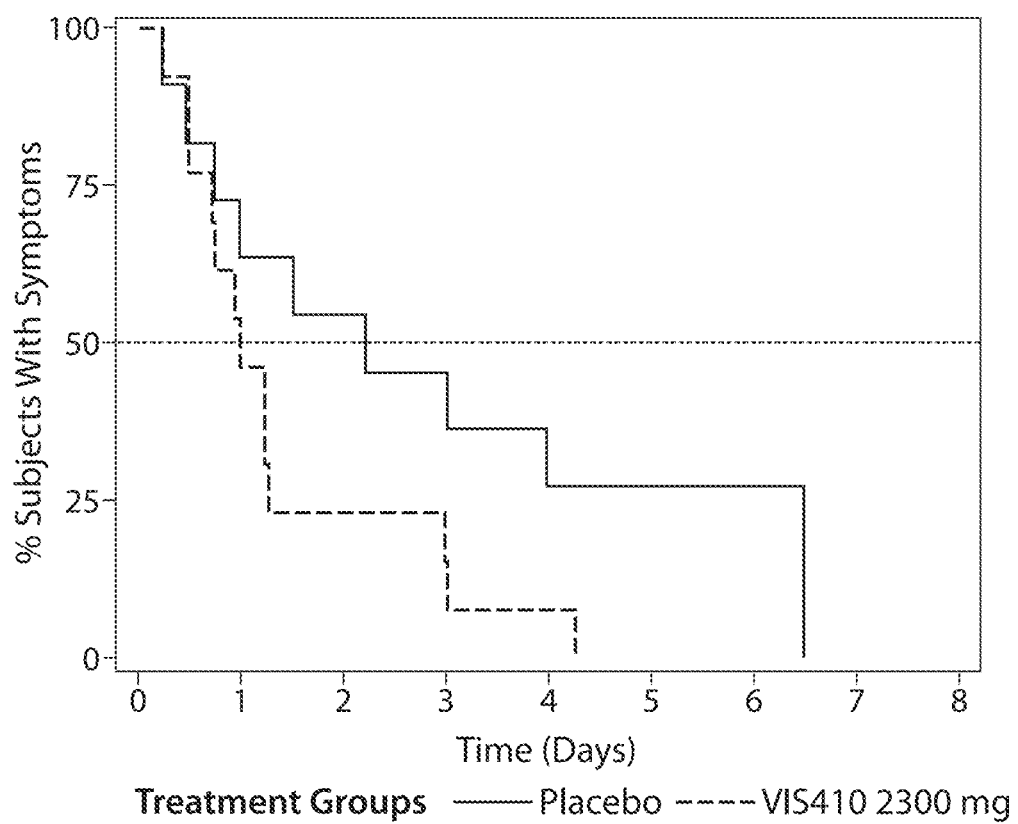
FIG. 13 depicts the time to resolution of upper respiratory tract symptom score in mITT population.
Figure 17:
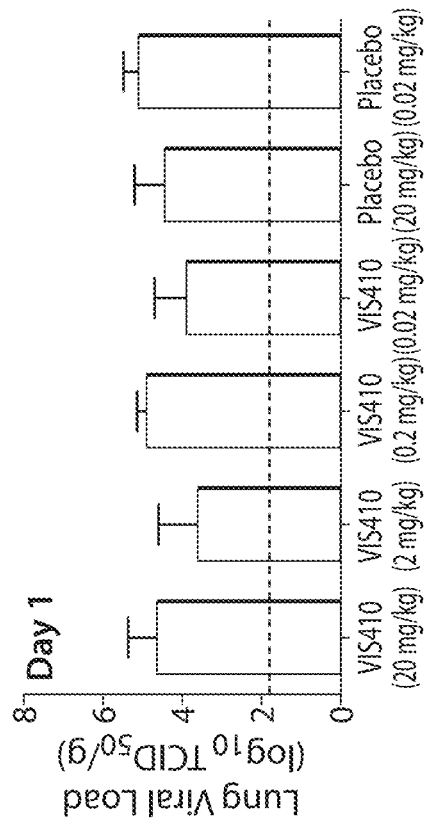
FIG. 17 depicts the average lung viral load on Days 1 and 14 pi in CD-1 mice treated with different doses of VIS410 and irrelevant human IgG1.
Figure 17:
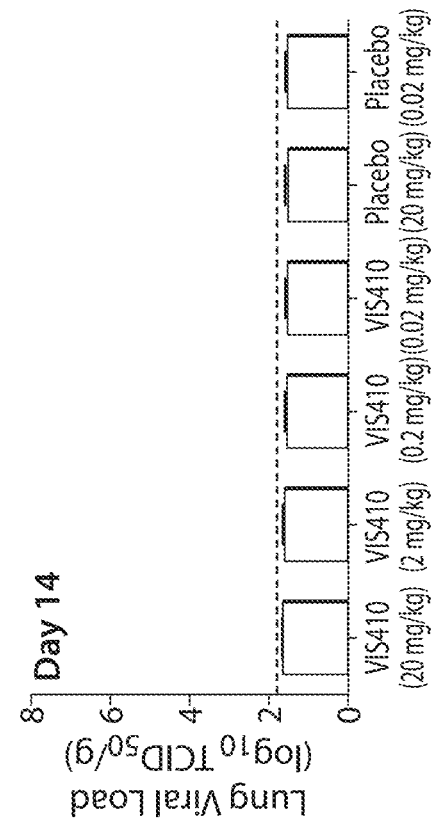
Figure 17:
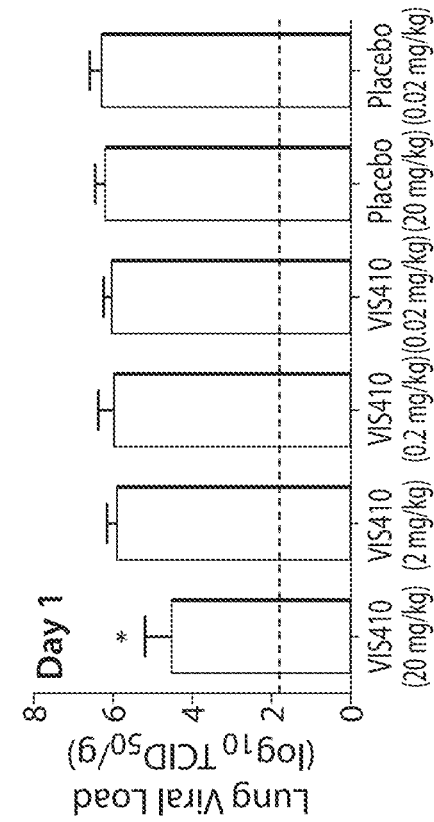
Figure 17:
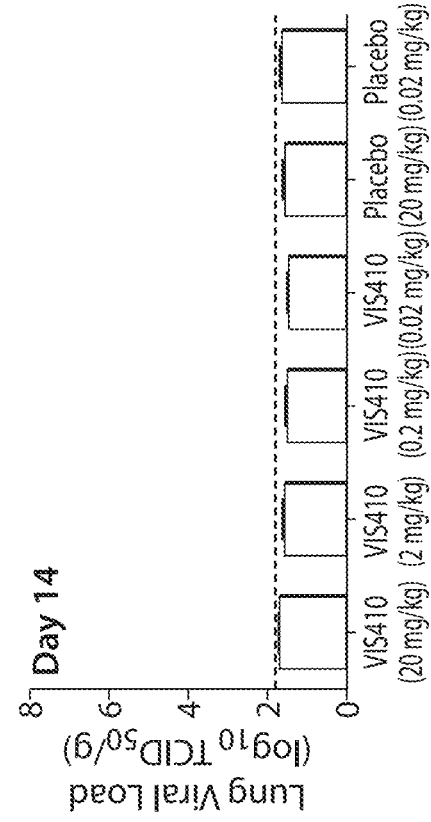

In an embodiment, an antibody molecule, e.g., an antibody featured in the disclosure has a variable heavy chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a heavy chain disclosed herein, e.g., from Table 3, Table 4A, or Table 4B, or FIG. 2, FIG. 13 or FIG. 17, of International Publication No. WO2013/170139 or U.S. Application Publication No. 2013/0302349, e.g. consensus sequence of SEQ ID NO: 161, and has a variable light chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a light chain disclosed herein, e.g., from Table 3, Table 4A, or Table 4B, or FIG. 3, FIG. 14 or FIG. 17, of International Publication No. WO2013/170139 or U.S. Application Publication No. 2013/0302349, e.g., the consensus sequence of SEQ ID NO: 62. The consensus sequences were determined through the analysis of biochemical and biophysical properties of several hundred computationally designed VH/VL combinations. The consensus sequences represent the amino acid sequences in which each amino acid is the one that occurs most frequently at that site when multiple sequences comprising desirable biochemical and biophysical data are aligned.

An exemplary anti-HA binding antibody has one or more CDRs, e.g., all three HC CDRs and/or all three LC CDRs of a particular antibody disclosed herein, or CDRs that are, in sum, at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to such an antibody. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the amino acid sequence of the HC and/or LC variable domain of an antibody described herein. The amino acid sequence of the HC and/or LC variable domain sequence can differ by at least one amino acid, but no more than ten, eight, six, five, four, three, or two amino acids from the corresponding sequence of an antibody described herein. For example, the differences may be primarily or entirely in the framework regions.

In certain embodiments, the amino acid differences are conservative amino acid differences (e.g., conservative amino acid substitutions). A "conservative" amino acid substitution is one in which the amino acid residue is replaced with an amino acid residue comprising a similar side chain. Families of amino acid residues comprising similar side chains have been defined in the art. These families include, e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (e.g., FR1, FR2, FR3, and/or FR4) of the HC and/or LC variable domain are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to corresponding framework regions of the HC and LC variable domains of an antibody described herein. In one embodiment, one or more heavy or light chain framework regions (e.g., HC FR1, FR2, and FR3) are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the sequence of corresponding framework regions from a human germline antibody.

Validation of Epitopes

In one embodiment, the antibodies featured in the disclosure are useful for validating a vaccine based on a particular epitope. For example, an epitope that is the target of an antibody featured in the disclosure can be assessed by computation methods to identify a peptide framework suitable for supporting the epitope conformation, such as to stabilize an epitope that is transient or minimally accessible in nature. Computational abstraction of the epitope and framework properties allows automated screening of databases to identify candidate acceptor peptide scaffolds. The acceptor scaffold can have a particular tertiary structure that includes, for example, one or more of a beta sheet, a beta sandwich, a loop, or an alpha or beta helix. The candidate epitope-scaffold antigens can be assayed in vitro, such as to identify binding properties with an antibody featured in the disclosure, e.g., binding affinity or structure analysis of the epitope-scaffold/antibody complex, or in vitro neutralization. The ability of the epitope-scaffold to generate an immune response (e.g., to generate antibodies) can be tested by administering the epitope-scaffold to an animal (e.g., in a mammal, such as a rat, a mouse, a guinea pig, or a rabbit), and then testing sera for the presence of anti-epitope-scaffold antibodies, e.g., by ELISA assay. The ability of the epitope-scaffold to elicit protection against infection by an influenza A Group 1 or Group 2 strain, or by both types of influenza strains, or an influenza B strain, can be assessed in vivo, such as in an animal (e.g., in a mammal). Thus, an antibody featured in the disclosure can provide validation that the epitope is functionally important and that targeting the epitope will provide protection from infection with a Group 1 or Group 2 influenza strain, or both types of strains, or an influenza B strain.

Production of Antibody Molecules

The nucleic acids (e.g., the genes) encoding an antibody molecule generated by a method described herein can be sequenced, and all or part of the nucleic acids can be cloned into a vector that expresses all or part of the nucleic acids. For example, the nucleic acids can include a fragment of the gene encoding the antibody, such as a single chain antibody (scFv), a $F(ab')_2$ fragment, a Fab fragment, or an Fd fragment. The disclosure also provides host cells comprising the nucleic acids encoding an antibody or fragment thereof as described herein. The host cells can be, for example, prokaryotic or eukaryotic cells, e.g., mammalian cells, or yeast cells, e.g., *Pichia* (see, e.g., Powers et al. (2001) *J. Immunol. Methods* 251:123-35), *Hanseula*, or *Saccharomyces*.

Antibody molecules, particularly full length antibody molecules, e.g., IgGs, can be produced in mammalian cells. Exemplary mammalian host cells for recombinant expression include Chinese Hamster Ovary (CHO) cells (including $dhfr^-$ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell. In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in $dhfr^-$ host cells with methotrexate selection/amplification) and the neo gene (for G418 selection).

In an exemplary system for recombinant expression of an antibody molecule (e.g., a full length antibody or an antigen-binding portion thereof), a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody molecule is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G. For example, purified antibodies can be concentrated to about 100 mg/mL to about 200 mg/mL using protein concentration techniques that are known in the art.

Antibody molecules can also be produced by a transgenic animal. For example, U.S. Pat. No. 5,849,992 describes a method for expressing an antibody molecule in the mammary gland of a transgenic mammal. A transgene is constructed that includes a milk-specific promoter and nucleic acid sequences encoding the antibody molecule of interest, e.g., an antibody described herein, and a signal sequence for secretion. The milk produced by females of such transgenic mammals includes, secreted therein, the antibody of interest, e.g., an antibody described herein. The antibody molecule can be purified from the milk, or for some applications, used directly. Antibody molecules can also be expressed in vivo, following administration of a vector containing nucleic acids encoding the antibody heavy chain and the antibody light chain. Vector mediated gene-transfer is then used to engineer secretion of the anti-HA antibody into circulation. For example, an anti-HA antibody heavy chain and an anti-HA antibody light chain as described herein are cloned into an adeno-associated virus (AAV)-based vector, and each of the anti-HA antibody heavy chain and the anti-HA antibody light chain are under control of a promoter, such as a cytomegalovirus (CMV) promoter. Administration of the vector to a subject, such as to a patient, e.g., a human patient, such as by intramuscular injection, results in expression of an anti-HA antibody, and secretion into the circulation.

Modifications of Binding Agents

Binding, agents, e.g., antibody molecules can be modified to have numerous properties, e.g., to have altered, e.g., extended half-life, to be associated with, e.g., covalently bound to detectable moieties, e.g., labels, to be associated with, e.g., covalently bound to toxins, or to have other properties, e.g., altered immune functions. Antibody molecules may include modifications, e.g., modifications that alter Fc function, e.g., to decrease or remove interaction with an Fc receptor or with Clq, or both. In one example, the human IgG1 constant region can be mutated at one or more residues.

For some antibody molecules that include an Fc domain, the antibody production system may be designed to synthesize antibody molecules in which the Fc region is glycosylated. The Fc domain can be produced in a mammalian expression system that appropriately glycosylates the residue corresponding to asparagine 297. The Fc domain can also include other eukaryotic post-translational modifications. Other suitable Fc domain modifications include those described in WO2004/029207. For example, the Fc domain can be an XmAb® Fc (Xencor, Monrovia, Calif.). The Fc domain, or a fragment thereof, can have a substitution in an Fcγ Receptor (FcγR) binding region, such as the domains and fragments described in WO05/063815. In some embodiments, the Fc domain, or a fragment thereof, has a substitution in a neonatal Fc Receptor (FcRn) binding region, such as the domains and fragments described in WO05047327. In other embodiments, the Fc domain is a single chain, or fragment thereof, or modified version thereof, such as those described in WO2008143954. Other suitable Fc modifications are known and described in the art.

Antibody molecules can be modified, e.g., with a moiety that improves its stabilization and/or retention in circulation, e.g., in blood, serum, lymph, bronchioalveolar lavage, or other tissues, e.g., by at least 1.5, 2, 5, 10, or 50 fold. For example, an antibody molecule generated by a method described herein can be associated with a polymer, e.g., a substantially non-antigenic polymer, such as a polyalkylene oxide or a polyethylene oxide. Suitable polymers will vary substantially by weight. Polymers comprising molecular number average weights ranging from about 200 to about 35,000 daltons (or about 1,000 to about 15,000, and 2,000 to about 12,500) can be used.

For example, an antibody molecule generated by a method described herein can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

Binding agents, e.g., antibody molecules, as disclosed herein, can by conjugated to another entity or moiety (e.g., to a cytotoxic or cytostatic moiety, a label or detectable moiety, or a therapeutic moiety). Exemplary moieties include: a cytotoxic or cytostatic agent, e.g., a therapeutic agent, a drug, a compound emitting radiation, molecules of plant, fungal, or bacterial origin, or a biological protein (e.g., a protein toxin) or particle (e.g., a recombinant viral particle, e.g., via a viral coat protein), a detectable agent; a pharmaceutical agent, and/or a protein or peptide that can mediate association of the antibody or antibody portion with another molecule (such as a streptavidin core region or a polyhistidine tag). A binding agent, e.g., an antibody molecule, as disclosed herein, can be functionally linked by any suitable method (e.g., chemical coupling, genetic fusion, covalent binding, noncovalent association or otherwise) to one or more other molecular entities.

Binding agents, e.g., antibody molecules, disclosed herein can be conjugated with a detectable moiety, e.g., a label or imaging agent. Such moieties can include enzymes (e.g., horseradish peroxidase, beta-galactosidase, luciferase, alkaline phosphatase, acetylcholinesterase, glucose oxidase and the like), radiolabels (e.g., $^{3}H$, $^{14}C$, $^{15}N$, $^{35}S$, $^{90}Y$, $^{99}Tc$, $^{111}In$, $^{125}I$, $^{131}I$ and the like), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, a moiety, e.g., a detectable moiety, e.g., a label, is attached by spacer arms of various lengths to reduce potential steric hindrance.

In some embodiments, a binding agent, e.g., antibody molecule, disclosed herein, is derivatized with a detectable enzyme and is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding agent, e.g., antibody molecule, disclosed herein, may also be derivatized with a prosthetic group (e.g., streptavidin/biotin and avidin/biotin). For example, an antibody may be derivatized with biotin, and detected through indirect measurement of avidin or streptavidin binding.

In some embodiments, the moiety comprises paramagnetic ions and NMR-detectable substances, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III). Binding agents, e.g., antibody molecules, as disclosed herein, can be modified to be associated with, e.g., conjugated to, a therapeutic agent, e.g., an agent comprising anti-viral activity, anti-inflammatory activity, or cytotoxic activity, etc. In some embodiments, therapeutic agents can treat symptoms or causes of influenza infection (e.g., for example, anti-viral, pain-relief, antiinflammatory, immuno-modulatory, sleep-inducing activities, etc).

Treatment Methods and Administration

The binding agents, e.g., antibody molecules, featured in the disclosure, can be used to treat a subject, e.g., a subject, e.g., a human subject, infected with, or at risk for becoming infected with, an influenza virus.

Any human is candidate to receive an antibody molecule featured in the disclosure for treatment or prevention of an infection by an influenza virus. Humans at high risk of infection, such as immunocompromised individuals, and humans who are at high risk of exposure to influenza virus are particularly suited to receive treatment with the antibody molecule. Immunocompromised individuals include the elderly (65 years and older) and children (e.g., 6 months to 18 years old), and people with chronic medical conditions. People at high risk of exposure include heath care workers, teachers and emergency responders (e.g., firefighters, policemen).

The antibody molecules described herein can also be used to prevent or reduce (e.g., minimize) secondary infection (e.g., secondary bacterial infection) or a risk of comprising secondary infection associated with influenza, or any effects (e.g., symptoms or complications) thereof on a subject. Opportunistic secondary bacterial infections (e.g., secondary bacterial pneumonia, e.g., primarily with *Streptococcus pneumonia*) contribute significantly to the overall morbidity and mortality associated with seasonal and pandemic influenza infections. The antibody molecules described herein can be used to prevent or reduce (e.g., minimize) the complications from secondary, opportunistic infections (e.g., bacterial infections) in a subject.

An antibody molecule can be administered to a subject, e.g., a human subject, by a variety of methods. For many applications, the route of administration is one of: intravenous injection or infusion, subcutaneous injection, or intramuscular injection. An antibody molecule can be administered as a fixed dose, or in a mg/kg dose. The antibody molecule can be administered intravenously (IV) or subcutaneously (SC). For example, the antibody molecule can be administered at a fixed unit dose of between about 50-600 mg IV, e.g., every 4 weeks, or between about 50-100 mg SC (e.g., 75 mg), e.g., at least once a week (e.g., twice a week). In one embodiment, the antibody molecule is administered IV at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more. Administration of the IV dose can be once or twice or three times or more per week, or once every two, three, four, or five weeks, or less frequently.

An anti-HA antibody molecule featured in the disclosure can also be administered intravenously, such as a fixed unit dose between 500 mg and 3000 mg, e.g., between 1000 mg and 3000 mg, between 1500 mg and 3000 mg, between 2000 mg and 3000 mg, between 1800 mg and 2500 mg, between 2500 mg and 3000 mg, between 500 mg and 2500 mg, between 500 mg and 2000 mg, between 500 mg and 1500 mg, between 500 mg and 1000 mg, between 1000 mg and 2500 mg, between 1500 mg and 2000 mg, or between 2000 mg and 2500 mg, e.g., 1500 mg, 1600 mg, 1700 mg, 1800 mg, 1900 mg, 2000 mg, 2100 mg, 2200 mg, 2300 mg, 2400 mg, or 2500 mg. In an embodiment, the antibody molecule is administered intravenously over a period of 1-3 hours, e.g., 1-2 hours or 2 to 3 hours, e.g., 2 hours. In an embodiment, the antibody molecule is administered as a single dose. In one embodiment, the antibody molecule is administered SC at a fixed unit dose of 50 mg, 60 mg, 70 mg, 75 mg, 80 mg, 100 mg, or 120 mg or more. Administration of the SC dose can be once or twice or three times or more per week, or once every two, three, four, or five weeks, or less frequently. An anti-HA antibody molecule featured in the disclosure can also be administered by inhalation, such as by intranasal or by oral inhalation, such as at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, or more.

In an embodiment, the antibody molecule is administered in an amount that does not cause an ADE in the subject, e.g., as determined by a method described herein. In an embodiment, the antibody molecule is administered in an amount that does not cause viral resistance, e.g., as determined by a method described herein. In one embodiment, an anti-HA antibody is administered to a subject via vector-mediated gene transfer, such as through the delivery of a vector encoding the heavy chain and the light chain of an anti-HA antibody, and the antibody is expressed from the heavy chain and light chain genes in the body. For example, nucleic acids encoding a heavy chain and a light chain can be cloned in a AAV vector, such as a self-complementary AAV vector, the scAAV vector administered to a human by injection, such as by IM injection, and the antibody is expressed and secreted into the circulation of the human.

An antibody molecule can also be administered in a bolus at a dose of between about 1 and 50 mg/kg, e.g., between about 1 and 10 mg/kg, between about 1 and 25 mg/kg or about 25 and 50 mg/kg, e.g., about 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg, or less. Modified dose ranges include a dose that is less than about 3000 mg/subject, about 1500 mg/subject, about 1000 mg/subject, about 600 mg/subject, about 500 mg/subject, about 400 mg/subject, about 300 mg/subject, about 250 mg/subject, about 200 mg/subject, or about 150 mg/subject, typically for administration every fourth week or once a month. The antibody molecule can be administered, for example, every three to five weeks, e.g., every fourth week, or monthly.

Dosing can be adjusted according to a patient's rate of clearance of a prior administration of the antibody. For example, a patient may not be administered a second or follow-on dose before the level of antibodies in the patient's system has dropped below a pre-determined level. In one embodiment, a sample from a patient (e.g., plasma, serum, blood, urine, or cerebrospinal fluid (CSF)) is assayed for the presence of antibodies, and if the level of antibodies is above a pre-determined level, the patient will not be administered a second or follow-on dose. If the level of antibodies in the patient's system is below a pre-determined level, then the patient is administered a second or follow-on dose. A patient whose antibody levels are determined to be too high (above the pre-determined level) can be tested again after one or two or three days, or a week, and if the level of antibody in the patient samples has dropped below the pre-determined level, the patient may be administered a second or follow-on dose of antibody.

In certain embodiments, the antibody may be prepared with a carrier that will protect the drug against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Controlled Drug Delivery (Drugs and the Pharmaceutical Sciences), Second Edition, J. Robinson and V. H. L. Lee, eds., Marcel Dekker, Inc., New York, 1987.

Pharmaceutical compositions can be administered with a medical device. For example, pharmaceutical compositions can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules are discussed in, e.g., U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system comprising multi-chamber compartments; and U.S. Pat. No. 4,475,196, which discloses an osmotic drug delivery system. Of course, many other such implants, delivery systems, and modules are also known. In some embodiments, the binding agent, e.g., an antibody molecule, is administered buccally, orally, or by nasal delivery, e.g., as a liquid, spray, or aerosol, e.g., by topical application, e.g., by a liquid or drops, or by inhalation.

An antibody molecule described herein can be administered with one or more additional therapeutic agents, e.g., a second drug, for treatment of a viral infection, or a symptom of the infection. The antibody molecule and the one or more second or additional agents can be formulated together, in the same formulation, or they can be in separate formulations, and administered to a patient simultaneously or sequentially, in either order.

Dosage regimens are adjusted to provide the desired response, such as a therapeutic response or a combinatorial therapeutic effect. Generally, any combination of doses (either separate or co-formulated) of an antibody molecule and a second or additional agent can be used in order to provide a subject with both agents in bioavailable quantities. Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with another agent.

A pharmaceutical composition may include a "therapeutically effective amount" of an agent described herein. In some embodiments, where the antibody molecule is administered in combination with a second or additional agent, such effective amounts can be determined based on the combinatorial effect of the administered first and second or additional agent. A therapeutically effective amount of an agent may also vary according to factors such as the disease state, age, sex, and weight of the individual, and the ability of the compound to elicit a desired response in the individual, such as amelioration of at least one infection parameter, or amelioration of at least one symptom of the infection, such as chills, fever, sore throat, muscle pain, headache, coughing, weakness, fatigue and general discomfort. A therapeutically effective amount is also one in which any toxic or detrimental effects of the composition are outweighed by the therapeutically beneficial effects.

In an embodiment, administration of a binding agent, e.g., antibody molecule, provided, e.g., as a pharmaceutical preparation, is by one of the following routes: oral, intravenous, intramuscular, intra-arterial, subcutaneous, intraventricular, transdermal, interdermal, rectal, intravaginal, intraperitoneal, topical (as by liquids, powders, ointments, creams, sprays, or drops), mucosal, nasal, buccal, enteral, sublingual; intratracheal instillation, bronchial instillation, and/or inhalation; and/or as an oral spray, nasal spray, and/or aerosol. In an embodiment, the method described herein further comprises determining the presence or absence of an anti-drug antibody (ADA) in the subject. In an embodiment, the subject is selected for administration of an antibody molecule described herein on the basis of the absence of an ADA in the subject. ADA can be detected, e.g., by ELISA, in a sample from the subject.

Combination Treatments and Exemplary Second or Additional Agents

Binding agents, e.g., antibody molecules, provided e.g., as pharmaceutical compositions, can be administered either alone or in combination with one or more other therapy, e.g., the administration of a second or additional therapeutic agent.

In some embodiments, the combination can result in a lower dose of the antibody molecule or of the other therapy being needed, which, in some embodiments, can reduce side effects. In some embodiments, the combination can result in enhanced delivery or efficacy of one or both agents. The agents or therapies can be administered at the same time (e.g., as a single formulation that is administered to a patient or as two separate formulations administered concurrently) or sequentially in any order. Such second or additional agents include vaccines, anti-viral agents, and/or additional antibodies. In typical embodiments the second or additional agent is not co-formulated with the binding agent, e.g., antibody molecule, though in others it is. In some embodiments, the binding agent, e.g., antibody molecule, and the second or additional agent are administered such that one or more of the following is achieved: therapeutic levels, or therapeutic effects, of one overlap the other; detectable levels of both are present at the same time; or the therapeutic effect is greater than what would be seen in the absence of either the binding agent, e.g., antibody molecule, or the second or additional agent. In some embodiments, each agent will be administered at a dose and on a time schedule determined for that agent.

The second or additional agent can be, for example, for treatment or prevention of influenza. For example, the binding agents, e.g., antibody molecules, e.g., therapeutic antibodies, provided herein can be administered in combination with a vaccine, e.g., a vaccine described herein or a mixture (a.k.a. a cocktail) of influenza peptides to stimulate the patient's immune system to prevent infection with particular strains of influenza A. In other examples, the second or additional agent is an anti-viral agent (e.g., an anti-NA or anti-M2 agent), a pain reliever, an anti-inflammatory, an antibiotic, a steroidal agent, a second therapeutic antibody molecule (e.g., an anti-HA antibody), an adjuvant, a protease or glycosidase (e.g., sialidase), etc.

Exemplary anti-viral agents include, e.g., vaccines, neuraminidase inhibitors or nucleoside analogs. Exemplary anti-viral agents can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (Relenza®), oseltamivir (Tamiflu®), laninamivir, peramivir), rimantadine. Exemplary second antibody molecules include, for example Ab 67-11 (U.S. Provisional application No. 61/645,453, FI6 (U.S. Application Publication No. 2010/0080813), FI28 (U.S. Application Publication No. 2010/0080813), C179 (Okuno et al., *J. Virol.* 67:2552-8, 1993), F10 (Sui et al., *Nat. Struct. Mol. Biol.* 16:265, 2009), CR9114 (Dreyfus et al., *Science* 337:1343, 2012), or CR6261 (Ekiert et al., *Science* 324:246, 2009). Thus, Ab 044 can be used in combination of any of those antibodies. In other embodiments, two or more binding agents, e.g., antibody molecules disclosed herein, can be administered in combination, e.g., Ab 044 can be administered in combination with Ab 032. In the case of combinations, two agents can be administered as part of the same dosage unit or administered separately. Other exemplary agents useful for treating the symptoms associated with influenza infection are acetaminophen, ibuprofen, aspirin, and naproxen.

In one embodiment, the antibody molecule and the second or additional agent are provided as a co-formulation, and the co-formulation is administered to the subject. It is further possible, e.g., at least 24 hours before or after administering the co-formulation, to administer separately one dose of the antibody formulation and then one dose of a formulation containing a second or additional agent. In another implementation, the antibody molecule and the second or additional agent are provided as separate formulations, and the step of administering includes sequentially administering the antibody molecule and the second or additional agent. The sequential administrations can be provided on the same day (e.g., within one hour of one another or at least 3, 6, or 12 hours apart) or on different days.

In some embodiments, the antibody molecule and the second or additional agent are each administered as a plurality of doses separated in time. The antibody molecule and the second or additional agent are generally each administered according to a regimen. The regimen for one or both may have a regular periodicity. The regimen for the antibody molecule can have a different periodicity from the regimen for the second or additional agent, e.g., one can be administered more frequently than the other. In one implementation, one of the antibody molecule and the second or additional agent is administered once weekly and the other once monthly. In another implementation, one of the antibody molecule and the second or additional agent is administered continuously, e.g., over a period of more than 30 minutes but less than 1, 2, 4, or 12 hours, and the other is administered as a bolus. In some embodiments, sequential administrations are administered. The time between administration of the one agent and another agent can be minutes, hours, days, or weeks. The use of an antibody molecule described herein can also be used to reduce the dosage of another therapy, e.g., to reduce the side-effects associated with another agent that is being administered. Accordingly, a combination can include administering a second or additional agent at a dosage at least 10, 20, 30, or 50% lower than would be used in the absence of the antibody molecule. The antibody molecule and the second or additional agent can be administered by any appropriate method, e.g., subcutaneously, intramuscularly, or intravenously.

In some embodiments, each of the antibody molecule and the second or additional agent is administered at the same dose as each is prescribed for monotherapy. In other embodiments, the antibody molecule is administered at a dosage that is equal to or less than an amount required for efficacy if administered alone. Likewise, the second or additional agent can be administered at a dosage that is equal to or less than an amount required for efficacy if administered alone. In some cases, the formulations described herein, e.g., formulations containing an antibody molecule featured in the disclosure, include one or more second or additional agents, or are administered in combination with a formulation containing one or more second or additional agents. In an embodiment a binding agent, e.g., antibody molecule, provided, e.g., as a pharmaceutical preparation, is administered by inhalation or aerosol delivery of a plurality of particles, e.g., particles comprising a mean particle size of 4, 5, 6, 7, 8, 9, 10, 11, 12, or 13 microns.

Pharmaceutical Compositions

The binding agents, e.g., antibody molecules, featured in the disclosure can be formulated as pharmaceutical compositions, such as for the treatment or prevention of influenza.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions comprising antibody molecules can be formulated according to methods known in the art. Pharmaceutical formulation is a well-established art, and is further described in Gennaro (ed.), Remington: The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

Pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions. Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular (IM), intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and by intrasternal injection or by infusion.

Pharmaceutical compositions may be provided in a sterile injectable form (e.g., a form that is suitable for subcutaneous injection or intravenous infusion). In some embodiments, pharmaceutical compositions are provided in a liquid dosage form that is suitable for injection or topical application. In some embodiments, pharmaceutical compositions are provided as in dry form, e.g., as powders (e.g. lyophilized and/or sterilized preparations). The Pharmaceutical composition can be provided under conditions that enhance stability, e.g., under nitrogen or under vacuum. Dry material can be reconstituted with an aqueous diluent (e.g., water, buffer, salt solution, etc.) prior to injection.

In one embodiment, the pharmaceutical composition containing an anti-HA antibody is administered intranasally. In another embodiment, the pharmaceutical composition containing an anti-HA antibody is administered by inhalation, such as by oral or by nasal inhalation. In some embodiments, the pharmaceutical composition is suitable for buccal, oral or nasal delivery, e.g., as a liquid, spray, or aerosol, e.g., by topical application, e.g., by a liquid or drops, or by inhalation). In some embodiments, a pharmaceutical preparation comprises a plurality of particles, suitable, e.g., for inhaled or aerosol delivery. In some embodiments, the mean particle size of 4, 5, 6, 7, 8, 9, 10, 11, 12, or 13 microns. In some embodiments, a pharmaceutical preparation is formulated as a dry powder, suitable, e.g., for inhaled or aerosol delivery. In some embodiments, a pharmaceutical preparation is formulated as a wet powder, through inclusion of a wetting agent, e.g., water, saline, or other liquid of physiological pH. In some embodiments, a pharmaceutical preparation is provided as drops, suitable, e.g., for delivery to the nasal or buccal cavity. In some embodiments, the pharmaceutical composition is disposed in a delivery device, e.g., a syringe, a dropper or dropper bottle, an inhaler, or a metered dose device, e.g., an inhaler.

In one embodiment, a pharmaceutical composition contains a vector, such as an adenovirus-associated virus (AAV)-based vector, that encodes a heavy chain of an anti-HA antibody molecule, and a light chain of an anti-HA antibody molecule featured in the disclosure. The composition containing the vector can be administered to a subject, such as a patient, such as by injection, e.g., IM injection. Genes encoding the anti-HA antibody under control of, for example, cytomegalovirus (CMV) promoters, are expressed in the body, and the recombinant anti-HA antibody molecule is introduced into the circulation. See, e.g., Balazs et al., *Nature* 30:481:81-84, 2011.

Pharmaceutical compositions typically should be sterile and stable under the conditions of manufacture and storage. A pharmaceutical composition can also be tested to insure it meets regulatory and industry standards for administration. The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A pharmaceutical composition may be provided, prepared, packaged, and/or sold in bulk, as a single unit dose, and/or as a plurality of single unit doses. Typically a bulk preparation will contain at least 2, 5, 10, 20, 50, or 100 unit doses. A unit dose is typically the amount introduced into the patient in a single administration. In some embodiments, only a portion of a unit dose is introduced. In some embodiments, a small multiple, e.g., as much as 1.5, 2, 3, 5, or 10 times a unit dose is administered. The amount of the active ingredient is generally equal to a dose which would be administered to a subject and/or a convenient fraction of such a dose such as, for example, one-half or one-third of such a dose.

Immunogens and Vaccines

Antibodies of the invention have elucidated epitopes that are useful for inducing immunity to, and in some embodiments, provide protection from, one or more, e.g., at least two, influenza strains. These epitopes are referred to herein as "broad range immunogens." As used herein, the term "broad range vaccine" refers to a preparation comprising a broad range immunogen, or a nucleic acid encoding a broad range immunogen, that can induce formation of antibodies or immunity against the broad range immunogen or an organism, e.g., an influenza virus. Additional immunogens and vaccines, and uses thereof, are described in International Publication No. WO2013/170139 or U.S. Application Publication No. 2013/0302349, the contents of which are hereby incorporated by reference in their entirety.

Epitope

HAs exist in nature as homotrimers of proteolytically processed mature subunits. Each subunit of the trimer is synthesized as a precursor. A precursor molecule is proteolytically processed into two disulfide bonded polypeptide chains to form a mature HA polypeptide. The mature HA polypeptide includes two domains: (1) a core HA-1 domain that extends from the base of the molecule through the fibrous stem to the membrane distal head region that contains the glycan receptor binding domain, returning to fibrous region ending in the cleavage site, and (2) HA-2 domain that includes the stem region and the transmembrane domain of HA. HA-1 includes a glycan binding site. The glycan binding site may be responsible for mediating binding of HA to the HA-receptor. The HA-2 domain acts to present the HA-1 domain. The HA trimer can be stabilized by polar and non-polar interactions between the three long HA alpha-helices of the stem of HA monomers.

HA sequences from all influenza subtypes share a set of amino acids in the interface of the HA-1 and HA-2 domains that are well conserved. The HA-1/HA-2 interface membrane proximal epitope region (MPER) that includes the canonical a-helix and residues in its vicinity are also conserved across a broad spectrum of subtypes. (Ekiert et al., Science., 324(5924):246, 2009; Sui et al., Nat Struct Mol Biol. 16(3):265, 2009).

Ab 044 has high affinity for HA's from Group 1 and Group 2. It binds a conformational epitope that is broadly conserved across a plurality of influenza strains. Numerous amino acid residues distributed along the linear sequences of HA from different strains/subtypes contribute the Ab 044 conformational epitope. The interaction of Ab 044 with H3 was analyzed by docking studies and residues bound by (or not bound by) Ab 044 were identified. The Fv of Ab 044 was docked against HA of group I and II strains using ZDOCK. The structure of the HA antigen was modeled using the SWISS MODEL homology modeling server keeping the solved crystal structure of H1N1 as the template. ZDOCK uses shape complementarity along with desolvation and electrostatic energy terms ('ZRANK') to rank docked poses. To ensure the docked poses do not deviate significantly from the native complex, mapped epitope and paratope residues by alanine scanning are forced to be included in the binding interface.

For comparison studies, amino acids that bind (or do not bind) FI6 were taken from published US patent application US 2011/0274702 A1, Neutralizing Anti-Influenza A Virus Antibodies and Uses Thereof, filed Jul. 18, 2011.

ZDOCK is a Fast Fourier Transform based protein docking program. It was developed by Zhiping Weng at the University of Massachusetts Medical School. In ZDOCK, two PDB files are input and the output is the predicted structure of their complex. The program searches all possible binding modes in the translational and rotational space between the two proteins and evaluates each by an energy scoring function. The protein's structure is converted to a digital signal and a Fast Fourier Transform technique used to reduce computational time. ZDOCK is discussed in Pierce B G, Hourai Y, Weng Z. (2011) Accelerating Protein Docking in ZDOCK Using an Advanced 3D Convolution Library. PLoS One 6(9): e24657, Pierce B, Tong W, Weng Z. (2005) M-ZDOCK: A Grid-based Approach for C Symmetric Multimer Docking. Bioinformatics 21(8): 1472-1476; Mintseris J, Pierce B, Wiehe K, Anderson R, Chen R, Weng Z. (2007) Integrating Statistical Pair Potentials into Protein Complex Prediction. Proteins 69(3): 511-520; and Chen R, Li L, Weng Z. (2003) ZDOCK: An Initial-stage Protein Docking Algorithm. Proteins 52(1): 80-7.

SWISS-MODEL is a fully automated protein structure homology-modeling server. It is accessible via the ExPASy web server, or from the program DeepView (Swiss Pdb-Viewer). Swiss-Model is discussed in Arnold K., Bordoli L., Kopp J., and Schwede T. (2006). The SWISS-MODEL Workspace: A web-based environment for protein structure homology modelling. Bioinformatics, 22, 195-201; Kiefer F, Arnold K, Kunzli M, Bordoli L, Schwede T (2009). The SWISS-MODEL Repository and associated resources. *Nucleic Acids Research.* 37, D387-D392; and Peitsch, M. C. (1995) Protein modeling by E-mail Bio/Technology 13: 658-660.

H3 residues that bind Ab 044 and H3 residues that bind FI6 are discussed below.

H3 HA1

The amino acid sequence of H3 HA1 is provided below, as SEQ ID NO: 173. Residues N38, I278, and D291 shown in dashed boxes, are bound by Ab 044 but not by FI6; Residues Q327, T328, and R329 shown in dotted boxes, are bound by FI6 but not by Ab 044; residues T318, R321, and V323 shown in solid boxes, are bound by both Ab 044 and FI6.

```
                                               (SEQ ID NO: 173)
QDLPGNDNST ATLCLGHHAV PNGTLVKTIT DDQIEVTNAT
ELVQSSSTGK ICNNPHRILD GIDCTLIDAL LGDPHCDVFQ
NETWDLFVER SKAFSNCYPY DVPDYASLRS LVASSGTLEF
ITEGFTWTGV TQNGGSNACK RGPGSGFFSR LNWLTKSGST
YPVLNVTMPN NDNFDKLYIW GIHHPSTNQE QTSLYVQASG
RVTVSTRRSQ QTIIPNIGSR PWVRGLSSRI SIYWTIVKPG
DVLVINSNGN LIAPRGYFKM RTGKSSIMRS DAPIDTCISE
CITPNGSIPN DKPFQNVNKI TYGACPKYVK QNTLKLATGM
RNVPEKQTR
```

H3 HA2

The amino acid sequence of H3 HA21 is provided below, as SEQ ID NO: 174 Residue N12 shown in a dash box, is bound by Ab 044 but not by FI6; Residues G1, L2, F3, G4, and D46 shown in dotted boxes, are bound by FI6 but not by Ab 044; residues A7, E11, I18, D19, G20, W21, L38, K39, T41, Q42, A43, I45, I48, N49, L52, N53, I56, and E57, shown in solid boxes, are bound by both Ab 044 and FI6.

```
                                               (SEQ ID NO: 174)
GLFGAIAGFI ENGWEGMIDG WYGFRHQNSE GTGQAADLKS
TQAAIDQING KLNRVIEKTN EKFHQIEKEF SEVEGRIQDL
EKYVEDTKID LWSYNAELLV ALENQHTIDL TDSEMNKLFE
KTRRQLRENA EEMGNGCFKI YHKCDNACIE SIRNGTYDHD
VYRDEALNNR FQIKG
```

H1 residues that bind Ab 044 and H1 residues that bind FI6 are discussed below.

H1 HA1

The amino acid sequence of H1 HA1 is provided below, as SEQ ID NO: 181. Residues H31, N279, and S292 shown in dashed boxes, are bound by Ab 044 but not by FI6. Residues Q328 and S329 shown in dotted boxes, are bound by FI6 but not by Ab 044. Residues T319, R322, and I324 shown in solid boxes, are bound by both Ab 044 and FI6.

```
                                               (SEQ ID NO: 181)
     TNADTI CIGYHANNST DTVDTVLEKN VTVTHSVNLL
EDSHNGKLCK LKGIAPLQLG KCNIAGWLLG NPECDLLLTA
SSWSYIVETS NSENGTCYPG DFIDYEELRE QLSSVSSFEK
FEIFPKTSSW PNHETTKGVT AACSYAGASS FYRNLLWLTK
KGSSYPKLSK SYVNNKGKEV LVLWGVHHPP TGTDQQSLYQ
NADAYVSVGS SKYNRRFTPE IAARPKVRDQ AGRMNYYWTL
LEPGDTITFE ATGNLIAPWY AFALNRGSGS GIITSDAPVH
DCNTKCQTPH GAINSSLPFQ NIHPVTIGEC PKYVRSTKLR
MATGLRNIPS IQS
```

H1 HA2

The amino acid sequence of H1 HA2 is provided below, as SEQ ID NO: 182. Residues G12 shown in a dashed box, is bound by Ab 044 but not by FI6. Residues G1, L2, F3, G4, and D46 shown in dotted boxes, are bound by FI6 but not by Ab 044. Residues A7, E11, 118, D19, G20, W21, Q38, K39, T41, Q42, N43, I45, I48, T49, V52, N53, I56, and E57 shown in solid boxes, are bound by both Ab 044 and FI6.

```
                                      (SEQ ID NO: 182)
GLFGAIAGF IEGGWTGMID GWYGYHHQNE QGSGYAADQK

STQNAIDGIT NKVNSVIEKM NTQFTAVGKE FNNLERRIEN

LNKKVDDGFL DIWTYNAELL VLLENERTLD FHDSNVRNLY

EKVKSQLKNN AKEIGNGCFE FYHKCDDACM ESVRNGTYDY

PKYSEESKLN REEIDGVKLE SMGVYQILAI YSTVASSLVL

LVSLGAISFW MCSNGSLQCR ICI
```

A three dimensional representation of H3 HA with the amino acids residues that are predicted to be part of Ab 044 epitope but not part of FI6's epitope highlighted (i.e., the highlighted amino acids are unique to Ab 044's epitope) is depicted in FIG. 26 of International Publication No. WO2013/170139 or U.S. Application Publication No. 2013/0302349. A three dimensional representation of H3 HA with the amino acid residues that are part of FI6's epitope but not predicted to be part of Ab 044's epitope highlighted is depicted in FIG. 27 of International Publication No. WO2013/170139 or U.S. Application Publication No. 2013/0302349.

Diagnostic Methods

The methods described herein can further include a diagnostic step as described herein. The binding agents, e.g., antibody molecules, provided herein are useful for identifying the presence of influenza in a biological sample, e.g., a patient sample, such as a fluid sample, e.g., a blood, serum, saliva, mucous, or urine sample, or a tissue sample, such as a biopsy. In one embodiment, a patient sample is contacted with a binding agent, e.g., an antibody molecule, featured in the disclosure, and binding is detected. Binding can be detected with a number of formats and means of detection, e.g., with an antigen capture assay, such as an ELISA assay or Western blot, or an immunohistochemistry assay. In some embodiments, the binding agent, e.g., an antibody molecule, is provided, e.g., coupled to an insoluble matrix, e.g., a bead or other substrate, and a detection molecule used to detect binding of HA.

Binding of binding agent, e.g., antibody molecule, to HA, can be detected with a reagent comprising a detectable moiety, e.g., a reagent, e.g., an antibody, which binds the binding agent, e.g., antibody molecule. In some embodiments, the binding agent, e.g., antibody molecule, has a detectable moiety. Suitable detectable moieties include enzymes (e.g., horseradish peroxidase, beta-galactosidase, luciferase, alkaline phosphatase, acetylcholinesterase, glucose oxidase and the like), radiolabels (e.g., $^{3}H$, $^{14}C$, $^{15}N$, $^{35}S$, $^{90}Y$, $^{99}Tc$, $^{111}In$, $^{125}I$, $^{113}I$), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, labels are attached by spacer arms of various lengths to reduce potential steric hindrance.

In some embodiments, a human is tested for presence of influenza virus be a method described herein, and if the test is positive, a binding agents, e.g., antibody molecules, e.g., an antibody, provided herein, is administered. The binding agents, e.g., antibody molecules, e.g., an antibody, provided herein can be used for cytology assays, such as to identify an HA in a cell. The assay can be a colorimetric assay. A biological sample from a normal (non-infected) individual is used as a control. The diagnostic assay can be performed in vitro. The diagnostic assay can also be performed to determine infection of cells in culture, e.g., of mammalian cells in culture. The antibody molecules can be used in in vitro assays.

Because the antibody molecules featured herein bind a broad spectrum of HA subtypes, the diagnostic assays featured in the disclosure can detect the presence of influenza virus in patients infected with a variety of distinct strains of influenza. A patient sample can be further tested with subtype specific antibodies, or other assays (e.g., RFLP (Restriction Fragment Length Polymorphism), PCR (Polymerase Chain Reaction), RT-PCR (Reverse Transcription coupled to Polymerase Chain Reaction), Northern blot, Southern blot or DNA sequencing) to further determine the particular strain of virus. In one embodiment, a patient determined to be infected with influenza A can be further administered an antibody molecule featured in the disclosure, to treat the infection. Also provided are solid substrates, e.g., beads, dipsticks, arrays, and the like, on which is disposed a binding agent, e.g., antibody molecule.

Kits

A binding agent, e.g., an antibody molecule, disclosed herein, e.g., generated by the methods described herein, can be provided in a kit, e.g., for use in a method described herein. The kit can include one or more other components, e.g., containers, buffers or other diluents, delivery devices, and the like.

In one embodiment, the kit includes materials for administering an antibody molecule to a subject, such as for treatment or prevention of infection by influenza viruses. For example, the kit can include one or more or all of: (a) a container that contains a composition that includes an antibody molecule, optionally (b) a container that contains a composition that includes a second therapeutic agent, and optionally (c) informational material. In another embodiment, the kit includes materials for using an antibody molecule in a diagnostic assay, such as for detection of HA in a biological sample. For example, the kit can include one or more or all of: (a) a container that contains a composition that includes an antibody molecule, optionally (b) a container that contains a reagents, e.g., labeled with a detectable moiety, to detect the antibody, e.g., for use in an ELISA or immunohistochemistry assay, and optionally (c) informational material. In other embodiments, the kit comprises a binding agent, e.g., antibody molecule, comprising a detectable moiety.

In an embodiment, the kit comprises a solid substrate, e.g., bead, dipstick, array, and the like, on which is disposed a binding agent, e.g., antibody molecule. The informational material can be descriptive, instructional, marketing or other material that relates to the methods described herein and/or the use of the agents for therapeutic benefit, or for a diagnostic assay. The informational material of the kits is not limited in its form. In one embodiment, the informational material can include information about production of the antibody, concentration, date of expiration, batch or production site information, and so forth. In one embodiment, the informational material relates to methods of administering the antibody, e.g., in a suitable dose, dosage form, or mode of administration (e.g., a dose, dosage form, or mode of administration described herein), to treat a subject who has an infection, e.g., viral infection or secondary infection (e.g., secondary bacterial infection). In another embodiment, the informational material relates to methods for using the antibody molecule for a diagnostic assay, e.g., to detect the presence of influenza viruses in a biological sample. The information can be provided in a variety of formats, including printed text, computer readable material, video recording, or audio recording, or information that provides a link or address to substantive material. In addition to the agent, the composition in the kit can include other ingredients, such as a solvent or buffer, a stabilizer, or a preservative. The agent can be provided in any form, e.g., a liquid, dried or lyophilized form, and substantially pure and/or sterile. When the agents are provided in a liquid solution, the liquid solution typically is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the antibody molecule and the second or additional agent, such as in a desired ratio. For example, the kit can include a plurality of syringes, ampoules, foil packets, blister packs, or medical devices each containing, for example, a single combination unit dose. The containers of the kits can be air tight, waterproof (e.g., impermeable to changes in moisture or evaporation), and/or light-tight.

The kit optionally includes a device suitable for administering the composition, e.g., a syringe or device for delivering particles or aerosols, e.g., an inhaler, a spray device, or a dropper or other suitable delivery device. The device can be provided pre-loaded with one or both of the agents or can be empty but suitable for loading. The invention is further illustrated by the following examples, which should not be construed as further limiting.

OTHER EMBODIMENTS

The antibody molecule described herein can be encoded by a nucleic acid molecule, e.g., an isolated nucleic acid molecule. In an embodiment, the nucleic acid molecule comprises a nucleotide sequence that encodes a heavy chain immunoglobulin variable region segment featured in the disclosure. In another embodiment, the nucleic acid molecule comprises a nucleotide sequence encoding a light chain immunoglobulin variable region segment featured in the disclosure. In yet another aspect, the nucleic acid molecule comprises a nucleotide sequence that encodes a heavy chain immunoglobulin variable region segment featured in the disclosure and a light chain immunoglobulin variable region segment featured in the disclosure. In an embodiment, the nucleic acid molecule is present in a vector, e.g., a recombinant vector (e.g., an expression vector). In an embodiment, the vector comprises a nucleic acid molecule that comprises a nucleotide sequence that encodes a heavy chain immunoglobulin variable region segment featured in the disclosure, a nucleotide sequence that encodes a light chain immunoglobulin variable region segment featured in the disclosure, or both. In one embodiment, the nucleic acid molecule in the recombinant vector includes a nucleotide sequence encoding (a) a heavy chain immunoglobulin variable region segment comprising the amino acid sequence of: S-Y-A-M-H (SEQ ID NO:68) in CDR1; V-V-S-Y-D-G-N-Y-K-Y-Y-A-D-S-V-Q-G (SEQ ID NO:69) in CDR2; and D-S-R-L-R-S-L-L-Y-F-E-W-L-S-Q-G-Y-F-N-P (SEQ ID NO:70) in CDR3; and (b) a light chain immunoglobulin variable region segment comprising the amino acid sequence of: Q-S-I-T-F-D-Y-K-N-Y-L-A (SEQ ID NO:145) in CDR1; W-G-S-Y-L-E-S (SEQ ID NO:72) in CDR2; and Q-Q-H-Y-R-T-P-P-S (SEQ ID NO:73) in CDR3.

In an embodiment, the antibody molecule described herein is produced from a cell containing a recombinant vector featured in the disclosure, such as a recombinant vector comprising a nucleic acid sequence that encodes a heavy chain immunoglobulin variable region, or a recombinant vector comprising a nucleic acid sequence that encodes a light chain immunoglobulin variable region. In one embodiment, the cell contains a recombinant vector comprising a nucleic acid sequence that encodes a heavy chain immunoglobulin variable region, and a recombinant vector comprising a nucleic acid sequence that encodes a light chain immunoglobulin variable region. In yet another embodiment, the cell contains a recombinant vector comprising a nucleic acid sequence that encodes a heavy chain immunoglobulin variable region, and a nucleic acid sequence that encodes a light chain immunoglobulin variable region. In an embodiment, the antibody molecule is produced, e.g., by providing a host cell comprising a nucleic acid sequence expressing a heavy chain segment and a nucleic acid sequence expressing a light chain segment, and expressing the nucleic acids in the host cell. In one embodiment, the nucleic acid sequence expressing the heavy chain segment and the nucleic acid sequence expressing the light chain segment are on the same recombinant expression vector. In another embodiment, the nucleic acid sequence expressing the heavy chain segment and the nucleic acid sequence expressing the light chain segment are on separate recombinant expression vectors.

In an embodiment, a pharmaceutical composition containing an antibody molecule featured in the disclosure, and a pharmaceutically acceptable carrier, is used in a method described herein.

In an embodiment, the method described herein treats or prevents an infection with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010), in a subject, e.g., a human subject, that comprises: administering a binding agent, e.g., an antibody molecule, featured in the disclosure to a subject, e.g., human subject, in need thereof. In one embodiment, the influenza A virus is an H1, H5, H9, H3 or H7 strain, such as an H1N1 strain, an H3N2 strain, or an H5N1 strain of influenza A virus. In an embodiment, the administration results in, or correlates with, one or more of a reduction in the incidence or severity of a symptom or manifestation of an influenza infection, or the delay or onset of a symptom or manifestation of an influenza infection. In an embodiment, the administration results in, or correlates with, one or more of a reduction in the incidence or severity of a symptom or manifestation of a secondary infection, or the delay or onset of a symptom or manifestation of a secondary infection. In some embodiments, the subject, e.g., a human subject, has been administered, or the method comprises, administering, or recommending the administration of, a second or additional therapy.

In some embodiments, the antibody molecule is administered in combination with a second or additional agent or therapy. In some embodiments, the second or additional therapy comprises administration of a vaccine or an antiviral therapy, e.g., an anti-NA or an anti-M2 therapy. In an embodiment, the second or additional therapy comprises an administration of a vaccine, e.g., a vaccine described herein or a mixture (a.k.a. a cocktail) of influenza peptides to stimulate the patient's immune system to prevent infection with particular strains of influenza A. In an embodiment, the second or additional agent comprises administering an antiviral agent, a pain reliever, an anti-inflammatory, an antibiotic, a steroidal agent, a second therapeutic antibody molecule (e.g., an anti-HA antibody), an adjuvant, a protease or glycosidase (e.g., sialidase). In an embodiment, the second or additional agent comprises, acyclovir, ribavirin, amantadine, remantidine, a neuraminidase inhibitor (e.g., zanamivir (Relenza®), oseltamivir (Tamiflu®), laninamivir, peramivir), or rimantadine.

In an embodiment, the second or additional agent comprises a second antibody molecule, e.g., Ab 67-11 (U.S. Provisional application No. 61/645,453, FI6 (U.S. Application Publication No. 2010/0080813), FI28 (U.S. Application Publication No. 2010/0080813), C179 (Okuno et al., *J. Virol.* 67:2552-8, 1993), F10 (Sui et al., *Nat. Struct. Mol. Biol.* 16:265, 2009), CR9114 (Dreyfus et al., *Science* 337: 1343, 2012), or CR6261 (see, e.g., Ekiert et al., *Science* 324:246, 2009). Thus, Ab 044 can be used in combination of any of those antibodies. In an embodiment, the second or additional agent comprises a second or additional binding agent, e.g., antibody molecule, e.g., an anti-HA antibody, e.g., an anti-HA antibody disclosed herein. E.g., two or more of Ab 044, Ab 069, Ab 032, and Ab 031 can be administered. E.g., Ab 044 can be administered in combination with Ab 069 or Ab 032. In the case of combinations, two agents can be administered as part of the same dosage unit or administered separately. Other exemplary agents useful for treating the symptoms associated with influenza infection are acetaminophen, ibuprofen, aspirin, and naproxen.

In an embodiment, the binding agent, e.g., an antibody molecule, is administered to a human subject suffering from or susceptible to an influenza infection. In an embodiment, the binding agent, e.g., an antibody molecule, is administered prior to known exposure to influenza, or to particular influenza subtypes or strains. In an embodiment, the binding agent, e.g., an antibody molecule, is administered prior to manifestation of effects or symptoms of influenza infection, or to one or more particular effects manifestation of effects or symptoms of influenza infection. In an embodiment, the binding agent, e.g., an antibody molecule, is administered after known exposure to influenza, or to particular influenza subtypes or strains. In an embodiment, the binding agent, e.g., an antibody molecule, is administered after manifestation of effects or symptoms of influenza infection, or after observation of one or more particular effects manifestation of effects or symptoms of influenza infection. In an embodiment, the binding agent, e.g., an antibody molecule, is administered in response to, or to treat or prevent, a manifestation of an effect or a symptom of influenza infection, e.g., inflammation, fever, nausea, weight loss, loss of appetite, rapid breathing, increase heart rate, high blood pressure, body aches, muscle pain, eye pain, fatigue, malaise, dry cough, runny nose, and/or sore throat.

In an embodiment, the method further comprises, testing the human subject for the influenza virus, e.g., with a method disclosed herein. In some embodiments, the administration is responsive to a positive test for influenza.

In an embodiment, the method described herein treats a subject, e.g., a human subject, an infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010) by administering a binding agent, e.g., an antibody molecule, featured in the disclosure. For example, the influenza A virus is an H1, H5, H9, H3 or H7 strain, such as an H1N1 strain, an H3N2 strain, or an H5N1 strain of influenza A virus. In one embodiment, a binding agent, e.g., an anti-HA antibody, described herein is administered instead of a vaccine for prevention of influenza. In another embodiment, the binding agent, e.g., anti-HA antibody molecule, is administered in combination with (simultaneously or sequentially with) a vaccine for prevention of the flu.

In an embodiment, the method further comprises detecting influenza (e.g., influenza A or influenza B) virions in a biological sample, such as by contacting the sample with a binding agent, e.g., an antibody molecule, featured in the disclosure, and then detecting the binding of the antibody molecule to the sample. In one embodiment, the method of detecting the influenza virus (e.g., influenza A or influenza B virus) is performed in vitro.

In an embodiment, the method further includes: (a) providing a sample from a patient; (b) contacting the sample with a binding agent, e.g., an antibody molecule, featured in the disclosure, and (c) determining whether the binding agent, e.g., an antibody molecule, featured in the disclosure binds a polypeptide in the sample, where if the binding agent, e.g., an antibody molecule, binds a polypeptide in the sample, then the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/ 2004, or an influenza B virus, e.g., e.g., B/Wisconsin/1/ 2010). In one embodiment, the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/ 04/2009, or an H5N1 strain, e.g., A/Indonesia/5/2005 or A/Vietnam/1203/2004, or an influenza B virus, e.g., B/Wisconsin/1/2010), and the patient is further administered a binding agent, e.g., an antibody molecule, disclosed herein, e.g., the binding agent, e.g., an antibody molecule, with which the test was performed.

In an embodiment, the method further includes inducing immunity to one or more influenza strains, or preventing, delaying or reducing infection with an influenza strain, or symptom thereof, in a vertebrate, e.g., a human. The method comprises administering to the vertebrate, e.g., a human, a broad range vaccine, or broad range immunogen, described herein.

In an embodiment, the broad range vaccine, or broad range immunogen, induces an immune response against, or confers protection against, one or more influenza strains. In an embodiment, the broad range vaccine, or broad range immunogen, induces an immune response against, or confers protection against, two influenza strains. In an embodiment, the broad range vaccine, or broad range immunogen, induces an immune response against, or confers protection against, two Group 1 influenza strains. In an embodiment, the broad range vaccine induces, or broad range immunogen, an immune response against, or confers protection against, at least one Group 1 strain, and a second strain from Group 1, Group 2 or an influenza B strain. In one embodiment, the influenza A virus is an H1, H5, H9, H3 or H7 strain, such as an H1N1 strain, an H3N2 strain, or an H5N1 strain of influenza A virus.

In an embodiment, the administration results in, or correlates with, one or more of: a reduction in the chance of an infection, a reduction in the incidence or severity of a symptom or manifestation of an influenza infection, or the delay or onset of a symptom or manifestation of an influenza infection. In an embodiment, the administration results in, or correlates with, one or more of: a reduction in the incidence or severity of a symptom or manifestation of a secondary infection, or the delay or onset of a symptom or manifestation of a secondary infection.

In some embodiments, the subject, e.g., a human subject, has been administered, or the method comprises, administering, or recommending the administration of, a second or additional therapy. In some embodiments, the broad range vaccine is administered in combination with a second or additional agent or therapy. In some embodiments, the second or additional agent comprises administration of another vaccine or another anti-viral therapy, e.g., an anti-NA or an anti-M2 therapy. In an embodiment, the second or additional agent comprises administration of a vaccine comprising a mixture (a.k.a. a cocktail) of influenza peptides to stimulate the patient's immune system to prevent infection with particular strains of influenza A. In an embodiment, the second or additional agent comprises administering an anti-viral agent, a pain reliever, an anti-inflammatory, an antibiotic, a steroidal agent, a second therapeutic antibody molecule (e.g., an anti-HA antibody), an adjuvant, a protease or glycosidase (e.g., sialidase). In an embodiment, the second or additional agent comprises, acyclovir, ribavirin, amantadine, remantidine, a neuraminidase inhibitor (e.g., zanamivir (Relenza®), oseltamivir (Tamiflu®), laninamivir, peramivir), or rimantadine. In an embodiment, the second or additional agent comprises an antibody molecule, e.g., Ab 67-11 (U.S. Provisional application No. 61/645,453, FI6 (U.S. Application Publication No. 2010/0080813), FI28 (U.S. Application Publication No. 2010/0080813), C179 (Okuno et al., *J. Virol.* 67:2552-8, 1993), F10 (Sui et al., *Nat. Struct. Mol. Biol.* 16:265, 2009), CR9114 (Dreyfus et al., *Science* 337:1343, 2012), or CR6261 (Ekiert et al., *Science* 324:246, 2009). In an embodiment, the second or additional agent comprises an antibody molecule disclosed herein, e.g., an antibody molecule selected from Ab-044, Ab 069, Ab 032, and Ab 031 antibody molecules. In the case of combinations, two agents can be administered as part of the same dosage unit or administered separately. Other exemplary second or additional agents useful for treating the symptoms associated with influenza infection are acetaminophen, ibuprofen, aspirin, and naproxen.

In an embodiment, the method further comprises, testing the human subject for the influenza virus, e.g., with a method disclosed herein. In some embodiments, the administration is responsive to a positive test for influenza. In an embodiment, the method further comprises reducing the severity of influenza in a population. The method includes administering a broad range vaccine, or broad range immunogen, to sufficient individuals in the population to prevent or decrease the chance of influenza virus transmission to another individual in the population.

Anti-HA antibody molecules described herein are also disclosed in International Publication No. WO2013/170139, U.S. Pat. Nos. 8,877,200, 9,096,657, and U.S. Patent Application Publication No. US 2013/0302349. The contents of the aforesaid publications are incorporated by reference in their entirety.

TABLE 4C

Nucleic acid and amino acid sequences

| SEQ ID NO. | Lab no. | Source | Comment | Sequence |
|---|---|---|---|---|
| 1 | n.a. | Table 2 | Consensus AA sequence of HC CDR1 | [S/T]Y[A/G]MH |
| 2 | n.a. | Table 2 | Consensus AA sequence of HC CDR2 | V[I/V/L]S[Y/F]DG[S/N][Y/N][K/R]YYADSVQG |
| 3 | n.a. | Table 2 | Consensus AA sequence of HC CDR3 | D[S/T][R/K/Q]LR[S/T]LLYFEWLS[Q/S]S[Y/L/V][F/L][N/D][P/Y] |
| 4 | n.a. | Table 2 | Consensus AA sequence of LC CDR1 | Q[S/T][V/L/I][T/S][Y/F/W][N/S/D]YKNYLA |
| 170 | n.a. | Table 2 | Consensus AA sequence of LC CDR1 | Q[S/T][V/L/I][T/S][Y/F/W][N/S/D/Q/R/E]YKNYLA |
| 5 | n.a. | Table 2 | Consensus AA sequence of LC CDR2 | W[A/G]S[T/A/Y/H/K/D][R/L]E[S/T] |
| 6 | n.a. | Table 2 | Consensus AA sequence of LC CDR3 | QQ[Y/H]YRTPP[T/S] |
| 7 | n.a. | Table 2 | Consensus AA sequence of HC FR1 | [E/Q]VQLLE[S/T]GGGLVKPGQSLKLSCAASGFTF[S/T] |
| 8 | n.a. | Table 2 | Consensus AA sequence of HC FR2 | WVRQPPGKGLEWVA |
| 9 | n.a. | Table 2 | Consensus AA sequence of HC FR3 | RFTISRDNSKNTLYLQMNSLRAEDTAVYYCAK |
| 10 | n.a. | Table 2 | Consensus AA sequence of HC FR4 | WG[A/Q][G[T/A][T/M][L/V]TVSS |
| 11 | n.a. | Table 2 | Consensus AA sequence of LC FR1 | [E/D][V/Q]MTQSP[D/S][S/T][L/V][A/S][V/A][S/T][L/V/R][G[E/D]R[A/V][T/S]I[N/T/Q/D/R/]C[K/R]SS |
| 12 | n.a. | Table 2 | Consensus AA sequence of LC FR2 | WYQQKPG[Q/K][P/A]PKLLIY |
| 13 | n.a. | Table 2 | Consensus AA sequence of LC FR3 | GVP[D/E/S]RFSGSGSGTDFTLTISSLQ[A/P]ED[V/F/K/D]A[V/T]YYC |
| 14 | n.a. | Table 2 | Consensus AA sequence of LC FR4 | FG[G/Q/T/S/N]GTK[L/V][D/E]IK |
| 15 | 15 VH15 | Table 4A, Table 4A, FIG. 2 | Table 3, AA sequence of HC VR of Ab A18; entire HC domain is in FIG. 1; ID version is in FIG. 13; NT sequence is in Example 1 | EVQLLESGGGLVKPGQSLKLSCAASGFTFTSYGMHWVRQPPGKGLEWVAVISYDGSYKYYADSVQGRFTISRDNSKNTLYLQMNSL RAEDTAVYYCAKDSRLRSLLYFEWLSQYFNPWGAGTTLTVSS |
| 28 | 28 VL28 | Table 4A, FIG. 3 | Table 3, AA sequence of LC VR of Ab A18; entire LC Table 4A domain is in FIG. 1; ID version is in FIG. 14; NT sequence is in Example 1 | EIVMTQSPDSLAVSLGERATINCKSSQSVTNYKNYLAWYQQKPGQPPKLLIYWASTRESGVPDRFSGSGSGTDFTLTISSLQAED VAVYYCQQYYRTPPTFGGGTKLDIK |
| 16 | 16 VH16 | Table 4A, FIG. 2 | Table 3, AA sequence of HC VR of Abs 014,028; ID Table 4A version is in FIG. 13; NT sequence is in Example 1 | EVQLLESGGGLVKPGQSLKLSCAASGFTFSSYGMHWVRQPPGKGLEWVAVVSYDGSNKYYADSVQGRFTISRDNSKNTLYLQMNSL RAEDTAVYYCAKDTKLRSLLYFEWLSSGLLDYWGQGAMVTSS |

TABLE 4C-continued

Nucleic acid and amino acid sequences

| SEQ ID NO. | Lab no. | Source Comment | Sequence |
|---|---|---|---|
| 29 | 29 VL29 | Table 3 AA sequence of LC VR of Abs 014, 154, 157; Table 4A ID version is in FIG. 14; NT sequence is in FIG. 3 Example 1 | EIVMTQSPDSLAVSLGERATINCKSSQVTFSYKNYLAWYQQKPGQPPKLLIYWASTRESGVPDRFSGSGSGTDFTLTISSLQAED VAVYYCQQYRTPPTFGGGTKLDIK |
| 30 | 30 VL30 | Table 3 AA sequence of LC VR of Abs 028, 155; ID Table 4A version is in FIG. 14; NT sequence is in FIG. 3 Example 1 | EIVMTQSPDSLAVSLGERATINCKSSQVTFDYKNYLAWYQQKPGQPPKLLIYWASTRESGVPDRFSGSGSGTDFTLTISSLQAED VAVYYCQQYRTPPTFGGGTKLDIK |
| 17 | 17 VH17 | Table 3 AA sequence of HC VR of Abs 001, 009, 017, Table 4A 025, 160, 186, 187, 188, 189, 190, 191, 192, FIG. 2 193, 202, 211; ID version is in FIG. 13. | EVQLLESGGGLVKPGQSLKLSCAASGFTFTSYGMHWRQPPGKGLEWVAVVSYDGNYKYYADSVQGRFTISRDNSKNTLYLQMNSL RAEDTAVYYCAKDSRLRSLLYFEWLSQGYFNPWGAGTTLTVSS |
| 31 | 31 VL31 | Table 3 AA sequence of LC VR of Abs 001, 002, 003; Table 4A ID version is in FIG. 14; FIG. 3 | EIVMTQSPDSLAVSLGERATINCKSSQVTVTFNYKNYLAWYQQKPGQPPKLLIYWASTRESGVPDRFSGSGSGTDFTLTISSLQAED VAVYYCQQHYRTPPSFGGGTKLDIK |
| 18 | 18 VH18 | Table 3 AA sequence of HC VR of Abs 002, 010, B18, Table 4A 026, 203, 212; ID version is in FIG. 13. FIG. 2 | EVQLLESGGGLVKPGQSLKLSCAASGFTFTSYGMHWRQPPGKGLEWVAVLSYDGNYKYYADSVQGRFTISRDNSKNTLYLQMNSL RAEDTAVYYCAKDSRLRSLLYFEWLSQGYFNPWGAGTTLTVSS |
| 19 | 19 VH19 | Table 3 AA sequence of HC VR of Abs 003, 011, 019, Table 4A 027, 194, 195, 196, 197, 198, 199, 200, 204, FIG. 2 213; ID version is in FIG. 13. | EVQLLESGGGLVKPGQSLKLSCAASGFTFTYAMHWRQPPGKGLEWVAVLSYDGNYKYYADSVQGRFTISRDNSKNTLYLQMNSL RAEDTAVYYCAKDSRLRSLLYFEWLSQGYFNPWGAGTTLTVSS |
| 32 | 32 VL32 | Table 3 AA sequence of LC VR of Abs 009, 010, 011, Table 4A ID version is in FIG. 14; FIG. 3 | EIVMTQSPDSLAVSLGERATINCKSSQTLSFNYKNYLAWYQQKPGQPPKLLIYWASTRESGVPDRFSGSGSGTDFTLTISSLQAED VAVYYCQQHYRTPPSFGGGTKLDIK |
| 33 | 33 VL33 | Table 3 AA sequence of LC VR of Abs 017, B18, 019; Table 4A ID version is in FIG. 14; FIG. 3 | EIVMTQSPDSLAVSLGERATINCKSSQTVTFNYKNYLAWYQQKPGQPPKLLIYFASTRESGVPDRFSGSGSGTDFTLTISSLQAED VAVYYCQQHYRTPPSFGGGTKLDIK |
| 34 | 34 VL34 | Table 3 AA sequence of LC VR of Abs 025, 026, 027, Table 4A 086; ID version is in FIG. 14; FIG. 3 | EIVMTQSPDSLAVSLGERATINCKSSQTLSFNYKNYLAWYQQKPGQPPKLLIYFASTRESGVPDRFSGSGSGTDFTLTISSLQAED VAVYYCQQHYRTPPSFGGGTKLDIK |
| 20 | 20 VH20 | Table 3 AA sequence of HC VR of Ab 086; ID version Table 4A is in FIG. 13. FIG. 2 | EVQLLESGGGLVKPGQSLKLSCAASGFTFTTYAMHWRQPPGKGLEWVAVVSFDGNNRYYADSVQGRFTISRDNSKNTLYLQMNSL RAEDTAVYYCAKDSQLRSLLYFEWLSSGVLDIWGQGAMVTVSS |
| 21 | 21 VH21 | Table 3 AA sequence of HC VR of Abs 154, 155; ID Table 4A version is in FIG. 13. FIG. 2 | EVQLLESGGGLVKPGQSLKLSCAASGFTFSSYGMHWRQPPGKGLEWVAVVSYDGNNKYYADSVQGRFTISRDNSKNTLYLQMNSL RAEDTAVYYCAKDSKLRSLLYFEWLSSGLLDIWGQGAMVTVSS |
| 22 | 22 VH22 | Table 3 AA sequence of HC VR of Abs 157, 159; ID Table 4A version is in FIG. 13. FIG. 2 | EVQLLESGGGLVKPGQSLKLSCAASGFTFTYAMHWRQPPGKGLEWVAVVSYDGNNKYYADSVQGRFTISRDNSKNTLYLQMNSL RAEDTAVYYCAKDSKLRSLLYFEWLSSGLLDIWGQGAMVTVSS |

TABLE 4C-continued

Nucleic acid and amino acid sequences

| SEQ ID NO. | Lab no. | Source Comment | Sequence |
|---|---|---|---|
| 35 | VL35 | Table 3 AA sequence of LC VR of Ab 159; ID version Table 4A is in FIG. 14; FIG. 3 | EIVMTQSPDSLAVSLGERATINCKSSQVTWSYKNYLAWYQQKPGQPPKLLIYWASTRESGVPDRFSGSGSGTDFTLTISSLQAED VAVYYCQQYYRTPPTFGGGTKLDIK |
| 36 | VL36 | Table 3 AA sequence of LC VR of Ab 160; ID version Table 4A is in FIG. 14; FIG. 3 | EIVMSQSPDTLAVTLGERASINCKSSQVTFNYKNYLAWYQQKPGQPPKVLIYWASARETGVPERFSGSGSGTDFTLTISSLQAED VAVYYCQQHYRTPPSFQGTKLEIK |
| 37 | VL37 | Table 3 AA sequence of LC VR of Abs 186, 194; ID Table 4A version is in FIG. 14; FIG. 3 | EIVMTQSPDSLAVSLGERATINCKSSQVTFNYKNYLAWYQQKPGQPPKLLIYWASTRESGVPDRFSGSGSGTDFTLTISSLQAED VAVYYCQQHYRTPPSFGTGTKLDIK |
| 38 | VL38 | Table 3 AA sequence of LC VR of Abs 187, 195; ID Table 4A version is in FIG. 14; FIG. 3 | EIVMTQSPDSLAVSLGERATINCKSSQVTFNYKNYLAWYQQKPGQPPKLLIYWASTRESGVPDRFSGSGSGTDFTLTISSLQAED VAVYYCQQHYRTPPSFGSGSGTKLDIK |
| 39 | VL39 | Table 3 AA sequence of LC VR of Abs 188, 196; ID Table 4A version is in FIG. 14; FIG. 3 | EIVMTQSPDSLAVSLGERATINCKSSQVTFNYKNYLAWYQQKPGQPPKLLIYWASTRESGVPDRFSGSGSGTDFTLTISSLQAED VAVYYCQQHYRTPPSFGQGTKLDIK |
| 40 | VL40 | Table 3 AA sequence of LC VR of Abs 189, 197; ID Table 4A version is in FIG. 14; FIG. 3 | EIVMTQSPDSLAVSLGERATINCKSSQVTFNYKNYLAWYQQKPGQPPKLLIYWASTRESGVPDRFSGSGSGTDFTLTISSLQAED VAVYYCQQHYRTPPSFGNGTKLDIK |
| 41 | VL41 | Table 3 AA sequence of LC VR of Abs 190, 198; ID Table 4A version is in FIG. 14; FIG. 3 | EIVMTQSPDSLAVSLGERATINCKSSQTLSFNYKNYLAWYQQKPGQPPKLLIYWASTRESGVPDRFSGSGSGTDFTLTISSLQAED VAVYYCQQHYRTPPSFGTGTKLDIK |
| 42 | VL42 | Table 3 AA sequence of LC VR of Abs 191, 199; ID Table 4A version is in FIG. 14; FIG. 3 | EIVMTQSPDSLAVSLGERATINCKSSQTLSFNYKNYLAWYQQKPGQPPKLLIYWASTRESGVPDRFSGSGSGTDFTLTISSLQAED VAVYYCQQHYRTPPSFGSGSGTKLDIK |
| 43 | VL43 | Table 3 AA sequence of LC VR of Abs 192, 200; ID Table 4A version is in FIG. 14; FIG. 3 | EIVMTQSPDSLAVSLGERATINCKSSQTLSFNYKNYLAWYQQKPGQPPKLLIYWASTRESGVPDRFSGSGSGTDFTLTISSLQAED VAVYYCQQHYRTPPSFGQGTKLDIK |
| 44 | VL44 | Table 3 AA sequence of LC VR of Abs 193; ID Table 4A version is in FIG. 14; FIG. 3 | EIVMTQSPDSLAVSLGERATINCKSSQTLSFNYKNYLAWYQQKPGQPPKLLIYWASTRESGVPDRFSGSGSGTDFTLTISSLQAED VAVYYCQQHYRTPPSFGNGTKLDIK |
| 45 | VL45 | Table 3 AA sequence of LC VR of Abs 202, 203, 204, Table 4A210, 031, 032, 033, 034; ID version is in FIG. 14; NT sequence is in Example 1 FIG. 3 | DIQMTQSPSSLSASVGDRVTITCRSSQSITFNYKNYLAWYQQKPGKAPKLLIYWGSYLESGVPSRFSGSGSGTDFTLTISSLQPED FATYYCQQHYRTPPSFQGTKVEIK |
| 46 | VL46 | Table 3 AA sequence of LC VR of Abs 211, 212, 213, Table 4A219, 037, 038, 039, 040; ID version is in FIG. 14; FIG. 3 | DIQMTQSPSSLSASVGDRVTITCRSSQSITFNYKNYLGWYQQKPGKAPKLLIYWGSYLESGVPSRFSGSGSGTDFTLTISSLQPED FATYYCQQHYRTPPSFQGTKVEIK |

TABLE 4C-continued

Nucleic acid and amino acid sequences

| SEQ ID NO. | Lab no. | Source | Comment | Sequence |
|---|---|---|---|---|
| 23 | 23 VH23 | Table 3 Table 4A FIG. 2 | AA sequence of HC VR of Abs 210, 219; ID version is in FIG. 13; | EVQLLESGGGLVKPGQSLKLSCAASGFTFTSYGMHWVRQPPGKGLEWVAVVSYDGNYKYYADSVQGRFTISRDNSKNTLYLQMNSL RAEDTAVYYCAKDSKLRSLLYFEWLSQGYFNPWGAGTTLTVSS |
| 24 | 24 VH24 | Table 3 Table 4AA003, A010, A011, 031, 037; ID version is in FIG. 2 FIG. 13; NT sequence is in Example 1 | AA sequence of HC VR of Abs A001, A002, | EVQLLESGGGLVKPGQSLKLSCAASGFTFTSYAMHWVRQPPGKGLEWVAVVSYDGNYKYYADSVQGRFTISRDNSKNTLYLQMNSL RAEDTAVYYCAKDSRLRSLLYFEWLSQGYFNPWGQGTTLTVSS |
| 47 | 47 VL47 | Table 3 Table 4A007, 016; ID version is in FIG. 14; FIG. 3 | AA sequence of LC VR of Abs A001, 004, | DIVMTQSPDTLAVTLGERATIQCKSSQTVTFNYKNYLAWYQQKPGQPPKLLIYWASTRESGVPDRFSGSGSGTDFTLTITSLQAED VAVYYCQQHYRTPPSFGQGTKLDIK |
| 48 | 48 VL48 | Table 3 Table 4AA017; ID version is in FIG. 14; FIG. 3 | AA sequence of LC VR of Abs 002, 005, 008, | DIVMTQSPDTVAVTVGERATINCKSSQTVTFNYKNYLAWYQQKPGQPPKLLIYWASTRESGVPDRFSGSGSGTDFTLTISSLQAED VAVYYCQQHYRTPPSFGQGTKLDIK |
| 25 | 25 VH25 | Table 3 Table 4A 012, 013, 032, 038, 043, 044, 045, 046, 047, FIG. 2 048, 049, 050, 051, 052, 067, 068, 069, 070, 073, 074, 075, 076, 077; ID version is in FIG. 13; NT sequence is in Example 1 | AA sequence of HC VR of Abs 004, 005, 006, | QVQLLETGGGLVKPGQSLKLSCAASGFTFTSYAMHWVRQPPGKGLEWVAVVSYDGNYKYYADSVQGRFTISRDNSKNTLYLQMNSL RAEDTAVYYCAKDSRLRSLLYFEWLSQGYFNPWGQGTTLTVSS |
| 49 | 49 VL49 | Table 3 Table 4AA009, C18; ID version is in FIG. 14; FIG. 3 | AA sequence of LC VR of Abs A003, 006, | DIVMTQSPDTVAVTLGERATIDCKSSQTVTFNYKNYLAWYQQKPGQPPKLLIYWASTRESGVPDRFSGSGSGTDFTLTISSLQAED VAVYYCQQHYRTPPSFGQGTKLDIK |
| 26 | 26 VH26 | Table 3 Table 4AA009, A14, 015, 033, 039; ID version is in FIG. 2 FIG. 13; | AA sequence of HC VR of Abs 007, 008, | EVQLLESGGGLVKPGQSLKLSCAASGFTFTSYAMHWVRQPPGKGLEWVAVVSYDGNYKYYADSVQGRFTISRDNSKNTLYLQMNSL RAEDTAVYYCAKDSQLRTLLYFEWLSQGYFNPWGQGTTLTVSS |
| 50 | 50 VL50 | Table 3 Table 4AA14, A019; ID version is in FIG. 14; FIG. 3 | AA sequence of LC VR of Abs A010 012, | DIVMTQSPDTLAVTVGERATIRCKSSQTVTFNYKNYLAWYQQKPGQPPKLLIYWASTRESGVPDRFSGSGSGTDFTLTISSLQAED VAVYYCQQHYRTPPSFGQGTKLDIK |
| 51 | 51 VL51 | Table 3 Table 4A015; ID version is in FIG. 14; FIG. 3 | AA sequence of LC VR of Ab A011, 013, | DIVMTQSPDTLAVSRGERATIDCKSSQTVTFNYKNYLAWYQQKPGQPPKLLIYWASTRESGVPDRFSGSGSGTDFTLTISSLQAED EAVYYCQQHYRTPPSFGQGTKLDIK |
| 27 | 27 VH27 | Table 3 Table 4AC18, A019, 034, 040; ID version is in FIG. FIG. 2 13; | AA sequence of HC VR of Abs 016, A017, | EVQLLESGGGLVKPGQSLKLSCAASGFTFTSYAMHWVRQPPGKGLEWVAVVSYDGNYKYYADSVQGRFTISRDNSKNTLYLQMNSL RAEDTAVYYCAKDSRLRTLLYFEWLSQGYFDPWGQGTTLTVSS |
| 60 | 60 VL60 | Table 3 Table 4A is in FIG. 14; FIG. 3 | AA sequence of LC VR of Ab 043; ID version | DIQMTQSPSSLSASVGDRVTITCRSSQSITFNYKNYLAWYQQKPAPKLLIWGSYLESGVPSRFSGSGSGTDFTLTISSLQPED FATYYCQQYRITPPSFGQGTKVEIK |

TABLE 4C-continued

Nucleic acid and amino acid sequences

| SEQ ID NO. | Lab no. | Source | Comment | Sequence |
|---|---|---|---|---|
| 52 | VL52 | Table 3 FIG. 3 | AA sequence of LC VR of Abs 044, 071, 072, 4A 078; ID version is in FIG. 14; NT sequence is in Example 1 | DIQMTQSPSSLSASVGDRVTITCRSSQSITFDYKNYLAWYQQKPGKAPKLLIYWGSYLESGVPSRFSGSGSGTDFTLTISSLQPED FATYYCQQHYRTPPSFGQGTKVEIK |
| 57 | VL57 | Table 3 Table 4A is in FIG. 14; FIG. 3 | AA sequence of LC VR of Ab 045; ID version | DIQMTQSPSSLSASVGDRVTITCRSSQSITFNYKNYLAWYQQKPGKAPKLLIYWGSYLESGVPSRFSGSGSGTDFTLTISSLQPED VATYYCQQHYRTPPSFGQGTKVEIK |
| 59 | VL59 | Table 3 Table 4A is in FIG. 14; FIG. 3 | AA sequence of LC VR of Ab 046; ID version | DIQMTQSPSSLSASVGDRVTITCRSSQSITFNYKNYLAWYQQKPGKAPKLLIYWGSYLESGVPSRFSGSGSGTDFTLTISSLQPED DATYYCQQHYRTPPSFGQGTKVEIK |
| 55 | VL55 | Table 3 Table 4A is in FIG. 14; FIG. 3 | AA sequence of LC VR of Ab 047; ID version | DIQMTQSPSSLSASVGDRVTITCRSSQSITFNYKNYLAWYQQKPGKAPKLLIYWGSKLESGVPSRFSGSGSGTDFTLTISSLQPED FATYYCQQHYRTPPSFGQGTKVEIK |
| 58 | VL58 | Table 3 Table 4A is in FIG. 14; FIG. 3 | AA sequence of LC VR of Ab 048; ID version | DIQMTQSPSSLSASVGDRVTITCRSSQSITFNYKNYLAWYQQKPGKAPKLLIYWGSHLESGVPSRFSGSGSGTDFTLTISSLQPED KATYYCQQHYRTPPSFGQGTKVEIK |
| 54 | VL54 | Table 3 Table 4A is in FIG. 14; FIG. 3 | AA sequence of LC VR of Ab 049; ID version | DIQMTQSPSSLSASVGDRVTITCRSSQSITFNYKNYLAWYQQKPGKAPKLLIYWGSDLESGVPSRFSGSGSGTDFTLTISSLQPED FATYYCQQHYRTPPSFGQGTKVEIK |
| 56 | VL56 | Table 3 Table 4A is in FIG. 14; FIG. 3 | AA sequence of LC VR of Ab 050; ID version | DIQMTQSPSSLSASVGDRVTITCRSSQSITFNYKNYLAWYQQKPGKAPKLLIYWGSTLESGVPSRFSGSGSGTDFTLTISSLQPED FATYYCQQHYRTPPSFGQGTKVEIK |
| 53 | VL53 | Table 3 Table 4A is in FIG. 14; FIG. 3 | AA sequence of LC VR of Ab 051; ID version | DIQMTQSPSSLSASVGDRVTITCRSSQSITFNYKNYLAWYQQKPGKAPKLLIYWGSTRESGVPSRFSGSGSGTDFTLTISSLQPED FATYYCQQHYRTPPSFGQGTKVEIK |
| 61 | VL61 | Table 3 Table 4A is in FIG. 14; FIG. 3 | AA sequence of LC VR of Ab 052; ID version | DIQMTQSPSSLSASVGDRVTITCRSSQSITFNYQYKNYLAWYQQKPGKAPKLLIYWGSYLESGVPSRFSGSGSGTDFTLTISSLQPED FATYYCQQHYRTPPSFGQGTKVEIK |
| 153 | VL153 | Table 3 Table 4A is in FIG. 14; FIG. 3 | AA sequence of LC VR of Ab 067; ID version | DIQMTQSPSSLSASVGDRVTITCRSSQSITFRYKNYLAWYQQKPGKAPKLLIYWGSYLESGVPSRFSGSGSGTDFTLTISSLQPED FATYYCQQHYRTPPSFGQGTKVEIK |
| 154 | VL154 | Table 3 Table 4A is in FIG. 14; FIG. 3 | AA sequence of LC VR of Ab 068; ID version | DIQMTQSPSSLSASVGDRVTITCRSSQSITFEYKNYLAWYQQKPGKAPKLLIYWGSYLESGVPSRFSGSGSGTDFTLTISSLQPED FATYYCQQHYRTPPSFGQGTKVEIK |
| 155 | VL155 | Table 3 Table 4A version is in FIG. 14; FIG. 3 | AA sequence of LC VR of Abs 069, 079; ID | DIQMTQSPSSLSASVGDRVTITCRSSQSITFEYKNYLAWYQQKPGKAPKLLIYWGSYLESGVPSRFSGSGSGTDFTLTISSLQPED FATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 156 | 156 VL156 | Table 3 Table 4A FIG. 3 | AA sequence of LC VR of Ab 070; ID version 4A is in FIG. 14; | DIQMTQSPSSLSASVGDRVTITCRSSQSITFDYKNYLAWYQQKPGKAPKLLIYWGSTRESGVPSRFSGSGSGTDFTLTISSLQPED FATYYCQQHYRTPPSFGQGTKVEIK |
| 162 | 162 VL162 | Table 3 Table 4A FIG. 17 | AA sequence of HC VR of Ab 071 | EVQLLESGGGLVKPGQSLKLSCAASGFSFSTYAMHWVRQPPGKGLEWVAVVSYDGNYKYYADTVQGRFTISRDNSKNTLYLQMNSL RAEDTAVYYCAKDSRLRSLLYFEWLSQGYFNPWGQGTTLTVSS |
| 163 | 163 VL163 | Table 3 Table 4A FIG. 17 | AA sequence of HC VR of Ab 072 | EVQLLESGGGLRKPGQSLKLSCAASGFSFSTYAMHWVRQPPGKGLEWVAVVSYDGNYKYYADSVQGRFTISRDNSKNTLYLQMNSL RAEDTAVYYCAKDSRLRSLLYFEWLSQGYFNPWGQGTTLTVSS |
| 165 | 165 VL165 | Table 3 Table 4A FIG. 17 | AA sequence of LC VR of Ab 073 | DIQMTQSPSSLSASVGDRVTITCRSSQSITWDYKNYLAWYQQKPGKAPKLLIYWGSYLESGVPSRFSGSGSGTDFTLTISSLQPED FATYYCQQHYRTPPSFGQGTKVEIK |
| 166 | 166 VL166 | Table 3 Table 4A FIG. 17 | AA sequence of LC VR of Ab 074, 080 | DIQMTQSPSSLSASVGDRVTITCRSSQSITWDYKNYLAWYQQKPGKAPKLLIYWGSYLESGVPSRFSGSGSGTDFTLTISSLQPED FATYYCQQHYRTPPSFGQGTKVEIK |
| 167 | 167 VL167 | Table 3 Table 4A FIG. 17 | AA sequence of LC VR of Ab 075 | DIQMTQSPSSLSASVGDRVTITCRSSQSITWQYKNYLAWYQQKPGKAPKLLIYWGSYLESGVPSRFSGSGSGTDFTLTISSLQPED FATYYCQQHYRTPPSFGQGTKVEIK |
| 168 | 168 VL168 | Table 3 Table 4A FIG. 17 | AA sequence of LC VR of Ab 076 | DIQMTQSPSSLSASVGDRVTITCRSSQSITWRYKNYLAWYQQKPGKAPKLLIYWGSYLESGVPSRFSGSGSGTDFTLTISSLQPED FATYYCQQHYRTPPSFGQGTKVEIK |
| 169 | 169 VL169 | Table 3 Table 4A FIG. 17 | AA sequence of LC VR of Abs 077, 081 | DIQMTQSPSSLSASVGDRVTITCRSSQSITWEYKNYLAWYQQKPGKAPKLLIYWGSYLESGVPSRFSGSGSGTDFTLTISSLQPED FATYYCQQHYRTPPSFGQGTKVEIK |
| 164 | 164 HC161 | Table 3 Table 4A FIG. 17 | AA sequence of HC VR of Abs 078, 079, 080, 081 | QVQLLETGGGLVKPGQSLKLSCAASGFTFTSYAMHWVRQPPGKGLEWVAVVSYDGNYKYYADSVQGRFTISRDNSKNTLYLQMNSL RAEDTAVYYCAKDSKLRSLLYFEWLSSGLLDVWGQGAMVTVSS |
| 161 | HC161 | Table 3 FIG. 2 | AAA sequence of HC VR consensus; ID version is in FIG. 13; | EVQLLESGGGLVKPGQSLKLSCAASGFTFSSYGMHWVRQPPGKGLEWVAVVSYDGSNKYYADSVQGRFTISRDNSKNTLYLQMNSL RAEDTAVYYCAKDSKLRSLLYFEWLSSGLLDVWGQGAMVTVSS |
| 62 | LC62 | Table 3 FIG. 3 | AAA sequence of LC VR consensus; ID version is in FIG. 14; | DIQMTQSPSSLSASVGDRVTITCRSSQSITFNYKNYLAWYQQKPGKAPKLLIYWGSYLESGVPSRFSGSGSGTDFTLTISSLQPED FATYYCQQHYRTPPSFGQGTKVEIK |
| 96 | 15-ID | Table 4B FIG. 13 | AA sequence of HC VR of Ab A18; non-ID version is in FIG. 2; | IDEVQLLESGGGLVKPGQSLKLSCAASGFTFTSYGMHWVRQPPGKGLEWVAVISYDGSYKYYADSVQGSYKYYADSVQGRFTISRDNSKNTLYLQMN SLRAEDTAVYYCAKDSRLRSLLYFEWLSQGYFNPWGAGTTLTVSS |
| 110 | 28-ID | Table 4B FIG. 14 | AA sequence of LC VR of Ab A18; non-ID version is in FIG. 3 | IDEIVMTQSPDSLAVSLGERATINCKSSQSVTYNYKNYLAWYQQKPGQPPKLLIYWASTRESGVPDRFSGSGSGTDFTLTISSLQA EDVAVYYCQQYRTPPTFGGGTKLDIK |

TABLE 4C-continued

Nucleic acid and amino acid sequences

| SEQ ID NO. | Lab ID no. | Source Comment | Sequence |
|---|---|---|---|
| 97 | 16-ID | Table 4B AA sequence of HC VR of Abs 014, 028; non-FIG. 13 ID version is in FIG. 2; | IDEVQLLESGGGLVKPGQSLKLSCAASGFTFSSYGMHWVRQPPGKGLEWVAVVSYDGSNKYYADSVQGRFTISRDNSKNTLYLQMN SLRAEDTAVYYCAKDTKLRSLLYFEWLSSGLLDYWGQAMVTVSS |
| 111 | 29-ID | Table 4B AA sequence of LC VR of Abs 014, 154,157; FIG. 14 non-ID version is in FIG. 3; | IDEIVMTQSPDSLAVSLGERATINCKSSQSVTFSYKNYLAWYQQKPGQPPKLLIYWASTRESGVPDRFSGSGSGTDFTLTISSLQA EDVAVYYCQQYYRTPPTFGGGTKLDIK |
| 98 | 17-ID | Table 4B AA sequence of HC VR of Abs 001, 009, 017, FIG. 13 025, 160, 186, 187, 188, 189, 190, 191, 192, 193, 202, 211; non-ID version is in FIG. 2; | IDEVQLLESGGGLVKPGQSLKLSCAASGFTFTSYGMHWVRQPPGKGLEWVAVVSYDGNYKYYADSVQGRFTISRDNSKNTLYLQMN SLRAEDTAVYYCAKDSRLRSLLYFEWLSQGYFNPWGAGTTLTVSS |
| 112 | 30-ID | Table 4B AA sequence of LC VR of Abs 028, 155; non-FIG. 14 ID version is in FIG. 3; | IDEIVMTQSPDSLAVSLGERATINCKSSQSVTFPDYKNYLAWYQQKPGQPPKLLIYWASTREGVPDRFSGSGSGTDFTLTISSLQA EDVAVYYCQQYYRTPPTFGGGTKLDIK |
| 99 | 18-ID | Table 4B AA sequence of HC VR of Abs 002, 010, B18, FIG. 13 026, 203, 212; non-ID version is in FIG. 2; | IDEVQLLESGGGLVKPGQSLKLSCAASGFTFTSYGMHWVRQPPGKGLEWVAVLSYDGNYKYYADSVQGRFTISRDNSKNTLYLQMN SLRAEDTAVYYCAKDSRLRSLLYFEWLSQGYFNPWGAGTTLTVSS |
| 113 | 35-ID | Table 4B AA sequence of LC VR of Ab 159; non-ID FIG. 14 version is in FIG. 3; | IDEIVMTQSPDSLAVSLGERATINCKSSQSVTWSYKNYLAWYQQKPGQPPKLLIYWASTRESGVPDRFSGSGSGTDFTLTISSLQA EDVAVYYCQQYYRTPPTFGGGTKLDIK |
| 100 | 19-ID | Table 4B AA sequence of HC VR of Abs 003, 011, 019, FIG. 13 027, 194, 195, 196, 197, 198, 199, 200, 204, 213; non-ID version is in FIG. 2; | IDEVQLLESGGGLVKPGQSLKLSCAASGFTFTTYAMHWVRQPPGKGLEWVAVLSYDGNNKYYADSVQGRFTISRDNSKNTLYLQMN SLRAEDTAVYYCAKDSRLRSLLYFEWLSQGYFNPWGAGTTLTVSS |
| 114 | 31-ID | Table 4B AA sequence of LC VR of Abs 001, 002, 003; FIG. 14 non-ID version is in FIG. 3; | IDEIVMTQSPDSLAVSLGERATINCKSSQTVTFNYKNYLAWYQQKPGQPPKLLIYWASTREGVPDRFSGSGSGTDFTLTISSLQA EDVAVYYCQQHYRTPSFGGGTKLDIK |
| 101 | 21-ID | Table 4B AA sequence of HC VR of Abs 154, 155; non-FIG. 13 ID version is in FIG. 2; | IDEVQLLESGGGLVKPGQSLKLSCAASGFTFSSYGMHWVRQPPGKGLEWVAVVSYDGNNKYYADSVQGRFTISRDNSKNTLYLQMN SLRAEDTAVYYCAKDSRLRSLLYFEWLSSGLLDYWGGAMVTVSS |
| 115 | 32-ID | Table 4B AA sequence of LC VR of Abs 009, 010, 011; FIG. 14 non-ID version is in FIG. 3; | IDEIVMTQSPDSLAVSLGERATINCKSSQTLSFNYKNYLAWYQQKPGQPPKLLIYWASTRESGVPDRFSGSGSGTDFTLTISSLQA EDVAVYYCQQHYRTPPTFGGGTKLDIK |
| 102 | 22-ID | Table 4B AA sequence of HC VR of Abs 157, 159; non-FIG. 13 ID version is in FIG. 2; | IDEVQLLESGGGLVKPGQSLKLSCAASGFTFTTYAMHWVRQPPGKGLEWVAVLSYDGNNKYYADSVQGRFTISRDNSKNTLYLQMN SLRAEDTAVYYCAKDSRLRSLLYFEWLSQGYFNPWGGAMVTVSS |
| 116 | 33-ID | Table 4B AA sequence of LC VR of Abs 017, B18, 019; FIG. 14 non-ID version is in FIG. 3; | IDEIVMTQSPDSLAVSLGERATINCKSSQTVTFPNYKNYLAWYQQKPGQPPKLLIYFASTRESGVPDRFSGSGSGTDFTLTISSLQA EDVAVYYCQQHYRTPPTFGGGTKLDIK |
| 103 | 20-ID | Table 4B AA sequence of HC VR of Ab 086; non-ID FIG. 13 version is in FIG. 2; | IDEVQLLESGGGLVKPGQSLKLSCAASGFTFSSYGMHWVRQPPGKGLEWVAVVSFDGNNRYYADSVQGRFTISRDNSKNTLYLQMN SLRAEDTAVYYCAKDSQLRSLLYFEWLSSGVLDYWGGQAMVTVSS |
| 117 | 34-ID | Table 4B AA sequence of LC VR of Abs 025, 026, 027, FIG. 14 086; non-ID version is in FIG. 3; | IDEIVMTQSPDSLAVSLGERATINCKSSQTLSFNYKNYLAWYQQKPGQPPKLLIYFASTRESGVPDRFSGSGSGTDFTLTISSLQA EDVAVYYCQQHYRTPPTFGGGTKLDIK |
| 104 | 23-ID | Table 4B AA sequence of HC VR of Abs 210, 219; non-FIG. 13 ID version is in FIG. 2; | IDEVQLLESGGGLVKPGQSLKLSCAASGFTFTSYGMHWVRQPPGKGLEWVAVVSYDGNYKYYADSVQGRFTISRDNSKNTLYLQMN SLRAEDTAVYYCAKDSKLRSLLYFEWLSQGYFNPWGAGTTLTVSS |

TABLE 4C-continued

Nucleic acid and amino acid sequences

| SEQ ID NO. | Lab no. | Source | Comment | Sequence |
|---|---|---|---|---|
| 118 | 36-ID | Table 4B AA | sequence of LC VR of Ab 160; non-ID version is in FIG. 3; | IDEIVMTQSPDTLAVTLGERASINCKSSQTVTFNYKNYLAWYQQKPGQPPKVLIYWASARETGVPERFSGSGSGTDFTLTISSLQA EDVAVYYCQQHYRTPPSFGQGTKLEIK |
| 105 | 24-ID | Table 4B AA FIG. 13 | sequence of HC VR of Abs A001, A002, A003, A010, A011, 031, 037; non-ID version is in FIG. 2; | IDEVQLLESGGGLVKPGQSLKLSCAASGFTFTSYAMHWVRQPPGKGLEWVAVVSYDGNYKYYADSVQGRFTISRDNSKNTLYLQMN SLRAEDTAVYYCAKDSRLRSLLYFEWLSQGYFNPWGQGTTLTVSS |
| 119 | 45-ID | Table 4B AA FIG. 13 | sequence of LC VR of Abs 202, 203, 204; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQP EDFATYYCQQHYRTPPSFGQGTKVEIK |
| 106 | 25-ID | Table 4B AA FIG. 13 | sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; non-ID version is in FIG. 2; | IDQVQLLETGGGLVKPGQSLKLSCAASGFTFTSYAMHWVRQPPGKGLEWVAVVSYDGNYKYYADSVQGRFTISRDNSKNTLYLQMN SLRAEDTAVYYCAKDSRLRSLLYFEWLSQGYFNPWGQGTTLTVSS |
| 120 | 46-ID | Table 4B AA FIG. 14 | sequence of LC VR of Abs 211, 212, 213, 219, 037, 038, 039, 040; non-ID version is in FIG. 3; | IDDIQMTQSPSSLSASVGDRVTITCRSSQSITFNYKNYLGWYQQKPGKAPKLLIYWASTRESGVPDRFSGSGSGTDFTLTISSLQA EDFATYYCQQHYRTPPSFGQGTKVEIK |
| 107 | 26-ID | Table 4B AA FIG. 13 | sequence of HC VR of Abs 007, 008, A009, A14, 015, 033, 039; non-ID version is in FIG. 2; | IDEVQLLESGGGLVKPGQSLKLSCAASGFTFTSYAMHWVRQPPGKGLEWVAVVSYDGNYKYYADSVQGRFTISRDNSKNTLYLQMN SLRAEDTAVYYCAKDSQLRTLLYFEWLSQGYFNPWGQGTTLTVSS |
| 121 | 37-ID | Table 4B AA FIG. 14 | sequence of LC VR of Abs 186, 194; non-ID version is in FIG. 3; | IDEIVMTQSPDSLAVSLGERATINCKSSQTVTFNYKNYLAWYQQKPGQPPKLLIYWASTRESGVPDRFSGSGSGTDFTLTISSLQA EDVAVYYCQQHYRTPPSFGTGTKLDIK |
| 108 | 27-ID | Table 4B AA FIG. 13 | sequence of HC VR of Abs 016, A017, C18, A019, 034, 040; non-ID version is in FIG. 2; | IDEVQLLESGGGLVKPGQSLKLSCAASGFTFTSYAMHWVRQPPGKGLEWVAVVSYDGNYKYYADSVQGRFTISRDNSKNTLYLQMN SLRAEDTAVYYCAKDSRLRTLLYFEWLSQGYFDPWGQGTTLTVSS |
| 122 | 38-ID | Table 4B AA FIG. 14 | sequence of LC VR of Abs 187, 195; non-ID version is in FIG. 3; | IDEVMTQSPDSLAVSLGERATINCKSSQTVTFNYKNYLAWYQQKPGQPPKLLIYWASTRESGVPDRFSGSGSGTDFTLTISSLQA EDVAVYYCQQHYRTPPSFGSGTKLDIK |
| 109 | 161-ID | Table 4B AA FIG. 13 | sequence of HC VR consensus ID; non-ID version is in FIG. 2; | IDEVQLLESGGGLVKPGQSLKLSCAASGFTFSSYGMHWVRQPPGKGLEWVAVVSYDGSNKYYADSVQGRFTISRDNSKNTLYLQMN SLRAEDTAVYYCAKDSRLRSLLYFEWLSSGLLDYWGQGAMVTVSS |
| 123 | 39-ID | Table 4B AA FIG. 14 | sequence of LC VR of Abs 188, 196; non-ID version is in FIG. 3; | IDEIVMTQSPDSLAVSLGERATINCKSSQTVTFNYKNYLAWYQQKPGQPPKLLIYWASTRESGVPDRFSGSGSGTDFTLTISSLQA EDVAVYYCQQHYRTPPSFGQGTKLDIK |
| 124 | 40-ID | Table 4B AA FIG. 14 | sequence of LC VR of Abs 189, 197; non-ID version is in FIG. 3; | IDEIVMTQSPDSLAVSLGERATINCKSSQTVTFNYKNYLAWYQQKPGQPPKLLIYWASTRESGVPDRFSGSGSGTDFTLTISSLQA EDVAVYYCQQHYRTPPSFGNGTKLDIK |
| 125 | 41-ID | Table 4B AA FIG. 14 | sequence of LC VR of Abs 190, 198; non-ID version is in FIG. 3; | IDEIVMTQSPDSLAVSLGERATINCKSSQTLSFNYKNYLAWYQQKPGQPPKLLIYWASTRESGVPDRFSGSGSGTDFTLTISSLQA EDVAVYYCQQHYRTPPSFGTGTKLDIK |

TABLE 4C-continued

Nucleic acid and amino acid sequences

| SEQ ID NO. | Lab no. | Source Comment | Sequence |
|---|---|---|---|
| 126 | 42-ID | Table 4BAA sequence of LC VR of Abs 191, 199; non-ID version is in FIG. 3; | IDEIVMTQSPDSLAVSLGERATINCKSSQTLSFNYKNYLAWYQQKPGQPPKLLIYWASTRESGVPDRFSGSGSGTDFTLTISSLQA EDVAVYYCQQHYRTPPSFGSGTKLDIK |
| 127 | 43-ID | Table 4BAA sequence of LC VR of Abs 192, 200; non-ID version is in FIG. 3; | IDEIVMTQSPDSLAVSLGERATINCKSSQTLSFNYKNYLAWYQQKPGQPPKLLIYWASTRESGVPDRFSGSGSGTDFTLTISSLQA EDVAVYYCQQHYRTPPSFGQGTKLDIK |
| 128 | 44-ID | Table 4BAA sequence of LC VR of Abs 193; non-ID version is in FIG. 3; | IDEIVMTQSPDSLAVSLGERATINCKSSQTLSFNYKNYLAWYQQKPGQPPKLLIYWASTRESGVPDRFSGSGSGTDFTLTISSLQA EDVAVYYCQQHYRTPPSFGNGTKLDIK |
| 129 | 47-ID | Table 4BAA sequence of LC VR of Abs A001, 004, 007, 016 | IDDIVMTQSPDTLAVLGERATIQCKSSQTVTFNYKNYLAWYQQKPGQPPKLLIYWASTRESGVPDRFSGSGSGTDFTLTISSLQA EDVAVYYCQQHYRTPPSFGQGTKLDIK |
| 130 | 48-ID | Table 4BAA sequence of LC VR of Abs 002, 005, 008, A017; non-ID version is in FIG. 3; | IDDIVMTQSPDTVAVTVGERATINCKSSQTVTFNYKNYLAWYQQKPGQPPKLLIYWASTRESGVPDRFSGSGSGTDFTLTISSLQA EDVAVYYCQQHYRTPPSFGQGTKLDIK |
| 131 | 49-ID | Table 4BAA sequence of LC VR of Abs A003, 006, A009, C18; non-ID version is in FIG. 3; | IDDIVMTQSPDTVAVTLGERATIDCKSSQTVTFNYKNYLAWYQQKPGQPPKLLIYWASTRESGVPDRFSGSGSGTDFTLTISSLQA EDVAVYYCQQHYRTPPSFGQGTKLDIK |
| 132 | 50-ID | Table 4BAA sequence of LC VR of Abs A010 012, A14, A019; non-ID version is in FIG. 3; | IDDIVMTQSPDTLAVTVGERATIRCKSSQTVTFNYKNYLAWYQQKPGQPPKLLIYWASTRESGVPDRFSGSGSGTDFTLTISSLQA EDVAVYYCQQHYRTPPSFGQGTKLDIK |
| 133 | 51-ID | Table 4BAA sequence of LC VR of Ab A011, 013, 015; non-ID version is in FIG. 3; | IDDIVMTQSPDTLAVSRGERATIDCKSSQTVTFNYKNYLAWYQQKPGQPPKLLIYWASTRESGVPDRFSGSGSGTDFTLTISSLQA EDEAVYYCQQHYRTPPSFGQGTKLDIK |
| 134 | 52-ID | Table 4BAA sequence of LC VR of Abs 044, 071, 072, 078; non-ID version is in FIG. 3; | IDDIQMTQSPSSLSASVGDRVTITCRSSQSITFDYKNYLAWYQQKPGKAPKLLIYWGSYLESVPSRFSGSGSGTDFTLTISSLQP EDFATYYCQQHYRTPPSFGQGTKVEIK |
| 135 | 53-ID | Table 4BAA sequence of LC VR of Ab 051; non-ID version is in FIG. 3; | IDDIQMTQSPSSLSASVGDRVTITCRSSQSITFNYKNYLAWYQQKPGKAPKLLIYWGSTLESGVPSRFSGSGSGTDFTLTISSLQP EDFATYYCQQHYRTPPSFGQGTKVEIK |
| 136 | 54-ID | Table 4BAA sequence of LC VR of Ab 049; non-ID version is in FIG. 3; | IDDIQMTQSPSSLSASVGDRVTITCRSSQSITFNYKNYLAWYQQKPGKAPKLLIYWGSHLESGVPSRFSGSGSGTDFTLTISSLQP EDFATYYCQQHYRTPPSFGQGTKVEIK |
| 137 | 55-ID | Table 4BAA sequence of LC VR of Ab 047; non-ID version is in FIG. 3; | IDDIQMTQSPSSLSASVGDRVTITCRSSQSITFNYKNYLAWYQQKPGKAPKLLIYWGSKLESGVPSRFSGSGSGTDFTLTISSLQP EDFATYYCQQHYRTPPSFGQGTKVEIK |
| 138 | 56-ID | Table 4BAA sequence of LC VR of Ab 050; non-ID version is in FIG. 3; | IDDIQMTQSPSSLSASVGDRVTITCRSSQSITFNYKNYLAWYQQKPGKAPKLLIYWGSDLESGVPSRFSGSGSGTDFTLTISSLQP EDFATYYCQQHYRTPPSFGQGTKVEIK |
| 139 | 57-ID | Table 4BAA sequence of LC VR of Ab 045; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQP EDFATYYCQQHYRTPPSFGQGTKVEIK |
| 140 | 58-ID | Table 4BAA sequence of LC VR of Ab 048; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQP EDKATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 141 | 59-ID | Table 4B FIG. 14 | AA sequence of LC VR of Ab 046; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQP EDFATYYCQQHYRTPPSFGQGTKVEIK |
| 142 | 60-ID | Table 4B FIG. 14 | AA sequence of LC VR of Ab 043; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQP EDFATYYCQQHYRTPPSFGQGTKVEIK |
| 143 | 61-ID | Table 4B FIG. 14 | AA sequence of LC VR of Ab 052; non-ID version is in FIG. 3; | IDDIQMTQSPSSLSASVGDRVTITCRSSQSITPQYKNYLAWYQQKPGKAPKLLIYWGSYLESGVPSRFSGSGSGTDFTLTISSLQP EDFATYYCQQHYRTPPSFGQGTKVEIK |
| 157 | 153-ID | Table 4B FIG. 14 | AA sequence of LC VR of Ab 067; non-ID version is in FIG. 3; | IDDIQMTQSPSSLSASVGDRVTITCRSSQSITFRYKNYLAWYQQKPGKAPKLLIYWGSYLESGVPSRFSGSGSGTDFTLTISSLQP EDFATYYCQQHYRTPPSFGQGTKVEIK |
| 158 | 154-ID | Table 4B FIG. 14 | AA sequence of LC VR of Ab 068; non-ID version is in FIG. 3; | IDDIQMTQSPSSLSASVGDRVTITCRSSQSITFEYKNYLAWYQQKPGKAPKLLIYWGSYLESGVPSRFSGSGSGTDFTLTISSLQP EDFATYYCQQHYRTPPSFGQGTKVEIK |
| 159 | 155-ID | Table 4B FIG. 14 | AA sequence of LC VR of Abs 069, 079; non-ID version is in FIG. 3; | IDDIQMTQSPSSLSASVGDRVTITCRSSQSITFDYKNYLAWYQQKPGKAPKLLIYWGSTRESGVPSRFSGSGSGTDFTLTISSLQP EDFATYYCQQHYRTPPSFGQGTKVEIK |
| 160 | 156-ID | Table 4B FIG. 14 | AA sequence of LC VR of Ab 070; non-ID version is in FIG. 3; | IDDIQMTQSPSSLSASVGDRVTITCRSSQSITFNYKNYLAWYQQKPGKAPKLLIYWGSTRESGVPSRFSGSGSGTDFTLTISSLQP EDFATYYCQQHYRTPPSFGQGTKVEIK |
| 144 | 624D | Table 4B FIG. 14 | AA sequence of LC VR consensus ID; non-ID version is in FIG. 3; | IDDIQMTQSPSSLSASVGDRVTITCRSSQSITFNYKNYLAWYQQKPGKAPKLLIYWGSYLESGVPSRFSGSGSGTDFTLTISSLQP EDFATYYCQQHYRTPPSFGQGTKVEIK |
| 63 | VH16 | Example 1 | NT sequence of HC VR of Abs 014, 028 | GAGGTACAGCTCCTCGAATCGGAGGAGGGACTGGTCAAACCGGTCAATCGCTCAAACTCTCTGTCAGCCTCAGGTTTTACGTT CAGCTCATATGGATGCACTGGGTCCGCCAGCCTCCGGGAAGGGACTGGAGTGGGTGGCAGTCGTGTCGTATGACGGAGCAATA AGTACTACGCCGATTCAGTGCAAGGTCCGTTTGCGCCAAAGACACAAGCTGCGATCCCTGTTGTACTTCAGATGTTGTCCGGCTT AGAGCCGAAGATACGGCTGTGTACTATTGCGCCAAAGACACAAAGCTGCGATCCCTGTTGTACTTCAGATGTTGTCTCGGCTT GCTTGACTATTGGGGGCCAGGGCGCCATGGTCACAGTATCCAGCGCGTCGACTAAGGGCCC |
| 64 | VL29 | Example 1 | NT sequence of LC VR of Abs 014, 154, 157 | GAGATCGTGATGACGCAGAGCCCCGATAGCCTCATTGGGAGGACTGGGAACCGGCCACGATTAACTGCAAATCCTCACAGTCGT GACTTTCAGCTATAAGAATTACTGGCATGGTATCAGCAGAGCCGGTCAACCCCAAAACTGTTGATCTACTGGGCCTCCACAC GCCAGTCGGAGTCCCGACCGATTTTCGGGTTCAGCGACTGCAGTCCTCGACTTTACCCTCACAATTTCATCGCTTCAAGCGAGGAT GTAGCAGTGACTATTGTCAGCAGTATATACAGAACACCTCCCACCTTCGGAGGGGAACGAAACTTGACATCAAGGATCC |
| 65 | VL30 | Example 1 | NT sequence of LC VR of Abs 028, 155 | NT: GAGACGTCGACTATAAGAATTACTGGCATGGTATCAGCAGAGCCGGTCAACCCCAAAACTGTTGATCTACTGGGCCTCCACAC GCCAGTCGGAGTCCCGACCGATTTTCGGGTTCAGCGACTGCAGTCCTCACAGATTTCATCGCTTCAAGCGAGGAT GTAGCAGTGACTATTGTCAGCAGTATATACAGAACACCTCCCACCTTCGGAGGGGAACGAAACTTGACATCAAGGATCC |
| 66 | VH15 | Example 1 | NT sequence of HC VR of Ab A18 | GAAGTGCAACTCCTCGAGTCAGGAGGAGGTTTGGTGAACAGCCGGTCAGTCCTTGAAACTCCTGTGCAGCAAGCGGTTCACGTT TACGTCGTACGGACATGCAGTGGGTTACGGCAGTCCTGCAGCCTCCCGGAAGGACTTGAATGGGTGCCCGTCATCATAACTAGGGTGTACA AATACTATGCCGATAGCCGTGCAAGGTCCGTCACAAATTCCCGGACAATTCGAAGAATACACTGTACTTTGTACTTTGTGCTGTCGAGGGTA AGGGCTGAGGACACGGCGGTCTATTACTGCGCGAAGGATTCGCGACTCAGATCCGTATCAAGCGCGTATCAAGCCTTTTGACTTTGTACTTTGTGCTGTCAGGGGTA TTTCAACCCATGGGGAGCCGGAACCACACACTTGACCGTATCAAGCGCGTATCAACAAAGGGCCC |

TABLE 4C-continued

Nucleic acid and amino acid sequences

| SEQ ID NO. | Lab no. | Source | Comment | Sequence |
|---|---|---|---|---|
| 67 | VL28 | Example 1 | NT sequence of LC VR of Ab A18 | GAAATTGTAATGACGCAGAGCCCTGATAGCCTTGCCGTGTCCCTGGGTGAGAGGGCGACAATCAATTGTAAGTCATCACAGTCGGT CACGTACAACTACAAGACTACCTGGCTGGTATCAACAGAAACCCGGGCAGCCCCCCAAATTGCTCATCTATTGGGCTTCGACAC GGGAGTCCGGGTCTGCCAGACCCGCTTCTCCGGGTCAGGATCGGAGACTTCACGTTGACTATTTCGTCCCTCCAGCAGAAGAT GTAGCCGTCTACTATTGCCAACAGTATTACAGAACCGCTCACATTTGGAGGCGACAAACTTGACATCAAGGATCCGTGGC CGCCCCAGCGTCTTCATCTTCCCGCCAGCAGCTGAGCAGCTTGAAACGGGCCAGCAGCGTGTGGTGTGCCTCTGAACAACTTCT ACCCCGGAGGCGAAGGTCCAGCAGGACACCCTGACGCTGAGCAAGGCCGATACGAGGAGACAAGCTACGAGAGCCAGGACACGCTACGCCTGCGAGGTGAC AAGGACAGCACCTACACCCTGAGCAAGGCCGATACGAGAAGCAACCAAGGCTACGCCTGCGAGGTGAC CCAACCAGGGCTCTCGAGCCCCGTGACCAAGAGCTTCAACCGGGGCGAGTG |
| 149 | VL52 | Example 1 | NT sequence of LCVR of Abs 044, 071, 072, 078 | GACATTCAGATGACTCAGTCGCCTTCGATTGTCCGCCTCCGTGGGTGATAGGGTCACGATCACGTGCCGGAGCAGCCAGTCCAT CACCTTCAATTACAAAACTATTTGGCATGGTATCAACAGAAACCCGGAAGCTCCTGATCTACTGGGTTCATATC TTGAGTCGGGGTGCCGTCGAGATTTCGGCAGCCGGATCAGGGACGGATTTCACGCTGACCATTTCGACCCAGCCGAGGAC TTTGCGACATATTACTGTCAACAGCACTACAGAGACACCCCCATCTTTCGACAGGGACTAAAGTAGAAATCAAGGGATCCGTGGC CGCCCCCAGCGTCTTCATCTTCCCGCCAGCAGCTGAAGTCGGGCACGGCCAGCGTGGAGAGCGTGACCAGGAGGCTGAACAACTTCT ACCCCGGAGGCGAAGGTCCAGCAGGACACCCTGACGCTGAGCAAGGCCGACTACGAGAAGCACCAAGGTCTACGCCTGCGAGGTGAC AAGGACAGCACCTACACCCTGAGCAAGGCCGACTACGAGAAGCACCAAGGTCTACGCCTGCGAGGTGAC CCACCAGGGCTCTCGAGCCCCGTGACCAAGAGCTTCAACCGGGGCGAGTGCTGCTGA |
| 150 | VL45 | Example 1 | NT sequence of LCVR of Abs 202, 203, 204, 210, 031, 032, 033, 034 | GACATTCAGATGACTCAGTCGCCTTCGATTGTCCGCCTCCGTGGGTGATAGGGTCACGATCACGTGCCGGAGCAGCCAGTCCAT CACCTTCAATTACAACGATATTTGGCATGGTATCAACAGAAACCCGGAAGCTCCTGATCTACTGGGTTCATATC TTGAGTCGGGGTGCCGTCGAGATTTCGGCAGCCGGATCAGGGACGGATTTCACGCTGACCATTTCGACCCAGCCGAGGAC TTTGCGACATATTACTGTCAACAGCACTACAGAGACACCCCCATCTTTCGACAGGGACTAAAGTAGAAATCAAGGGATCCGTGGC CGCCCCCAGCGTCTTCATCTTCCCGCCAGCAGCTGAAGTCGGGCACGGCCAGCGTGGAGAGCGTGACCAGGAGGCTGAACAACTTCT ACCCCGGAGGCGAAGGTCCAGCAGGACACCCTGACGCTGAGCAAGGCCGACTACGAGAAGCACCAAGGTCTACGCCTGCGAGGTGAC AAGGACAGCACCTACACCCTGAGCAAGGCCGACTACGAGAAGCACCAAGGTCTACGCCTGCGAGGTGAC CCACCAGGGCTCTCGAGCCCCGTGACCAAGAGCTTCAACCGGGGCGAGTGCTGAGAATTC |
| 151 | VH25 | Example 1 | NT sequence of HCVR of Abs 004, 005, 006, 012, 013, 032, 038, 043, 044, 045, 046, 047, 048, 049, 050, 051, 052, 067, 068, 069, 070, 073, 074, 075, 076, 077 | CAGGTACAATTGCTTGAGACAGGTGAGGACTCGTGAAGCCAGGTCAGTCATTGAAACTGACTGCCGCATCCGGTTCACATT CACTTCCTTACGCCATGACACTGGGTCCGCCAGCCTCCCGGAAAGGGACTTGAGTGGGTCGTGTATATCGTATGATGGAATTACA AATACTATGCAGACTCCGTGCAAGGCCGGTTTACGATTAGCAGGACAACTGAAGATAACCCTTTACCTCCAAATGAACTGCTC CGAGCGGAGGACACCGCCGTCTATTATCGCGCAAGGATTGAGATTCACGGTTGAGATCGTGTCTCTATTTGAATGGTGTCACAGGGGTA CTTCAACCCTGGGGTCAGGGGAACCAGCACTGGGCGTCAGCTGCCTCAGCCTGACTAAAGGCCAGCGTGTTCCCGCTGGCCTGCCTGGAACAG GCGGCCTGACAGCCAGCTGGGGCACGCCAAGAGCACCTCTGGGGGCACAGCGGCCCTGACCAGCGGCGTGGTCACCGTGG CAGCAGCAGCCTGGGCACAAAACTCACATGTCCCCAGGACTACTCATGATCTGTAACTCCTGGGGTGGGACCGTGAGCCACGACACCCTCAGTGG AAACCCAAGGACACCACCCTCATGATCTCCCGGACCCCCGAGGTCACATGCGTGGTGGTGGACGTGAGCCACGACACCCCTCAGTGTGG GTTCAACTGGTACGTGGACGGTGTGGAGGTGCATAATGCCAAGACACGCCGGAGGAGCAGTACAACAGCACGTACCGTGTGG TCAGCGTCCTCACCGTCCTGCACCAGGACTGGCTGAATGGCAAGGAGTACAAGGTGCAAGGTCTCCCAACAAAGCCCTCAGCCCTC ATCGAGAAAACCATCTCCAAAGCCAAAGGTCAGCCCCGAGAACCACAGGTGTACACCCTGCCCCCATCCCGGGATGAGCTGACCAA GAACCAGGTCAGCCTGACCTGCCTGGTCAAAGGCTTCTATCCCAGCGACATCGCCGTGGAGTGGGAGAGCAATGGGCAGCCGGAGA ACAACTACAAGACCACGCCTCCCGTGCTGGACTCCGACGGCTCATAATGCCTGACCGTGGACAAGAGCAGGTGG CAGCAGGGGAACGTCTTCTCATGCTCCGTGATGCATGAGGCTCTGCACAACCACTACACGCAGAAGAGCCTCTCCCTGTCTCCGGG TAAATGA |

TABLE 4C-continued

Nucleic acid and amino acid sequences

| SEQ ID NO. | Lab no. | Source | Comment | Sequence |
|---|---|---|---|---|
| 152 | VH24 | Example 1 | NT sequence of HCVR of Abs A001, A002, A003, A010, A011, 031, 037 | GAAGTACAATTGCTTGAGTCGGTGGAGGACTCTGAAGCCAGGTCAGTCATTGAAACTGAGCTGTCGCCATCCGGGTTCACATT CACTTCCTACGGCATGCACTGGTTCCGTGCAAGGCCGGTTACAGGCTCCAGCCTCCCGGAAAGGACTTGAGTGGGTCGCTGTGATCAGTTACGA AATACTATGCAGACTCCAGACTCCGTGCAAGGCCGGTTATTACTGCGAAGAATACCCTTACCTCAAATGAACTGCTC CGAGCGGAGGACACGGCCGTGTATTACTGCGACGATCGACTCGACGTTGAGATTCACGGTGCTCTCTATTTGAATGGTTGTCACAGGGTA CTTCAACCCTGGGGTCAGGGGAACCACACTGGTCACCGTCTCCAGCGGTGTTCCCAGCGTGTTCCCCTGGCCCCCAGCA GCAAGAGCACCAGCGGGAGCGGGACCGCGCCCACCACCTTCCCGGCCGTCCTGCTGTGCTGCTGACCACTTCCCCGAGCCGTCACCTGCC GGCGTGACCAGCAGCTGGGGACTCACCACCGAGCCCGTGACCCTGACCTGCAACGTGGACCACAAGCCCAGCAACACCAAGGTGGACAAGCGC CAGAGAGTCGACGACCACCATGCCCAGCTACTCCAACGACCAATGCTCCAGTCTTCCTCTTCCCCCA CGAGAGAGTCGACGACCACCATGCCCAGCTACTCCAACGACCGTCAGTCCTCCAGGACCCCTGAGGTCACCTGCGTGGTGGTGGACGTGAGCCACGAAGACCCTGAGGTCAA GTTCAACTGGTACGTGACGGCGTGGAGGTGCATAATGCCAAGACAAAGCCGCGGGAGGAGCAGTACAACAGCACGTACCGTGTGG TCAGCGTCCTCACCGTCCTGCACCAGGACTGGCTGAATGGCAAGGAGTACAAGTGCAAGGTCTCCAACAAAGCCCTCCCAGCCCC ATCGAGAAAAACCATCTCCAAAGCCAAAGGGCAGCCCCGAGAACCACAGGTGTACACCCTGCCCCCATCCCGGGATGAGCTGACCAA GAACCAGGTCAGCCTGACCTGCCTGGTCAAAGGCTTCTACCCCAGCGACATCGCCGTGGAGTGGGAGAGCAATGGGCAGCCGGAGA ACAACTACAAGACCACGCCTCCCGTGCTGGACTCCGACGGCTCCTTCTTCCTCTACAGCAAGCTCACCGTGGACAAGAGCAGGTGG CAGCAGGGGAACGTCTTCTCATGCTCCGTGATGCATGAGGCTCTGCACAACCACTACACGCAGAAGAGCCTCTCCCTGTCTCCGGG TAAATGA |
| 94 | 15 | FIG. 1 | AA sequence of HC of Ab A18 | EVQLLESGGGLVKPGQSLKLSCAASGFTFTSYGMHWVRQPPGKGLEWVAVISYDGSYKYYADSVQGRFTISRDNSKNTLYLQMNSL RAEDTAVYYCAKDSRLRSLLYFEWLSQGYFNPWGAGTTLTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKKVEPKSCDKTHTCPPCPELLGGPSVFLFPP KPKDTLMISRTPEVTCVVVDVSHEDPEVKFNWYVDGVEVHNAKTKPREEQYNSTYRVVSVLTVLHQDWLNGKEYKCKVSNKALPAP IEKTISKAKGQPREPQVYTLPPSRDELTKNQVSLTCLVKGFYPSDIAVEWESNGQPENNYKTTPPVLDSDGSFFLYSKLTVDKSRW QQGNVFSCSVMHEALHNHYTQKSLSLSPGK |
| 95 | 28 | FIG. 1 | AA sequence of LC of Ab A18 | EIVMTQSPDSLAVSLGERATINCKSSQSVTNYNKYLAWYQQKPGQPPKLLIYWASTRESGVPDRFSGSGSGTDFTLTISSLQAED VAVYYCQQYRTPTFGGGTKLDIKGSVAAPSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGE |
| 145 | n.a. | see text | AA sequence of LC CDR1 of Ab 044 | QSITFDYKNYLA |
| 146 | n.a. | see text | AA sequence of LC CDR1 of F16 VK | KSSQSVTFNYKNYLA |
| 147 | n.a. | see text | AA sequence of LC CDR2 of F16 VK | WASARES |
| 148 | n.a. | see text | AA sequence of LC CDR3 of F16 VK | QQHYRTPT |
| 68 | n.a. | see text | AA sequence of HC CDR1 of Abs 044, 069, 032, 031 | SYAMH |
| 69 | n.a. | see text | AA sequence of HC CDR2 of Abs 044, 069, 032, 031 | VVSYDGNYKYYADSVQG |
| 70 | n.a. | see text | AA sequence of HC CDR3 of Abs 044, 069, 032, 031 | DSRLRSLLYFEWLSQGYFNP |
| 71 | n.a. | see text | AA sequence of LC CDR1 of Abs 032, 031 | QSITFNYKNYLA |

TABLE 4C-continued

Nucleic acid and amino acid sequences

| SEQ ID NO. | Lab no. | Source | Comment | Sequence |
|---|---|---|---|---|
| 72 | n.a. | see text | AA sequence of LC CDR2 of Abs 044, 069, 032, 031 | WGSYLES |
| 73 | n.a. | see text | AA sequence of LC CDR3 of Abs 044, 069, 032, 031 | QQHYRTPPS |
| 74 | n.a. | see text | AA sequence of HC FR1 of Ab 069 | QVQLLETGGGLVKPGGSLKLSCAASGFTFT |
| 75 | n.a. | see text | AA sequence of HC FR2 of Ab 069 | WVRQPPGKGLEWVA |
| 76 | n.a. | see text | AA sequence of HC FR3 of Ab 069 | RFTISRDNSKNTLYLQMNSLRAEDTAVYYCAK |
| 77 | n.a. | see text | AA sequence of HC FR4 of Ab 069 | WGQGTTLTVSS |
| 78 | n.a. | see text | AA sequence of LC FR1 of Ab 069 | DIQMTQSPSSLSASVGDRVTITCRSS |
| 79 | n.a. | see text | AA sequence of LC FR2 of Ab 069 | WYQQKPGKAPKLLIY |
| 80 | n.a. | see text | AA sequence of LC FR3 of Ab 069 | GVPSRFSGSGSGTDFTLTISSLQPEDFATYYC |
| 81 | n.a. | see text | AA sequence of LC FR4 of Ab 069 | FGGGTKVEIK |
| 82 | n.a. | see text | AA sequence of HC FR1 of Ab 031 | EVQLLESGGGLVKPGGSLKLSCAASGFTFT |
| 83 | n.a. | see text | AA sequence of LC CDR1 of Ab A18 et al. | KSSQSVTNYKNYLA |
| 84 | n.a. | see text | AA sequence of LC CDR2 of Ab A18 et al. | WASTRES |
| 85 | n.a. | see text | AA sequence of LC CDR3 of Ab A18 et al. | QQYYRTPPT |
| 86 | n.a. | see text | AA sequence of HC CDR1 of Ab A18 et al. | SYGMH |
| 87 | n.a. | see text | AA sequence of HC CDR2 of Ab A18 et al. | VISYDGSYKYYADSVQG |
| 88 | n.a. | see text | AA sequence of an HC CDR3 | DSELRSLLYFEWLSQGYFNP |
| 89 | n.a. | see text | AA sequence of HC FR4 of Ab A18 et al. | WGAGTTLTVSS |
| 90 | n.a. | see text | AA sequence of LC FR1 of Ab A18 et al. | EIVMTQSPDSLAVSLGERATINC |
| 91 | n.a. | see text | AA sequence of LC FR2 of Ab A18 et al. | WYQQKPGQPPKLLIY |
| 92 | n.a. | see text | AA sequence of LC FR3 of Ab A18 et al. | GVPDRFSGSGSGTDFTLTISSLQAEDVAVYYC |
| 93 | n.a. | see text | AA sequence of LC FR4 of Ab A18 et al. | FGGGTKLDIK |

TABLE 4C-continued

Nucleic acid and amino acid sequences

| SEQ ID NO. | Lab no. | Source | Comment | Sequence |
|---|---|---|---|---|
| 171 | n.a. | see text | AA sequence of HC FR4 of Ab 078 et al | WGQGTTVTVSS |
| 172 | n.a. | see text | AA sequence of LC CDR1 of Ab 069 | QSITFEYKNYLA |
| 173 | n.a. | see text | AA sequence of H3 HA] | QDLPGNDNSTATLCLGHHAVPNGTLVKTITDDQIEVTNATELVQSSSTGKICNNPHRILDGIDCTLIDALLGDPHCDVFQNETWDL FVERSKAFSNCYPYDVPDYASLRSLVASSGTLEFITEGFTWTGVTQNGGSNACKRGPGSGFFSRLNWLITKSGSTYPVLNVTMPNND NFDKLYIWGIHHPSTNQEQTSLYVQASGRVTVSTRRSQQTIIPNIGSRPWVRGLSSRISIYWTIVKPGDVLVINSNGNLIAPRGYF KMRTGKSSIMRSDAPIDTCISECITPNGSIPNDKPFQNVNKITYGACPKYVKQNTLKLATGMRNVPEKQTR |
| 174 | n.a. | see text | AA sequence of H3 HA2 | GLFGAIAGFIENGWEGMIDGWYGFRHQNSEGTGQAADLKSTQAAIDQINGKLNRVIEKTNEKFPHQIEKEFSEVEGRIQDLEKYVED TKIDLWSYNAELLVALENQHTIDLTDSEMNKLFEKTRRQLRENAEEMGNGCFKIYHKCDNACIESIRNGTYDHDVRDEALNNRFQ IKG |
| 175 | n.a. | FIG. 12 | AA sequence of HC VR of F16 | QVQLVQSGGGVVQPGRSLRLSCVASGFTFSTYAMHWVRQAPGRGLEWVAVISYDGNYKYYADSVKGRPSISRDNSNNTLHLEMNTL RTEDTALYYCAKDSQLRSLLYFEWLSQGYFDPWGQGTLVTVTS |
| 176 | n.a. | FIG. 12 | AA sequence of HC VR of F1370 | QVQLVQSGGGVVQPGRSLRLSCAASGFTFSTYGMHWVRQAPGKGLEWVAVISYDGNYKYYADSVRGRFTISRDNSKNTLNLDMNSL RTEDTALYYCAKDSQLRSLLYFDWLSQGYFDHWGQGTLVTVSS |
| 177 | n.a. | FIG. 12 | AA sequence of HC VR of F16 variant 1 | QVQLVESGGGVVQPGRSLRLSCAASGFTFSSYGMHWVRQAPGKGLEWVAVISYDGSNKYYADSVKGRFTISRDNSKNTLYLQMNSL RAEDTAVYYCAKDSQLRSLLYFDWLSQGYFDYWGQGTLVTVSS |
| 178 | n.a. | FIG. 12 | AA sequence of HC VR of F16 variant 3 | QVQLVESGGGVVQPGRSLRLSCAASGFTFSTYAMHWVRQAPGKGLEWVAVISYDANYKYYADSVKGRFTISRDNSKNTLYLQMNSL RAEDTAVYYCAKDSQLRSLLYFDWLSQGYFDYWGQGTLVTVSS |
| 179 | n.a. | FIG. 12 | AA sequence of HC VR of F16/370 | QVQLVQSGGGVVQPGRSLRLSCAASGFTFSTYGMHWVRQAPGKGLEWVAVISYDGNYKYYADSVKGRFTISRDNSKNTLYLEMNSL RTEDTALYYCAKDSQLRSLLYFDWLSQGYFDHWGQGTLVTVSS |
| 180 | n.a. | FIG. 12 | AA sequence of kappa LC VR of F16 | DIQMTSQPDSLAVSLGARATINCKSSQSVTFNYKNYLAWYQQKPGQPPKVLIYWASARESGVPDRFSGSGSGTDFTLTISSLQAED VAVYYCQQHYRTPPTFGQGTKVEIK |
| 181 | | See text | AA sequence of H1 HA1 | TNADTICIGYHANNSTDTVDTVLEKNVTVTHSVNLLEDSHNGKLCKLKGIAPLQLGKCNIAGWLLGNPECDLLLTASSWSYIVETS NSENGTCYPGDFIDYEELREQLSSVSSFEKFEIFPKITSSWPNHETTKGVTAACSYAGASSFYRNLLWLITKKGSSYPKLSKSYVNNK GKEVLVLWGVHHPPTGTDQQSLYQNADAYVSVGSSKYNRRFTPEIAARPKVRDQAGRMNYWTLLEPGDTITFEATGNLIAPWYAF ALNRGSGSGIITSDAPVHDCNTKCQTPHGAINSSLPFQNIHPVTIGECPKYVRSTKLRMATGLRNIPSIQS |
| 182 | | See text | AA sequence of H1 HA2 | GLFGAIAGFIEGGWTGMIDGWYGYHHQNEQGSGYAADQKSTQNAIDGITNKVNSVIEKMNTQFTAVGKEFNNLERRIENLNKKVDD GFLDIWTYNAELLVLLENERTLDFHDSNVRNLYEKVKSQLKNNAKEIGNGCFEFYHKCDDACMESVRNGTYDYPKYSEESKLNREE IDGVKLESMGVYQILAIYSTVASSLVLIVSLGAISFWMCSNGSLQCRICI |

EXAMPLES

Example 1: Safety and Upper Respiratory Pharmacokinetics of the Hemagglutinin Antibody VIS410 Support Treatment and Prophylaxis Based on Population Modeling of Seasonal Influenza A Outbreaks Summary Background.

Seasonal influenza is a major public health concern in vulnerable populations. Monoclonal antibody therapies represent a modality for treatment and prophylaxis given their safe profile and broad neutralizing ability.

Methods.

Using a single-ascending dose study (n=41) at dose levels from 2 mg/kg-50 mg/kg, the safety and pharmacokinetics (e.g., serum and upper respiratory pharmacokinetics) of a broadly-neutralizing antibody (VIS410, also known as Ab 044 herein) against influenza A were characterized (ClinicalTrials.gov identifier NCT02045472). The primary endpoints were safety and tolerability of VIS410 compared to placebo. An epidemic microsimulation model was developed for testing the ability of VIS410 to mitigate attack rates and severe disease in at risk-populations.

Findings.

VIS410 was found to be generally safe and well-tolerated at all dose levels, from 2-50 mg/kg. Overall, 27 of 41 subjects (65.9%) reported a total of 67 treatment emergent adverse events (TEAEs). TEAEs were reported by 20 of 30 subjects (66.7%) who received VIS410 and by 7 of 11 subjects (63.6%) who received placebo. 14 of 16 TEAEs related to study drug were considered mild (Grade 1) and 2 were moderate (Grade 2). Two subjects (1 subject who received 30 mg/kg VIS410 and 1 subject who received placebo) experienced serious AEs (grade 3 or 4 TEAEs) that were not related to study drug. VIS410 exposure was approximately dose-proportional with a mean half-life of 12.9 days. Mean VIS410 $C_{max}$ levels in the upper respiratory tract were 20.0 and 25.3 µg/ml at the 30 mg/kg and 50 mg/kg doses, respectively, with corresponding serum $C_{max}$ levels of 980.5 and 1316 µg/mL. Using these pharmacokinetic data, the microsimulation model showed that median attack rate reductions ranged from 8.6% (interquartile range (IQR): 4.7%-11.0%) for 2% coverage to 22.6% (IQR: 12.7-30.0%) for 6% coverage. The overall benefits to the elderly, a vulnerable subgroup, are largest when VIS410 is distributed exclusively to elderly individuals, resulting in reductions in hospitalization rates between 11.4% (IQR: 8.2%-13.3%) for 2% coverage and 30.9% (IQR: 24.8%-35.1%) for 6% coverage among those more than 65 years of age.

Interpretation.

VIS410 was generally safe and well tolerated and had good relative exposure in both serum and upper respiratory tract, supporting its use as either a single-dose therapeutic or prophylactic for influenza A. Including VIS410 prophylaxis among the public health interventions for seasonal influenza can be used to lower attack rates and substantially reduce hospitalizations in individuals over the age of 65.

To summarize, in this Example, the safety, tolerability, and pharmacokinetics of a broadly neutralizing, stalk-binding monoclonal antibody (VIS410) against Influenza A were investigated in a Phase 1 clinical trial. Based on these results and preclinical data, a mathematical modeling approach was used to investigate whether VIS410 could be used prophylactically to lessen the burden of a seasonal influenza epidemic and to protect at-risk groups from associated complications.

VIS410 is a broadly neutralizing monoclonal antibody that was engineered to bind a conserved region on the influenza A hemagglutinin protein that is used by the virus to bind and enter infected cells. VIS410 has a direct mechanism of action, inhibiting HA-mediated cell fusion, neutralizing the virus and preventing cell infection. For a drug to be an effective prophylactic against seasonal influenza it should have a strong neutralizing effect against both group 1 viruses, such as H1N1, and group 2 viruses, such as H3N2, target an epitope that is conserved and widely shared among influenza subtypes, have a PK/PD profile that affords sufficient protection for a typical flu season, and have a good safety profile. The pre-clinical and phase 1 clinical data demonstrates that VIS410 possesses these properties. It was shown that VIS410 is safe and well tolerated in a phase 1 clinical trial in healthy adult volunteers who were given a single infusion of the drug. Measurements of the drug levels of VIS410 in the upper respiratory tract demonstrated that protective levels were achieved at the site of influenza infection. Given the phase 1 trial results, Epidemic modeling analyses indicate that for a sufficiently potent and long-lasting antibody, such as VIS410, that prophylactic administration to 4-6% of the population, focused on high risk individuals (e.g., elderly individuals), would be sufficient to lower (e.g., substantially suppress overall) hospitalizations related to severe influenza. Seasonal influenza A infection results in significant morbidity and mortality especially in high risk groups such as the elderly. Notably, given the current state-of-the-art in the production of antibodies, it is possible to rapidly ensure availability of adequate supply of monoclonal antibody to protect such a population during an influenza season in a much shorter time scale than that for production of a vaccine, incorporating novel strains (generally >6 months).

Introduction

Severe influenza occurs each winter especially in high-risk groups such as young children, older adults, patients with pulmonary conditions, inflammatory conditions, malignancies, and pregnant women (Newton et al. The American journal of managed care 2000; 6(5 Suppl): S265-75; Schanzer et al. Vaccine 2008; 26(36): 4697-703). Despite available therapy with neuraminidase inhibitors, including oseltamivir, zanamivir, and peramivir; 10%-44% of hospitalized patients require intensive care and 25%-50% of these patients die. In the United States, it is estimated that as many as to 400,000 patients are hospitalized with influenza each year, with as many as 50,000 deaths per year (Centers for Disease Control U. Hamborsky et al., editors. Epidemiology and Prevention of Vaccine-Preventable Diseases. 13th ed. Washington, D.C.: Public Health Foundation; 2015). Furthermore, as evidenced by pandemic influenza A infections such as the 2009 "swine flu" pandemic, newly emerging influenza subtypes represent a considerable threat to global public health as they have the potential to cause significant morbidity and mortality.

The majority of the severe disease burden during seasonal influenza is experienced by individuals over the age of 65, who are susceptible to a number of complications following infection with influenza virus (Reed et al. PloS one 2015; 10(3): e0118369; Thompson et al. Jama 2004; 292(11): 1333-40). Currently available public health interventions have not significantly mitigated disease burden for the elderly. Vaccination with trivalent or tetravalent killed influenza has historically had lower measured efficacy in elderly individuals compared to adults and children (Darvishian et al. The Lancet Infectious diseases 2014; 14(12): 1228-39; Breteler Vaccine 2013; 31(45): 5168-77; Osterholm The Lancet Infectious diseases 2012; 12(1): 36-44). Prophylaxis or early treatment with neuraminidase inhibitors are the current de facto standard of care however, some controversy exists as to whether a direct link can be established between early oseltamivir treatment and lower hospitalization rates (Jefferson et al. Bmj 2014; 348: g2545). Based on these shortfalls in care, there is a need to develop countermeasures to reduce or mitigate the effects of influenza in the elderly and other susceptible populations.

The benefits of broadly neutralizing antibodies are that they can protect elderly individuals from influenza infection regardless of immune response and potentially provide a reliable option when considering the vaccine mismatches that occur against influenza every three to five years. Using an antibody engineering approach, a broadly neutralizing antibody (VIS410) that targets a unique, conserved epitope on influenza hemagglutinin and binds to and neutralizes influenza A virus across group 1 and group 2 subtypes was developed. In vitro, VIS410 has been shown to neutralize groups 1 and 2 influenza strains; over 40 different virus strains have been tested to date, with $EC_{50}$ values ranging from 0.1-60 µg/mL and representing broad temporal/geographical, subtype, and epitope diversity (Tharakaraman et al. Proc Natl Acad Sci USA. 2015; 112(35):10890-5; Baranovich et al. Antimicrob Agents Chemother. 2016; pii: AAC.02457-15). Additionally, in vivo studies in mouse models demonstrated that VIS410 administered as a prophylactic or therapeutic protects mice challenged with lethal doses of influenza A, including A/Puerto Rico/8/1934 [H1N1], A/California/04/2009 [H1N1], A/Victoria/3/1975 [H3N2], and A/Vietnam/1203/2004 [H5N1]. VIS410 also demonstrated protection against newly emerging pathogenic H7N9 strains, A/Anhui/1/2013 and oseltamivir-resistant A/Shanghai/1/2013 in a lethal BALB/c mouse model (Baranovich et al. Antimicrob Agents Chemother. 2016; pii: AAC.02457-15). VIS410 is being developed as a single dose treatment for hospitalized patients with influenza A is currently in phase 2 studies.

Described herein are the safety and pharmacokinetics of VIS410 in the serum and the upper respiratory tract, the primary target organ of infection of influenza A. Furthermore, this information was utilized to model the application of a broadly neutralizing antibody, such as VIS410, during an influenza outbreak to mitigate severe disease, especially for at risk-populations. Evidence has been provided that VIS410 is generally safe and well-tolerated in healthy subjects with protective levels of antibody achieved in the upper respiratory tract, and that it has a pharmacokinetic/pharmacodynamic (PK/PD) profile that may allow it to be used as a prophylactic during or prior to a period of high influenza activity. Taken together, these data support the development of a broadly neutralizing monoclonal antibody as a strategy for reducing the severity of seasonal influenza.

Methods

Production of Antibody.

VIS410 was produced under current Good Manufacturing Practice (cGMP) at Gallus Biopharmaceuticals (Princeton, N.J.) in a CHO cell line. After production at a 200 L scale, VIS410 was purified by protein A and ion exchange polishing steps. Testing of bulk drug substance indicated that the material was >99% monomer, containing <0.1 pg/mg residual DNA and <0.1 ng/mg of host cell proteins. VIS410 materials were formulated at 25 mg/mL in 40 mM Citrate-Sodium Phosphate, 150 mM NaCl, pH 6.0, containing 0.025% Tween-80.

Phase I Clinical Trial.

A Phase 1, double-blind, placebo-controlled, single ascending dose-escalation study was completed in healthy adult subjects (ClinicalTrials.gov identifier NCT02045472). This study was conducted according to the International Conference on Harmonisation harmonised tripartite guideline E6(R1): Good Clinical Practice. Institutional Research Board approval for the study was obtained in writing before the study began. The primary endpoint for the study was the safety and tolerability of VIS410 compared to placebo and the secondary endpoint was the serum pharmacokinetics of a single dose of VIS410. Eligible subjects were admitted to the clinic for dose administration and were discharged 24-hours post-infusion. Overall, 30 subjects were dosed with VIS410 and 11 subjects were dosed with a placebo control infusion. Nine subjects were dosed in the first cohort (Cohort 1); 6 subjects received VIS410 (2 mg/kg) and 3 subjects received placebo (sodium chloride 0.9%). Eight subjects were dosed in the subsequent cohorts (Cohorts 2 through 5) and were randomly assigned in a 6:2 ratio to receive either VIS410 or placebo. The detailed phase 1 protocol is also presented herein.

Briefly, in the first cohort (Cohort 1) the first four sentinel subjects were randomly assigned to receive either VIS410 (2 mg/kg; n=2) or placebo (n=2) and received study drug at least 48 hours before the remaining subjects in the cohort were dosed. After the investigator had assessed that the infusions were well tolerated, the remaining subjects in the cohort were dosed concurrently (VIS410 n=4 and placebo n=1). In each subsequent cohort, the first 3 subjects were randomly assigned to receive either VIS410 (n=2) or placebo (n=1) and received study drug at least 48 hours before the remaining subjects in the cohort were dosed. After the investigator had assessed that the infusions were well tolerated, the remaining members of the cohort (VIS410 n=4 and placebo n=1) were dosed concurrently. Dose escalation to the next dosing level occurred after the Safety Monitoring Committee (SMC) comprised of the investigator, an independent medical monitor, and the sponsor reviewed the safety data through Day 7 after the infusion.

Assessment of safety by the SMC was determined from vital sign measurements; physical examinations; hematology, chemistry, and urinalysis laboratory testing; 12-lead triplicate electrocardiograms (ECGs); use of concomitant medications; and review of adverse events (AEs). Blood samples for pharmacokinetic (PK) analysis and for assessment of antidrug antibodies (ADA) to VIS410 were obtained before and after the infusion during the 120-day study period (Days 1, 2, 3, 7, 14±1, 28±3, 56±7, and 120±7). Nasopharyngeal (NP) swabs, to assess upper respiratory VIS410 concentrations, were collected before and after the infusion from subjects in the 15, 30, and 50 mg/kg cohorts (Days 1, 3 and 7).

Pharmacokinetic and Antidrug Antibody Assays.

Blood samples were collected at the time points described herein. Serum was aliquoted and stored at −20° C. to −80° C. All samples were tested for IgG antibody concentrations using an enzyme-linked immunosorbent assay. Nasopharyngeal swabs (one from each nostril) for the analysis of the local concentration of VIS410 were taken using COPAN flocked swabs from subjects in the 15, 30, and 50 mg/kg cohorts at the time points described herein. The swabs from each nostril were combined in 1 transport tube containing 3 mL COPAN Universal Transport Medium and stored at −70°

C. Samples were tested for VIS410 by an immunoassay. The samples for ADA analysis were collected in serum separator tubes. Serum was aliquoted and stored at −20° C. to −80° C. The enzyme-linked immunosorbent assay was performed. Descriptive statistics were used to summarize data between groups. Statistical comparisons of the frequency of adverse events for placebo versus VIS410 receiving subjects used Fisher's exact test. All statistical analyses were conducted using SAS® software Version 9.3 (SAS Institute, Inc, Cary, N.C.), and the PK analysis was conducted using Phoenix WinNonlin® Version 6.2.1 (Pharsight Corporation, St Louis, Mo.).

Individual-Based Population Model.

An individual-based microsimulation was developed based on a previously developed model, and is similar in structure and design to an array of microsimulation models that have been developed over the past decade (Boni et al. Philosophical transactions of the Royal Society of London Series B, Biological sciences 2013; 368(1614): 20120207; Ferguson et al. Nature 2005; 437(7056): 209-14; Germann et al. Proceedings of the National Academy of Sciences of the United States of America 2006; 103(15): 5935-40; Longini et al. Science 2005; 309(5737): 1083-7). Individual-based microsimulation methods were used to test the population-level effects of deploying VIS410 during a typical winter influenza epidemic and to perform sensitivity analyses on key unknown parameters, Briefly, the model simulates an age-structured population of one million individuals living in a city with 100 pre-defined neighborhoods or locations. Daily work commutes, random within-city travel, household structure, pre-existing immunity, and age-based social contacts are included in the model. Influenza infection and potential hospitalization are modeled by randomly infecting individuals by location or household, in proportion to the current level of infections and contacts in that location or household. Infection, seasonality, contact structure, hospitalization, and the clinical course and epidemiology of influenza in the model were validated using characteristics of past influenza epidemics of influenza A, as described herein.

Figure 4:
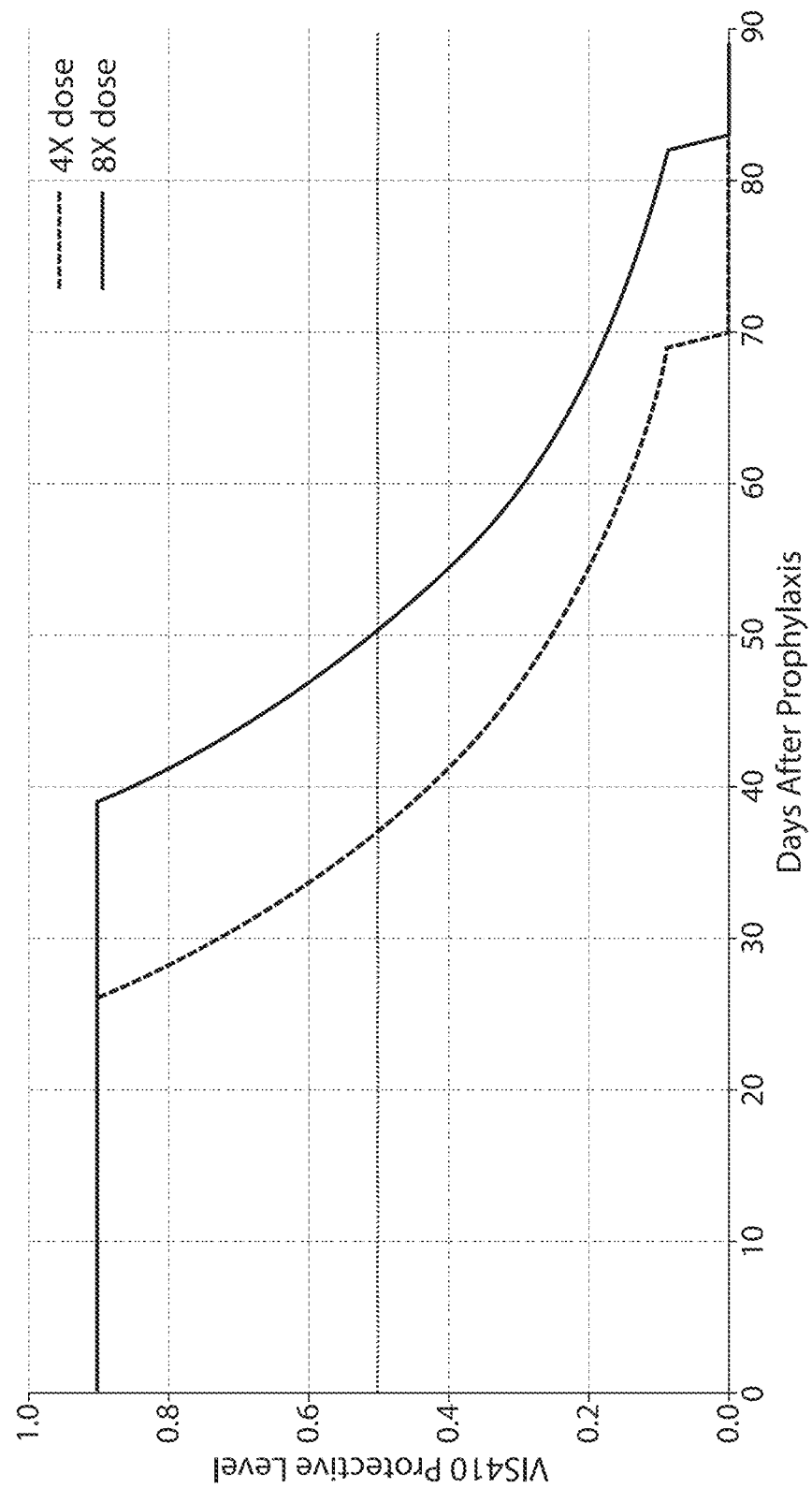
FIG. 4 depicts the protective levels conferred by VIS410 as a function of time (half-life of 13 days).

In the microsimulation, VIS410 was deployed as a population-wide prophylaxis strategy. A small percentage of individuals received VIS410 prophylaxis (between 0% and 6%) in the early stages of the epidemic, and two modes of distribution were included: randomly to all individuals or randomly to only elderly individuals (>65 years old). The distribution time was varied between eight weeks prior to the epidemic peak and the date of the modelled epidemic peak. VIS410 levels in individuals were modeled using an exponential decay function, with a half-life of 13 days. VIS410 was modeled to be administered at a level that was 8-fold over a minimally protective dose of approximately 1-2 mg/kg based on preclinical estimates, corresponding to over 3 half-lives of protection. Levels of VIS410 over the protective threshold confer a 90% reduction in the probability of being infected, with the protection decreasing exponentially as a function of VIS410 levels below the minimally protective threshold. Levels of VIS410 below 0.1-fold of the protective threshold were considered to be non-protective. This behavior is shown in FIG. 4.

Results

Figure 8:
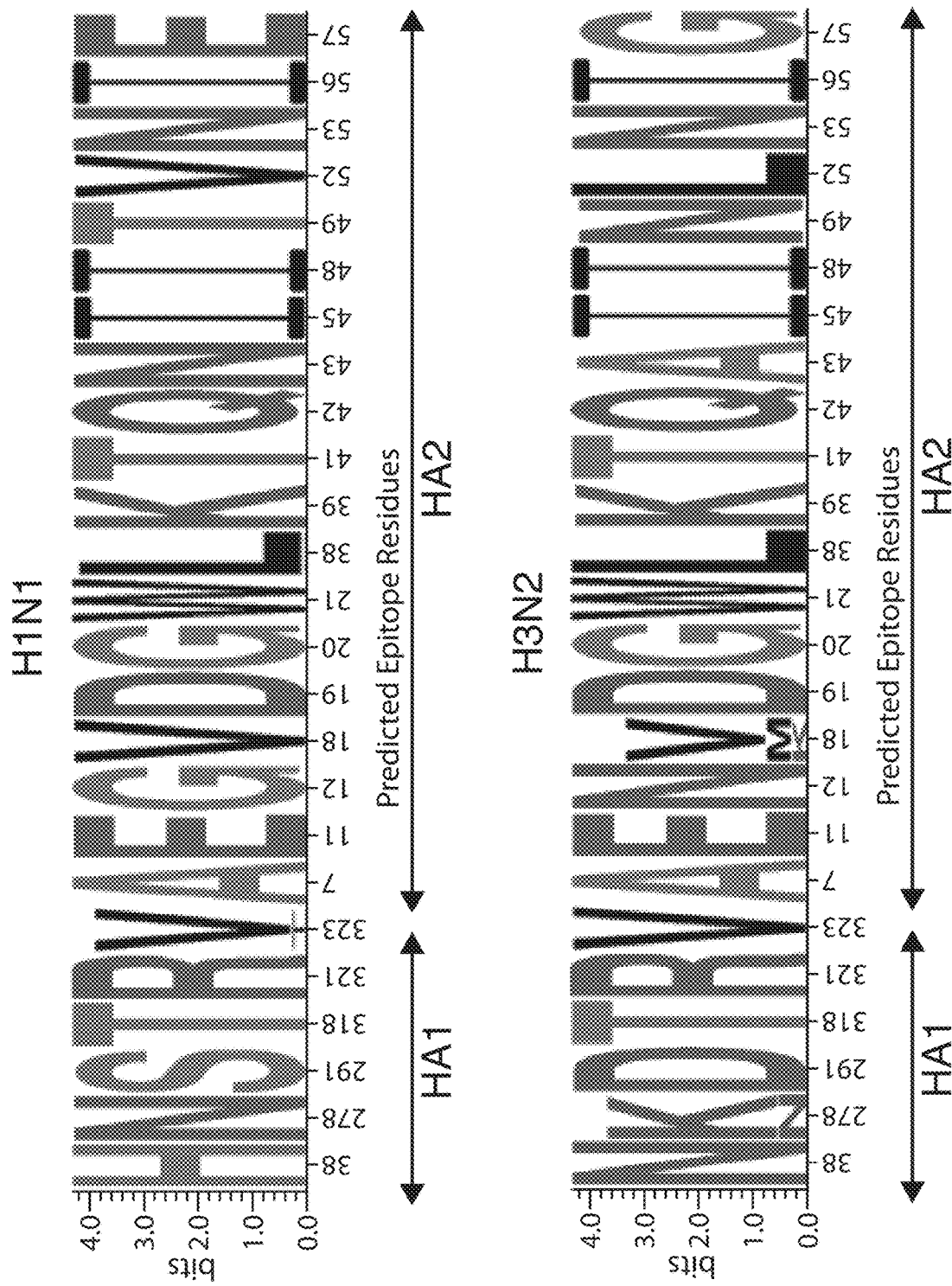
FIG. 8 depicts the sequence logo of predicted VIS410 epitope positions for H1N1 (top) and H3N2 (bottom) for influenza A strains collected from 2012 through 2015.

VIS410 is an engineered human IgG1 antibody that targets a unique, conserved conformational epitope on the stem of Influenza A virus HA protein. Previous studies have identified that VIS410 has broad reactivity against both group 1 and group 2 influenza A. A bioinformatics analysis of over 26,500 H1N1 and H3N2 HA sequences demonstrates the conserved nature of the targeted epitope within H1 and H3 subgroups (Tharakaraman et al. Proc Natl Acad Sci USA. 2015; 112(35):10890-5). FIG. 8 shows the observed residue composition of this epitope based on a sequence analysis of currently circulating strains (collected since 2012), supporting the pre-clinical in vitro and in vivo analyses which indicates that VIS410 is effective against a broad panel of seasonal H1 and H3 influenza viruses as well as H7N9 virus.

A Phase 1, placebo-controlled, single ascending dose study of VIS410 in healthy volunteers was initiated at a single site in North America. Five cohorts were dosed with levels ranging from 2 to 50 mg/kg (Table 5). A total of 41 subjects were enrolled in the phase 1 study. Overall, 36 subjects (87.8%) completed the study and 5 subjects (12.2%) discontinued early. All 41 subjects (100.0%) who received study drug (VIS410 or placebo) were included in the safety analysis set. All 30 subjects (100.0%) who received a dose of VIS410 and had at least one evaluable PK parameter were included in the PK analysis set. Five subjects (12.2%) withdrew consent (4 of 30 subjects [13.3%] who received VIS410 and 1 of 11 subject [9.1%] who received placebo). For 1 subject (Subject 402; 30 mg/kg VIS410), the investigator was unblinded to the subject's treatment due to serious adverse events (SAEs) of leukopenia and herpes simplex esophagitis. This SAE was ultimately found to be unrelated to the study drug as a primary herpes simplex virus type 1 infection was confirmed based on analysis of pre and post event serology.

TABLE 5

Summary of Subject Disposition

| | VIS410 | | | | | | | |
|---|---|---|---|---|---|---|---|---|
| | 2 mg/kg (n = 6) | 5 mg/kg (n = 6) | 15 mg/kg (n = 6) | 30 mg/kg (n = 6) | 50 mg/kg (n = 6) | Total (N = 30) | Placebo (N = 11) | Overall (N = 41) |
| Total number of subjects, No. (%) | | | | | | | | |
| Completed | 6 (100.0) | 4 (66.7) | 5 (83.3) | 5 (83.3) | 6 (100.0) | 26 (86.7) | 10 (90.9) | 36 (87.8) |
| Discontinued | 0 | 2 (33.3) | 1 (16.7) | 1 (16.7) | 0 | 4 (13.3) | 1 (9.1) | 5 (12.2) |
| Primary reason for discontinuation, No. (%) | | | | | | | | |
| Subject withdrew consent | 0 | 2 (33.3) | 1 (16.7) | 1 (16.7) | 0 | 4 (13.3) | 1 (9.1) | 5 (12.2) |

TABLE 5-continued

Summary of Subject Disposition

| | VIS410 | | | | | | | |
|---|---|---|---|---|---|---|---|---|
| | 2 mg/kg (n = 6) | 5 mg/kg (n = 6) | 15 mg/kg (n = 6) | 30 mg/kg (n = 6) | 50 mg/kg (n = 6) | Total (N = 30) | Placebo (N = 11) | Overall (N = 41) |
| | Study Population, No. (%) | | | | | | | |
| Safety analysis set[a] | 6 (100.0) | 6 (100.0) | 6 (100.0) | 6 (100.0) | 6 (100.0) | 30 (100.0) | 11 (100.0) | 41 (100.0) |
| Pharmacokinetic analysis set[b] | 6 (100.0) | 6 (100.0) | 6 (100.0) | 6 (100.0) | 6 (100.0) | 30 (100.0) | 0 | 30 (73.2) |

Note:
Percentages were based on the number of subjects within each group and overall.
[a]The safety analysis set included all subjects who received a dose of VIS410 or placebo.
[b]The pharmacokinetic analysis set included all subjects who received a dose of VIS410 and had at least 1 evaluable pharmacokinetic parameter.

Safety Results.

Overall, 27 of 41 subjects (65.9%) reported a total of 67 treatment emergent adverse events (TEAEs). TEAEs were reported by 20 of 30 subjects (66.7%) who received VIS410 and by 7 of 11 subjects (63.6%) who received placebo. 18 of 41 subjects (43.9%) overall (16 of 30 subjects [53.3%] who received VIS410 and 2 of 11 subjects [18.2%] who received placebo; p>0.05) experienced TEAEs related to study drug. 14 of 16 TEAEs related to study drug were considered mild (Grade 1) and 2 were moderate (Grade 2).

Overall, the highest percentage of subjects that reported TEAEs were classified as nervous system disorders (11 subjects; 26.8%) followed by gastrointestinal (GI) disorders and infections and infestations (10 subjects; 24.4% each). The percentage of subjects reporting nervous system disorders was similar following administration of VIS410 (7 of 30 subjects; 23.3%) compared with placebo (4 of 11 subjects; 36.4%) and did not reach statistical significance; no notable differences were observed across VIS410 dose levels. Gastrointestinal disorders were reported by subjects who received VIS410 only (10 of 30 subjects; 33.3% for VIS410 receiving subjects, compared to 0% for placebo, p<0.05). The percentage of subjects reporting GI disorders was highest in the 50 mg/kg VIS410 cohort (5 of 6 subjects; 83.3%). The percentage of subjects reporting infections and infestations was similar following administration of VIS410 (6 of 30 subjects; 20.0%) compared with placebo (4 of 11 subjects; 36.4%); no notable differences were observed across VIS410 dose levels (See Tables 6 and 7).

TABLE 6

Summary of Gastrointestinal Adverse Events

| | VIS410 | | | | | | | |
|---|---|---|---|---|---|---|---|---|
| Adverse Event | 2 mg/kg (N = 6) | 5 mg/kg (N = 6) | 15 mg/kg (N = 6) | 30 mg/kg (N = 6) | 50 mg/kg (N = 6) | Total (N = 30) | Placebo (N = 11) | Overall (N = 41) |
| Diarrhea | 0 | 2 (33.3%) | 1 (16.7%) | 2 (33.3%) | 5 (83.3%) | 10 (33.3%) | 0 | 10 (24.4%) |
| Nausea | 0 | 0 | 0 | 2 (33.3%) | 2 (33.3%) | 4 (13.3%) | 0 | 4 (9.8%) |
| Vomiting | 0 | 0 | 0 | 0 | 2 (33.3%) | 2 (6.7%) | 0 | 2 (4.9%) |

TABLE 7

Summary of Gastrointestinal Adverse Events by Severity

| | VIS410 | | | | | | | |
|---|---|---|---|---|---|---|---|---|
| Adverse Event/ Severity* | 2 mg/kg (N = 6) | 5 mg/kg (N = 6) | 15 mg/kg (N = 6) | 30 mg/kg (N = 6) | 50 mg/kg (N = 6) | Total (N = 30) | Placebo (N = 11) | Overall (N = 41) |
| Diarrhea | 0 | 2 (33.3%) | 1 (16.7%) | 2 (33.3%) | 5 (83.3%) | 10 (33.3%) | 0 | 10 (24.4%) |
| Grade 1 | 0 | 2 (33.3%) | 1 (16.7%) | 2 (33.3%) | 5 (83.3%) | 10 (33.3%) | 0 | 10 (24.4%) |
| Grade 2 | 0 | 0 | 0 | 0 | 0 | 0 | 0 | 0 |
| Grade 3 | 0 | 0 | 0 | 0 | 0 | 0 | 0 | 0 |
| Grade 4 | 0 | 0 | 0 | 0 | 0 | 0 | 0 | 0 |

TABLE 7-continued

Summary of Gastrointestinal Adverse Events by Severity

| Adverse Event/ Severity* | VIS410 | | | | | Total (N = 30) | Placebo (N = 11) | Overall (N = 41) |
|---|---|---|---|---|---|---|---|---|
| | 2 mg/kg (N = 6) | 5 mg/kg (N = 6) | 15 mg/kg (N = 6) | 30 mg/kg (N = 6) | 50 mg/kg (N = 6) | | | |
| Nausea | 0 | 0 | 0 | 2 (33.3%) | 2 (33.3%) | 4 (13.3%) | 0 | 4 (9.8%) |
| Grade 1 | 0 | 0 | 0 | 2 (33.3%) | 1 (16.7%) | 3 (10.0%) | 0 | 3 (7.3%) |
| Grade 2 | 0 | 0 | 0 | 0 | 1 (16.7%) | 1 (3.3%) | 0 | 1 (2.4%) |
| Grade 3 | 0 | 0 | 0 | 0 | 0 | 0 | 0 | 0 |
| Grade 4 | 0 | 0 | 0 | 0 | 0 | 0 | 0 | 0 |
| Vomiting | 0 | 0 | 0 | 0 | 2 (33.3%) | 2 (6.7%) | 0 | 2 (4.9%) |
| Grade 1 | 0 | 0 | 0 | 0 | 1 (16.7%) | 1 (3.3%) | 0 | 1 (2.4%) |
| Grade 2 | 0 | 0 | 0 | 0 | 1 (16.7%) | 1 (3.3%) | 0 | 1 (2.4%) |
| Grade 3 | 0 | 0 | 0 | 0 | 0 | 0 | 0 | 0 |
| Grade 4 | 0 | 0 | 0 | 0 | 0 | 0 | 0 | 0 |

*Grade 1 = mild; Grade 2+ moderate; Grade 3 = Severe; Grade 4 = Life-threatening Additional summary safety data from the Phase I study is shown in Tables 8 and 9.

TABLE 8

Subjects with Confirmed ADA and TEAE

| Subject # | VIS410 Cohort | ADA Titer (Day) | TEAE | Severity* | Relationship | Onset Time from Start of Infusion |
|---|---|---|---|---|---|---|
| 204 | 2 mg/kg | 10 (Day 120) | Headache | Grade 2 | Related | 7 hrs 50 mins |
| | | | Headache | Grade 1 | Not related | 50 days |
| 205 | 2 mg/kg | 10 (Day 14) 40 (Day 120) | None reported | | | |
| 208 | 2 mg/kg | 40 (Day 120) | Diarrhea | Grade 1 | Related | 11 hrs 21 mins |
| 305 | 15 mg/kg | 10 (Day 120) | None reported | | | |

*Grade 1 = mild; Grade 2+ moderate; Grade 3 = severe; Grade 4 = serious adverse event Subjects who developed clinically significant upper respiratory infections had viral testing of their nasopharyngeal swabs by the site investigator for the duration of the study (Day 120). None were found to have influenza although the 30 mg/kg and 50 mg/kg cohorts were dosed from December 2014 to January 2015 where, based on state reported epidemiology, there were high relative incidences of

TABLE 9

Summary of Infections and Infestations

| Adverse Event | VIS410 | | | | | Total VIS410 (N = 30) | Placebo (N = 11) | Overall (N = 41) |
|---|---|---|---|---|---|---|---|---|
| | 2 mg/kg (N = 6) | 5 mg/kg (N = 6) | 15 mg/kg (N = 6) | 30 mg/kg (N = 6) | 50 mg/kg (N = 6) | | | |
| All Infections and Infestations | 0 | 0 | 1 (16.7%) | 3 (50.0%) | 2 (33.3%) | 6 (20.0%) | 4 (36.4%) | 10 (24.4%) |
| Upper respiratory tract infection | 0 | 0 | 0 | 1 (16.7%) | 1 (16.7%) | 2 (6.7%) | 2 (18.2%) | 4 (9.8%) |
| Appendicitis | 0 | 0 | 0 | 0 | 0 | 0 | 1 (9.1%) | 1 (2.4%) |

TABLE 9-continued

Summary of Infections and Infestations

| | VIS410 | | | | | | | |
|---|---|---|---|---|---|---|---|---|
| Adverse Event | 2 mg/kg (N = 6) | 5 mg/kg (N = 6) | 15 mg/kg (N = 6) | 30 mg/kg (N = 6) | 50 mg/kg (N = 6) | Total VIS410 (N = 30) | Placebo (N = 11) | Overall (N = 41) |
| Corona virus infection | 0 | 0 | 0 | 1 (16.7%) | 0 | 1 (3.3%) | 0 | 1 (2.4%) |
| Gastroenteritis | 0 | 0 | 1 (16.7%) | 0 | 0 | 1 (3.3%) | 0 | 1 (2.4%) |
| Herpes simplex esophagitis | 0 | 0 | 0 | 1 (16.7%) | 0 | 1 (3.3%) | 0 | 1 (2.4%) |
| Herpes zoster | 0 | 0 | 0 | 0 | 0 | 0 | 1 (9.1%) | 1 (2.4%) |
| Rhinitis | 0 | 0 | 0 | 0 | 1 (16.7%) | 1 (3.3%) | 0 | 1 (2.4%) |
| Rhinovirus Infection | 0 | 0 | 0 | 0 | 0 | 0 | 1 (9.1%) | 1 (2.4%) |

Pharmacokinetic Results.

Figure 1B:
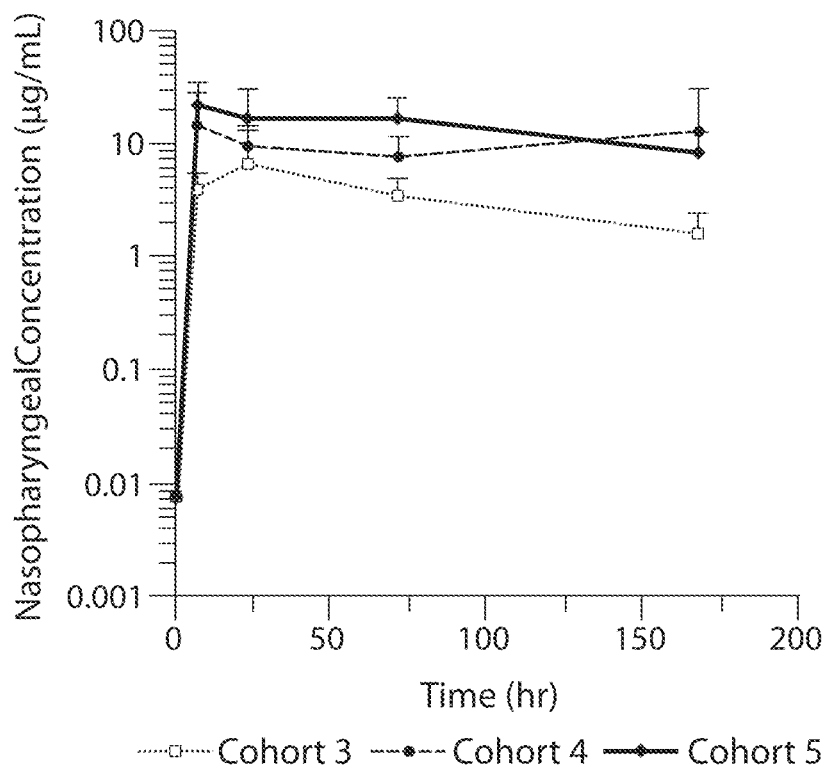

Mean $AUC_{0-t}$, $AUC_{0-\infty}$, and $C_{max}$ for VIS410 increased approximately proportional to dose (FIGS. 1A-1B and Table 10). Across the dose cohorts, mean $t_{1/2}$ values of VIS410 ranged between 250.72 to 376.38 hours and median $T_{max}$ values ranged between 1.92 and 3.50 hours. The mean clearance values of VIS410 ranged from 11.41 to 14.07 mL/hr and mean volume of distribution values ranged from 4,914.4 to 6,189.8 mL, across all of the doses tested. A dose proportional increase in the $C_{max}$ for VIS410 was observed, which ranged from 58.6 μg/mL at a 2 mg/kg dose to 1316 μg/mL at a 50 mg/kg dose. Additionally, PK samples were examined for the presence of anti-drug antibodies (ADA). Of note, no preexisting ADAs were detected before administration of VIS410. It was found that four subjects (three at 5 mg/ml and one at 15 mg/ml dose levels) developed low titer ADA, 120 days after administration of VIS410. Notably, the presence of ADA did not alter drug PK as exclusion of ADA-positive subject data from the analysis did not substantially affect calculated PK parameters, including half-life and drug exposure.

Nasopharyngeal (NP) swabs were collected for the 15, 30, and 50 mg/kg VIS410 treatment groups but not for the 2 and 5 mg/kg groups. Following a single IV infusion of VIS410 over 120 minutes, across the dose cohorts tested, NP VIS410 concentrations appeared to increase with each increasing dose level, in a similar manner to serum $C_{max}$ levels (Table 11 and FIG. 1A-1B). Mean NP VIS410 concentrations reached peak levels within 24 hours after dosing for all the dose cohorts tested and remained measurable throughout the collection period. Mean NP VIS410 concentrations for the ADA-negative subset were comparable to the PK analysis set demonstrating that the ADA status did not influence VIS410 NP concentrations.

TABLE 11

VIS410 Nasopharyngeal Pharmacokinetic $C_{max}$ Statistics

| Cohort | Dose (mg/kg) | n | Mean $C_{max}$ ± SD (μg/mL) |
|---|---|---|---|
| 3 | 15 | 6 | 7.6 ± 5.2 |
| 4 | 30 | 6 | 20.0 ± 16.3 |
| 5 | 50 | 6 | 25.3 ± 10.4 |

$C_{max}$ - Maximum observed nasal concentration.

TABLE 10

Mean (CV) Serum Pharmacokinetic Parameters of VIS410

| | VIS410 | | | | |
|---|---|---|---|---|---|
| Parameter (unit) | 2 mg/kg (N = 6) | 5 mg/kg (N = 6) | 15 mg/kg (N = 6) | 30 mg/kg (N = 6) | 50 mg/kg (N = 6) |
| $AUC_{0-t}$ (hr · μg/mL) | 10828 (11) | 28026 (50) | 90332 (33) | 163914 (41) | 322070 (16) |
| $AUC_{0-\infty}$ (hr · μg/mL) | 11074 (12) | 36086 (25) | 100410 (20) | 190921 (10) | 323451 (16) |
| $C_{max}$ (μg/mL) | 58.6 (16.8) | 180.5 (29.6) | 446.1 (13.6) | 980.5 (16.7) | 1316.0 (14.3) |
| $T_{max}$ (hr)[a] | 3.00 (1.92, 3.00) | 3.50 (1.92, 4.00) | 3.00 (1.92, 3.08) | 2.46 (1.92, 4.00) | 1.92 (1.92, 3.00) |
| $t_{1/2}$ (hr)[b] | 250.7 (11.6) | 293.1 (38.5) | 341.2 (17.1) | 288.6 (15.3) | 376.4 (16.0) |
| CL (mL/hr) | 14.1 (10.4) | 12.6 (28.6) | 12.9 (40.8) | 11.7 (19.7) | 11.4 (6.4) |
| Vd (mL) | 5089 (16) | 4914 (21) | 6027 (22) | 4779 (15) | 6190 (17) |

Abbreviations: AUC, area under the curve; $C_{max}$, maximal concentration of VIS410; $T_{max}$, time at which maximal concentration is achieved; $t_{1/2}$, half-life; CL, clearance; Vd, volume of distribution; CV, coefficient of variation; hr, hours; $K_{el}$, terminal elimination rate constant.
Note:
$K_{el}$-associated pharmacokinetic parameters for Subject 202 (5 mg/kg VIS410) and Subject 306 (15 mg/kg VIS410) were set to missing due to >20% extrapolation of $AUC_{0-\infty}$.
[a]For $T_{max}$, the median (minimum, maximum) values are presented.
[b]VIS410 serum half-life (12.9 days), was calculated by averaging the mean $t_{1/2}$ of all cohorts.

Modelling of Population-Level Benefits.

Figure 9:
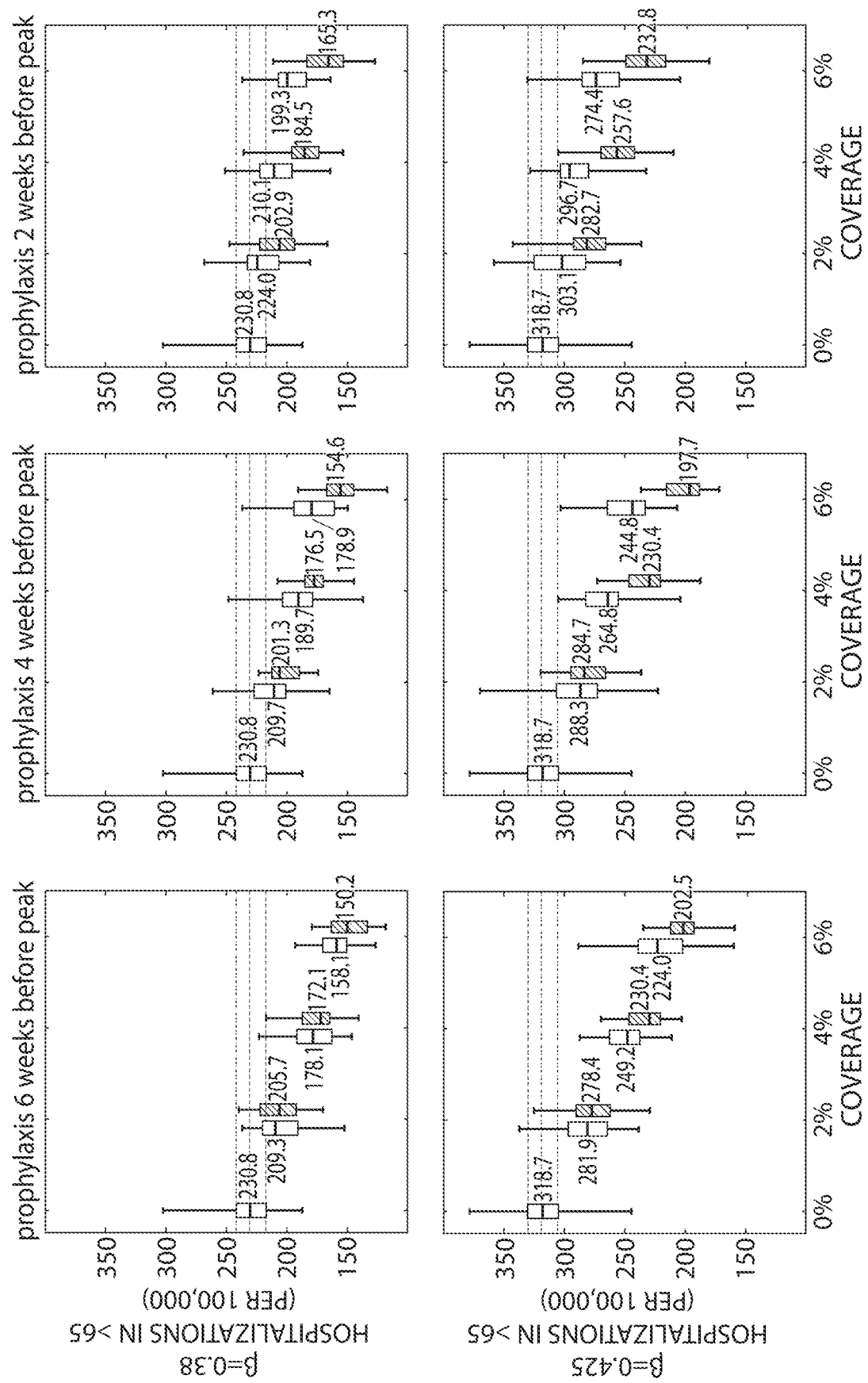
FIG. 9 depicts the effect of VIS410 administration on elderly hospitalization events for a low transmission (top panel) and high transmission (bottom panel) epidemic. The effect of VIS410 administration was modeled when prophylaxis was initiated 6 weeks (left), 4 weeks (center), and 2 weeks (right) prior to the peak of the epidemic.

Using the measured half-life and biodistribution information as well as information on protective levels in animals, it was modeled if a population-level prophylaxis strategy with VIS410 would be able to reduce influenza burden during a single influenza season. The microsimulation results indicated that prophylaxis of even a small percentage of the population can have a substantial impact on the outcome of the epidemic as measured by the reduction in both attack rates and hospitalization rates for the elderly. Simulations were carried out for a range of temperate-zone influenza epidemic scenarios corresponding to attack rates between 4.8% and 27%. Attack rates and hospitalization rates for the 3 coverage levels explored in this study are shown in Table 12. For a prophylactic dose of 8-fold over a protective threshold of 1-2 mg/kg as estimated from preclinical prophylactic experiments and with administration initiated 0-8 weeks prior to the epidemic peak, median reductions in attack rates from 50 simulations were 8.6% (IQR: 4.7%41.0%) for 2% coverage, 16.1% (IQR: 8.1%-20.9%) for 4% coverage, and 22.6% (IQR: 12.7%-30.0%) for 6% coverage (FIG. 2A). The associated reductions in hospitalization of the elderly were 8.8% (IQR: 4.9%41.6%), 16.5% (IQR: 8.8%-21.9%) and 22.9% (IQR: 13.0%-30.6%), respectively, for the three coverage scenarios (FIG. 2C).

reductions in >65 years old hospitalizations were 11.4% (IQR: 8.2%-13.3%) for 2% coverage, 21.6% (IQR: 17.4%-24.9%) for 4% coverage, and 30.9% (IQR: 24.8%-35.1%) for 6% coverage when VIS410 was administered to the elderly only. Hospitalization rate in the elderly is an important outcome measure as this age group makes up the majority of influenza hospitalizations and is particularly vulnerable to severe outcomes. Hospitalization rates across all age groups differed by a small amount (±4%) when comparing general-population prophylaxis to prophylaxis of the elderly only (FIG. 2B). The impact of VIS410 prophylaxis on seasonal influenza epidemics shown in FIGS. 2A-2B represents an aggregation across a number of simulation variables (including severity of the epidemic, and date of administration of VIS410 relative to the date of peak activity). When the analysis is restricted to a single epidemic scenario, the effect of VIS410 on the severity of the epidemic is much more pronounced (FIG. 9).

An additional critical parameter that had a large influence on attack rates and hospitalizations was the timing of VIS410 deployment (FIG. 3). For an influenza season of

TABLE 12

Results of Microsimulation Measurements

| Metric | Age | Admin | Untreated | 2% (IQR) | 4% (IQR) | 6% (IQR) |
|---|---|---|---|---|---|---|
| Attack Rate (%) | 0-5 | all | 9.1 (6.7-12.7) | 8.4 (6.0-11.7) | 7.8 (5.4-10.8) | 7.2 (5.0-10.1) |
| | | elderly | | 8.9 (6.4-12.3) | 8.6 (6.2-12.0) | 8.4 (6.0-11.7) |
| | 6-15 | all | 15.6 (11.6-21.8) | 14.5 (10.4-20.1) | 13.6 (9.4-18.6) | 12.6 (8.7-17.5) |
| | | elderly | | 15.3 (11.2-21.1) | 14.9 (10.7-20.7) | 14.7 (10.5-20.2) |
| | 16-25 | all | 13.1 (9.5-18.3) | 12.1 (8.6-16.8) | 11.3 (7.8-15.5) | 10.4 (7.2-14.6) |
| | | elderly | | 12.8 (9.2-17.6) | 12.4 (8.9-17.3) | 12.2 (8.6-16.9) |
| | 26-34 | all | 11.4 (8.2-15.9) | 10.5 (7.4-14.6) | 9.8 (6.7-13.5) | 9.0 (6.2-12.7) |
| | | elderly | | 11.1 (8.0-15.4) | 10.8 (7.7-15.0) | 10.5 (7.5-14.6) |
| | 35-49 | all | 18.6 (13.5-25.5) | 17.1 (12.3-23.5) | 16.0 (11.1-21.8) | 14.8 (10.3-20.5) |
| | | elderly | | 18.1 (13.1-24.7) | 17.5 (12.6-24.2) | 17.2 (12.3-23.6) |
| | 50-64 | all | 12.3 (9.0-17.1) | 11.4 (8.2-15.7) | 10.7 (7.4-14.5) | 9.8 (6.8-13.6) |
| | | elderly | | 12.1 (8.7-16.5) | 11.7 (8.4-16.1) | 11.4 (8.1-15.6) |
| | >65 | all | 7.2 (5.2-10.0) | 6.6 (4.7-9.1) | 6.2 (4.3-8.4) | 5.7 (4.0-7.8) |
| | | elderly | | 6.5 (4.7-8.8) | 5.8 (4.1-7.8) | 5.2 (3.7-6.9) |
| | All Ages | all | 13.1 (9.5-18.2) | 12.1 (8.6-16.7) | 11.3 (7.8-15.4) | 10.4 (7.2-14.5) |
| | | elderly | | 12.7 (9.2-17.4) | 12.3 (8.8-17.0) | 11.9 (8.5-16.5) |
| Hospitalization Rate (per 100K) | 0-5 | all | 72.1 (52.1-102.8) | 67.5 (46.0-95.1) | 62.9 (42.9-87.4) | 58.3 (38.3-81.3) |
| | | elderly | | 70.6 (49.1-98.2) | 70.6 (47.5-96.6) | 67.5 (47.5-95.1) |
| | 6-15 | all | 5.3 (2.6-7.9) | 4.4 (2.6-7.0) | 4.4 (2.6-6.2) | 4.4 (2.6-6.2) |
| | | elderly | | 5.3 (3.5-7.0) | 4.4 (2.6-7.0) | 4.4 (2.6-7.0) |
| | 16-25 | all | 27.0 (19.0-37.2) | 24.8 (16.8-35.0) | 22.6 (15.3-32.1) | 21.2 (13.9-29.9) |
| | | elderly | | 26.3 (18.2-36.5) | 25.5 (17.5-35.7) | 24.8 (16.8-35.0) |
| | 26-34 | all | 23.5 (16.1-31.6) | 21.3 (14.4-29.3) | 19.5 (13.2-27.6) | 17.8 (12.1-25.3) |
| | | elderly | | 22.4 (15.5-31.0) | 21.8 (14.9-30.4) | 21.3 (14.4-29.3) |
| | 35-49 | all | 31.5 (22.3-43.1) | 29.1 (20.3-39.7) | 27.1 (18.5-37.3) | 24.7 (16.9-34.9) |
| | | elderly | | 31.0 (21.8-42.1) | 30.0 (20.8-41.2) | 29.5 (20.3-40.2) |
| | 50-64 | all | 55.0 (38.7-74.7) | 51.1 (35.4-69.6) | 47.2 (32.0-64.6) | 43.2 (29.8-60.1) |
| | | elderly | | 53.3 (37.6-73.0) | 51.7 (36.5-70.7) | 50.5 (35.4-69.1) |
| | >65 | all | 272.4 (198.3-370.6) | 249.2 (178.1-339.5) | 230.8 (161.3-315.5) | 212.5 (148.6-296.3) |
| | | elderly | | 243.6 (174.1-331.5) | 217.7 (154.2-294.7) | 194.1 (137.4-262.0) |
| | All Ages | all | 63.5 (46.1-86.7) | 58.5 (41.4-79.4) | 54.2 (37.5-74.0) | 49.7 (34.5-69.1) |
| | | elderly | | 59.0 (42.3-80.6) | 55.1 (39.1-75.3) | 51.8 (36.6-69.7) |

In addition to investigating coverage levels, it was assessed whether administration of VIS410 prophylaxis to the elderly would be an improvement over general population administration. In the microsimulations, general-population administration results in larger reductions in attack rate than administration to the elderly alone, partially because of the nature of social contacts by which individuals are more likely to associate with those in their same age group. However, prophylaxis of elderly populations was associated with a larger reduction in elderly hospitalizations than distribution to the population at large. The median moderate intensity, in the model described herein, administration of VIS410 four to eight weeks prior to peak prevalence resulted in a reduction of hospitalizations of 34.3% (IQR: 31.9%-36.6%) for 6% coverage, but the impact on hospitalizations was more marginal when administered zero to two weeks prior to the peak, with the reduction of hospitalizations at 13.9% (IQR: 12.1%-15.4%). The absolute case reduction of a prophylaxis strategy is very sensitive to the individual protective period assumed for an administered dose of VIS410, which is longer than 40 days in the model (FIG. 4). If prophylaxis is distributed too late, the majority of individuals will have already been infected, but if given too early, the prophylactic effects of VIS410 administration would wane before the major part of the epidemic wave passes through the population. Administration just prior to the peak is not optimal for population prophylaxis. At this period, approximately 30-40% of the season's infections have already occurred, and the opportunity is lost to protect individuals who become infected during the early and slow phase of the epidemic.

Influenza A remains a major public health threat based on seasonal infections and the potential for pandemic infection. Monoclonal antibody therapies like VIS410 that target broadly neutralizing epitopes represent a powerful class of therapies with multiple mechanisms of anti-viral activity, including direct neutralization of either viral attachment or viral fusion, and Fc-mediated activity including complement deposition and recruitment of cells of the innate immune system that enable the destruction of virus-infected cells (Longini et al. Science 2005; 309(5737): 1083-7; Brandenburg et al. PLoS one 2013; 8(12): e80034). Additionally, as demonstrated here, the relatively safe profile of an antibody therapy enables dosing at high levels through bolus administration compared to many small molecule therapies.

VIS410 was initially developed for the treatment of hospitalized patients with influenza A for at least the following reasons. (1) There are no approved treatments for hospitalized influenza patients, representing a large unmet need. (2) Administration of polyclonal antisera has demonstrated the ability to reduce morbidity and mortality in this population (Hung et al. Chest 2013; 144(2): 464-73). (3) The data from VIS410 in several preclinical models have demonstrated the ability to rapidly reduce viral titers by greater than one $\log_{10}$ and reduce ARDS in lethal models of H7N9 (Tharakaraman et al. Proc Natl Acad Sci USA. 2015; 112(35):10890-5). (4) Pre-clinical data in the ferret suggest that VIS410 can also prevent aerosol transmission of influenza (H1N1) despite its short half-life in this animal model (Lakdawala et al. Therapy or prophylaxis with an HA-stem antibody (VIS410) limits respiratory droplet transmission of influenza viruses in the ferret model. Options for the Control of Influenza VIII. Cape Town, South Africa: International Society for Influenza and Other Respiratory Virus Diseases; 2013). (5) As demonstrated in this Phase 1 study, the relatively safe profile of an antibody therapy enables dosing at high levels through bolus administration that can potentially enable a more rapid drop in viral loads compared to many small molecule therapies.

In this study, it was investigated whether VIS410 could be a useful therapy and/or prophylactic countermeasure. To this end, it was demonstrated here that VIS410 is generally safe and well tolerated, even at the relatively high dose levels of 30 mg/kg and 50 mg/kg. The most common AE related to study drug was loose stool or diarrhea (10° F. 40 subjects; 24.4%). Most subjects had minor and transient loose stool that resolved spontaneously. Two of the six subjects at the highest dose of 50 mg/ml had moderate diarrhea with associated nausea and vomiting that resolved within 6 hours. None of the subjects with diarrhea had any clinically significant issues such as hypotension and there were no associated laboratory abnormalities. The time of onset and transient nature of these AEs suggest that they may be related to an infusion reaction and options such as slowing infusion or pretreatment can be explored in future development to further mitigate these AEs.

There is precedence for infusion reaction related GI events as previously observed in both IVIG therapy and other monoclonal antibodies and appears to be related to mast cell activation that correlates to the period around the $C_{max}$ phase of the initial infusion. Serum PK was approximately dose proportional, and nasal PK of the target organ (nasopharyngeal/upper respiratory tract) demonstrated a partitioning compared to serum of 1:53. ADA was observed at very low levels in 4/30 subjects treated with VIS410. The presence of ADA in response to treatment with IgG1 monoclonal antibodies such as VIS410 is not unique and has been observed in marketed human monoclonal antibodies such as adalimumab.[36] If ADAs were to have a clinically-relevant impact on efficacy, it would be expected to observe a change in the PK of VIS410 as a result of ADA appearance. This was not observed in this study. While this was a small study in healthy volunteers, and ADAs will continue to be monitored thru the development program, these observations would suggest that an impact of ADAs on acute treatment or a one-time prophylaxis of influenza is unlikely. However, it may be likely that the 13% (4 of 30) of subjects who produced ADAs, upon re-exposure to VIS410, would elicit a similar immune response and produce ADAs again. Because the time-course to elicit the ADA response upon re-exposure and clinical significance of this hypothetical concern is unknown, it would be difficult to speculate on the potential impact that re-administration may have for VIS410 therapy either as a treatment or prophylactic modality.

Given the phase 1 trial results, another question was addressed, that is, whether VIS410 could be successfully deployed in the event of an epidemic outbreak to improve public health outcomes. Given VIS410's half-life, it was predicted that its distribution to the primary site of influenza A infection (nasopharynx), and its potency, that limited, directed use of the agent would reduce the total burden of disease. It is noted that universal prophylaxis is unlikely to be practical or feasible. To test the hypothesis of the ability of VIS410 to reduce influenza disease burden, a microsimulation of seasonal influenza that is in good general agreement with observed attack rates was developed. In multiple scenarios, administration of a broadly neutralizing antibody like VIS410 at an estimated dose of 8-16 mg/kg to the at-risk elderly, for example in nursing homes and within the hospital, prior to an influenza outbreak reduces the frequency of serious influenza. This effect can be achieved even with administration of VIS410 at a relatively low coverage (between 2% and 6%), having a measurable impact on mitigating hospitalization events in an influenza outbreak.

Sensitivity analysis of the models indicates that timing of administration may be a crucial component of the decision-making process for the deployment of VIS410 as a prophylaxis. The analysis suggests that between four to eight weeks prior to an epidemic peak is the optimal timing for deployment, and this is also dependent on the dose given which determines the length of an individual's protective period. As recently developed climate-based models have made wintertime influenza peak forecasting possible with a four to six week lead time, it can in fact be possible to have accurate enough influenza prediction to begin the early roll-out of a prophylaxis (Shaman et al. Nature communications 2013; 4: 2837; Shaman et al. Proceedings of the National Academy of Sciences of the United States of America 2012; 109(50): 20425-30). Another factor may be determining whether an influenza season will be short or long, and the forecasting exercises would need to be re-run with this exact scenario in mind: timed deployment of a population-level prophylactic whose aim is to stem transmission and reduce hospitalizations in the elderly.

Desirable outcomes for influenza public health interventions include reductions in attack rates and hospitalizations across all age groups. For hospitalization reductions in particular, it is usually not possible to prioritize one age group over another, and for this reason there is a long unresolved question in influenza about the age-targeting of public health interventions (e.g., targeting high-contact or high-vulnerability individuals for intervention). Targeting high-contact individuals may have a larger impact on mitigating the epidemic as a whole, including larger attack-rate reductions in high-vulnerability individuals (FIG. 2A). On the other hand, targeting high-vulnerability individuals has a more direct and measurable impact on the individuals that receive prophylaxis (FIG. 2C), and it may make it easier to argue for higher coverage levels if it can be clearly seen that protection is highly efficacious on an individual level.

The general indirect benefits seen in this population modeling exercise are seen in all population-level analyses of public health interventions for infectious disease. Precise outcomes from the population exercise may be affected by, for example, geographic, demographic, and contact structure of the population in question; individual variation in the protective period; interaction between VIS410 therapy and acquisition/loss of influenza-specific immunity; and the sometimes unpredictable shape of influenza epidemics. For long-term effects of VIS410 as a public health strategy and the relationship with immunity, it is noted that VIS410 targets a non-immunodominant epitope. As such, in animals, there is no measureable difference in the strength of the native immunological response between infected, untreated animals, and infected VIS410-treated animals. In both cases, re-challenge with the same virus results in no infection due to a memory response. For short-term effects (single epidemic season), the general prophylaxis principles described in this analysis can be robust to different characteristics of temperate-zone influenza epidemics, and individual cities or states can perform analyses and make decisions that are specific to their populations and their past experience with influenza.

In summary, based on the results presented here, it was found that the safety and pharmacokinetic profile of VIS410 allow for not only treating influenza on an individual level but also as a public health strategy to mitigate the effects of seasonal or pandemic influenza based on its ability to reduce the overall burden of disease when strategically administered in a vulnerable population.

Model Description

An individual-based epidemic microsimulation was developed in C++. The simulation was based on a previously developed model (Boni et al. (2013) *Phil Trans R Soc L B* 368: 20120207) and is similar in structure and design to an array of microsimulation models that have been developed over the past decade (Ferguson et al. (2005) *Nature* 437: 209-214; Germann et al. (2006) *Proc Natl Acad Sci USA* 103: 5935-5940; Longini and Koopman (1982) *Biometrics* 38: 115-126). The simulation has a 6-hourly time step and asynchronous updating which is implemented with a special scheduler class that keeps track of which individuals need updating at every time step. The population is structured into households, and locations (neighborhoods). Individuals spend 12 hours a day in their household potentially infecting household contacts (nighttime), and 12 hours a day (daytime) in a pre-assigned location potentially infecting others in the general population who are in the same location; general-population daytime contact rates are age-specific (Mossong et al. (2008) *PLoS Med* 5: e74). Individuals also engage in travel to random locations with a probability of 0.001 per timestep. The model has 1,000 locations and one million individuals.

Individuals in the model can pass through any of eight clinical states: susceptible to infection, exposed to influenza virus, latently infected (i.e. infectious but with mild or no symptoms), infected with symptoms, severe influenza, hospitalized with severe influenza, recovered and immune, and deceased. Individuals can be assigned to one of seven age groups: 0-5, 6-15, 16-25, 26-34, 35-49, 50-64, and >65 years of age.

During the daytime time steps, a location-specific force of infection (FOI) is computed using the population contact structure and the age structure of the infected individuals in that location. The FOI is multiplied by a scaling parameter ($\beta$) and a Poisson random number (mean=$\beta \cdot$FOI) of new individuals-to-be-infected (challenged by virus) is generated at each location at each daytime time step; each individual is then selected for infection or non-infection according to their immunity and protection by VIS410 (see below). The parameter $\beta$ is used to calibrate the attack rates and epidemic shape/duration in the model (see below). In order to simulate the introduction of infected individuals from other populations, 10 random susceptible individuals (0.001%) were infected each day.

A seasonal forcing function for $\beta$ was implemented using the positive part of a cosine function to ensure that simulated epidemics peaked at times consistent with observed epidemics. Although influenza epidemics can peak at any point between December and March in northern temperate countries, it was not necessary to include all of this variation, as the important feature for VIS410 administration will be how close to the epidemic peak the therapy is distributed and used.

Susceptible individuals in the model carry some level of natural partial immunity to influenza which is based on their age and likelihood of past infection/vaccination. Natural or partial immunity is modeled simply on a scale of zero to one that describes an individual's relative immunity to infection if she/he encounters an infected contact. In other words, a completely naïve individual would have an immunity of 0.0 and would meet infectious individuals and contract an influenza infection proportional to some rate $\beta$ (general scaling parameter for transmission, from above). An individual that is partially immune with an immunity level of 0.67, for example, would be three times (1/(1−0.67)) less likely to become infected under the same pattern of contacts as a completely naïve individual; this individual would only have a 33% chance of becoming infected if he were challenged by virus. The mean immune levels for different age classes are shown in the table below. These are modeled as normal distributions with standard deviations set to 0.05. For the younger age classes a fraction of individuals are assumed to be completely naïve (immunity=0.0); age-specific rates for being considered completely naïve are listed in Table 13. These assumptions are based on an average 15% annual attack rate (Keitel et al. (1997) *Vaccine* 15: 1114-1122; Edwards et al. (1994) *J Infect Dis* 169: 68-76; Neuzil et al. (2002) *J Infect Dis* 185: 147-152) and vaccination rates in the US and Europe which are in the 15% to 50% range depending on country, season, and age group (Report M W (2012) Influenza Vaccination Coverage Among Health-Care Personnel—2011-12 Influenza Season, United States. 61: 2008-2011; Blank et al. (2008) *BMC Public Health* 8: 272).

TABLE 13

Age-based immunity levels used in the microsimulations

| Age Group | Mean Immunity-Level | Fraction Naïve |
|---|---|---|
| 0-5 | 0.50 | 0.3000 |
| 6-15 | 0.50 | 0.2019 |
| 16-25 | 0.40 | 0.0398 |
| 26-34 | 0.40 | 0.0100 |
| 35-49 | 0.40 | 0.0100 |
| 50-64 | 0.30 | 0.0100 |
| >65 | 0.20 | 0.0100 |

For each individual, the level of VIS410 antibody circulating in that person's blood was tracked. A therapeutic dose is set to (1-2 mg/kg) and this blood-concentration decays exponentially with a half-life of 13 days. If an individual is selected for infection in a particular timestep, that individual will be refractory to infection (i.e., protected by VIS410) with probability equal to—

$$(\text{Protective Efficacy}_{VIS410}) * (\text{blood concentration}) / (\text{blood therapeutic concentration})$$

In these simulations, the protective efficacy of VIS410 was set to 0.9, providing a maximum of 90% reduction in the probability of being infected when VIS410 levels are equal to or above the prophylactic dose (1-2 mg/ml). Individuals can receive 4-fold or 8-fold the prophylactic dose at the time of prophylaxis. A concentration below 0.1-fold the prophylactic dose is set to zero in the simulation. This behavior is shown in FIG. 4.

Age-specific hospitalization and mortality (given hospitalization) rates are taken from previous studies (section below). Age and household size distributions were set for the US population (US_Census_Bureau (2014) Age Demographic and Housing Estimates; Statista.com (n.d.) Distribution of Households in the US by Household Size Accessed 6 Nov. 2015).

Strategy Definitions

VIS410 prophylaxis strategies were modeled by considering the fraction of the population that would receive prophylaxis (the coverage f), the time before the epidemic peak at which the treatment is distributed (between 0 to 8 weeks before the peak), and whether the treatment was distributed to individuals of all ages or only individuals over the age of 65. VIS410 deployment for a given coverage level was spread equally over a 14 day period after the desired date of administration. Coverage levels of 2%, 4%, and 6% of the total population size were explored.

Model Validation

Infection Duration

Mean infection duration was set to a 1 day latent and infectious period and 2.75 days (with a standard deviation of 0.75 days) of a symptomatic and infectious period, for non-severe patients based on the known course of influenza infections (Carrat et al. (2008) Am J Epidemiol 167: 775-785; Hien et al. (2010) PLoS Med 7: e1000277). Although some of these studies show viremia out to day 7, these data also show a reduction in symptoms after days 3 or 4, and a difference in whether influenza can be molecularly confirmed or virologically confirmed in the late stages of infection. For individuals progressing to severe influenza, the duration of the severe stage of disease was set to 3.0 days. A fraction (5%) of individuals progressed to severity, thus the mean duration of a non-hospitalized influenza infection was 3.90 in the simulation.

Household Infection Rates

During the nighttime time steps, household infections occur according to previously inferred probabilities of household infection (Philip et al. (1961) Am J Hyg 73: 123-137; Longini et al. (1988) Am J Epidemiol 128: 845-859; Longini and Koopman (1982) Biometrics 38: 115-126; Cowling et al. Ann Intern Med 151: 437-446; Cowling et al. (2010) N Engl J Med 362: 2175-2184; Papenburg et al. (2010) Clin Infect Dis 51: 1033-1041; Petrie et al. (2013) PLoS One 8: e75339; Suess et al. (2012) BMC Infect Dis 12: 26; Klick et al. (2011) Epidemiology 22: 793-796). Note that the results in these studies vary substantially depending on whether the strain was pandemic or seasonal, prior immunity in household contacts, oseltamivir use in the study, and whether and at what time point influenza was molecularly/virologically confirmed. A probability of infection (given an infected contact in a household) of 0.0216 per individual in a six-hour time step was chosen; this corresponds to an average 13% household attack rate for the duration of an infection for families with 4 or 5 members.

Epidemics Duration and Attack Rate

The epidemic duration and attack rate are affected by $\beta$ (the transmission scaling parameter), migration between locations, immunity levels, and household contact rates. Household infection rates were calibrated separately so that the expected household attack rates were achieved. Between-location movement rates affect the duration of the epidemic. Individuals moved on a daily basis to workplaces, schools, or other daily locations that were pre-determined. This movement rate was set so that 1 in 250 individuals had random travel patterns assigned per day and calibrated so that the size and duration of the epidemic correspond to US influenza epidemic patterns.

Influenza attack rates in the US range from 5% to 25% (Longini et al. (1988) Am J Epidemiol 128: 845-859; Keitel et al. (1997) Vaccine 15: 1114-1122; Edwards et al. (1994) J Infect Dis 169: 68-76; Neuzil et al. (2002) J Infect Dis 185: 147-152; Monto et al. (1985) Am J Epidemiol 121: 811-822). These vary by age group and can be as high as 30% for children, depending on the influenza season. As most serological studies on seasonal influenza do not break individuals out into narrow age bands (with exceptions (Monto et al. (1985) Am J Epidemiol 121: 811-822; Hayward et al. (2014) Lancet Resp Med 2600: 16-19), it is difficult to know much about age-specific attack rates except that (1) children generally have higher attack rates than adults, and (2) elderly groups tend to have lower attack rates, but this needs to evaluated in light of the fact that elderly individuals can have low serological responses to influenza infection.

The duration of an influenza-like illness (ILI) season can be calibrated using CDC's ILINet, which shows weekly ILI incidence, for the past 11 years in 10 different regions in the US. Median duration is 15 weeks, and inter-quartile range is 10-20 weeks. These are epidemics of "influenza-like illness" which is defined syndromically, so the true influenza season may be slightly shorter (this depends on the season, subtype, and other circulating viruses). To compute these ILI durations, region-specific baselines were computed from the ILI trends (bottom two terciles of the data), and ILI rates that were two standard deviations above the baseline were considered as high ILI activity and used to define the ILI season.

15 different epidemic scenarios were defined based on the transmission parameter $\beta$ (five different values) and on host immunity levels (three different values). The five $\beta$ values considered are: 0.36, 0.38, 0.40, 0.425, and 0.45. And, three different scenarios of "relative levels of pre-existing immunity": 1.0 (a baseline or reference value), 0.94, and 1.06, were considered.

The levels of pre-existing immunity differ in the age groups according to Table 14.

TABLE 14

Age-Based Pre-Existing Immunity Levels Used in the Microsimulation

|  | Ages 0-15 | Ages 16-49 | Ages 50-64 | Ages ≥65 |
| --- | --- | --- | --- | --- |
| Mean Immunity in Scenario 1 | 0.470 | 0.376 | 0.282 | 0.188 |
| Mean Immunity in Scenario 2 | 0.5 | 0.4 | 0.3 | 0.2 |
| Mean Immunity in Scenario 3 | 0.530 | 0.424 | 0.318 | 0.212 |

Here, the value represents the reduction in susceptibility to infection if a person comes into sufficient contact with an infectious individual. The percentage naïve does not change for the different scenarios.

The age specific and overall attack rates for the fifteen different transmission scenarios are shown in Table 15.

TABLE 15

Median Attack Rates by Age Groups

| $\beta$ | Relative immunity | Ages 0-15 | Ages 16-49 | Ages 50-64 | Ages >= 65 | All Ages |
| --- | --- | --- | --- | --- | --- | --- |
| 0.36 | 0.94 | 15.87 | 17.40 | 14.49 | 8.26 | 15.45 |
|  | 1.00 | 10.03 | 11.04 | 9.25 | 5.31 | 9.84 |
|  | 1.06 | 5.92 | 6.43 | 5.46 | 3.24 | 5.77 |
| 0.38 | 0.94 | 17.93 | 19.79 | 16.47 | 9.49 | 17.56 |
|  | 1.00 | 11.51 | 12.63 | 10.62 | 6.11 | 11.24 |
|  | 1.06 | 7.10 | 7.72 | 6.54 | 3.84 | 6.91 |
| 0.40 | 0.94 | 19.83 | 21.71 | 18.22 | 10.57 | 19.35 |
|  | 1.00 | 13.23 | 14.60 | 12.24 | 7.12 | 13.01 |
|  | 1.06 | 8.12 | 8.98 | 7.56 | 4.41 | 8.00 |
| 0.425 | 0.94 | 22.82 | 25.16 | 21.17 | 12.34 | 22.45 |
|  | 1.00 | 15.63 | 17.24 | 14.50 | 8.48 | 15.34 |
|  | 1.06 | 9.95 | 10.99 | 9.35 | 5.44 | 9.83 |
| 0.45 | 0.94 | 25.58 | 28.37 | 23.96 | 14.06 | 25.31 |
|  | 1.00 | 18.61 | 20.44 | 17.25 | 10.10 | 18.22 |
|  | 1.06 | 11.99 | 13.26 | 11.36 | 6.56 | 11.88 |

Figure 5:
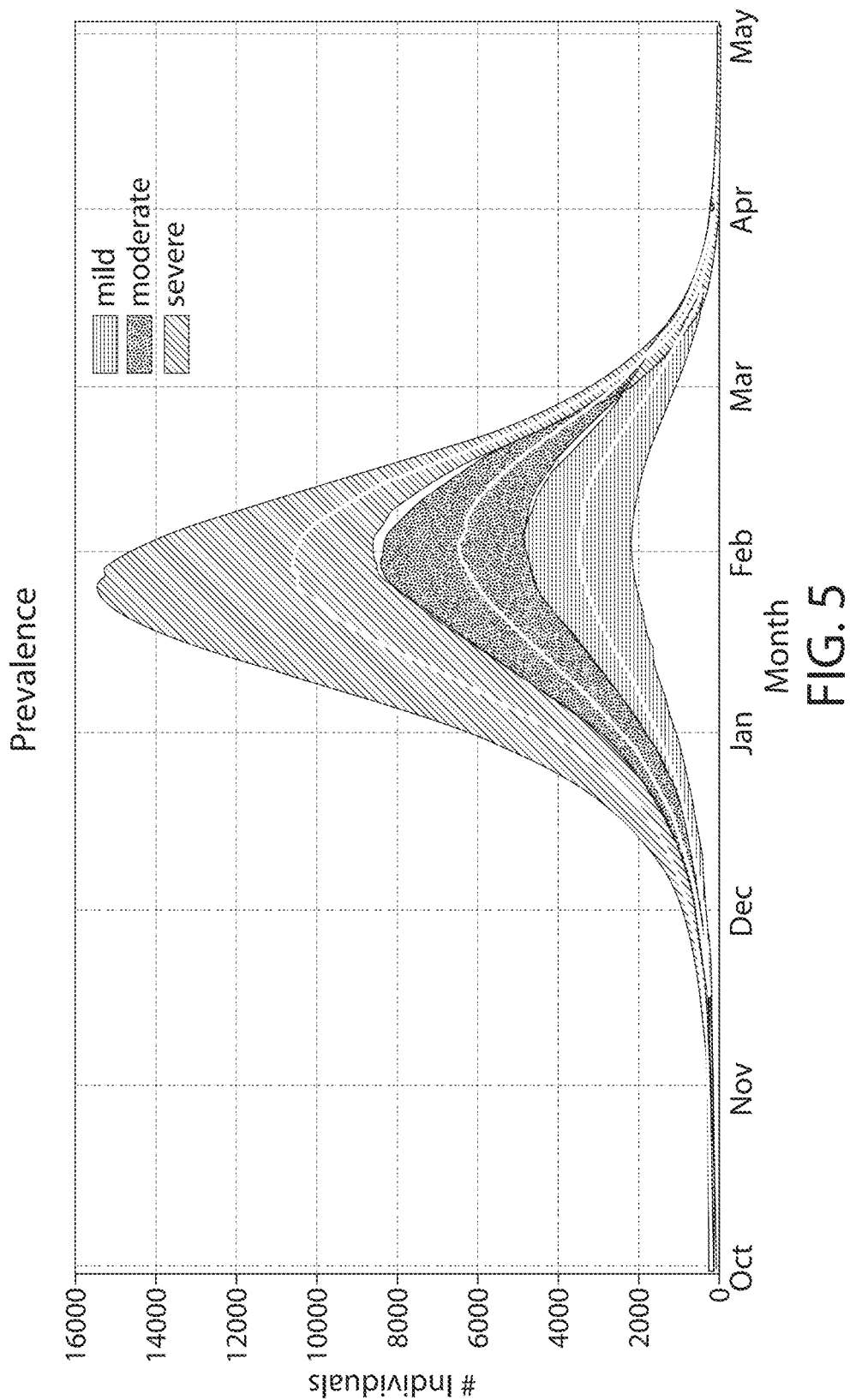
FIG. 5 depicts the prevalence curves (375 simulations) of seasonal influenza for varying transmission scenarios. Filled colors show the middle 90% ranges of simulation outputs classified into three transmission intensities: attack rate >16% (red/severe), attack rate between 10% and 16% (blue/moderate), attack rate <10% (green/mild).
Figure 6:
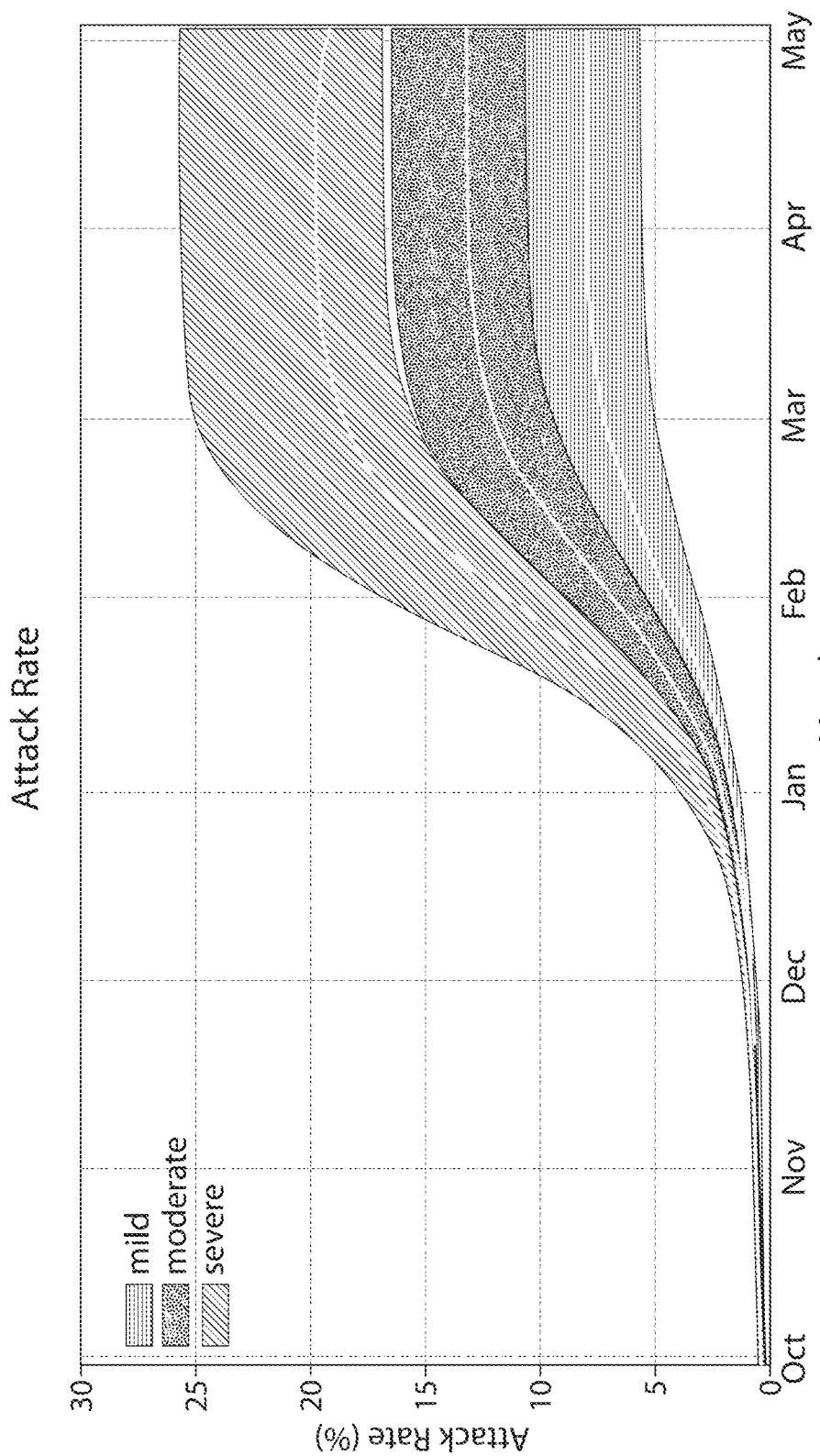
FIG. 6 depicts the cumulative prevalence curves (375 simulations) of seasonal influenza for varying transmission scenarios. Filled colors show the middle 90% ranges of simulation outputs classified into three transmission intensities: attack rate >16% (red/severe), attack rate between 10% and 16% (blue/moderate), attack rate <10% (green/mild).
Figure 7:
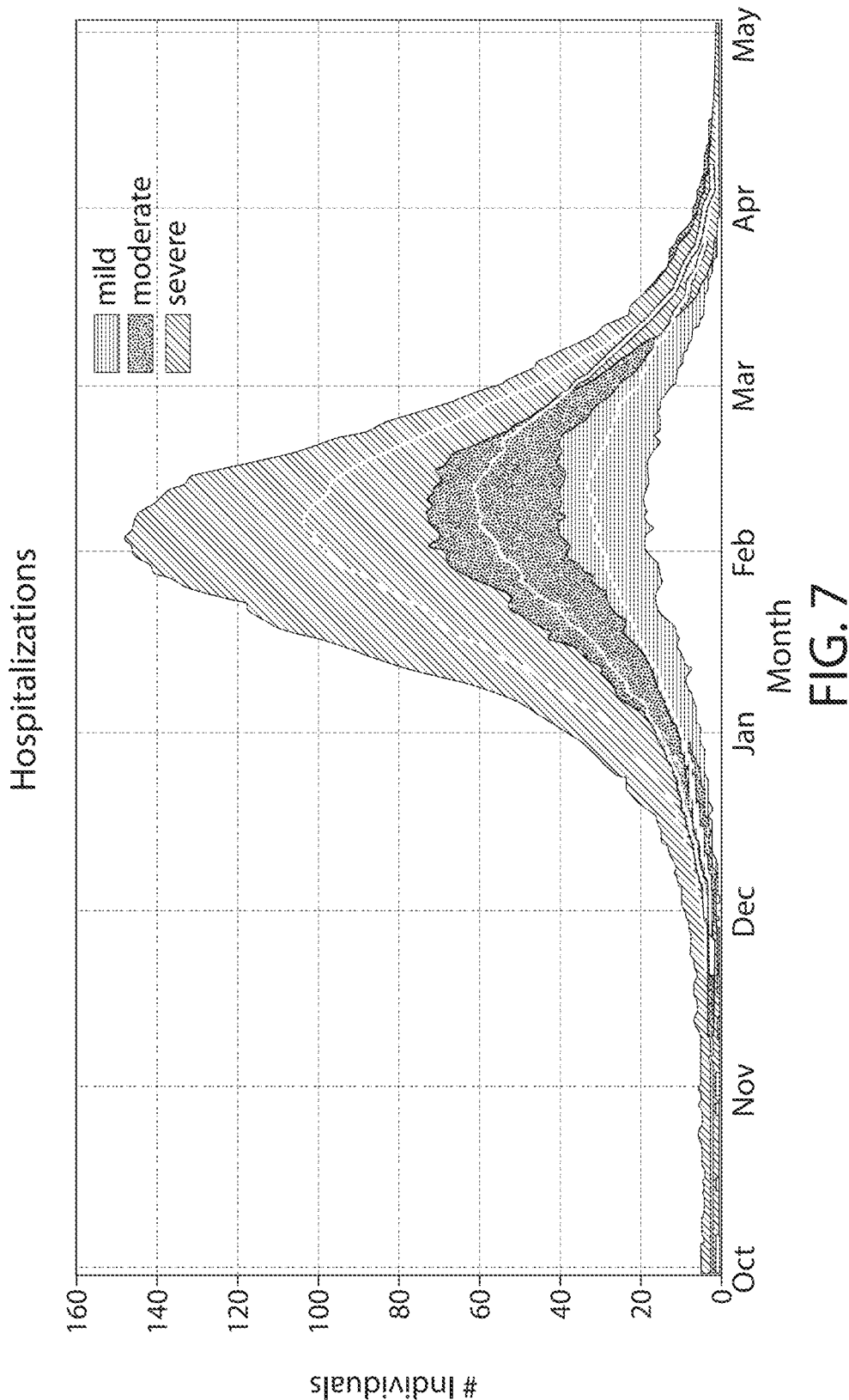
FIG. 7 depicts the hospitalization curves (375 simulations) of seasonal influenza for varying transmission scenarios. Vertical axis shows total number of hospitalized patients, of all ages, in a population of one million individuals. Filled colors show the middle 90% ranges of simulation outputs classified into three transmission intensities: attack rate >16% (red/severe), attack rate between 10% and 16% (blue/moderate), attack rate <10% (green/mild).

These fifteen scenarios were chosen (i.e., calibrated) in order to achieve attack rates in the 5% to 25% range and epidemic durations in agreement with CDC data on influenza-like illness incidence in the United States. Typical prevalence rates, attack rates, hospitalization rates, and epidemic durations are shown in FIGS. 5-7.

Age-Specific Hospitalization and Mortality

The model construction requires us to assign the probability of an influenza infection becoming severe, the probability of a severe influenza infection being hospitalized, and the probability of a hospitalized influenza patient dying. The probability of progressing from non-severe symptomatic influenza to severe influenza is poorly defined, as typically severity is measured in hospitalized patients but not in the general patient pool. In the calibrations below, this fraction was set to 5%; in other words, 5% of influenza infections progress from "normal influenza" to "severe, but not necessarily hospitalized or not yet hospitalized, influenza." From these 5% the hospitalization and mortality rates can be calibrated as these data are collected at national levels in the US and most other countries. Using US data these rates/probabilities were set to values shown Table 16.

TABLE 16

Age-Based Hospitalization and Mortality Rates Used in the Microsimulation

| Age Group | Hospitalization Prob | Mortality Prob |
| --- | --- | --- |
| 0-5 | 0.1600 | 0.010 |
| 6-15 | 0.0065 | 0.020 |
| 16-25 | 0.0410 | 0.025 |
| 26-34 | 0.0400 | 0.033 |
| 35-49 | 0.0340 | 0.050 |
| 50-64 | 0.0880 | 0.066 |
| >65 | 0.7500 | 0.066 |

Here, the hospitalization probability in the second column is the probability of becoming hospitalized if one has a severe influenza infection. The mortality probability is the probability of a hospitalized patient dying as a result of complications resulting from influenza infection.

Hospitalization rates were taken from previous studies of influenza associated hospitalization in the US (Thompson et al. (2004) J Am Med Assoc 292: 1333-1340; Bhat et al. (2005) N Engl J Med: 2559-2567; Dawood et al. (2010) J Pediatr 157: 808-814; Jhung et al. (2011) Clin Infect Dis 52 Suppl 1: S13-S26; Zhou et al. (2012) Clin Infect Dis 54: 1427-1436). Depending on the hospital classifications used and the severity of the influenza season, annual influenza-attributed hospitalization rates in the United States fall between 20 and 120 per 100,000 individuals. For individuals over the age of 65, this rate falls between 200 and 400 per 100,000.

For the fifteen transmission scenarios chosen for the analysis, general-population hospitalization rates fall between 28 and 123 per 100,000. For the over 65 age group, these rates are between 200 and 370 per 100,000 individuals.

Model calibration was performed for influenza A, where possible. A low transmission season in the model can also be considered one that is predominantly influenza B. For a season that is mixed or approximately equally split between influenza A and influenza B, the reductions in attack rate and hospitalization resulting from VIS410 prophylaxis would be lower.

Sensitivity Analysis

To perform a basic sensitivity analysis to various epidemiological scenarios, the transmission scenario (the transmission parameter $\beta$ and the pre-existing population immunity), the coverage level (2%, 4%, 6%), the date of administration of VIS410 prophylaxis (0, 2, 4, 6, and 8 weeks prior to the peak), the dose given (4-fold or 8-fold), and whether VIS410 was administered to all age groups or targeted only to the elderly, were varied. This represents 900 scenarios. Performing 50 stochastic runs for each scenario yields 45,000 simulation outputs.

The Pearson partial correlation coefficients between a simulation output and a simulation input (parameter), holding the other parameters constant, are shown in Table 17.

TABLE 17

Partial Correlation Coefficients

|  | β | Pre-existing immunity | VIS410 Administration group (0 = all ages, 1 = elderly) | Dose (4- or 8-fold) | Population Coverage | VIS410 administration, days prior to epidemic peak |
|---|---|---|---|---|---|---|
| Attack Rate (all ages) | 0.912 | −0.967 | 0.411 | −0.089 | −0.384 | −0.419 |
| Hospitalization Rate (all ages) | 0.889 | −0.955 | 0.077 | −0.115 | −0.450 | −0.408 |
| Hospitalization Rate (>65 only) | 0.859 | −0.938 | −0.208 | −0.134 | −0.488 | −0.394 |

The signs and magnitudes in the first two columns are as expected. Increasing the transmission parameter or pre-existing population immunity has substantial effects on overall attack rates and hospitalizations.

As the administration parameter was "increased" from 0 (all ages) to 1 (elderly only), a clear positive effect was seen on the attack rate, and a small positive effect on the total hospitalization numbers. The reason the hospitalization effect is small is that the increase in attack rate comes in the least likely groups to be hospitalized, children and young adults. As the administration parameter is "increased" from 0 to 1, hospitalizations in the elderly decline (PCC=−0.208) as expected as this group benefits from direct protection due to VIS410 prophylaxis. This effect is seen in the three panels of FIGS. 2A-2C.

As expected, increasing the dose or increasing coverage reduces attack rates and hospitalizations (fourth and fifth columns).

The final column shows the partial correlation between administration time and the attack rate/hospitalization outcomes. However, FIG. 3 already shows that this relationship is non-monotonic. Hence, the negative correlations should not be taken to mean that earlier administration will always be associated with a reduction in attack rate or hospitalizations.

Epitope Analysis of Currently Circulating Strains of Influenza A

To assess the diversity of the amino acids comprising the predicted epitope of hemagglutinin (HA) targeted by VIS410, all HA sequences from H1N1 and H3N2 collected from Jan. 1, 2012 through Jun. 30, 2015 were analyzed. Sequences were obtained from the EpiFlu database provided by the Global Initiative on Sharing Avian Influenza Data (GISAID). 5,782 H1N1 sequences and 10,210 H3N2 sequences were obtained. A multiple sequence alignment (MSA) for both H1N1 and H3N2 was created using HMMalign version 3.1b1 against a curated sequence profile of HA. Using this MSA, the amino acid variation at positions predicted to be in the epitope were computed. Sequence variation at these positions is shown in the sequence logo plots shown in FIG. 8, illustrating that the 25 positions comprising the predicted epitope are highly conserved.

Detailed Phase I Study Design

VIS410 was administered as an IV infusion over at least 120 minutes. Randomization was used to reduce selection bias, double-blinding was employed to reduce potential bias during data collection and evaluation of safety variables, and the placebo group served as the control group. The dose-escalation design and the safety evaluation period within cohorts and between successive cohorts allowed for incremental safety review. In this study, subjects received the following doses: 2, 5, 15, 30, and 50 mg/kg. These doses were consistent with serum concentrations of VIS410 that were achieved during in vivo studies and demonstrated protection from challenge with various influenza A strains and prevention of influenza spreading via respiratory droplets. See Table 18 for the schedule of events.

Institutional research board approval was obtained prior to start of the study. Informed consent and Health Insurance Portability and Accountability Act (HIPAA) authorization were obtained at the screening visit. The screening visit was conducted within 30 days of study product infusion (Days −30 to −1).

Inclusion Criteria

For inclusion in the study, each subject was required to meet all of the following criteria at screening:

1. After the nature of the study was fully explained, the subject read, understood, and signed the IRB-approved ICF which provided written informed consent and HIPAA authorization.
2. Aged ≥18 and ≤55 years.
3. Had a body mass index ≥18 and ≤33 $kg/m^2$, inclusive, and weighed ≤90 kg for subjects in Cohort 5 receiving a 50-mg/kg dose.
4. Was in general good health without history of any of the conditions listed in the exclusion criteria.
5. Nonsmoker for at least 6 months.
6. A woman agreed not to become pregnant from the time of study enrollment until at least 3 months after the completion of the monoclonal antibody infusion. If a woman was sexually active and had no history of hysterectomy or tubal ligation, she agreed to use hormonal birth control, barrier method of birth control with spermicidal gel, or an intrauterine device and continued using approved contraception for at least 3 months after the completion of the VIS410 infusion. These birth control measures were not applicable for postmenopausal women, defined as either having amenorrhea for ≥12 months or follicle-stimulating hormone >40 MIU/mL.
7. Sexually active male subjects agreed to use a barrier method of birth control with spermicidal gel during the course of the study and continued using a barrier method of birth control for at least 3 months after the completion of the VIS410 infusion.
8. Subject had screening laboratory values that met the following criteria:
   a. White blood cells: 3000 to 12 000/$mm^3$
   b. Platelets: >150 000/$mm^3$
   c. Hemoglobin: >13 g/dL (male) or >12 g/dL (female)
   d. Creatinine: ≤1.40 mg/dL e. Blood urea nitrogen: ≤25 mg/dL
f. Aspartate aminotransferase: ≤50 IU/L
g. Alanine aminotransferase: ≤67 IU/L
h. Alkaline phosphatase: ≤150 IU/L
i. Bilirubin: ≤1.4 mg/dL
j. Glucose (fasting): <115 mg/dL
k. Drug and alcohol screen: Negative Exclusion Criteria Any of the following was regarded as a criterion for exclusion of a subject from the study:

1. Previously received an antibody or biologic therapy, whether licensed or investigational (e.g., immunoglobulin products, monoclonal antibodies, or antibody fragments).
2. History of any of the following illnesses or conditions: cancer, heart disease, diabetes mellitus, respiratory condition (such as asthma requiring daily medication), autoimmune disorder, blood dyscrasias, or psychiatric disorder that precluded compliance with protocol.
3. Any chronic condition that required daily prescription or over-the-counter medicine, except for vitamins and birth control products.
4. Abused drugs or alcohol within the previous 12 months.
5. History of a previous severe allergic reaction with generalized urticaria, angioedema, or anaphylaxis.
6. Physical finding on an examination considered clinically significant, such as murmur (other than functional), hepatosplenomegaly, lymphadenopathy, or focal neurological deficit.
7. Blood pressure >160/100 or <90/50 on 2 separate readings.
8. Urinalysis results determined to be clinically significant per investigator discretion.
9. Positive serology for human immunodeficiency virus antibody, hepatitis C virus antibody, or hepatitis B surface antigen.
10. Positive urine pregnancy test during screening or within 24 hours of monoclonal antibody administration or an unwillingness to undergo pregnancy testing for female subjects.
11. Positive drug or alcohol testing at screening or within 24 hours of monoclonal antibody administration.
12. Breastfeeding.
13. Received another investigational study agent within 30 days or 5 half-lives, whichever was longer, before administration of the study product.
14. Received any live virus or bacterial vaccinations within 3 months prior to screening or was expected to receive any live virus or bacterial vaccinations during the study.
15. Received inactivated influenza vaccines within 2 weeks of Day 0 or was expected to receive an inactivated influenza virus during the study.
16. Any other condition that, in the opinion of the investigator, would have jeopardized the safety or rights of the subject participating in the study, or made it unlikely the subject could have completed the protocol.

TABLE 18

Schedule of Events

| Procedure | Screening | | Study Time After Infusion (days) | | | | | | |
|---|---|---|---|---|---|---|---|---|---|
| Time Point (Day) | −30 to −1 | 0$^a$ | 1 | 2 | 3 | 7 | 14 | 28 | 56 | 120 |
| Study Visit | 1 | 2 | 3 | 4 | 5 | 6 | 7 | 8 | 9 | 10 |
| Informed consent/HIPAA authorization | X | | | | | | | | | |
| Inclusion/exclusion criteria | X | | | | | | | | | |
| Demographics and medical history | X | | | | | | | | | |
| Serum for hepatitis panel and HIV | X | | | | | | | | | |
| Drug and alcohol toxicology screen$^b$ | X | X | | | | | | | | |
| Pregnancy test | X | X | | | | | | | | |
| Vital signs$^c$ | X | X | X | X | X | X | X | X | X | |
| Electrocardiogram$^d$ | X | X | | | | | | | | |
| Physical examination$^e$ | X | X | X | | X | | X | | X | |
| Clinic admission$^f$ | | X | | | | | | | | |
| PK sampling$^g$ | | X | X | X | X | X | X | X | X | X |
| ADA sampling$^h$ | | X | | | | | X | | X | X |
| Study infusion | | X | | | | | | | | |
| Hematology$^i$ | X | X | X | | X | X | X | X | | |
| Serum chemistry/liver function tests$^i$ | X | X | X | | X | X | X | X | | |
| Urinalysis$^i$ | X | X | X | | X | X | X | X | | |
| Concomitant medications | X | X | X | X | X | X | X | X | X | X |
| Adverse events$^j$ | | X | X | X | X | X | X | X | X | X |
| Nasopharyngeal swabs$^k$ | | X | X | | X | X | | | | |

Example 2: Preclinical Animal Data Supporting Prophylactic Dose Level

Methodology

An A/Puerto Rico/8/1934(H1N1) lethal mouse models was employed Animals were administered antibody IP in a volume of 200 µL as prophylaxis one day prior to infection. Then, mice were anaesthetized under isoflurane and challenged i.n. with 50 µL viral suspension (~100 pfu). Weight and appearance of the animals were recorded daily. Animals were euthanized upon loss of considerable weight (>20%) in conjunction with high body score indicating illness. Lungs were harvested from a subgroup of animals on day four post-infection for the determination of viral load by plaque assay. In addition, lungs on day eight were submitted for histological examination.

Results
The study was completed as follows (Table 19).

TABLE 19

Experimental Design

| Agent | Dose (mg/kg) | Administration |
|---|---|---|
| PBS (Vehicle) | — | — |
| Ribavirin | 75 (3 doses) | −24 hours, +24 hours, +48 hours |
| VIS410 | 10 | 24 h prior to infection |
| VIS410 | 2.5 | 24 h prior to infection |
| VIS410 | 0.6 | 24 h prior to infection |

Visual Cues

Figure 10A:
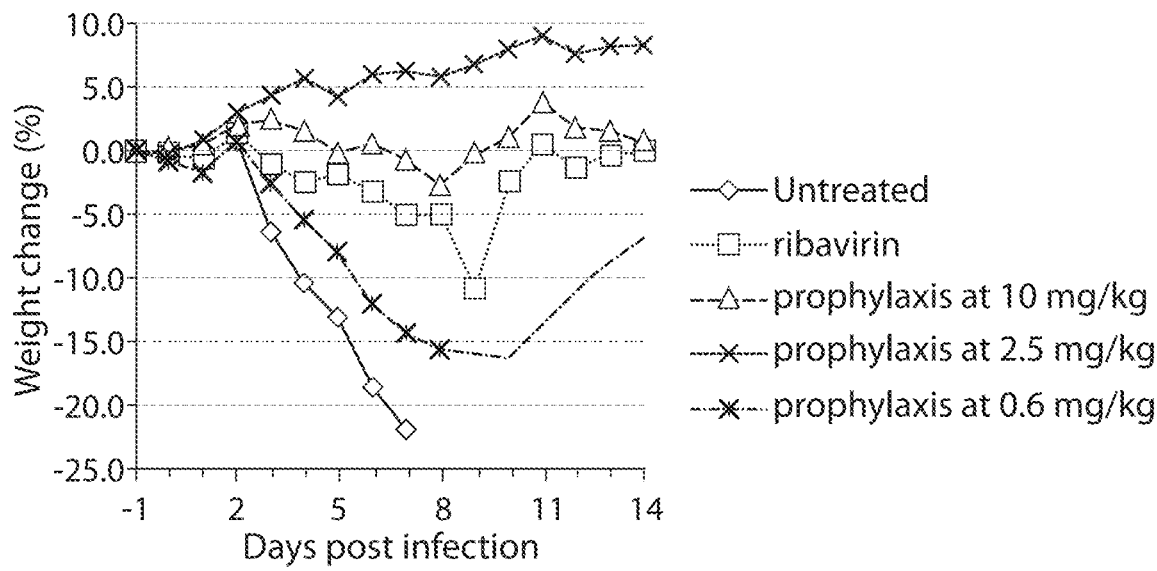
FIG. 10A depicts the weight loss of animals infected with H1N1 PR8 and untreated or treated with ribavirin or a prophylactic dose of VIS410 (0.6, 2.5, or 10 mg/kg).
Figure 10B:
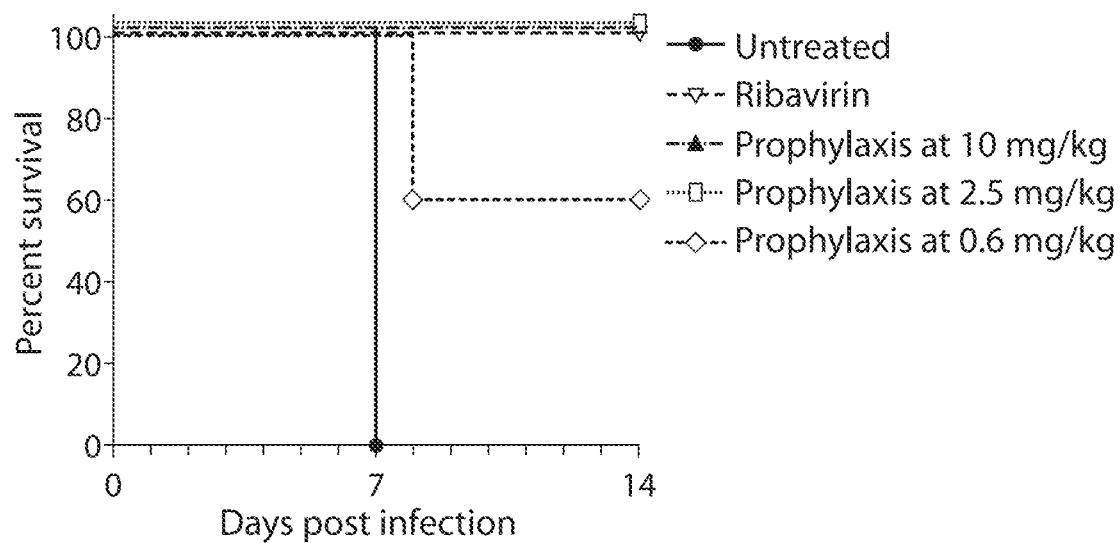
FIG. 10B depicts the Kaplan-Meier survival curves for animals infected with H1N1 PR8 and untreated or treated with ribavirin or a prophylactic dose of VIS410 (0.6, 2.5, or 10 mg/kg).
Figure 11A:
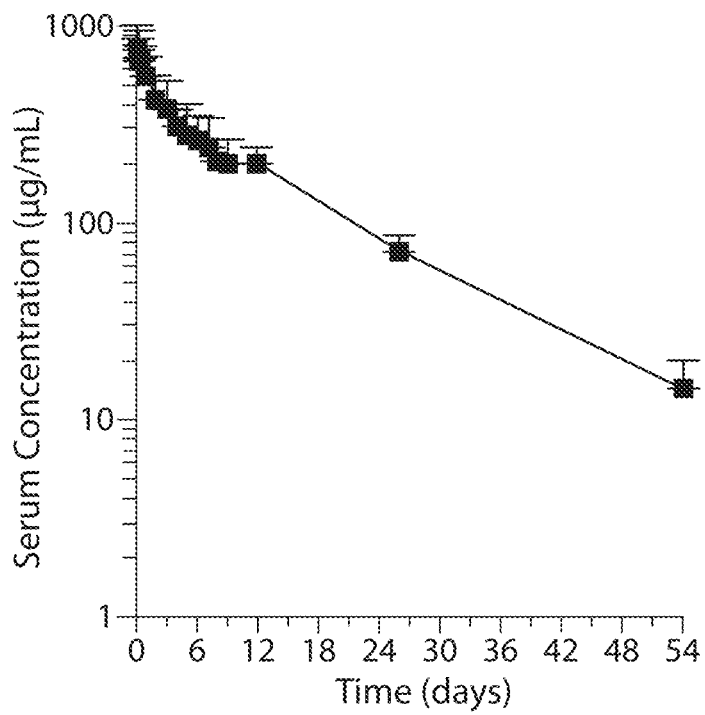
FIGS. 11A-11B depict the mean (+SD) serum (FIG. 11A) and nasopharyngeal (FIG. 11B) VIS410 concentration versus time profiles (log-linear scale).
Figure 11B:
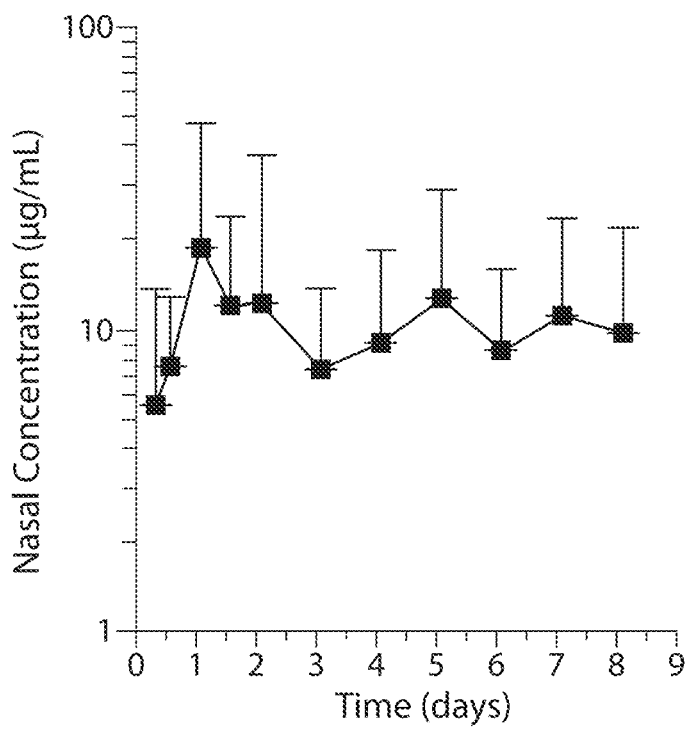

Animals were monitored for signs of illness (ruffled fur, hunching) daily. Untreated mice that were challenged with H1N1 appeared sick three days post-infection and were euthanized on day seven, as expected. Mice that were challenged with H1N1 and treated with three doses of ribavirin exhibited negligible signs of illness and recovered fully (FIGS. 10A-10B). Mice that were treated with VIS410 one day prior to challenge at 2.5 mg/kg or 10 mg/kg exhibited no sign of illness. Mice that were treated with VIS410 at 0.6 mg/kg one day prior exhibited some signs of illness, with 60% of animals surviving.

Viral Load

The lung viral loads four days after H1N1 infection were assessed in a single plaque assay (Table 20). Comparisons were made between treatment groups to assess the significance of the reductions in lung viral load. Significance ($p<0.05$) was determined Mann Whitney U test. The lung viral load in all treatment arms was significantly different from that in the untreated group.

TABLE 20

Lung Viral Load in Mice Four Days after Challenge with H1N1 PR8

| Group | Dose (mg/kg) | Lung Viral Load |
|---|---|---|
| Untreated | — | 6.03 |
| Ribavirin | 75(x3) | 4.38 |
| VIS410 | 10 | 4.45 |
| VIS410 | 2.5 | 4.08 |
| VIS410 | 0.6 | 5.38 |

Example 3: Evaluation of Efficacy and Emergence of Resistance to an Anti-HA Antibody Molecule in a Human Challenge Model of Infection with a p2009 H1N1 Virus In this study, the efficacy and emergence of resistance to an exemplary anti-HA antibody molecule (i.e., VIS410) was evaluated.

Methods

The efficacy and emergence of viral resistance to VIS410 were evaluated in a Phase 2a human challenge study in healthy volunteers with an H1N1 strain isolated during the 2009 pandemic (p2009 H1N1). Eighteen subjects received a single intravenous 2300 mg dose of VIS410 24 hours after viral inoculation. Influenza virus replication from nasopharyngeal swab specimens was measured by tissue culture infectious dose 50 (TCID50) assay and quantitative PCR methods. Emergence of resistance was assessed by using both phenotypic and genotypic approaches to characterize influenza viruses in nasopharyngeal swab specimens from subjects. Briefly, phenotypic resistance was assessed by culturing virus in the presence or absence of pre-defined concentrations of VIS410 and detecting virus outgrowth by nucleoprotein ELISA and viral foci immunostaining. Genotypic resistance was assessed by performing nested Sanger population sequencing of the full-length HA gene and next generation sequencing to detect potential minority species.

Results

VIS410 demonstrated potent antiviral activity at 2300 mg with a 91% and 76% reduction in median viral load AUC compared to placebo for $TCID_{50}$ and qPCR, respectively. There was no emergence of resistance following administration of a single 2300 mg dose of VIS410. Influenza viruses cultured from nasopharyngeal swab specimens were uniformly sensitive to VIS410 neutralization in vitro. Additionally, Sanger and next generation sequencing did not reveal any deleterious adaptations that would affect VIS410 binding/function.

Thus, a single dose IV administration of VIS410 at 2300 mg provided potent antiviral activity and no viral resistance exhibited in this study.

Example 4: Pharmacokinetics of an Anti-HA Antibody Molecule in a Human Challenge Model of Infection with p2009 H1N1 Virus In this study, the pharmacokinetics of an exemplary anti-HA antibody molecule (i.e., VIS410) was evaluated.

Methods

Serum and nasal pharmacokinetics (PK) of VIS410 have been characterized in a Phase 2a human challenge study in healthy volunteers, with an H1N1 strain isolated during the 2009 pandemic (p2009 H1N1). This randomized, placebo-controlled, double-blind study evaluated the PK of a single 2 h IV infusion of VIS410 (2300 mg) administered 24 h after inoculation. Blood samples for PK analysis and for assessment of antidrug antibodies (ADA) to VIS410 were collected before and up to 84 days post infusion in all VIS41.0 subjects (n=18). Nasopharyngeal samples were collected for nasal PK up to Day 10 to assess VIS410 concentration at the site of infection. VIS410 concentrations were analyzed using a validated ELBA method, Standard non-compartmental methods were used to estimate PK parameters in serum and nasal mucosa.

Study Design

This study was a randomized, double-blind, placebo controlled, Phase 2a human challenge study. Data presented are from the interim analysis of the 31 healthy volunteers. Subjects were inoculated intranasally (Day 1) with approximately 106 tissue culture infective dose (TCID50) of influenza A (H1N1) strain isolated during the 2009 pandemic. One day (24 hours) after inoculation (Day 2), subjects received a single intravenous administration of 2300 mg of VIS410 (n=18) or placebo (0.9% sodium chloride) (n=13).

Serial blood samples for determination of VIS410 serum concentration were collected. Serum VIS410 concentrations were determined using a validated ELISA with a lower limit of quantification of 50 ng/mL. Serial nasopharyngeal swabs for determination of VIS410 nasal concentration and viral shedding were collected. Nasal mucosa VIS410 concentrations were determined using a validated ELISA with a lower limit of quantification of 0.50 ng/mL.

Nasal and serum PK parameters were determined using standard non-compartmental methods using Phoenix WinNonlin software. Serum PK samples were collected pre-dose and at serial times relative to the end of infusion. Nasal PK and viral samples were collected Day −2 (prior to inoculation), pre-dose and at serial times relative to the end of infusion. Non-parametric Mann Whitney U test was used to assess the difference between treatment groups in the area under the viral load time curve (AUC) for H1N1 based on qRT-PCR and TCID50 from nasopharyngeal swabs.

Results

All 18 VIS410 subjects were included in the PK analysis. Of the 31 randomized and treated subjects, 20 (7 placebo and 13 VIS410) were included in the analysis of viral shedding. Seven subjects (4 placebo and 3 VIS410) were excluded due to baseline HAI titer of >10 to the challenge virus and 4 subjects (2 placebo and 2 VIS410) were excluded for not being infected post inoculation. Mean serum and nasal PK parameters are presented in Table 21. The mean serum and nasal concentration versus time profiles are presented in FIGS. 11A-11B, respectively. Statistically significant reduction in viral AUC and peak viral load was observed with a single dose of VIS410 2300 mg vs. placebo (Table 22). All data are presented as mean (CV %).

and a clear elimination phase was not evident in the majority of profiles. A single VIS410 dose of 2300 mg resulted in a statistically significant reduction in both viral AUC and peak viral load compared to placebo. Thus, a single dose IV administration of VIS410 at 2300 mg provides potent antiviral activity, which is consistent with the observed high and sustained systemic and nasopharyngeal exposures in relation to the in vitro $EC_{50}$.

Example 5: Safety and Efficacy of the Monoclonal Antibody VIS410 in a Human Volunteer Challenge Model of Infection with an H1N1 Influenza A Virus Methods The efficacy of VIS410 was tested in a Phase 2a human challenge study with an H1N1 strain isolated during the 2009 pandemic. This randomized, placebo-controlled, double-blind study was designed to assess the efficacy and safety of VIS410 in healthy human volunteers challenged

TABLE 21

Mean Serum and Nasopharyngeal VIS410 PK Parameters

| | Treatment | | $C_{max}$ (μg/mL) | $T_{max}$ (day) | $AUC_{0-last}$ (day*μg/mL) | $T_{last}$ (day) | $AUC_{0-\infty}$ (day*μg/mL) | $AUC_{\%extrap}$ (%) | Vd (mL) | CL (mL/day) |
|---|---|---|---|---|---|---|---|---|---|---|
| Serum | VIS410 | N | 18 | 18 | 18 | 18 | 18 | 18 | 18 | 18 |
| | 2300 | Mean | 792 | 0.260 | 6,900 | 55.2 | 7,150 | 3.49 | 5530 | 334 |
| | mg | CV % | 32.3 | 94.1 | 19.5 | 5.87 | 19.4 | 42.9 | 25.8 | 20.0 |
| Nasal | VIS410 | N | 18 | 18 | 18 | 18 | | | | |
| | 2300 | Mean | 28.4 | 3.73 | 81.6 | 8.04 | | | | |
| | mg | CV % | 112 | 72.8 | 92.2 | 0.507 | | | | |

TABLE 22

Interim Analysis of Antiviral Effect of VIS410 2300 mg Compared to Placebo (mITT population)

| Viral Measure | Placebo (N = 7) | VIS410 (N = 13) | Reduction | p Value |
|---|---|---|---|---|
| Median Viral AUC $TCID_{50}$ ($log_{10}X$ hours) | 552 | 47.1 | 91% | 0.019 |
| Median Viral AUC qPCR ($log_{10}X$ hours) | 1033 | 232 | 76% | 0.024 |
| Median Peak Viral Load $TCID_{50}$ ($log_{10}$) | 5.00 | 2.75 | 2.3 | 0.009 |
| Median Peak Viral Load qPCR ($log_{10}$) | 7.14 | 5.61 | 1.5 | 0.043 |

Based on preliminary data following a 2300 mg dose (n=18) the serum $C_{max}$ was 792 (32%) μg/mL, $AUC_{0-last}$ 7150 (19%) μg*d/mL, clearance 334 (20%) mL/d, and a long half-life of approximately 12 days. Nasopharyngeal concentrations of VIS410 exceeded the in vitro $EC_{50}$ (0.3-11 μg/mL) of the majority of influenza strains tested within 6 hours of dosing (mean [CV %] concentration after 6 h was 5.6 [140%] μg/mL; $C_{max}$ for nasopharyngeal concentrations was 28.4 [112%] μg/mL and remained elevated through Day 8 [9.7 (120%) μg/mL]). VIS410 also demonstrated potent antiviral activity at 2300 mg with a 2.3 and 1.5 $log_{10}$ reduction in median peak viral load compared to placebo for $TCID_{50}$ and PCR, respectively. None of the subjects were tested positive for ADA.

Serum PK in this study is consistent with those of a human IgG1 antibody. The observed half-life of approximately 12 days supports a single dose administration of VIS410 in patients with influenza A infection. Nasopharyngeal concentration versus time profiles were highly variable with influenza A. Twenty-four hours after viral inoculation, subjects were randomized to receive either VIS410 or placebo and monitored for viral shedding by nasopharyngeal swabs, clinical symptoms and pharmacokinetics. A total of 31 subjects were randomized, all of whom either received VIS410 as an intravenous infusion at a dose of 2300 mg or placebo.

Study Design

This study was a randomized, double-blind, placebo controlled, Phase 2a human challenge study. The primary objectives were to assess the safety and tolerability of VIS410 and the effect of VIS410 on the area under the curve of viral shedding over time (viral AUC).

Healthy adult volunteers (N=31) were inoculated intranasally (Day 1) with approximately 106 tissue culture infective dose (TCID) of influenza A (H1N1) strain isolated during the 2009 pandemic. One day (24 hours) after inoculation (Day 2), subjects received a single intravenous administration of 2300 mg of VIS410 (n=18) or placebo (0.9% sodium chloride) (n=13). Nasopharyngeal swabs for determination of viral shedding were collected on Day −1 (prior to inoculation), pre-dose and at 0, 6, 12, 24, 30, 36, 48, 54, 60, 72, 78, 84, 96, 102, 108, 120, 126, 132, 144, 150, 156, 168, 174, 180, 192, 198, and 204 hours relative to the end of infusion.

The quantity of influenza virus from nasopharyngeal swab specimens was measured by tissue culture infectious dose 50 (TCID50) assay and quantitative RT-PCR (qRT-PCR) methods. A symptom score card was used to record the incidence, severity and duration of signs and symptoms of influenza-like illness through Day 10.

The modified intent-to-treat (mITT) population used in the PD analysis was defined as all randomized subjects who received study drug who met the inclusion criterion of seronegativity by hemagglutinin inhibition assay (HA1) (≤10) on Day 1 and were infected, defined by either seroconversion (≥4×HA1 titers from baseline) or measurable viral load (2 consecutive qRT-PCR time points above the level of quantification). Standard non-compartmental approaches using Phoenix WinNonlin (Pharsight Corporation, Princeton, N.J., USA; Version 6.3) were used to calculate peak viral load (VL) and VL AUC. Non-parametric Mann Whitney U test was used to assess the difference between treatment groups in the area under the viral load time curve (AUC) for H1N1 based on qRT-PCR and TCID50 from nasopharyngeal swabs Results All 31 subjects received study drug and were included in the safety analysis. Of the 31 randomized and treated subjects, 20 (7 placebo and 13 VIS410) were included in the mITT PD analysis of viral shedding. Seven subjects (4 placebo and 3 VIS410) were excluded due to baseline HA1 titer of >10 to the challenge virus and 4 subjects (2 placebo and 2 VIS410) were excluded for not being infected post inoculation.

A robust H1N1 infection model was achieved with median peak viral load of >4.5 log 10 by TCID50 and >7 log 10 by qPCR. VIS410 was generally safe and well tolerated with adverse events reported in 76.9% and 94.4% of the subjects in the placebo and VIS410 treatment arm, respectively.

There were no drug-related discontinuations, serious adverse events, or deaths in the study. Gastrointestinal disorders were the most commonly reported events in the VIS410 arm (88.9%) vs. placebo (15.4%). Abdominal pain and loose stool were the most commonly reported GI events (61.1% and 50%, respectively in the VIS410 arm). Use of a pretreatment regimen containing a histamine blocker (diphenhydramine 50 mg PO) reduced the severity of the GI events with majority (54.5%) being mild Statistically significant reduction in viral AUC and peak viral load was observed with a single dose of VIS410 2300 mg vs. placebo (Table 22)

The median duration of viral shedding measured by qRT-PCR was 5.29 days (mean=4.92 days) for VIS410 2300 mg and 7.78 days (mean=6.52 days) for placebo, while the median time to resolution of viral shedding was 5.21 days (mean=5.23 days) and 8.24 (mean=7.37 days) for VIS410 2300 mg and placebo, respectively (FIG. 12A). The $TCID_{50}$ versus time profiles of VIS410 compared to Placebo as measured by a cell based assay are shown in FIG. 12B.

Upper respiratory symptoms resolved a median of 2 days faster in the VIS410 treatment group versus placebo (FIG. 13).

VIS410 was generally safe and well tolerated with a pre-treatment regimen that included over-the-counter oral anti-histamines and NSAIDs. There were no drug-related discontinuations, serious adverse events, or deaths reported in this study. The overall area-under-the-curve (AUC) of viral shedding for the VIS410 treated subjects was 91% (p=0.019) lower than the placebo group, as measured by the cell based assay $TCID_{50}$, and 76% (p=0.024) lower than the placebo group, as measured by viral RNA quantitation (qPCR). Peak viral levels for the VIS410 treatment groups were 2.2 logs (p=0.009) lower than placebo, as measured by the cell based assay $TCID_{50}$, and 1.5 logs (p=0.043) lower, as measured by qPCR. Furthermore, subject-reported upper respiratory symptoms resolved a median of 2 days faster in the VIS410 treatment group versus placebo.

Figure 14A:
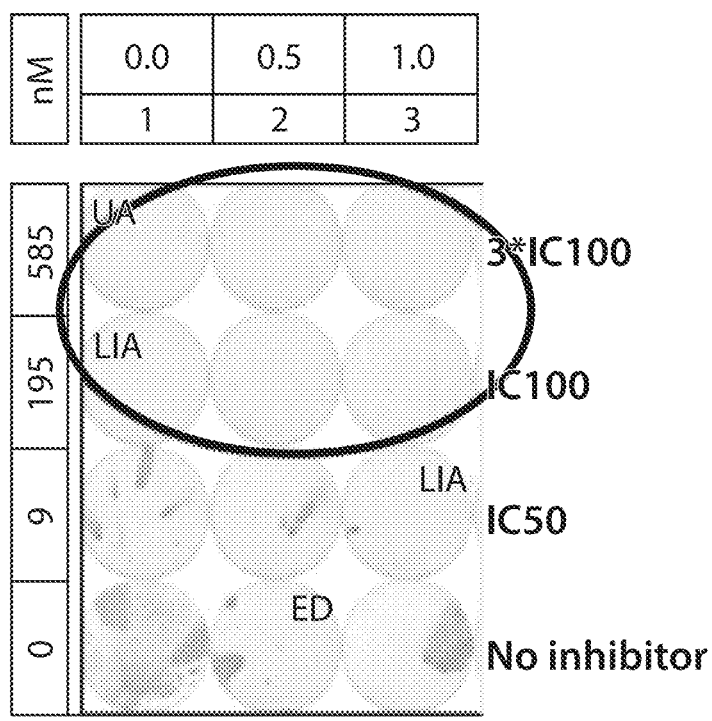
FIG. 14A depicts the result of phenotypic resistance testing using ViroSpot™ assay.
Figure 14B:
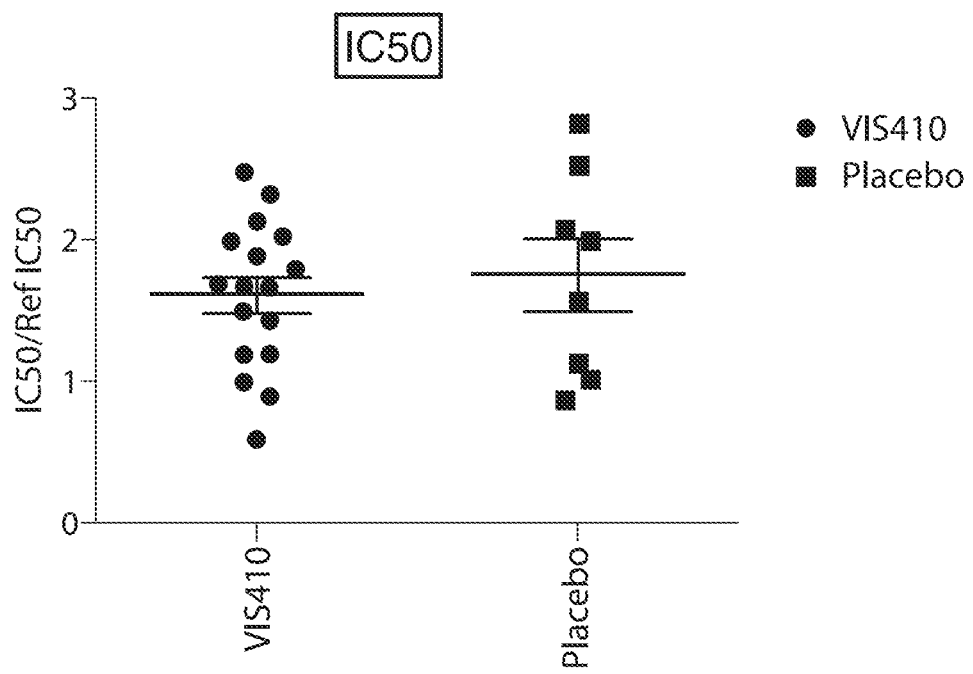
FIG. 14B depicts the result of phenotypic resistance testing based on $IC_{50}$.
Figure 15:
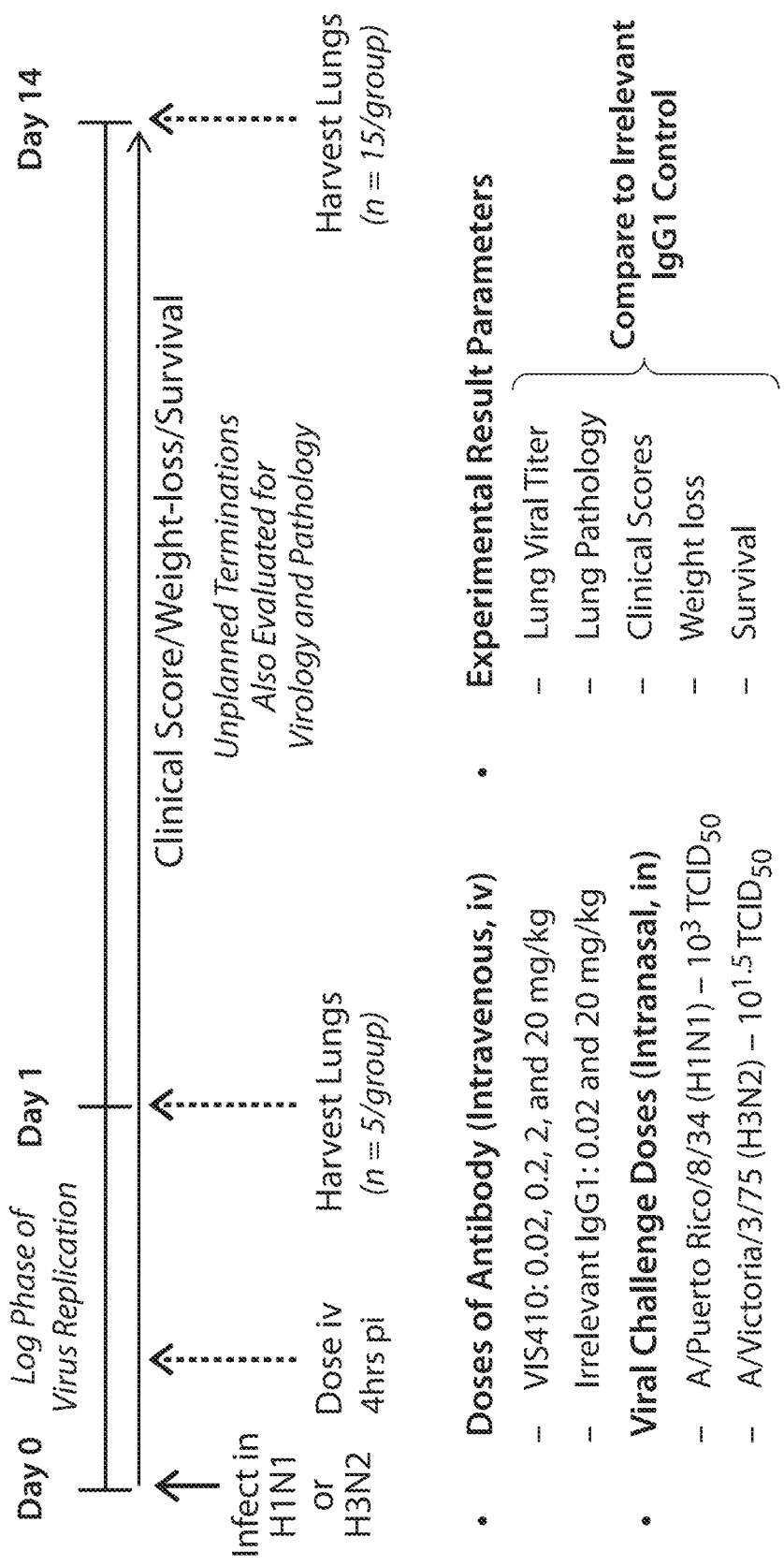
FIG. 15 depicts the in vivo ADE study design.
Figure 16A:
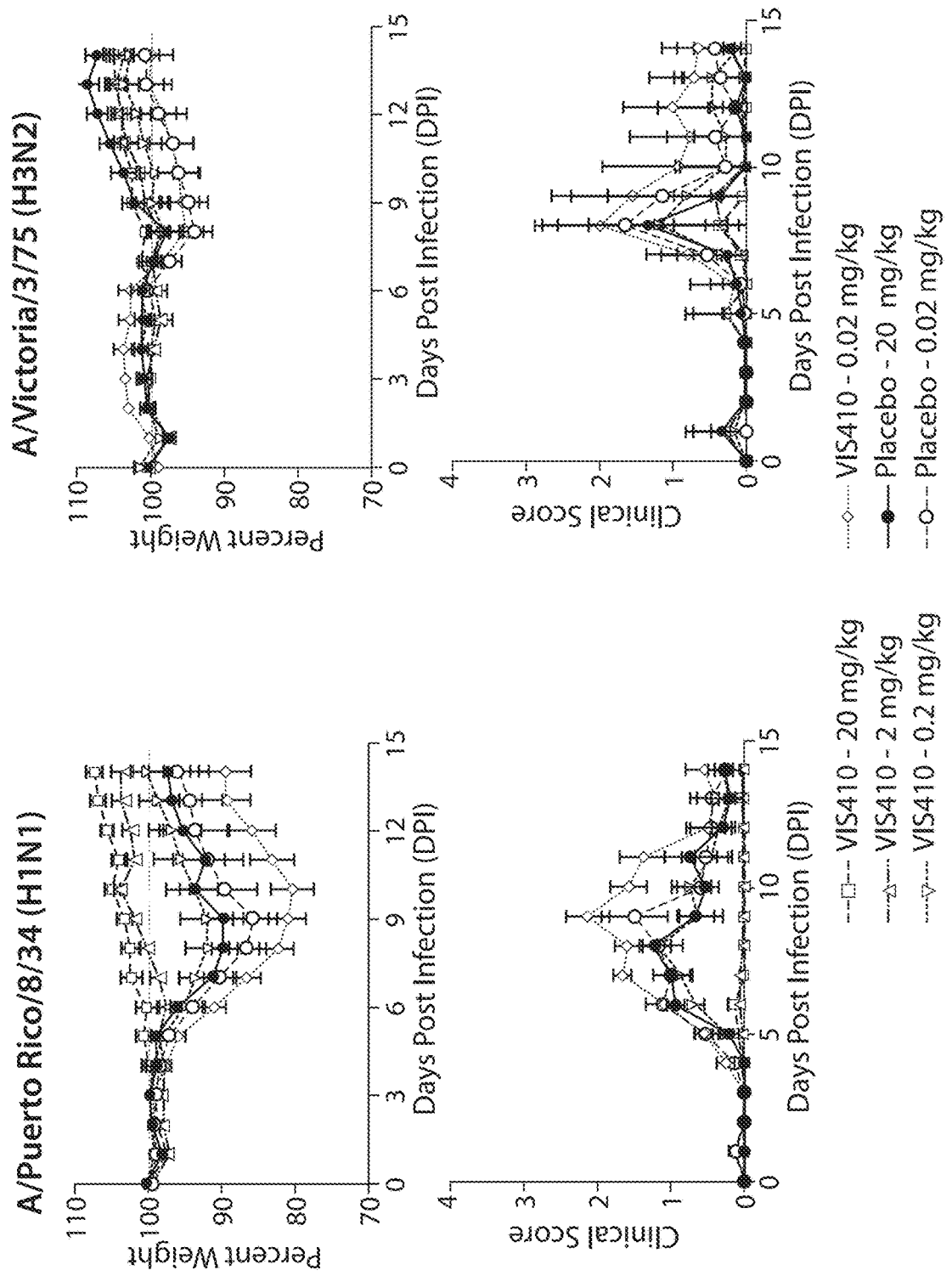
FIGS. 16A-16B depict the protection of CD-1 mice from influenza A virus-induced morbidity by VIS410 in a dose dependent manner as compared to irrelevant human IgG1.
Figure 16B:
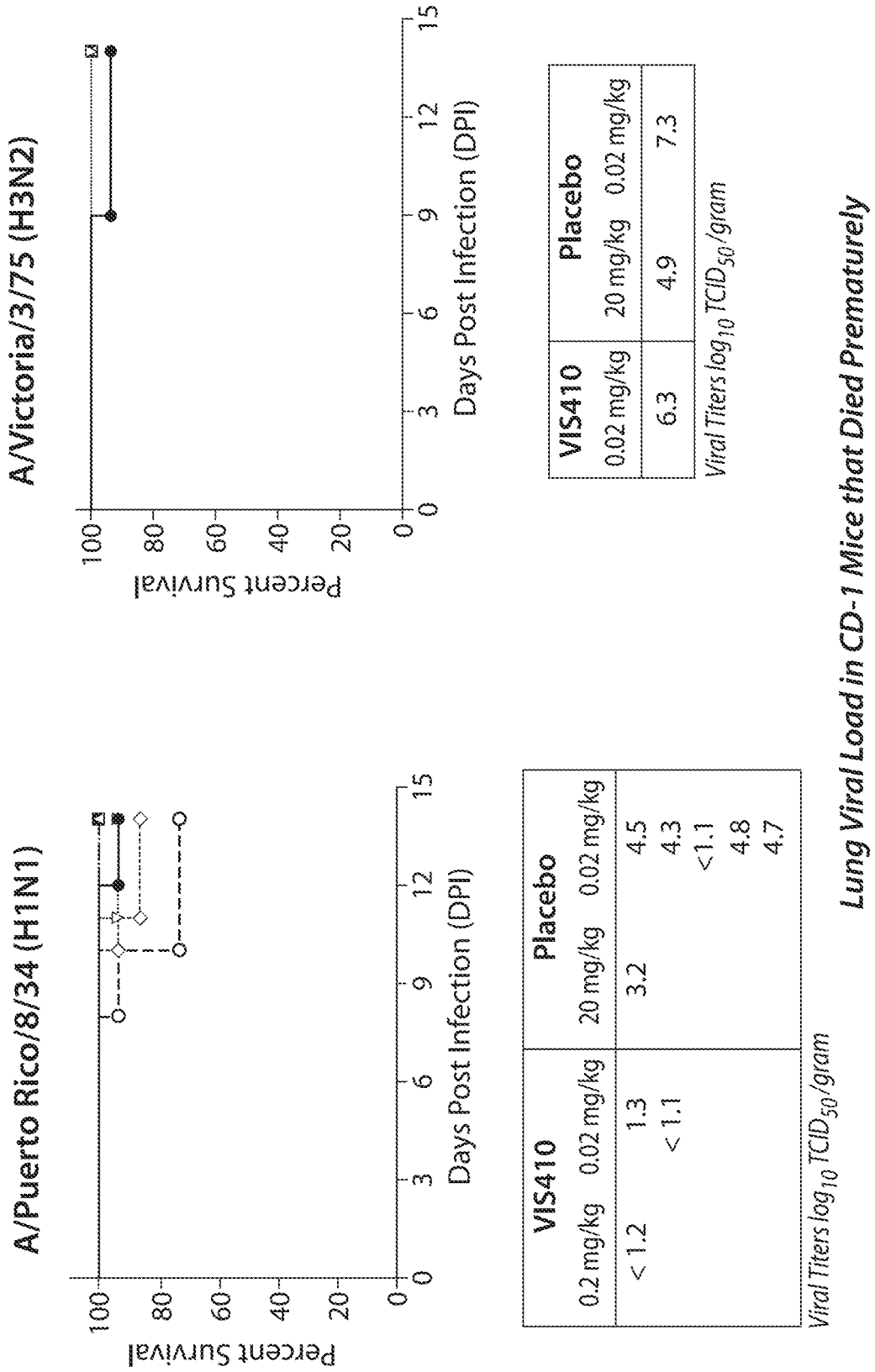

Phenotypic resistance was tested using ViroSpot™ assay and based on IC50 values. No phenotypic variants were identified by ViroSpot™ assay (27 samples assessed). Phenotypic assessment of IC50 revealed similar median of Placebo vs. VIS410 (25 samples). The results are shown in FIGS. 14A-14B. No resistant variants were identified.

The study achieved its primary endpoint of reducing the viral shedding area-under-the-curve in the VIS410 treatment group and showed a trend towards a shorter duration and lesser magnitude of upper-respiratory symptoms. VIS410 was generally safe and well tolerated with a pre-treatment regimen that included over-the-counter oral anti-histamines. A single VIS410 dose of 2300 mg resulted in a statistically significant reduction in both viral AUC and peak viral load compared to placebo. VIS410 showed a trend towards reduction in duration of viral shedding and the duration and severity of upper respiratory symptoms compared to placebo.

Example 6: Evaluation of Antibody Dependent Enhancement (ADE) in Preclinical Models of Influenza A Virus Infection Treated with an Anti-HA Antibody Molecule Antibody dependent enhancement (ADE) is the phenomena where non-neutralizing concentrations of antibodies can bind to virus particles and enhance disease by mediating entry into Fc-bearing cells, such as macrophages, consequently increasing virus tropism and pathogenesis. Data describing ADE during influenza infection in vivo is limited to preclinical and retrospective clinical vaccine studies, where polyclonal immune responses were found to elicit increased inflammation and pathology during heterologous influenza virus infection. With the advent of broadly neutralizing anti-viral monoclonal antibody therapies there is an increased need to understand the proposed therapeutic mechanisms and unintentional immunologic and virologic impact of these antibodies on disease progression. In this study, ADE potential of an exemplary anti-HA antibody molecule (i.e., VIS410) was evaluated in an in vivo efficacy model.

Methods

VIS410 was evaluated in 6-8 week old female CD-1 mice challenged with a lethal dose 25 ($LD_{25}$) of mouse-adapted A/Puerto Rico/8/34 (H1N1) or A/Victoria/3/75 (H3N2). Four hours after virus inoculation, doses of VIS410 (0.02, 0.2, 2, 20 mg/kg) and irrelevant human IgG1 antibody (0.02, 20 mg/kg) were administered intravenously. This dose range represented both protective and sub-neutralizing levels of VIS410, which could be compared for efficacy or enhancement to the corresponding doses of control antibody. Groups of mice were either harvested at the peak of infection or monitored for 14 days for weight-loss, clinical score and survival, all mice were evaluated for lung viral load and pathology.

Study Design

The study design is illustrated in FIG. 15.

Results

VIS410 treatment in mice demonstrated a dose dependent protection from weight-loss, clinical signs, and mortality during infection with H1N1 and H3N2 influenza A viruses. As shown in FIGS. 16A-16B, VIS410 protected CD-1 mice from influenza A virus-induced morbidity in a dose dependent manner as compared to irrelevant human IgG1. FIG. 14 shows the average lung viral load on Days 1 and 14. As shown in FIG. 17, lung viral loads were equivalent between 0.02 mg/kg VIS410 and placebo treated animals on Day 1 post infection (pi) (H1N1 6.1±0.4 vs. 6.3±0.6 TCID$_{50}$/g; H3N2 3.9±1.8 vs. 5.1±0.8 TCID$_{50}$/g, respectively), with all animals that survived to Day 14 pi successfully resolving infection.

Immunohistochemistry and pathology also correlated with dose, with animals receiving the higher doses of VIS410 displaying less viral antigen staining and decreased inflammation while animals treated with 0.02 mg/kg VIS410 or placebo had the greatest viral antigen staining at Day 1 pi and highest pathology scores at Day 14 pi.

TABLE 23

Day 1 IHC and Day 14 pi Lung Pathology in H1N1 Influenza Infected CD-1 Mice Treated with Different Doses of VIS410 and Irrelevant Human IgG1

| | VIS410 | | | | Placebo | |
|---|---|---|---|---|---|---|
| | 20 mg/kg | 2 mg/kg | 0.2 mg/kg | 0.02 mg/kg | 20 mg/kg | 0.02 mg/kg |
| | Immunohistochemistry | | | | | |
| Trachea/Primary Bronchus (IHC) | NP | – | +/– | ++ | NP | – |
| | NP | – | + | NP | – | NP |
| | – | NP | NP | NP | + | ++ |
| | +/– | NP | + | – | – | +/– |
| | +/– | NP | – | +/– | + | ++ |
| Bronchioles (IHC) | – | – | – | +/– | – | ++ |
| | – | – | – | – | – | – |
| | – | – | +/– | – | – | ++ |
| | – | – | – | – | – | – |
| | – | – | – | +/– | + | – |
| | Pathology | | | | | |
| Extend of Alveolitis (Score 0-3) | 0.07 ± 0.26$^b$ | 0.67 ± 0.49$^a$ | 1.36 ± 0.84 | 1.92 ± 1.04 | 1.50 ± 0.76 | 1.80 ± 0.92 |
| Severity of Alveolitis (Score 0-3) | 0.13 ± 0.52$^b$ | 1.13 ± 0.99 | 2.07 ± 1.14 | 2.00 ± 0.89 | 2.21 ± 0.89 | 2.00 ± 0.67 |
| Alveolar Edema (% Positive Slides) | 0 ± 0$^a$ | 0 ± 0$^a$ | 57.1 ± 51.4 | 61.5 ± 50.6 | 50.0 ± 51.9 | 50.0 ± 52.7 |
| Alveolar Hemorrhage (% Positive Slides) | 0 ± 0 | 0 ± 0 | 0 ± 0 | 7.7 ± 27.7 | 7.1 ± 26.7 | 0 ± 0 |
| Presence of Type II Pneumocyte Hyperplasia (% Positive Slides) | 6.7 ± 25.8$^b$ | 66.7 ± 48.8 | 78.6 ± 42.6 | 84.6 ± 37.6 | 85.7 ± 36.3 | 80.0 ± 42.2 |
| Severity of Bronchiolitis (Score 0-3) | 0.07 ± 0.26$^a$ | 0.47 ± 0.52 | 0.78 ± 0.58 | 0.77 ± 0.44 | 0.71 ± 0.47 | 0.70 ± 0.48 |
| Extent of Lymphocytic Cuffing (Score 0-3) | 0.53 ± 0.64 | 0.33 ± 0.62 | 1.00 ± 0.55 | 0.92 ± 0.86 | 0.93 ± 0.73 | 1.00 ± 0.67 |
| Severity of Tracheitis/ Bronchitis (Score 0-3) | 0 ± 0 | 0 ± 0 | 0 ± 0 | 0 ± 0 | 0 ± 0 | 0 ± 0 |

IHC Immunohistochemistry for influenza A Virus Nucleoprotein (NP) Demonstrating Virus Replication
NP Not Present, Therefor Not Evaluated
IHC Score: – All negative
+/– 1-Few Nuclei Stain Faintly Positive for IAV-NP or 'Suspect Positive'
+ Few Nuclei Stain Positive for IAV-NP
++ Several Nuclei Stain Positive for IAV-NP
+++ Many Nuclei Stain Positive for IAV-NP
Data Represent Mean ± Std Dev
$^a$P < 0.05 vs. Irrelvant Human IgG1 Groups
One-Way ANOVA (Kruskal-Wallis test) and Dunn's Post Hoc Test
$^b$P < 0.005 vs. Irrelvant Human IgG1 Groups

TABLE 24

Day 1 IHC and Day 14 pi Lung Pathology in H3N2 Influenza Infected CD-1
Mice Treated with Different Doses of VIS410 and Irrelevant Human IgG1

| | VIS410 | | | | Placebo | |
|---|---|---|---|---|---|---|
| | 20 mg/kg | 2 mg/kg | 0.2 mg/kg | 0.02 mg/kg | 20 mg/kg | 0.02 mg/kg |
| Immunohistochemistry | | | | | | |
| Trachea/Primary Bronchus (IHC) | + | − | − | − | ++ | − |
| | NP | NP | ++ | − | ++ | ++ |
| | − | NP | + | ++ | NP | ++ |
| | − | ++ | ++ | − | + | − |
| | − | − | − | − | ++ | ++ |
| Bronchioles (IHC) | − | − | − | − | − | − |
| | − | − | − | − | − | + |
| | − | − | − | − | − | − |
| | − | − | − | − | − | − |
| Pathology | | | | | | |
| Extend of Alveolitis (Score 0-3) | 0.14 ± 0.36b | 0.60 ± 0.63 | 1.07 ± 0.59 | 1.71 ± 0.91 | 1.29 ± 0.61 | 1.57 ± 0.94 |
| Severity of Alveolitis (Score 0-3) | 0.14 ± 0.36b | 0.73 ± 0.80 | 1.60 ± 0.98 | 2.14 ± 1.03 | 1.64 ± 0.74 | 1.64 ± 0.93 |
| Alveolar Edema (% Positive Slides) | 0 ± 0 | 6.7 ± 25.8 | 6.7 ± 25.8 | 35.7 ± 49.7 | 21.4 ± 42.6 | 28.6 ± 46.9 |
| Alveolar Hemorrhage (% Positive Slides) | 0 ± 0 | 0 ± 0 | 0 ± 0 | 0 ± 0 | 0 ± 0 | 7.1 ± 26.7 |
| Presence of Type II Pneumocyte Hyperplasia (% Positive Slides) | 0 ± 0a | 20.0 ± 41.4a | 53.3 ± 51.6 | 78.6 ± 42.6 | 78.6 ± 42.6 | 57.1 ± 51.4 |
| Severity of Bronchiolitis (Score 0-3) | 0 ± 0b | 0.20 ± 0.41 | 0.53 ± 0.52 | 0.64 ± 0.63 | 0.71 ± 0.61 | 0.50 ± 0.65 |
| Extent of Lymphocytic Cuffing (Score 0-3) | 0.71 ± 0.73 | 0.67 ± 0.62 | 0.93 ± 0.70 | 1.07 ± 0.73 | 0.78 ± 0.78 | 0.93 ± 0.73 |
| Severity of Tracheitis Bronchitis (Score 0-3) | 0.07 ± 0.27 | 0 ± 0 | 0.7 ± 0.26 | 0.14 ± 0.36 | 0 ± 0 | 0.08 ± 0.28 |

IHC Immunohistochemistry for influenza A Virus Nucleoprotein (NP) Demonstrating Virus Replication
NP Not Present, Therefor Not Evaluated
IHC Score: − All negative
+/− 1-Few Nuclei Stain Faintly Positive for IAV-NP or 'Suspect Positive"
+ Few Nuclei Stain Positive for IAV-NP
++ Several Nuclei Stain Positive for IAV-NP
+++ Many Nuclei Stain Positive for IAV-NP
Data Represent Mean ± Std Dev
aP < 0.05 vs. Irrelvant Human IgG1 Groups
One-Way ANOVA (Kruskal-Wallis test) and Dunn's Post Hoc Test
bP < 0.005 vs. Irrelvant Human IgG1 Groups Thus, in a sub-lethal mouse model of influenza A virus infection, VIS410 was protective at the highest doses (e.g., 2 and 20 mg/kg) while at suboptimal (e.g., sub-therapeutic) doses VIS410 neither protected nor elicited ADE, e.g., as measured by morbidity, mortality, virology and pathology assessments.

Example 7: Anti-Influenza Antibody VIS410 Targets a Broadly Conserved Epitope on Hemagglutinin Given the rapid evolution of HA, a sequence analysis of historical and currently circulating influenza strains was performed to monitor the conservation and evolution of VIS410 epitope residues, and the impact of these observed polymorphisms on binding and neutralization was assessed.

Methods

The VIS410 epitope was predicted using experimental data and in silico antibody docking methods. Sequences of influenza HA from various subtypes were collected from GenBank and the Global Initiative on Sharing Avian Influenza Data (GISAID). A bioinformatics analysis was performed to analyze the composition and evolution of amino acids found at VIS410 epitope positions in HA. ELISA was used to assay VIS410 for binding to HAs that differ in epitope amino acids, and virus neutralization assays were used to assess VIS410's ability to neutralize influenza viruses with epitope variation.

Results

VIS410 binds to an epitope that is highly conserved in group 1 and group 2 HAs and an analysis of over 44,000 sequences shows that the natural variability in these residues is limited within each group. Polymorphisms at epitope positions that occur at >1% were identified and interrogated in the context of existing strains harboring these mutations. VIS410 neutralized influenza virus strains that together covered >97% of the observed positional variability at each epitope position in H1 strains and >93% of the positional variability at each epitope position in H3 strains. Furthermore, when combined with ELISA binding data, VIS410 was empirically shown to bind to epitopes with amino acid content found in >99% of HA sequences.

Figure 18:
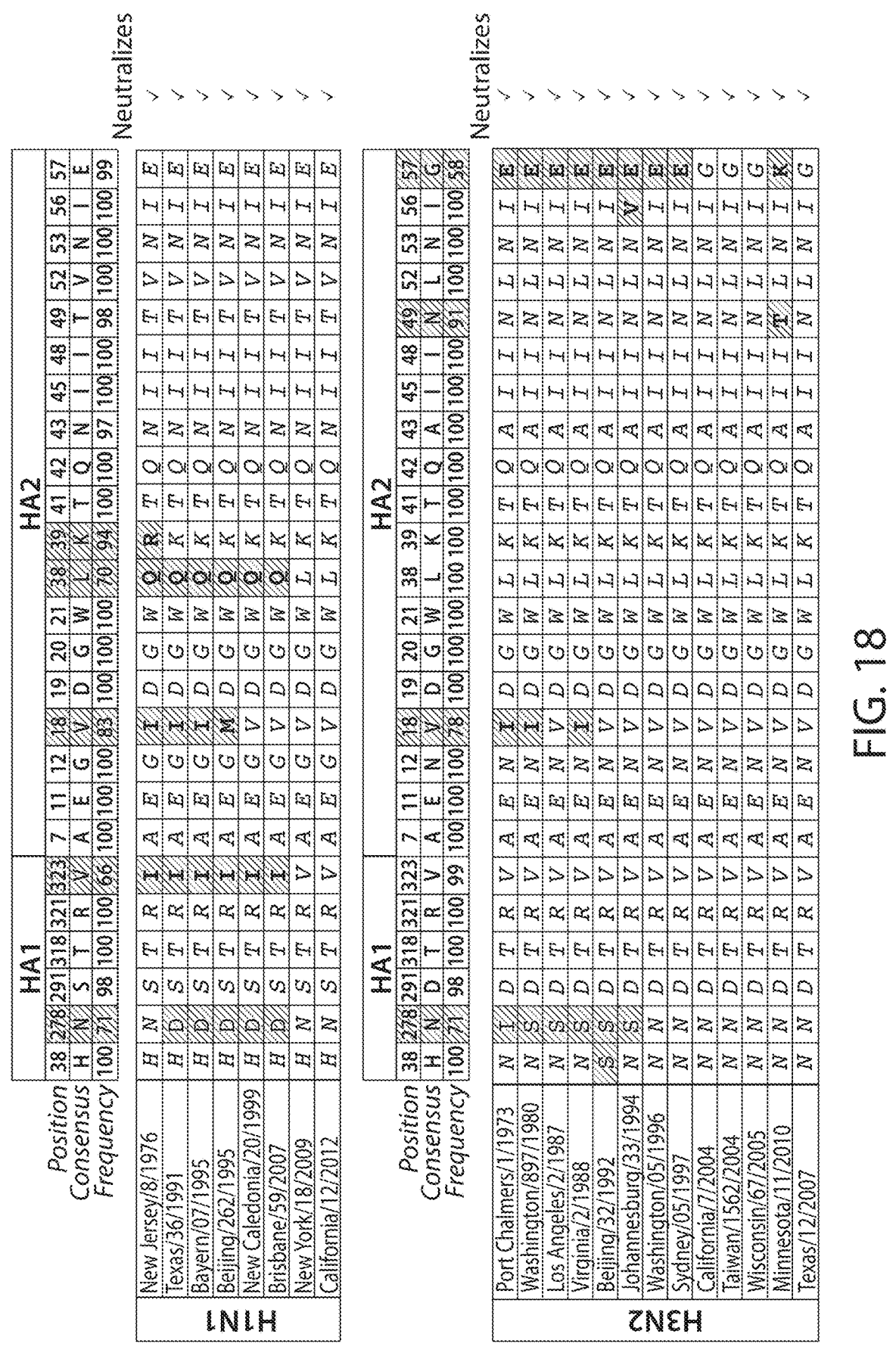

Specifically, to assess VIS410's breadth of binding and tolerance to sequence variation, a panel of seasonal influenza strains were selected with diverse geographic origin and spanning 4 decades. Strains exhibiting polymorphisms at the VIS410 epitope were identified based on a sequence analysis of available HA sequences, and were included in the panel. Strains were included that contain sequence diversity at epitope positions where the most frequently amino acid was observed at <95% (orange columns below). VIS410 successfully neutralized this diverse panel of strains in a cell-based microneutralization assay. The results are shown in FIG. 18.

Figure 19:
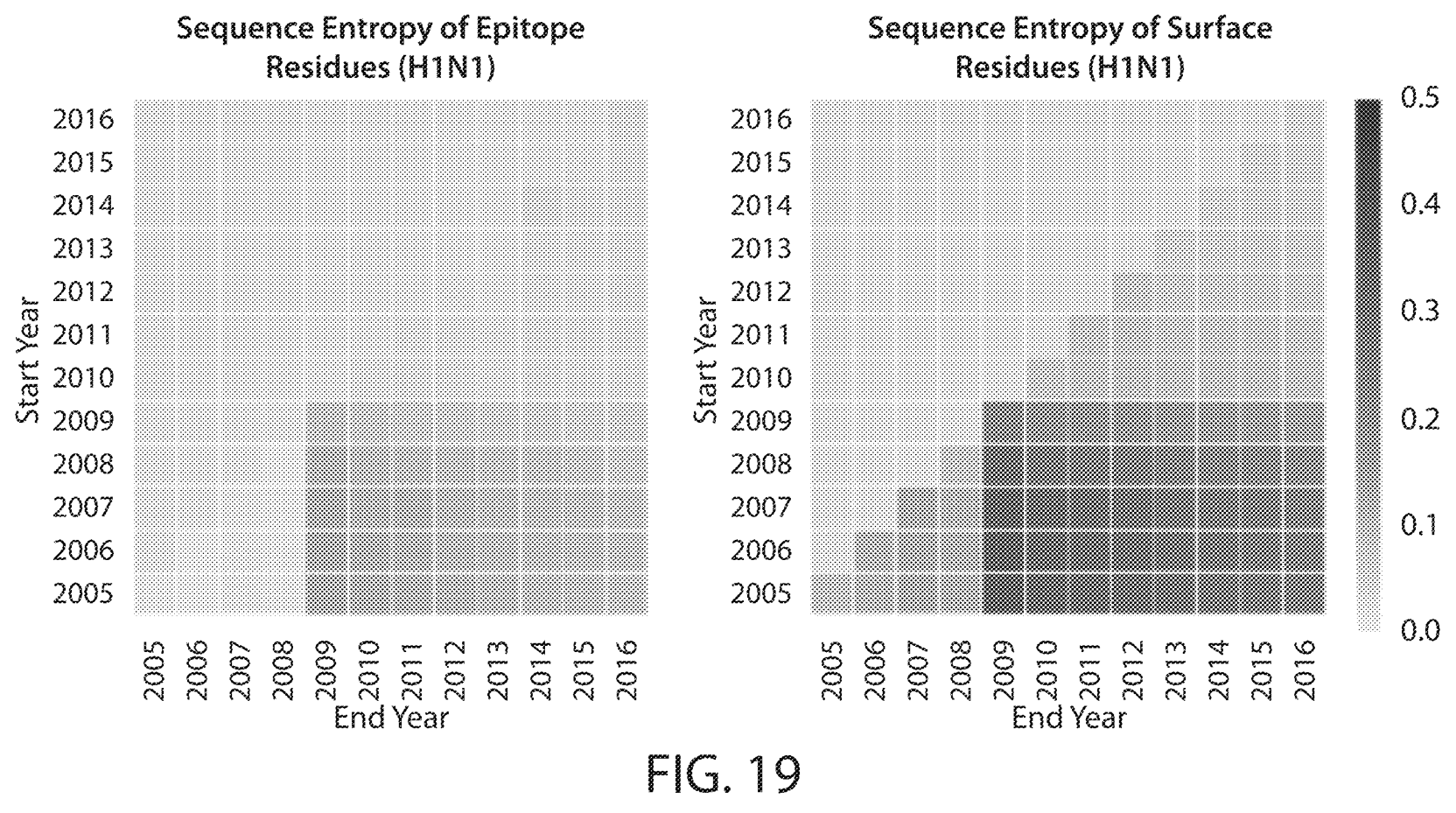

H1N1 sequences were analyzed for isolates collected from 2005 through 2016 (obtained from EpiFlu). In order to monitor the trajectory of the sequence diversity, the sequence entropy for epitope residues as well as all surface residues were calculated over this time period. The mean sequence entropy is shown using a heatmap (FIG. 19). VIS410 epitope residues show lower sequence entropy (higher conservation) than non-epitope surface residues. Of note in this analysis, even during the 2009 H1N1 pandemic, the VIS410 epitope showed little sequence variability.

Thus, VIS410 displays broad binding and neutralization and is tolerant to observed polymorphisms in its epitope including newly emerging mutations found in currently circulating strains.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of protecting a population of human subjects from influenza, the method comprising administering an anti-hemagglutinin (HA) antibody molecule comprising:
   (a) a heavy chain immunoglobulin variable region segment comprising: a CDR1 comprising the sequence of SEQ ID NO:68; a CDR2 comprising the sequence of SEQ ID NO:69; and a CDR3 comprising the sequence of SEQ ID NO:70, and
   (b) a light chain immunoglobulin variable region segment comprising: a CDR1 comprising the sequence of SEQ ID NO:145; a CDR2 comprising the sequence of SEQ ID NO:72; and a CDR3 comprising the sequence of SEQ ID NO:73,
   to at least 2%, but not more than 10%, of the subjects in the population, at a dose of at least 8-16 mg/kg, thereby protecting the population,
   wherein the subjects are 65 years of age or above and are present in a predefined area; and
   wherein the antibody molecule is administered 1 to 15 weeks prior to the date of an epidemic peak of influenza in a region where the subjects reside.

2. The method of claim 1, wherein the antibody molecule is administered to (i) at least 2%, but not more than 5%, or (ii) at least 4%, but nor more than 8%, of the subjects of the population.

3. The method of claim 1, wherein the protection comprises decreasing, or the method decreases, in the population, one, two, three, or all of: (a) the number of hospital admissions of influenza infected individuals; (b) the number incidents of influenza infection; (c) the attack rate; or (d) the number of deaths of influenza infected individuals.

4. The method of claim 3, wherein (i) the percentage decrease in the number of hospital admissions, the number of incidents of influenza infection, the attack rate, or the number of deaths, for the population, is at least 2 times greater than (ii) the percentage of subjects in the population receiving the antibody molecule.

5. The method of claim 1, wherein the predefined area is or comprises one, two, or all of: (a) a city, state, province or other political geographic area; (b) an area having a predefined number of subjects; or (c) an area within a preselected distance of a preselected place or landmark.

6. The method of claim 1, wherein the antibody molecule is administered at a dose of between 8 and 16 mg/kg.

7. The method of claim 1, wherein the date of the epidemic peak is an expected date for the epidemic peak determined prior to the occurrence of the epidemic peak.

8. The method of claim 7, wherein the epidemic peak is in a region that includes the city, province or state, in which the subjects live.

9. The method of claim 1, wherein the antibody molecule is administered 4 to 8 weeks prior to the date of an epidemic peak of influenza in a region where the subjects reside.

10. The method of claim 1, wherein the subjects reside in: (a) a single family residence; or (b) an institution, assisted living facility, a hospital, nursing home; or an institution in which more than 2 unrelated people reside.

11. The method of claim 1, wherein administering comprises a single intravenous infusion.

12. The method of claim 1, wherein the antibody molecule is administered at a dose of between 10 and 15 mg/kg 4 to 8 weeks prior to the expected date of an epidemic peak of influenza in a region where the subjects reside.

13. The method of claim 1, wherein the antibody molecule is administered at a dose of between 14.5 and 15.5 mg/kg 4 to 8 weeks prior to the expected date of an epidemic peak of influenza in a region where the subjects reside.

14. The method of claim 1, wherein said antibody molecule comprises (a) a heavy chain immunoglobulin variable region segment that comprises SEQ ID NO: 25; (b) a light chain immunoglobulin variable region segment that comprises SEQ ID NO: 52; or both (a) and (b).

15. A method of treating a human subject for influenza, the method comprising administering to the subject an anti-HA antibody molecule at a dose of at least 8-16 mg/kg,
   wherein the anti-HA antibody is administered to the subject 1 to 15 weeks prior to the expected date of an epidemic peak of influenza in a region where the subject resides,
   wherein the subject is 65 years of age or above, and
   wherein the anti-HA antibody molecule comprises: (a) a heavy chain immunoglobulin variable region segment comprising: a CDR1 comprising the sequence of SEQ ID NO:68; a CDR2 comprising the sequence of SEQ ID NO:69; and a CDR3 comprising the sequence of SEQ ID NO:70; and (b) a light chain immunoglobulin variable region segment comprising: a CDR1 comprising the sequence of SEQ ID NO:145; a CDR2 comprising the sequence of SEQ ID NO:72; and a CDR3 comprising the sequence of SEQ ID NO:73,
   thereby treating the subject.

16. The method of claim 15, wherein the antibody molecule is administered 2 to 10 weeks prior to the date of an epidemic peak of influenza in a region where the subject resides.

17. The method of claim 15, wherein the subject resides in: (a) a single family residence; or (b) an institution, assisted living facility, a hospital, nursing home; or an institution in which more than 2 unrelated people reside.

18. The method of claim 15, wherein the antibody molecule is administered at a dose of between 11 and 16 mg/kg.

19. The method of claim 15, wherein the antibody molecule is administered at a dose of between 8 and 16 mg/kg.

20. The method of claim 15, wherein the date of the epidemic peak is an expected date for the epidemic peak determined prior to the occurrence of the epidemic peak.

21. The method of claim 20, wherein the epidemic peak is in a region that includes the city, province or state, in which the subject lives.

22. The method of claim 15, wherein the antibody molecule is administered 4 to 8 weeks prior to the date of an epidemic peak of influenza in a region where the subject resides.

* * * * *